(12) United States Patent
Hedstrom et al.

(10) Patent No.: US 9,447,134 B2
(45) Date of Patent: Sep. 20, 2016

(54) COMPOUNDS AND METHODS FOR TREATING MAMMALIAN GASTROINTESTINAL MICROBIAL INFECTIONS

(71) Applicants: Brandeis University, Waltham, MA (US); The Brigham and Women's Hospital, Inc., Boston, MA (US)

(72) Inventors: Lizbeth K. Hedstrom, Newton, MA (US); Gregory D. Cuny, Houston, TX (US); Suresh K. Gorla, Gurgaon (IN); Mandapati Kavitha, Gurgaon (IN)

(73) Assignees: Brandeis University, Waltham, MA (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 14/421,818

(22) PCT Filed: Aug. 19, 2013

(86) PCT No.: PCT/US2013/055585
§ 371 (c)(1),
(2) Date: Feb. 14, 2015

(87) PCT Pub. No.: WO2014/028931
PCT Pub. Date: Feb. 20, 2014

(65) Prior Publication Data
US 2015/0210727 A1    Jul. 30, 2015

Related U.S. Application Data

(60) Provisional application No. 61/684,263, filed on Aug. 17, 2012.

(51) Int. Cl.
| | |
|---|---|
| *A61K 31/535* | (2006.01) |
| *C07H 15/203* | (2006.01) |
| *A61K 31/502* | (2006.01) |
| *C07D 413/14* | (2006.01) |
| *C07D 213/75* | (2006.01) |
| *C07D 319/18* | (2006.01) |
| *C07D 405/12* | (2006.01) |
| *C07D 413/04* | (2006.01) |
| *C07D 413/12* | (2006.01) |
| *C07D 417/04* | (2006.01) |
| *A61K 31/4184* | (2006.01) |
| *A61K 31/423* | (2006.01) |
| *C07C 275/30* | (2006.01) |

(Continued)

(52) U.S. Cl.
CPC ............ *C07H 15/203* (2013.01); *A61K 31/17* (2013.01); *A61K 31/277* (2013.01); *A61K 31/325* (2013.01); *A61K 31/4184* (2013.01); *A61K 31/4192* (2013.01); *A61K 31/423* (2013.01); *A61K 31/427* (2013.01); *A61K 31/44* (2013.01); *A61K 31/4409* (2013.01); *A61K 31/4439* (2013.01); *A61K 31/47* (2013.01); *A61K 31/4709* (2013.01); *A61K 31/496* (2013.01); *A61K 31/502* (2013.01); *A61K 31/5375* (2013.01); *A61K 31/7036* (2013.01); *A61K 45/06* (2013.01); *C07C 271/44* (2013.01); *C07C 271/50* (2013.01); *C07C 271/52* (2013.01); *C07C 275/28* (2013.01); *C07C 275/30* (2013.01); *C07C 275/34* (2013.01); *C07C 275/36* (2013.01); *C07C 275/38* (2013.01); *C07C 275/40* (2013.01); *C07C 275/42* (2013.01); *C07C 381/00* (2013.01); *C07D 213/75* (2013.01); *C07D 215/38* (2013.01); *C07D 237/32* (2013.01); *C07D 249/18* (2013.01); *C07D 263/57* (2013.01); *C07D 295/088* (2013.01); *C07D 295/135* (2013.01); *C07D 319/18* (2013.01); *C07D 401/04* (2013.01); *C07D 401/12* (2013.01); *C07D 405/12* (2013.01); *C07D 413/04* (2013.01); *C07D 413/12* (2013.01); *C07D 413/14* (2013.01); *C07D 417/04* (2013.01); *C07C 2101/02* (2013.01); *C07C 2103/74* (2013.01)

(58) Field of Classification Search
None
See application file for complete search history.

(56) References Cited

U.S. PATENT DOCUMENTS

| | | |
|---|---|---|
| 3,931,203 A | 1/1976 | Kilbourn et al. |
| 4,143,061 A | 3/1979 | Kubo et al. |

(Continued)

FOREIGN PATENT DOCUMENTS

| | | |
|---|---|---|
| DE | 2 200 325 | 7/1973 |
| DE | 26 59 404 | 7/1977 |

(Continued)

OTHER PUBLICATIONS

Bosanac et al., "A Photoactivated Precipiton for Reagent Sequestration in Solution-Phase Synthesis," J. Am. Chem. Soc., 124(16):4194-4195 (2002).

(Continued)

*Primary Examiner* — Patrick Lewis
(74) *Attorney, Agent, or Firm* — Foley Hoag LLP

(57) ABSTRACT

Disclosed are compounds and pharmaceutically acceptable salts thereof, which are useful as inhibitors of IMPDH. In certain embodiments, a compound selectively inhibits a parasitic IMPDH versus a host IMPDH. Also disclosed are pharmaceutical compositions comprising one or more compounds of the invention. Related methods of treating various parasitic and bacterial infections in mammals are disclosed. Moreover, the compounds may be used alone or in combination with other therapeutic or prophylactic agents, such as anti-virals, anti-inflammatory agents, antimicrobials and immunosuppressants.

20 Claims, 80 Drawing Sheets

(51) Int. Cl.

| | | |
|---|---|---|
| *C07C 275/36* | (2006.01) | |
| *C07C 275/38* | (2006.01) | |
| *C07C 275/40* | (2006.01) | |
| *C07C 275/42* | (2006.01) | |
| *C07C 381/00* | (2006.01) | |
| *A61K 31/17* | (2006.01) | |
| *A61K 31/277* | (2006.01) | |
| *A61K 31/325* | (2006.01) | |
| *A61K 31/4192* | (2006.01) | |
| *A61K 31/427* | (2006.01) | |
| *A61K 31/44* | (2006.01) | |
| *A61K 31/4409* | (2006.01) | |
| *A61K 31/4439* | (2006.01) | |
| *A61K 31/47* | (2006.01) | |
| *A61K 31/4709* | (2006.01) | |
| *A61K 31/496* | (2006.01) | |
| *A61K 31/5375* | (2006.01) | |
| *A61K 31/7036* | (2006.01) | |
| *A61K 45/06* | (2006.01) | |
| *C07C 271/44* | (2006.01) | |
| *C07C 271/50* | (2006.01) | |
| *C07C 271/52* | (2006.01) | |
| *C07C 275/28* | (2006.01) | |
| *C07C 275/34* | (2006.01) | |
| *C07D 215/38* | (2006.01) | |
| *C07D 237/32* | (2006.01) | |
| *C07D 249/18* | (2006.01) | |
| *C07D 263/57* | (2006.01) | |
| *C07D 295/088* | (2006.01) | |
| *C07D 295/135* | (2006.01) | |
| *C07D 401/04* | (2006.01) | |
| *C07D 401/12* | (2006.01) | |

(56) References Cited

U.S. PATENT DOCUMENTS

| | | |
|---|---|---|
| 5,807,876 A | 9/1998 | Armistead et al. |
| 8,969,342 B2 * | 3/2015 | Hedstrom et al. .... C07C 233/15 504/113 |
| 2003/0195202 A1 | 10/2003 | Armistead et al. |
| 2005/0197368 A1 | 9/2005 | Leban et al. |
| 2008/0167340 A1 | 7/2008 | deLong et al. |

FOREIGN PATENT DOCUMENTS

| | | |
|---|---|---|
| GB | 1 332 102 | 10/1973 |
| WO | WO-00/25768 | 5/2000 |
| WO | WO-2009/018344 | 2/2009 |
| WO | WO-2009/137404 | 11/2009 |
| WO | WO-2010/108187 A2 | 9/2010 |

OTHER PUBLICATIONS

Chen et al., "Identification of Novel and Potent Isoquinoline Aminooxazole-Based IMPDH Inhibitors," Bioorganic & Medicinal Chemistry Letters, 13(7):1345-1348 (2003).

Corbin et al., "Complexation-Induced Unfolding of Heterocyclic Ureas. Simple Foldamers Equilibrate with Multiply Hydrogen-Bonded Sheetlike Structures," J. Am. Chem. Soc., 123(43):10475-10488 (2001).

Gollapalli et al., "Structural determinants of inhibitor selectivity in prokaryotic IMP dehydrogenases," Chem Biol, 17:1084-91 (2010).

Gorla et al., "Optimization of benzoxazole-based inhibitors of *Cryptosporidium parvum* inosine 5'-monophosphate dehydrogenase," J Med Chem, 56:4028-43 (2013).

Gorla et al., "Selective and potent urea inhibitors of *Cryptosporidium parvum* inosine 5'-monophosphate dehydrogenase," J Med Chem, 55:7759-71 (2012).

Hall et al., "Ure Host Monomers for Stoichiometric Molecular Imprinting of Oxyanions," J. Org. Chem., 70:1732-1736 (2005).

Hosseinzadeh et al., "Copper-catalyzed arylation of phenylurea using KF/Al$_2$O$_3$," Tetrahedron Letters, 49(5):840-843 (2008).

International Search Report from corresponding international application No. PCT/US2013/055585, mailed Aug. 12, 2014.

Johnson et al., "Phthalazinone inhibitors of inosine-5'-monophosphate dehydrogenase from *Cryptosporidium parvum*," Bioorg Med Chem Lett, 23:1004-7 (2013).

Lambert et al., "Aliphatic Nitro-compounds. Part XIX. Friedel-Crafts Reactions with α- and β-Nitro-olefins," J. Chem. Soc., 42-46 (1949).

Makowska-Grzyska et al., "*Bacillus anthracis* inosine 5'-monophosphate dehydrogenase in action: The first bacterial series of structures of phosphate ion-, substrate-, and product-bound complexes," Biochem, 51:6148-63 (2012).

Supplementary European Search Report dated Oct. 9, 2012 from EP 10754239.1.

* cited by examiner

Figure 1

Correlation of Compounds from Schemes 1-5 with P Series Numbering

| Compound |
|:---:|
| 5a = P38 |
| 5b = P11 |
| 5c = P12 |
| 5d = P15 |
| 5e = P39 |
| 5f = P102 |
| 5g = P104 |
| 5h = P13 |
| 5i = P106 |
| 5j = P105 |
| 5k = P16 |
| 5l = P42 |
| 5m = P41 |
| 5n = P113 |
| 5o = P14 |
| 5p = P17 |
| 5q = P55 |
| 5r = P19 |
| 5s = P59 |
| 5t = P57 |
| 5u = P36 |
| 6a = P80 |
| 6b = P25 |
| 7a = P82 |
| 7b = P96 |
| 7c = P32 |

FIG. 2
| Code | Compounds | $IC_{50}$ (nM) |
|---|---|---|
| P-93 | 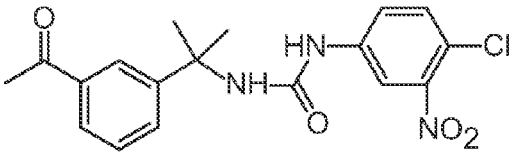 | 4.1 |
| P94 | 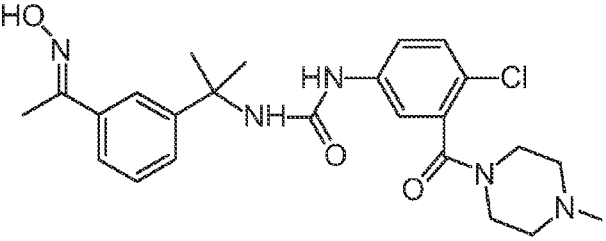 | 383 |
| P95 | 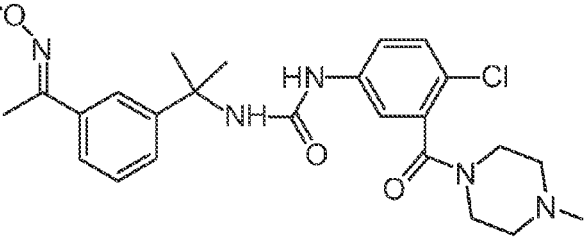 | 453 |
| P-96 | 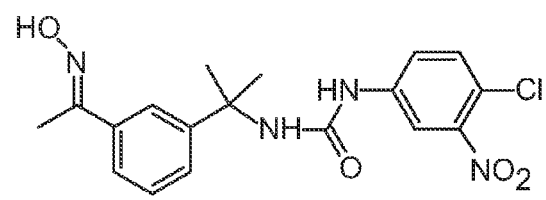 | 1.3 |
| P-97 | 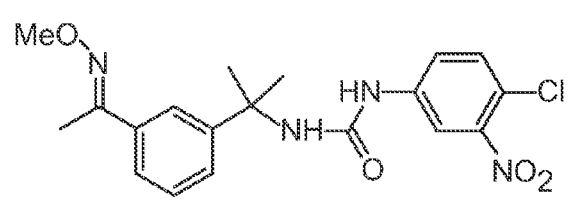 | 1.0 |

FIG. 2 (continued)

| Code | Compounds | $IC_{50}$ (nM) |
|---|---|---|
| P-98 | | 294 |
| P99 | | 9.2 |
| P100 | | 2.8 |
| P-101 | | 54 |
| P102 | | 10 |

FIG. 2 (continued)
| Code | Compounds | IC$_{50}$ (nM) |
|---|---|---|
| P103 | 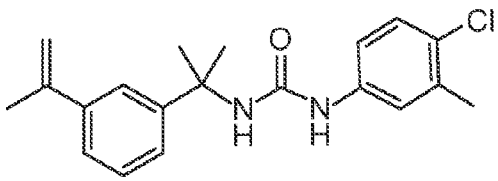 | 3.1 |
| P104 | 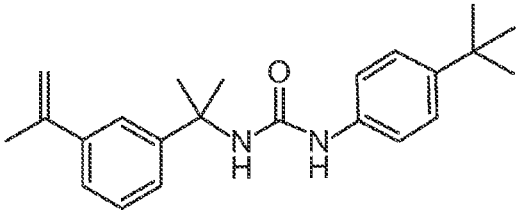 | >5000 |
| P105 | 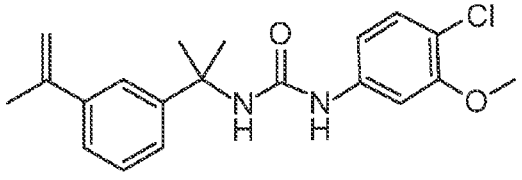 | 3.4 |
| P106 | 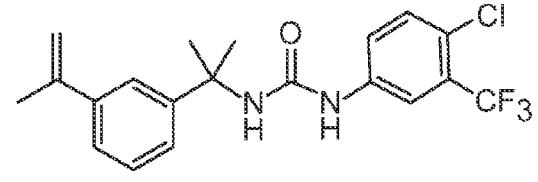 | 5.4 |
| P107 | 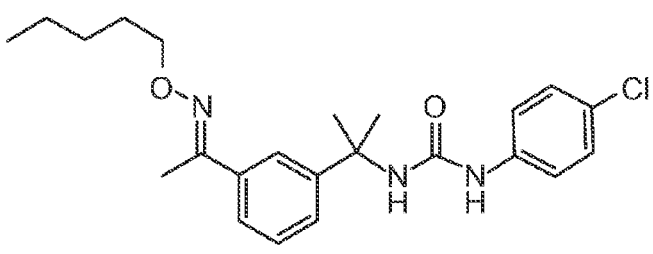 | 56 |

FIG. 2 (continued)

| Code | Compounds | IC$_{50}$ (nM) |
|---|---|---|
| P108=P138 | | 8.4 |
| P109 | | 1.3 |
| P110 | | 2.1 |
| P111 | | 13 |
| P112 | | 115 |

FIG. 2 (continued)
| Code | Compounds | IC$_{50}$ (nM) |
|---|---|---|
| P113 | 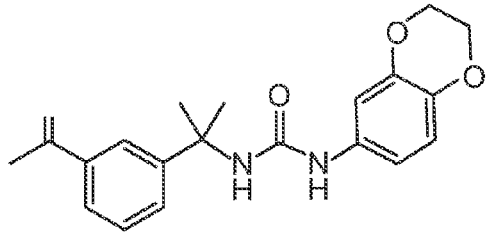 | 7.6 |
| P114 | 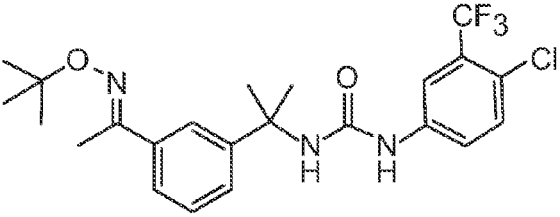 | 79 |
| P115 | 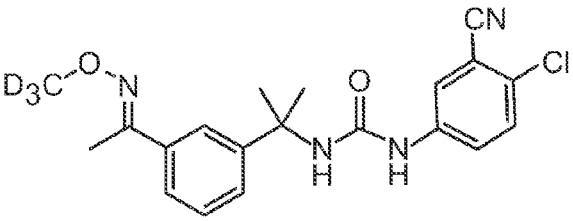 | 8.2 |
| P116 | 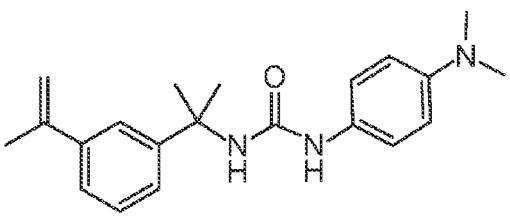 | 630 |

FIG. 2 (continued)
| Code | Compounds | IC$_{50}$ (nM) |
|---|---|---|
| P117 | 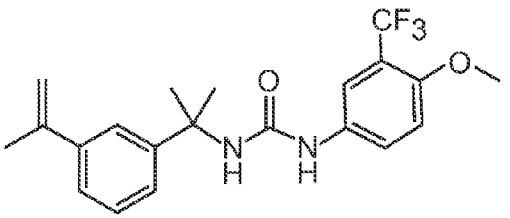 | >5000 |
| P118 | 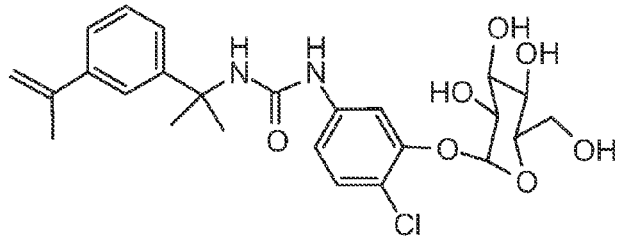 | 524 |
| P119 | 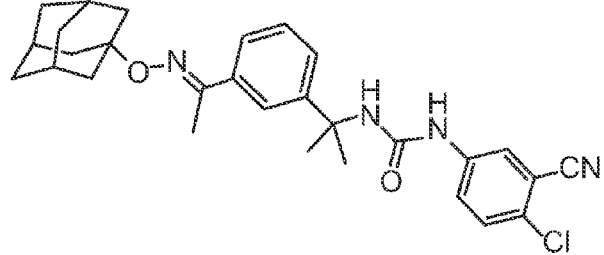 | 32 |
| P120 | 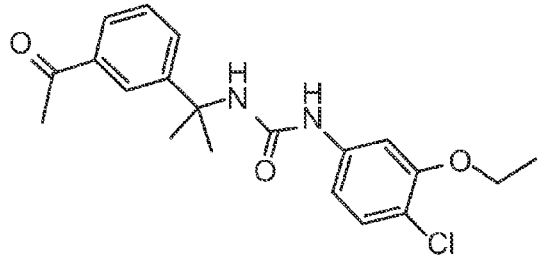 | 22 |
| P121 | 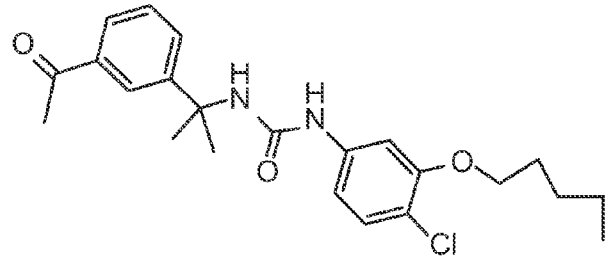 | 140 |

FIG. 2 (continued)

| Code | Compounds | IC$_{50}$ (nM) |
|---|---|---|
| P122 | | 17 |
| P123 | | 1.0 |
| P124 | | 10 |
| P125 | | >5000 |

FIG. 2 (continued)
| Code | Compounds | IC$_{50}$ (nM) |
|---|---|---|
| P126 | 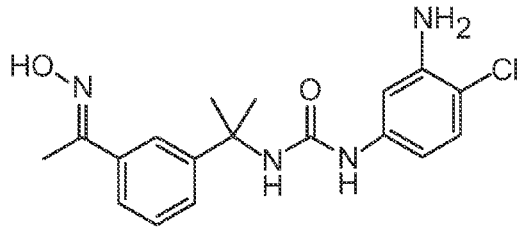 | 1.3 |
| P127 | 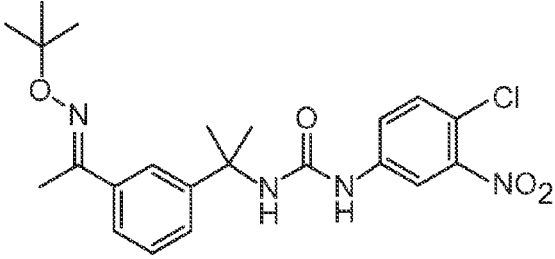 | 11 |
| P128 | 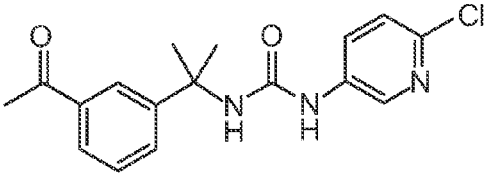 | 186 |
| P129 | 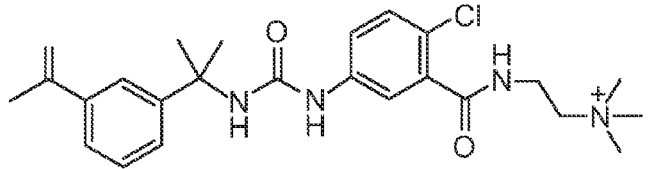 | >5000 |
| P130 | 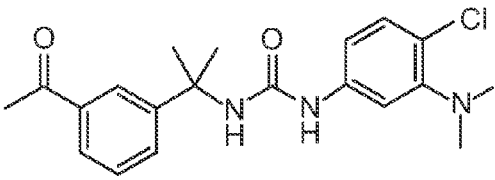 | 70 |

FIG. 2 (continued)
| Code | Compounds | IC$_{50}$ (nM) |
|---|---|---|
| P131 | 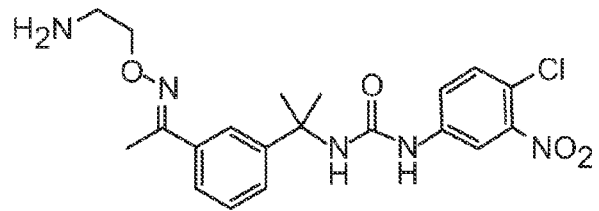 | 18 |
| P132 | 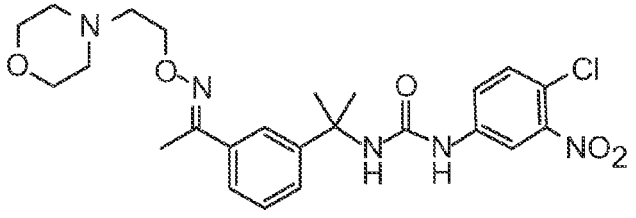 | 503 |
| P133 | 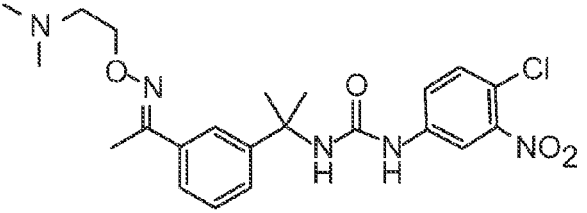 | 300 |
| P134 | 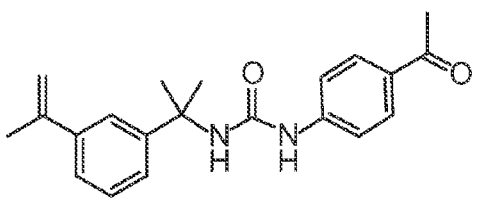 | 69 |
| P135 | 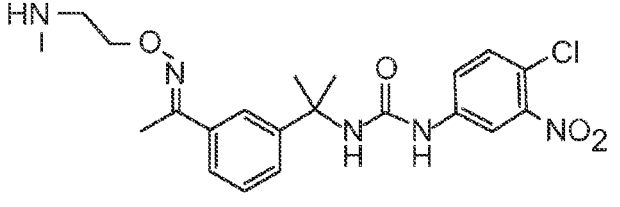 | 81 |

FIG. 2 (continued)

| Code | Compounds | IC$_{50}$ (nM) |
|---|---|---|
| P136 | | >5000 |
| P137 | | - |
| P138=P108 | | 8.4 |
| P139 | | - |

| ID | R | IC$_{50}$ (nM) | |
|---|---|---|---|
| | | (-) BSA | (+) BSA |
| 5a | Ph | 250 ± 20 | 410 ± 20 |
| 5b | 4-Cl-Ph | 20 ± 7 | 37 ± 7 |
| 5c | 4-Br-Ph | 10 ± 4 | 20 ± 10 |
| 5d | 3-Cl-Ph | 70 ± 10 | 330 ± 30 |
| 5e | 2-Cl-Ph | >5000 [a] | n.d. |
| 5f | 4-OMe-Ph | 9 ± 1 | 21 ± 7 |
| 5g | 4-tBu-Ph | >5000 [a] | n.d. |
| 5h | 3,4-di-ClPh | 6 ± 1 | 50 ± 20 |
| 5i | 3-CF$_3$-4-Cl-Ph | 4 ± 1 | 20 ± 6 |
| 5j | 3-OMe,4-Cl-Ph | 1.3 ± 0.2 | 5 ± 1 |
| 5k | 3-CONH$_2$,4-Cl-Ph | 2.3 ± 0.8 | 3 ± 1 |
| 5l | 3-CONHCH$_3$,4-Cl-Ph | 7 ± 2 | 14 ± 3 |
| 5m | 3-CON(Me)$_2$,4-Cl-Ph | 8 ± 1 | 11.7 ± 0.5 |
| 5n | 3,4-(OCH$_2$CH$_2$O)-Ph | 7.2 ± 0.6 | 110 ± 30 |
| 5o | 2-Naphthyl | 2.1 ± 0.8 | 40 ± 20 |
| 5p | 1-Naphthyl | >5000 [a] | n.d. |
| 5q | 6-Quinolyl | 1.8 ± 0.4 | 4 ± 1 |
| 5r | 7-Quinolyl | 0.8 ± 0.1 | 6 ± 2 |
| 5s | 3-Quinoline | 70 ± 10 | 308 ± 8 |
| 5t | 2-Quinoline | 250 ± 20 | 1100 ± 300 |

Figure 4

| Compound | Structure | IC$_{50}$ (nM) | |
|---|---|---|---|
| | | (-) BSA | (+) BSA |
| 38 | 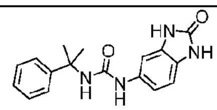 | >5000 | n.d. |
| 11 | 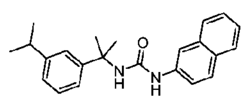 | >5000 | n.d. |
| 10 | 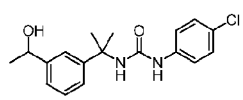 | 80 ± 20 | 120 ± 10 |
| 36a | 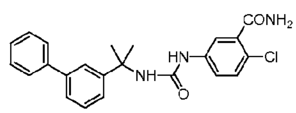 | 4 ± 4 | 14 ± 3 |
| 36b | 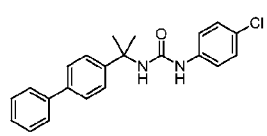 | >5000 [a] | n.d. |
| 6a | 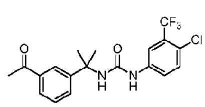 | 9 ± 5 | 20 ± 2 |
| 6b | 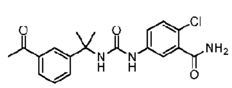 | 54 ± 7 | 52 ± 4 |

Figure 5

| Compound | Structure | IC$_{50}$ (nM) | |
|---|---|---|---|
| | | (−) BSA | (+) BSA |
| 17 | 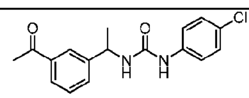 | 70 ± 20 | 110 ± 40 |
| 23 | 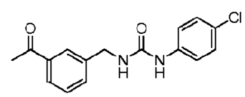 | ~5000 [a] | n.d. |
| 37 | 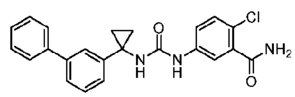 | 40 ± 10 | 90 ± 30 |
| 5u | 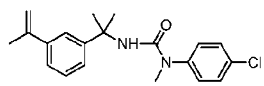 | 900 ± 400 | 5000 |
| 25 | 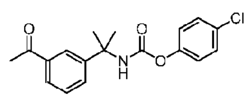 | >5000 | n.d. |
| 26 | 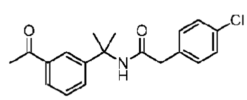 | >5000 | n.d. |
| 28 | 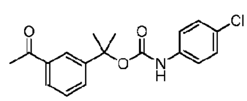 | 90 ± 20 | 120 ± 10 |

| ID | X | R | IC$_{50}$ (nM) | |
|---|---|---|---|---|
| | | | (-) BSA | (+) BSA |
| 7a | N-OH | 3-CF$_3$,4-Cl-Ph | 1.0 ± 0.1 | 4 ± 2 |
| 7b | N-OH | 3-NO$_2$,4-Cl-Ph | 0.66 ± 0.08 | 2.0 ± 0.4 |
| 7c | N-OH | 3-CONH$_2$, 4-Cl-Ph | 5 ± 1 | 6 ± 2 |
| 7d | N-OH | 2-Naphthyl | 1.0 ± 0.2 | 2.3 ± 0.6 |
| 7e | N-OH | 7-Quinolyl | 0.9 ± 0.2 | 1.2 ± 0.3 |
| 8a | N-OMe | 3-CF$_3$, 4-Cl-Ph | 5 ± 1 | 18 ± 3 |
| 8b | N-OMe | 3-CONH$_2$, 4-Cl-Ph | 5 ± 2 | 5 ± 1 |
| 8c | N-OMe | 2-Naphthyl | 1.6 ± 0.1 | 13 ± 4 |
| 9 | N-O(CH$_2$)$_2$NH$_2$ | 3-NO$_2$,4-Cl-Ph | 20 ± 3.4 | 24 ± 17 |

Figure 7

| Compound | Mouse Microsomal Stability ($t_{1/2}$, min) | Mouse Plasma Stability ($t_{1/2}$, min) |
|---|---|---|
| 5k | 25 | >120 |
| 5r | 5.9 | >120 |
| 6b | >700 | >120 |
| 7a | 88 | n.d. |
| 7c | 190 | >120 |
| 7e | 45 | >120 |
| 8a | 33 | n.d. |
| 7b | 11 | n.d. |
| 9 | 121 | n.d |

Figure 8

| Compound | EC$_{50}$ (μM) | | Selectivity [a] |
|---|---|---|---|
| | Toxo/WT | Toxo/CpIMPDH | |
| 5a | 6 ± 4 | 0.77 ± 0.06 | 8 |
| 5b | > 25 | 0.18 ± 0.02 | > 140 |
| 5c | > 25 | 0.2 ± 0.01 | > 120 |
| 5d | 0.402 ± 0.002 | 0.38 ± 0.01 | 1.0 |
| 5g | 20 ± 2 [b] | 7.2 ± 0.4 [b] | 3 |
| 5h | 4 ± 2 | 0.22 ± 0.04 | 20 |
| 5j | 2.3 ± 0.2 [b] | 0.018 ± 0.002 [b] | 127 |
| 5k | 15 ± 3 | 0.23 ± 0.04 | 65 |
| 5l | 19 ± 6 | 0.18 ± 0.03 | 100 |
| 5m | 9 ± 1 | 0.09 ± 0.03 | 100 |
| 5n | 8 ± 1 | 0.2 ± 0.2 | 50 |
| 5o | > 25 | 0.20 ± 0.03 | > 120 |
| 5q | 7.6 ± 0.8 | 0.02 ± 0.01 | ≥ 80 |
| 5r | 3.0 ± 0.1 [b] | < 0.2 | > 15 |
| 5s | 2 ± 1 | 1.1 ± 0.4 | 2.3 |
| 5t | 3 ± 1 | 3.4 ± 0.3 | 0.9 |
| 6a | 3.2 ± 0.7 | 0.2 ± 0.1 | 16 |
| 6b | > 25 | 0.38 ± 0.05 [b] | > 66 |
| 7a | 2.7 ± 0.2 | 0.01 ± 0.01 | 250 |
| 7b | 4 ± 2 | 0.006 ± 0.005 | 670 |
| 7c | > 25 | 1.9 ± 0.6 | > 12 |

Figure 8 (continued)

| | | | |
|---|---|---|---|
| 7d | 5 ± 4 | 0.08 ± 0.01 | 63 |
| 7e | 14 ± 6 | 0.058 ± 0.003 | 230 |
| 8a | 1.4 ± 0.4 | 0.016 ± 0.008 | 86 |
| 8b | >25 | 0.2 ± 0.1 | >120 |
| 8c | 2.3 ± 0.8 | 0.013 ± 0.009 | 180 |
| 9 | 10.1 ± 1.9 | 0.51 ± 0.007 | 20 |
| 10 | 19 ± 6 | 0.9 ± 0.4 | 20 |
| 17 | 8 ± 4 | 2.3 ± 0.6 | 4 |
| 23 | 7 ± 5 | 11 ± 3 | 0.6 |
| 36a | 6 ± 3 | 0.21 ± 0.09 | 30 |
| 37 | 9 ± 6 | 0.6 ± 0.2 | 15 | a. Selectivity is the ratio of $EC_{50}$ Toxo/$Cp$IMPDH to $EC_{50}$ Toxo/WT. b. Two determinations.

Figure 9

| Compound | Retention time (min) | Purity (%) |
|---|---|---|
| 5a | 1.83 | 98 |
| 5b | 1.83 | 98 |
| 5c | 1.69 | 98 |
| 5d | 1.84 | 98 |
| 5e | 1.65 | 98 |
| 5f | 1.58 | 97 |
| 5g | 1.97 | 98 |
| 5h | 1.91 | 98 |
| 5i | 1.74 | 97 |
| 5j | 1.84 | 98 |
| 5k | 1.54 | 98 |
| 5l | 1.59 | 98 |
| 5m | 1.22 | 97 |
| 5n | 1.57 | 96 |
| 5o | 1.86 | 98 |
| 5p | 1.66 | 97 |
| 5q | 1.50 | 97 |
| 5r | 1.34 | 98 |
| 5s | 1.39 | 96 |
| 5t | 1.50 | 97 |
| 5u | 1.32 | 98 |
| 6a | 1.62 | 98 |
| 6b | 1.60 | 97 |
| 7a | 1.55 | 98 |
| 7b | 1.54 | 98 |
| 7c | 1.61 | 97 |
| 7d | 1.61 | 98 |

Figure 9 (continued)

| | | |
|---|---|---|
| 7e | 1.78 | 98 |
| 8a | 1.70 | 97 |
| 8b | 1.68 | 98 |
| 8c | 1.80 | 97 |
| 9 | 1.44 | 96 |
| 10 | 1.68 | 98 |
| 11 | 1.96 | 98 |
| 17 | 1.52 | 98 |
| 23 | 1.43 | 98 |
| 25 | 1.56 | 98 |
| 26 | 1.46 | 97 |
| 28 | 1.85 | 97 |
| 36a | 1.46 | 98 |
| 36b | 1.69 | 98 |
| 37 | 1.40 | 97 |
| 38 | 2.1 | 96 |

FIG. 10
| Code | Compounds | IC$_{50}$ (nM) |
|---|---|---|
| D61 | 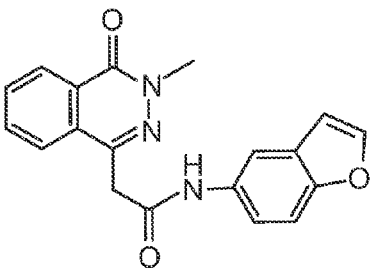 | 272 |
| D62 | 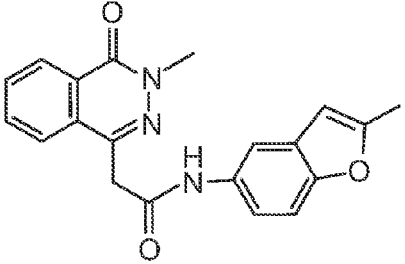 | 95 |
| D63 | 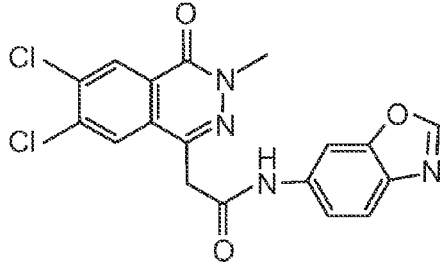 | >5000 |
| D64 | 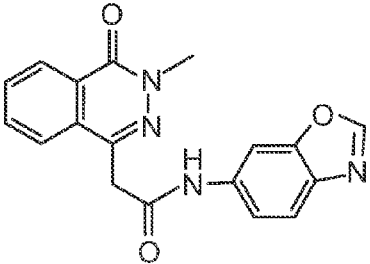 | >5000 |

FIG. 10 (continued)

| Code | Compounds | IC$_{50}$ (nM) |
|---|---|---|
| D65 | (6,7-dichloro-3-methyl-1-oxo-phthalazin-4-yl)-CH$_2$-C(=O)-NH-(benzofuran-5-yl) | >5000 |
| D66 | (6,7-dichloro-3-methyl-1-oxo-phthalazin-4-yl)-CH$_2$-C(=O)-NH-(2-methylbenzofuran-5-yl) | >5000 |
| D67 | (3-methyl-1-oxo-phthalazin-4-yl)-CH$_2$-C(=O)-NH-(tetrahydrodibenzofuran-yl) | 11 |
| D68 | (3-methyl-1-oxo-phthalazin-4-yl)-CH$_2$-C(=O)-NH-(4-chloro-3-methylphenyl) | 92 |

FIG. 10 (continued)
| Code | Compounds | IC$_{50}$ (nM) |
|---|---|---|
| D69 | 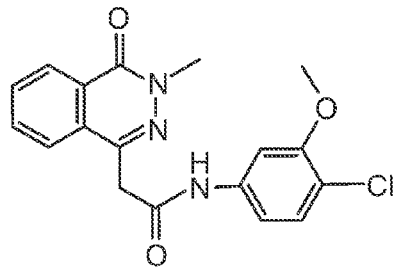 | 31 |
| D70 | 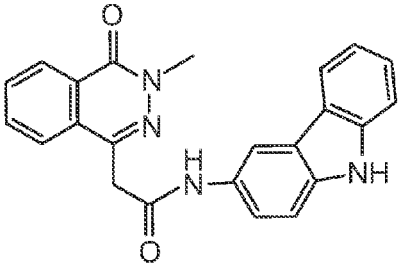 | >5000 |
| D71 | 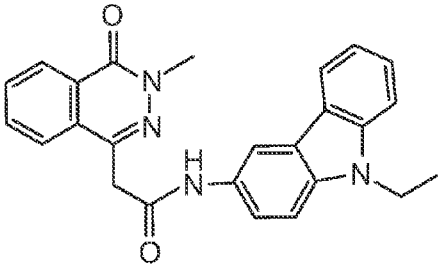 | >5000 |
| D72 | 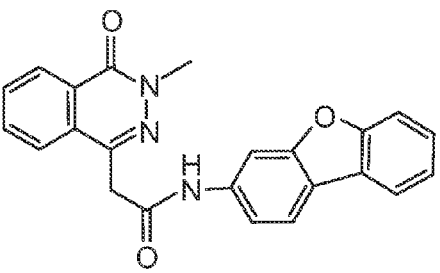 | >5000 |

FIG. 10 (continued)

| Code | Compounds | IC$_{50}$ (nM) |
|---|---|---|
| D73 | | 4 |
| D74 | | 82 |
| D75 | | 950 |
| D76 | | 650 |

FIG. 10 (continued)
| Code | Compounds | IC$_{50}$ (nM) |
|---|---|---|
| D77 | 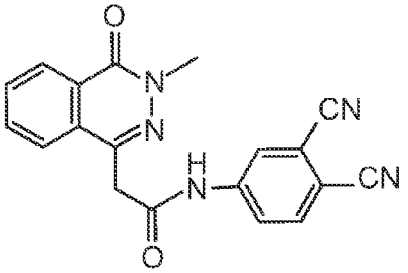 | 2500 |
| D78 | 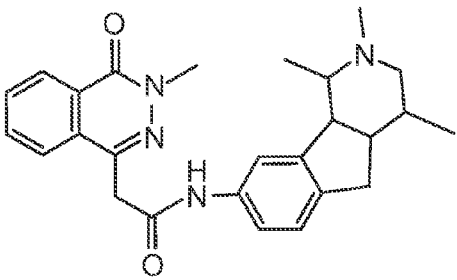 | 1900 |
| D79-D83 | Do not exist | |
| D84 | 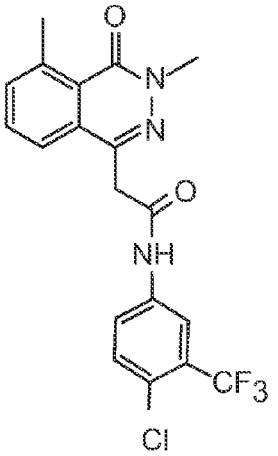 | 40 |

FIG. 10 (continued)

| Code | Compounds | IC$_{50}$ (nM) |
|---|---|---|
| D85 | | 45 |
| D86 | | 1360 |
| D87 | | 2.0 |
| D88 | | 84 |

FIG. 10 (continued)
| Code | Compounds | IC$_{50}$ (nM) |
|---|---|---|
| D89 | 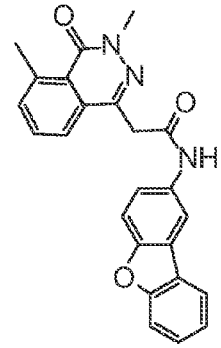 | - |
| D90 | 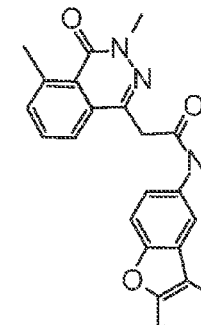 | >5000 |
| D91 | 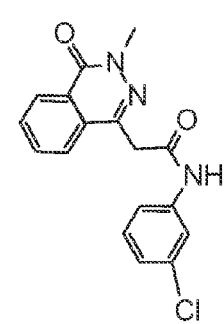 | >5000 |

Figure 11

| Compound | R | R¹ | (−)-BSA (nM) | (+)-BSA (nM) |
|---|---|---|---|---|
| D1 | Me | 4-OMePh | 1000 ± 200 | 930 ± 180 |
| D21 | Me | 2-OMePh | >5000 | ND |
| D20 | Me | 3-OMePh | >5000 | ND |
| D22 | Me | 4-OEtPh | >5000 | ND |
| D40 | Me | 4-OCF$_3$Ph | >5000 | ND |
| D34 | Me | 4-MePh | >5000 | ND |
| D6 | Me | 4-i-PrPh | >5000 | ND |
| D14 | Me | t-Bu | >5000 | ND |
| D8 | Me | NH$_2$ | >5000 | ND |
| D23 | Me | CH$_2$(4-OMePh) | >5000 | ND |
| D24 | Me | 4-ClPh | 270 ± 60 | 208 ± 50 |
| D29 | Me | 4-BrPh | 130 + 30 | 130 + 20 |
| D30 | Me | 4-FPh | >5000 | ND |
| D75 | Me | 4-CNPh | 950 ± 90 | 940 ± 90 |
| D39 | Me | 4-CF$_3$Ph | >5000 | ND |
| D19 | Me | 4-SO$_2$MePh | >5000 | ND |
| D51 | Me | 3-CF$_3$Ph | >5000 | ND |
| D91 | Me | 3-Cl | >5000 | ND |
| D27 | Me | 3,4-di-ClPh | 60 ± 4 | 95 ± 2 |
| D31 | Me | 3-Cl-4-BrPh | 42 ± 12 | 110 ± 30 |
| D45 | Me | 3-CF$_3$-4-BrPh | 23 ± 3 | 41 ± 5 |
| D48 | Me | 3-CF$_3$-4-ClPh | 13 ± 1 | 25 ± 5 |
| D50 | Me | 3-CF$_3$-4-CNPh | 81 ± 22 | 130 ± 70 |
| D49 | Me | 3-Cl-4-CNPh | 290 ± 40 | 470 ± 120 |
| D60 | Me | 3-CF$_3$-4-FPh | 150 ± 20 | 150 ± 30 |
| D53 | Me | 3-CF$_3$-4-OMePh | >5000 | ND |
| D54 | Me | 3-CF$_3$-4-NH$_2$Ph | >5000 | ND |
| D52 | Me | 3-F-4-ClPh | 200 ± 30 | 240 ± 30 |
| D68 | Me | 3-Me-4-ClPh | 79 ± 9 | 96 ± 19 |
| D74 | Me | 3-Me-4-BrPh | 82 ± 4 | 150 ± 10 |
| D76 | Me | 3-Me-4-CNPh | 620 ± 30 | 620 ± 30 |

Figure 11 (continued)

| D69 | Me | 3-OMe-4-ClPh | 31 ± 2 | 31 ± 2 |
|---|---|---|---|---|
| D77 | Me | 3,4-di-CNPh | >2500 | >2500 |
| D57 | Me | 2-CF$_3$-4-ClPh | >5000 | ND |
| D56 | Me | 2-CF$_3$-4-BrPh | >5000 | ND |
| D33 | Me | 2-F-4-BrPh | 1500 ± 100 | 1700 ± 100 |
| D38 | Me | 2,4-BrPh | >5000 | ND |
| D32 | Me | 2,4-di-ClPh | >5000 | ND |
| D43 | Me | 3,5-di-ClPh | >5000 | ND |
| D42 | Me | 3,4,5-tri-ClPh | >5000 | ND |
| D46 | Me | 3,4,5-tri-FPh | >5000 | ND |
| D41 | Me | 2-naphthyl | 61 + 4 | 134 + 9 |
| D58 | H | 3-CF$_3$-4-ClPh | 40 ± 1 | 61 ± 1 |
| D59 | H | 3-CF$_3$-4-BrPh | 17 ± 2 | 42 ± 6 |

Figure 12

| Compound | R | (-)-BSA (nM) | (+)-BSA (nM) |
|---|---|---|---|
| D61 | benzofuran-5-yl | 160 ± 60 | 140 ± 60 |
| D64 | benzoxazol-5-yl | >5000 | ND |
| D62 | 2-methylbenzofuran-5-yl | 70 ± 20 | 100 ± 30 |
| D67 | 6,7,8,9-tetrahydrodibenzofuran-yl | 20 ± 5 | 150 ± 20 |
| D73 | dibenzofuran-3-yl | 4 ± 1 | 30 ± 10 |
| D72 | dibenzofuran-2-yl | >5000 | ND |
| D70 | 9H-carbazol-3-yl | >5000 | ND |
| D71 | 9-ethyl-9H-carbazol-3-yl | >5000 | ND |

Figure 13

| Compound | EC$_{50}$$^a$ (μM) | | Selectivity $^b$ |
|---|---|---|---|
| | Toxo/WT | Toxo/*Cp*IMPDH | |
| D45 | 4 ± 3 * | 0.3 ± 0.2 | 14 |
| D48 | 23 ± 4 | 0.4 ± 0.3 | 60 |
| D67 | 1 ± 1 * | 0.5 ± 0.2 | 2 |
| D73 | 3 ± 1 | 0.4 ± 0.1 | 7 |

FIG. 14    Q-Series
| Code | Compounds | IC$_{50}$ (nM) |
|---|---|---|
| Q1 | 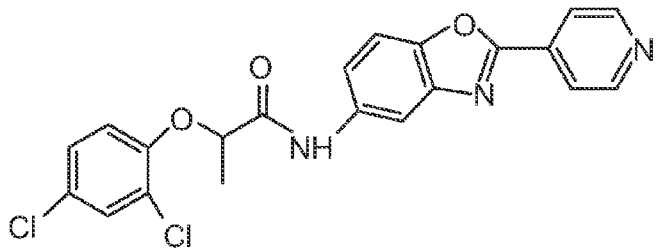 | 144 |
| Q2 | 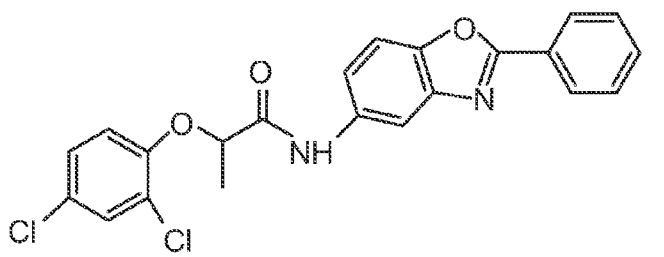 | >5000 |
| Q3 | 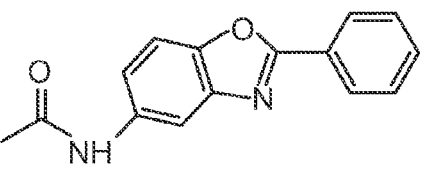 | >5000 |
| Q4 | 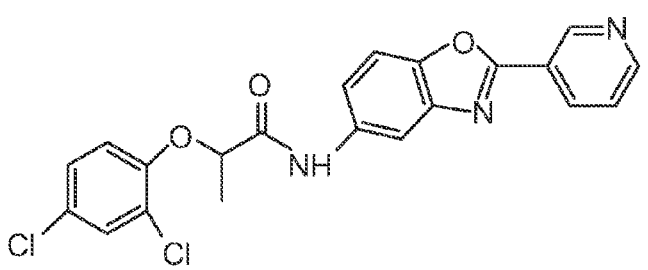 | 155 |

FIG. 14 (continued)
| Code | Compounds | $IC_{50}$ (nM) |
|---|---|---|
| Q5 | 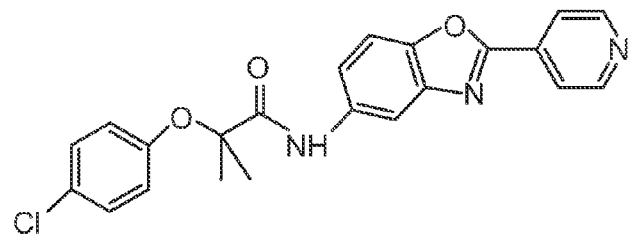 | >5000 |
| Q6 | 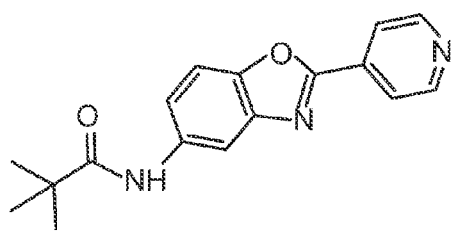 | >5000 |
| Q7 | 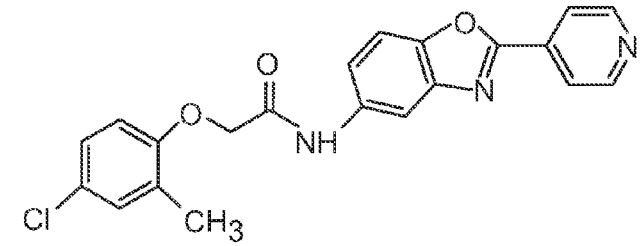 | >5000 |
| Q8 | 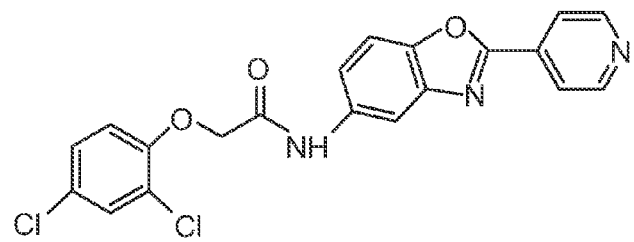 | >5000 |

FIG. 14 (continued)
| Code | Compounds | IC$_{50}$ (nM) |
|---|---|---|
| Q9 | 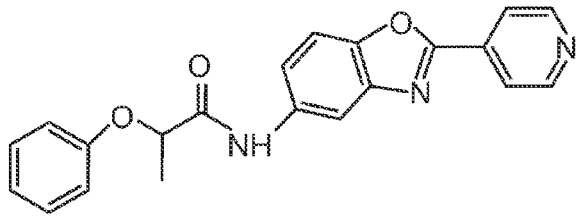 | 41 |
| Q10 | 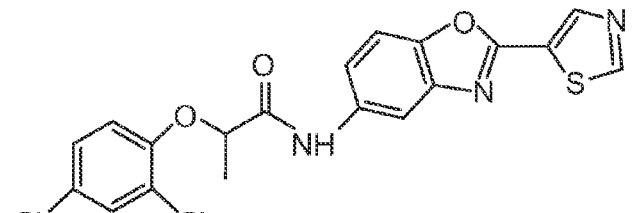 | 26 |
| Q11 | 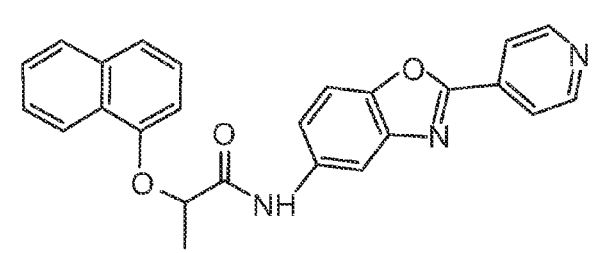 | 12 |
| Q12 | 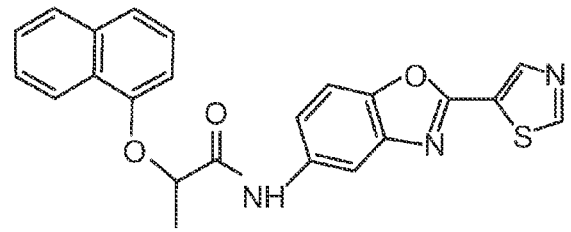 | 16 |

FIG. 14 (continued)
| Code | Compounds | IC$_{50}$ (nM) |
|---|---|---|
| Q13 | 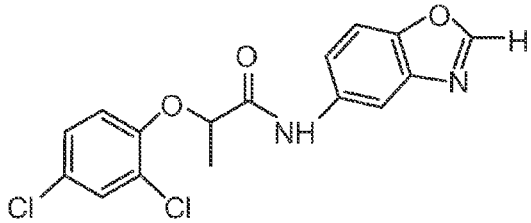 | >5000 |
| Q14 | 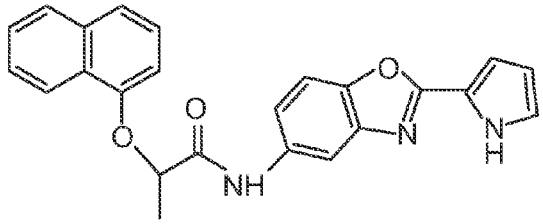 | 28 |
| Q15 | 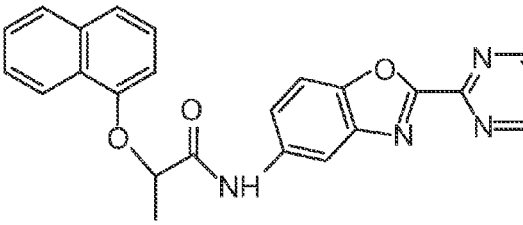 | >5000 |
| Q16 | 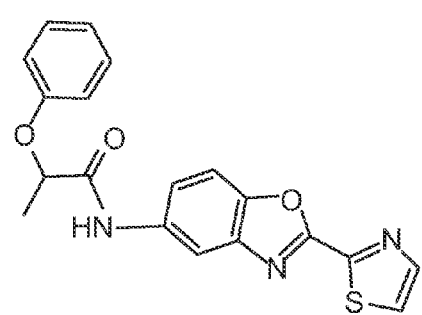 | 175 |

FIG. 14 (continued)
| Code | Compounds | IC$_{50}$ (nM) |
|---|---|---|
| Q17 | 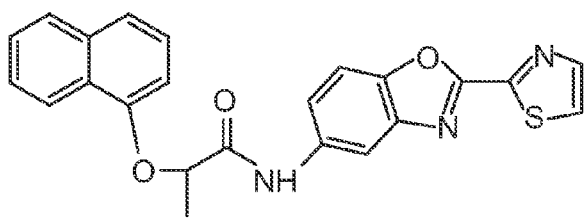 | >5000 |
| Q18 | 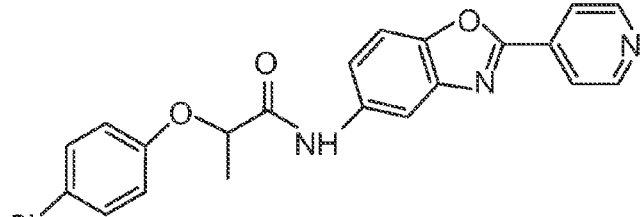 | 70 |
| Q19 | 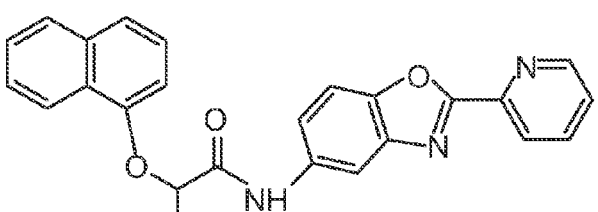 | 119 |
| Q20 | 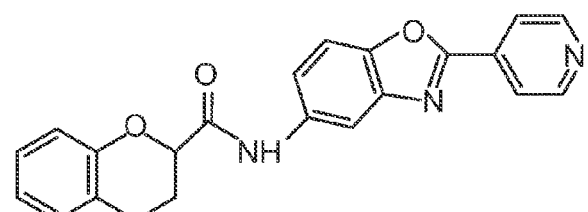 | >5000 |

FIG. 14 (continued)

| Code | Compounds | IC$_{50}$ (nM) |
|---|---|---|
| Q21 | (1-naphthyloxy)propanamide-N-(2-(pyridin-4-yl)benzoxazol-5-yl), (S)-configuration | 5.9 |
| Q22 | 2-(2,4-dichlorophenoxy)propanamide-N-(2-(pyridin-2-yl)benzoxazol-5-yl) | 183 |
| Q23 | (1-naphthyloxy)propanamide-N-(2-(pyridin-4-yl)benzoxazol-5-yl), (R)-configuration | 750 |
| Q24 | 2-(1-naphthyloxy)propanamide-N-(2-phenylbenzoxazol-5-yl) | 324 |

FIG. 14 (continued)

| Code | Compounds | IC$_{50}$ (nM) |
|---|---|---|
| Q25 | | >5000 |
| Q26 | | 1.7 |
| Q27 | | 20 |
| Q28 | | 23 |

FIG. 14 (continued)

| Code | Compounds | IC$_{50}$ (nM) |
|---|---|---|
| Q29 | (4-chloronaphthalen-1-yloxy)propanamide linked to 2-(pyridin-4-yl)benzoxazole | 26 |
| Q30 | (4-chloronaphthalen-1-yloxy)propanamide linked to 2-(thiazol-5-yl)benzoxazole | 19 |
| Q31 | quinolin-4-yloxy ethyl-triazole linked to 2-(pyridin-4-yl)benzoxazole | ~5000 |
| Q32 | (2,3-dichlorophenoxy)propanamide linked to 2-(pyridin-4-yl)benzoxazole | 1.5 |

FIG. 14 (continued)
| Code | Compounds | IC$_{50}$ (nM) |
|---|---|---|
| Q33 | 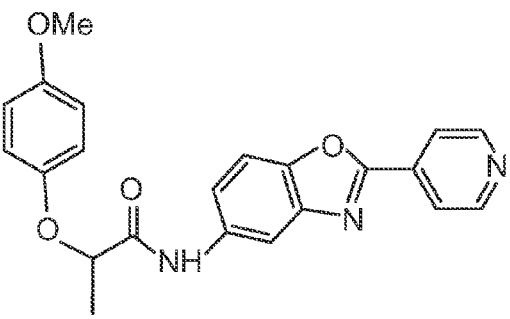 | 27 |
| Q34 | 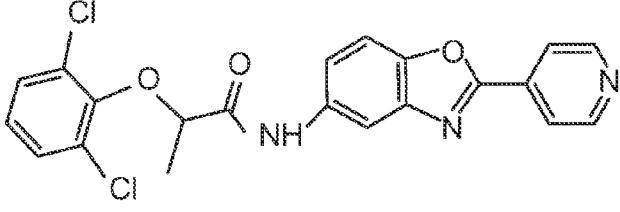 | >5000 |
| Q35 | 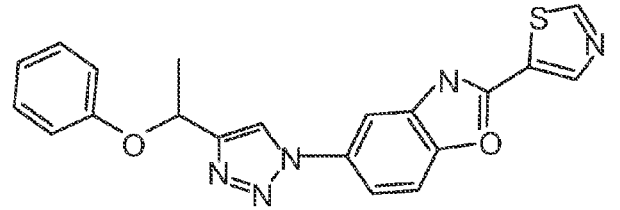 | >5000 |
| Q36 | 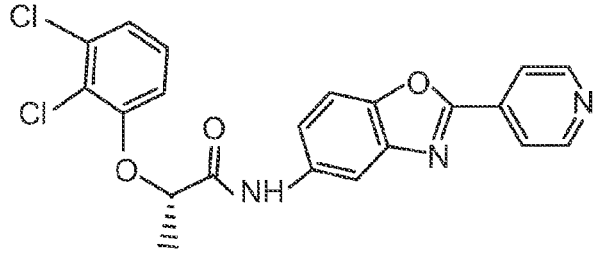 | 0.93 |

FIG. 14 (continued)
| Code | Compounds | IC$_{50}$ (nM) |
|---|---|---|
| Q37 | 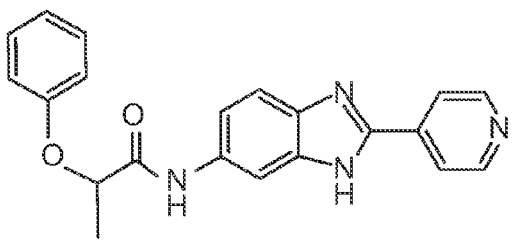 | >5000 |
| Q38 | 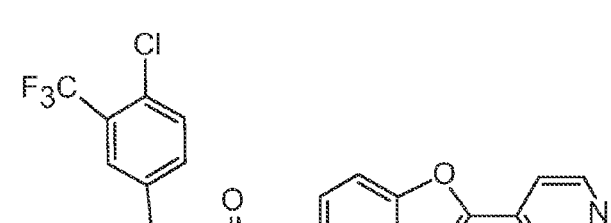 | 74 |
| Q39 | 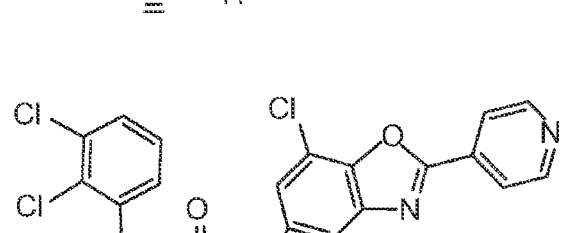 | 350 |
| Q40 | 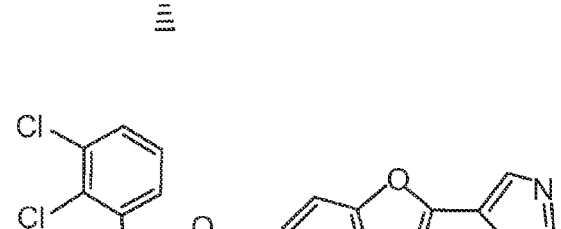 | 1.0 |

FIG. 14 (continued)
| Code | Compounds | IC$_{50}$ (nM) |
|---|---|---|
| Q41 | 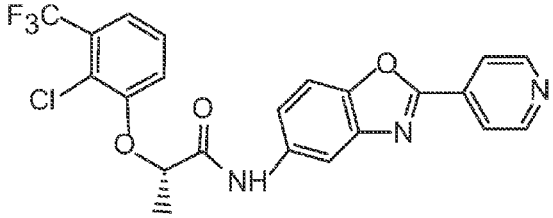 | 9.1 |
| Q42 | 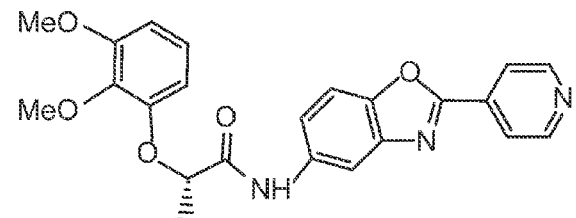 | 63 |
| Q43 | 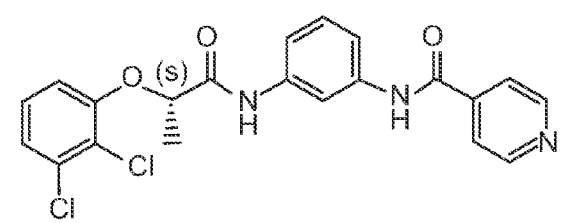 | >5000 |
| Q44 | 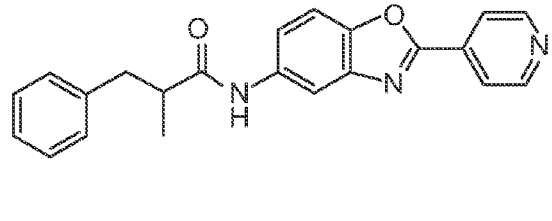 | >5000 |
| Q45 | 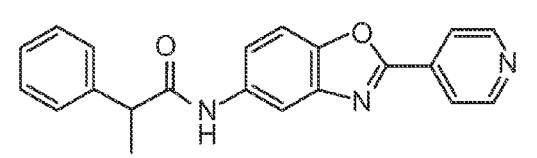 | 124 |

FIG. 14 (continued)
| Code | Compounds | IC$_{50}$ (nM) |
|---|---|---|
| Q46 | 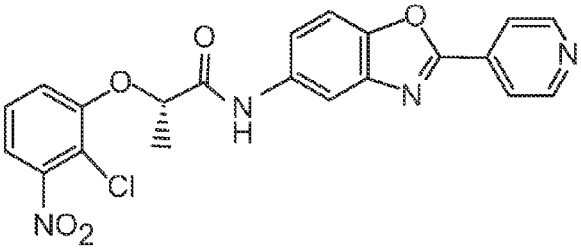 | 1.6 |
| Q47 | 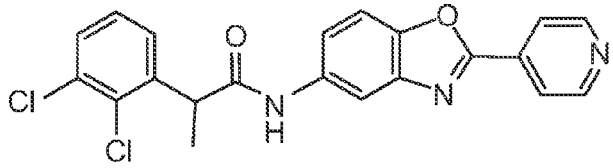 | 37 |
| Q48 | 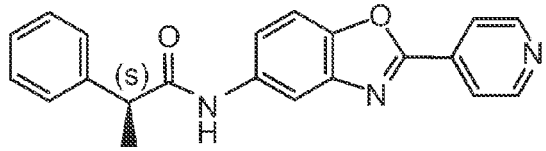 | >5000 |
| Q49 | 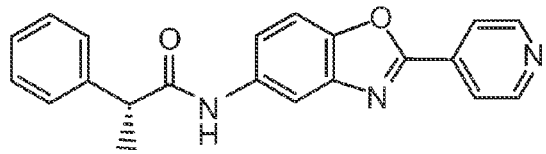 | 34 |
| Q50 | 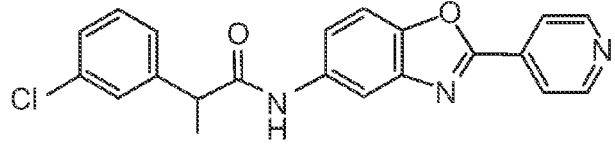 | 42 |

FIG. 14 (continued)
| Code | Compounds | IC$_{50}$ (nM) |
|---|---|---|
| Q51 | 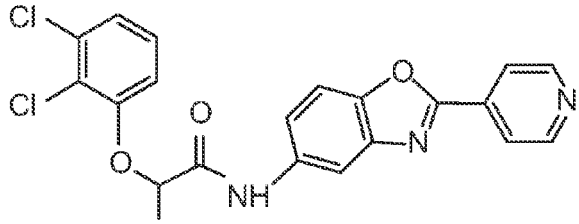 | 9.7 |
| Q52 | 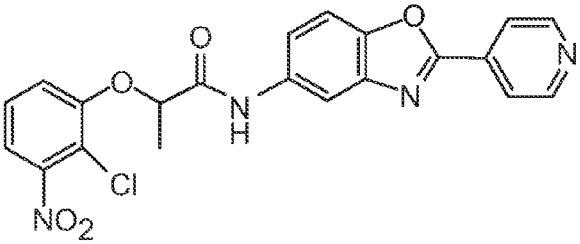 | 2.6 |
| Q53 | 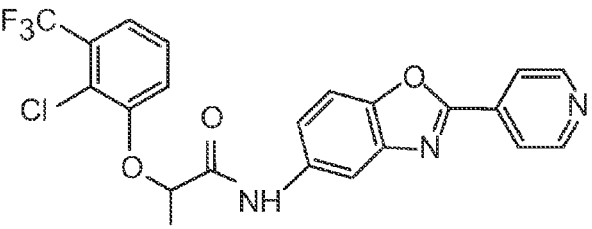 | 12 |
| Q54 | 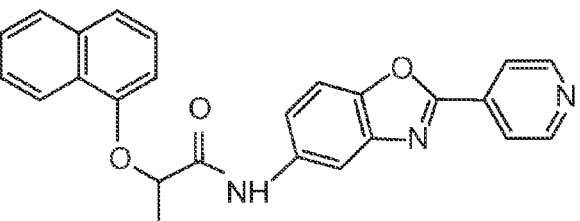 | 21 |

FIG. 14 (continued)
| Code | Compounds | $IC_{50}$ (nM) |
|---|---|---|
| Q55 | 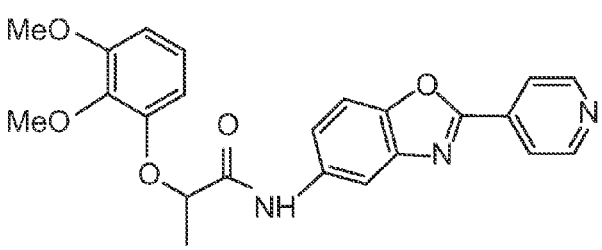 | 52 |
| Q56 | 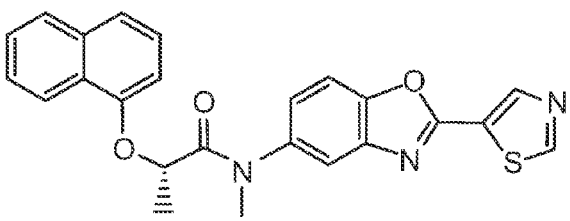 | >5000 |
| Q57 | 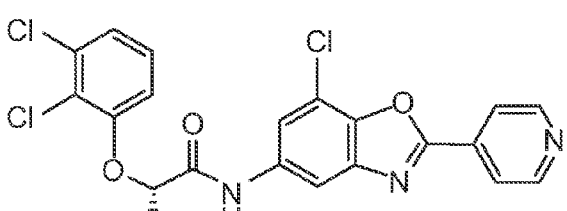 | 277 |
| Q58 | 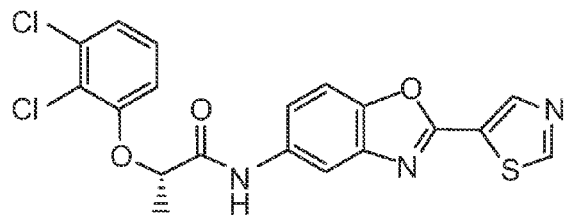 | 7.7 |
| Q59 | 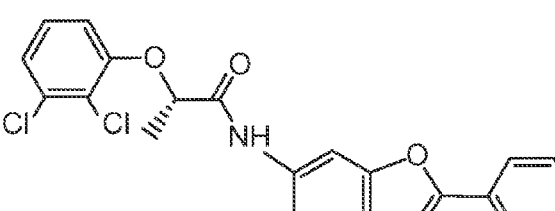 | 1.3 |

FIG. 14 (continued)

| Code | Compounds | IC$_{50}$ (nM) |
|---|---|---|
| Q60 | [structure: 2,3-dichlorophenyl-NH-CH(CH$_3$)-C(O)-NH-benzoxazole-2-(4-pyridyl)] | 1.1 |
| Q61 | No compound exist | - |
| Q62 | [structure: 2,3-dichlorophenoxy-CH(CH$_3$)-C(O)-NH-benzoxazole-2-(4-pyridyl)] | 52 |
| Q63 | [structure: phenyl-CH(CH$_3$)-NH-C(O)-benzoxazole-2-(4-pyridyl)] | >5000 |
| Q64 | [structure: 2,3-dichlorophenoxy-CH(CH$_3$)-C(O)-NH-benzoxazole-2-(5-thiazolyl)] | 6.3 |

FIG. 14 (continued)
| Code | Compounds | IC$_{50}$ (nM) |
|---|---|---|
| Q66 | 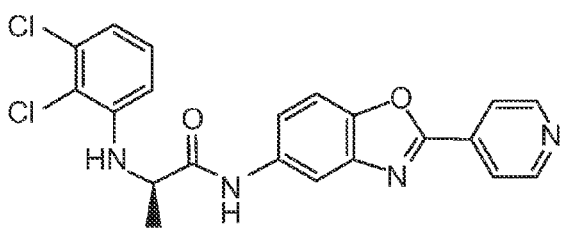 | 115 |
| Q67 | 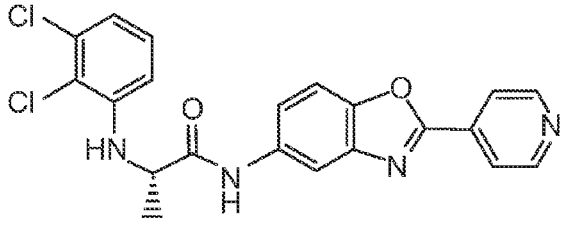 | 0.73 |
| Q68 | No compound exist | - |
| Q69 | No compound exist | - |
| Q70 | No compound exist | - |
| Q71 | 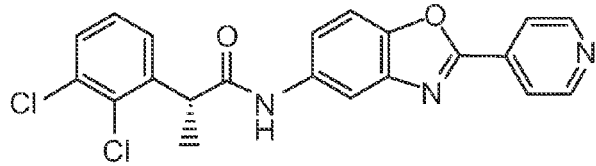 | 63 |
| Q72 | 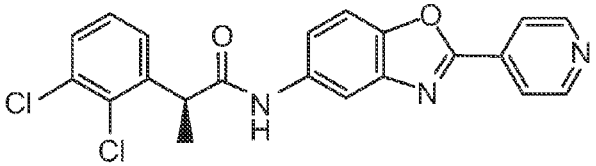 | 5000 |

FIG. 14 (continued)

| Code | Compounds | IC$_{50}$ (nM) |
|---|---|---|
| Q74 | | 14.6 |
| Q75 | | |
| Q76 | .HCl | |

| ID | $R_1$ | IC$_{50}$ (nM) | | EC$_{50}$ (μM) | | |
| --- | --- | --- | --- | --- | --- | --- |
| | | (-) BSA | (+) BSA | WT | CpIMPDH | Sel |
| (Q1) | 2,4-di-Cl-Ph | 44.6 ± 8.3 | 119.6 ± 12.2 | 1.3 ± 0.1# | 0.65 ± 0.03# | 2# |
| (Q27) | 2-Cl-Ph | 19.0 ± 1.87 | 50.5 ± 13.57 | 2.77 ± 1.37 | 0.94 ± 0.41 | 2.9 |
| (Q18) | 4-Cl-Ph | 70.0 ± 0.0 | 122.0 ± 0.0 | -- | -- | -- |
| (Q33) | 4-OMe-Ph | 27.66 ± 1.69 | 34.0 ± 4.96 | 25.3 ± 0.57 | 0.46 ± 0.22 | 55 |
| (Q9) | Ph | 40.3 ± 5.03 | 54.0 ± 16.0 | 7.4 ± 3.5 | 4.0 ± 2.4 | 1.8 |
| (Q28) | 3-Cl-Ph | 19.75 ± 7.18 | 31.66 ± 8.01 | 1.14 ± 0.41 | 0.53 ± 0.10 | 2.2 |
| (Q32) | 2,3-di-ClPh | 3.3 ± 1.46 | 11.0 ± 0.81 | 7.79 ± 2.40 | 0.22 ± 0.03 | 35.4 |
| (Q34) | 2,6-di-ClPh | >5000* | n.d | -- | -- | -- |
| (Q11) | 2-Naphthyl | 8.8 ± 2.61 | 13.7 ± 6.20 | 2.42 ± 0.28 | 0.07 ± 0.12 | 34.8 |
| | 4-OMe-Ph | 28 ± 2 | 34 ± 5 | | | |
| | 1-Naphthyl | 9 ± 3 | 14 ± 6 | | | |
| | 1-(4-Cl-naphthyl) | 27 ± 1 | 53 ± 1 | | | |

* One determination point, n.d = not determined.

| ID | X | R₁ | IC$_{50}$ (nM) | | EC$_{50}$ (µM) | | |
| --- | --- | --- | --- | --- | --- | --- | --- |
| | | | (-) BSA | (+) BSA | WT | CpIMPDH | Scl |
| (Q8) | H | 2,4-di-Cl-Ph | >5000* | n.d. | | | |
| (Q5) | Gem-di-Methyl | 4-Cl-Ph | >5000* | n.d. | | | |
| (Q54) | Isopropyl | 2-Naphthyl | 24.0 ± 2.16 | 57.33 ± 5.73 | | | |
| (Q23) | (R)-Me | 2-Naphthyl | 396.66 ± 73.72 | 384.0 ± 58.12 | -- | -- | -- |
| (Q21) | (S)-Me | 2-Naphthyl | 6.1 ± 0.50 | 8.23 ± 2.68 | 2.19 ± 0.61 | 0.44 ± 0.31 | 5 |
| (Q36) | (S)-Me | 2,3-di-Cl-Ph | 1.24 ± 0.23 | 3.5 ± 0.72 | 4.73 ± 2.31 | 0.30 ± 0.10 | 15 |
| (Q41) | (S)-Me | 2-Cl,3-CF$_3$-Ph | 9.4 ± 1.20 | 52.0 ± 5.09 | 1.70 ± 0.62 | 0.78 ± 0.39 | 2.1 |
| (Q46) | (S)-Me | 2-Cl,3-NO$_2$-Ph | 2.3 ± 0.92 | 5.5 ± 3.89 | 2.61 ± 1.49 | 0.18 ± 0.02 | 13.8 |
| (Q42) | (S)-Me | 2,3-di-OMe-Ph | 51.0 ± 12.0 | 58.5 ± 16.5 | 21.3 ± 6.14 | 0.70 ± 0.17 | 30.29 |

* One determination point, n.d. = not determined.

| ID | X | R1 | R2 | IC$_{50}$ (nM) | | EC$_{50}$ (µM) | | |
|---|---|---|---|---|---|---|---|---|
| | | | | (-) BSA | (+) BSA | WT | CpIMPDH | Sel |
| Q2 rac-Me | | 2,4-di-Cl-Ph | phenyl | >5000* | n.d | -- | -- | -- |
| Q4 rac-Me | | 2,4-di-Cl-Ph | pyridyl | 150.0 ± 18.7 | 577.6 ± 160.2 | -- | -- | -- |
| Q22 rac-Me | | 2,4-di-Cl-Ph | pyrimidyl | 212.0 ± 21.18 | 773.3 ± 225.9 | 3.81 ± 2.58 | 2.95 ± 2.18 | 1.3 |
| Q26 (S)-Me | | 2-Naphthyl | thiazolyl | 2.76 ± 0.75 | 4.0 ± 0.99 | 3.24 ± 0.79 | 0.30 ± 0.29 | 11 |
| Q40 (S)-Me | | 2,3-di-Cl-Ph | thiazolyl | 1.4 ± 0.32 | 2.33 ± 0.44 | 3.33 ± 0.48 | 0.18 ± 0.03 | 18.2 |
| Q58 (S)-Me | | 2,3-di-Cl-Ph | pyrrolyl | 16.56 ± 6.47 | 26.33 ± 10.53 | 2.26 ± 1.19 | 0.25 ± 0.01 | 8.7 |
| Q14 (S)-Me | | 2-Naphthyl | cyclohexyl | 26.0 ± 5.09 | 50 ± 5 | 1.66 ± 0.67 | 0.98 ± 0.14 | 1.7 |
| Q15 rac-Me | | 2-Naphthyl | pyrazinyl | 3750 ± 1250 | 2500.0 ± 0.0 | -- | -- | -- |

* One determination point, n.d = not determined.

| ID | R1 | R2 | IC$_{50}$ (nM) | | | | Sel |
|---|---|---|---|---|---|---|---|
| | | | (-) BSA | (+) BSA | WT | CpIMPDH | |
| Q29 | 4-Cl-Naph | | 27.33 ± 1.24 | 53.0 ± 9.09 | 2.86 ± 0.95 | 0.57 ± 0.26 | 5 |
| Q30 | 4-Cl-Naph | | 28.25 ± 5.88 | 71.0 ± 11.24 | 4.65 ± 3.58 | 1.82 ± 1.71 | 2.6 |

Figure 19

| ID | Structure | IC$_{50}$ (nM) | | EC$_{50}$ (µM) | | |
|---|---|---|---|---|---|---|
| | | (-) BSA | (+) BSA | WT | CpIMPDH | Sel |
| Q44 | | >5000 | n.d | -- | -- | -- |
| Q20 | | >5000 | n.d | -- | -- | -- |
| Q35 | | >5000 | n.d | -- | -- | -- |
| Q56 | | >5000 | n.d | -- | -- | -- |
| Q59 | | 0.68 ± 0.53 | 3.9 ± 1.70 | 2.73±1.17 | 0.018±0.020 | 152 |
| Q64 | | 7 ± 1.12 | 58 ± 21.7 | -- | -- | -- |
| Q39 | | 240.0 ± 94.16 | 633.3± 261.5 | -- | -- | -- |
| Q37 | | >5000* | n.d | 9.49 ± 2.74 | 9.02 ± 3.41 | 1 |
| Q43 | | >5000* | n.d | -- | -- | -- |
| Q63 | | >5000* | n.d | -- | -- | -- |

* One determination point, n.d = not determined.

| ID | X | R1 | IC$_{50}$ (nM) | | EC$_{50}$ (μM) | | |
| --- | --- | --- | --- | --- | --- | --- | --- |
| | | | (−) BSA | (+) BSA | WT | CpIMPDH | sel |
| (Q45) | Me | Phenyl | 123.4 ± 19.90 | 129.4 ± 27.35 | 4.77 ± 3.04 | 2.51 ± 0.22 | 1.9 |
| (Q48) | S(Me) | Phenyl | >5000* | n.d | -- | -- | -- |
| (Q49) | R(Me) | Phenyl | 34.0 ± 0.0 | 35.0 ± 0.0 | 2.20 ± 0.58 | 0.43 ± 0.10 | 5.06 |
| (Q71) | R(Me) | 2,3-di-Cl-Ph | 60 ± 3 | 49±13 | -- | -- | -- |
| | Me | CH$_2$Ph | >5000 | nd | | | |

| ID | X | R1 | IC$_{50}$ (nM) | | EC50 ($\mu$M) | | |
|---|---|---|---|---|---|---|---|
| | | | (−) BSA | (+) BSA | WT | CpIMPDH | Sel |
| Q60 | Me | 2,3-di-Cl-Ph | 1.9 ± 1.13 | 1.8 ± 0.52 | 3.92 ± 1.67 | 0.015± 0.017 | 261 |
| Q67 | S(Me) | 2,3-di-Cl-Ph | 0.53 ± 0.19 | 1.1 ± 0.05 | -- | -- | -- |
| Q74 | S(Me) | 2-Naphthyl | 14.6 ± 6.3 | 15 ± 3.60 | -- | -- | -- |

Figure 22

| Compound ID | NADPH dependent Mouse Microsomal Stability (t1/2, min) |
|---|---|
| (Q21) | 29.9 |
| (Q36) | 9 |
| (Q40) | 7 |
| (Q49) | 42.7 |
| (Q67) | 43.7 |
| (Q71) | 24.5 |
| (Q74) | 17.5 |

Figure 23

| Cmpd | Dose mg/kg | # Oocysts/100 μL | | | % Inhib | Vehicle |
| --- | --- | --- | --- | --- | --- | --- |
| | | Vehicle Ctrl | Paromomycin Ctrl | Cmpd | | |
| P96 | 250 | 5100 ± 2900 | 170 ± 20 | 1400 ± 600 | 72 | 5% DMSO/corn oil |
| P96 | 250 | 3800 ± 3400 | 100 ± 60 | 3000 ± 4000 | 21 | 5% DMSO/corn oil |
| P96 | 250 | 2200 ± 1100 | 150 ± 140 | 1400 ± 1000 | 37 | 5% DMSO/corn oil |
| P131 | 83 3x | 300 ± 200 | 70 ± 50 | 21 ± 22 | 93 | 5% DMSO/corn oil |
| P131 | 83 3x | 220 ± 170 | 200 ± 150 | 14 ± 13 | 94 | 5% DMSO/corn oil |
| P131 | 83 3x | 2200 ± 2600 | 110 ± 102 | 24 ± 37 | 99 | 5% DMSO/corn oil |
| P131 | 83 3x | 1400 ± 1200 | 390 ± 240 | 86 ± 53 | 94 | 5% DMSO/corn oil |
| P131 | 250 | 2200 ± 610 | 390 ± 250 | 850 ± 580 | 62 | 5% DMSO/corn oil |

Figure 24

| | IMPDH IC50 (molar) | | | |
|---|---|---|---|---|
| Cmpd | C. parvum | F.tularensis | B.anthracis | A. baumanii |
| D45 | 2.30E-08 | 2.70E-07 | n.d. | n.d. |
| D52 | 2.50E-07 | 4.00E-06 | 9.00E-07 | n.d. |
| D73 | 4.00E-09 | 6.00E-08 | 2.70E-07 | n.d. |
| P112 | 1.2E-07 | 3.9E-07 | 5.2E-07 | n.d. |
| P113 | 7.6E-09 | 4.1E-08 | 1.1E-07 | n.d. |
| P114 | 7.9E-08 | 6.9E-06 | 5.6E-08 | n.d. |
| P127 | 1.1E-08 | 1.8E-06 | 9.4E-08 | n.d. |
| P131 | 1.8E-08 | 1.0E-06 | 2.1E-07 | 7.1E-07 |
| P138 | n.d. | 1.2E-07 | 6.7E-08 | n.d. |
| Q63 | 0.0002 | 0.0002 | 0.0002 | n.d. |
| Q64 | 6.3E-09 | 9.37E-08 | 2.03E-07 | n.d. |
| Q67 | 2.6E-09 | 2.71E-08 | 2.68E-08 | n.d. |
| Q75 | n.d. | 1.92E-07 | 1.51E-07 | n.d. |

| | IMPDH IC50 (molar) | | |
|---|---|---|---|
| Cmpd | Ca. jejuni | S. pyogenes | Bu. mallei |
| D45 | 2.50E-07 | 0.7 | n.d. |
| D52 | 1.10E-06 | 1.2 | 0.0000004 |
| D73 | n.d. | >1E-4 | 1.00E-07 |
| P112 | n.d. | n.d. | n.d. |
| P113 | n.d. | n.d. | n.d. |
| P114 | n.d. | n.d. | n.d. |
| P127 | n.d. | n.d. | n.d. |
| P131 | n.d. | n.d. | n.d. |
| P138 | n.d. | n.d. | n.d. |
| Q63 | n.d. | n.d. | n.d. |
| Q64 | n.d. | n.d. | n.d. |
| Q67 | n.d. | n.d. | n.d. |
| Q75 | n.d. | n.d. | n.d. |

Figure 24 (continued)

| | Antibacterial activity MIC Summary | | |
|---|---|---|---|
| | MIC ≤2uM | MIC>2uM | |
| D41 | Ft | Ba | |
| D67 | Ft | | Key |
| D73 | Ft | Ba, Sa | Buth, Burkholderia thailandensis |
| D85 | Ft | | Bucp, Burkholderia cenocepacia |
| P11 | | Lm | Ft, F. tularensis |
| P13 | | Lm | Hp, Helicobacter pylori |
| P16 | | Ba,Sa | Lm, Listeria monocytogenes |
| P27 | | Ft, Mtb, Ba, Sa, Lm | Mtb, Mycobacterium tuberculosis |
| P32 | | Mtb | Pa, Pseudomonas aeruginosa |
| P41 | | Mtb | Sa, Staphylococcus aureus |
| P47 | | Ba, Sa, Lm, Hp | |
| P48 | | Buce, | |
| P55 | | Ba, Sa | |
| P64 | | Mtb | |
| P67 | | Mtb | |
| P69 | | Ba, Sa, Lm | |
| P70 | | Ba, Sa, Hp | |
| P74 | | Ba | |
| P82 | | Ba | |
| P83 | | Ba, Lm | |
| P86 | | Ba | |
| P90 | Hp | | |
| P94 | | Mtb, Buth, Buce, Pa, Ba | |
| P96 | Cp | Ft, Ba, Sa, Lm | |
| P114 | | Ba | |
| P118 | | Hp | |
| P119 | | Lm | |
| P120 | | Hp | |
| P123 | | Ba, Sa, Hp | |
| P127 | | Ft, Ba, Sa, Lm | |

Figure 24 (continued)

| | | |
|---|---|---|
| P131 | Cp, | |
| Q9 | | Ft |
| Q10 | | Mtb |
| Q21 | Ft | |
| Q26 | | Hp |
| Q27 | | Mtb |
| Q28 | | Mtb |
| Q32 | | Lm, Hp |
| Q33 | Ft | Mtb |
| Q40 | | Hp |
| Q41 | | Ba, Lm |
| Q42 | | Mtb |
| Q45 | | Mtb |
| Q46 | Ft | Mtb, Ba, Sa, |
| Q50 | | Mtb |
| Q54 | | Lm |
| Q55 | | Lm |
| Q59 | | Mtb, Sa |
| Q67 | | Ba, Sa |
| Q71 | | Hp |

FIG. 26

| ID | Structure | IC$_{50}$ (nM) | |
|---|---|---|---|
| | | (-) BSA | (+) BSA |
| 30 | 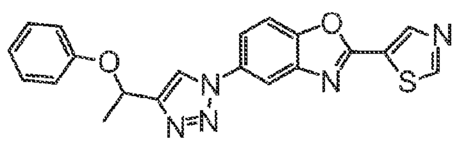 | >5000* | n.d. |
| 9 | 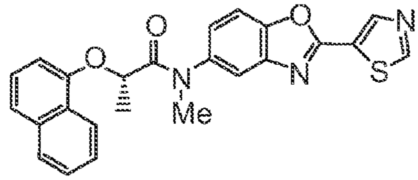 | >5000* | n.d. |
| 36 | 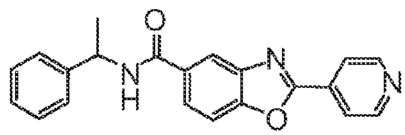 | >5000* | n.d. |
| 40a | 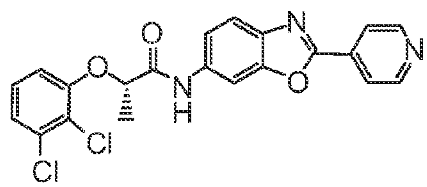 | 0.6 ± 0.5 | 4 ± 2 |
| 40b | 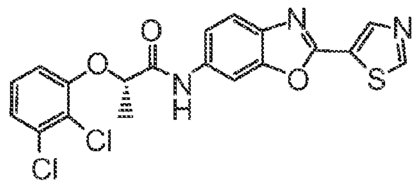 | 7 ± 1 | 60 ± 20 |
| 68 | 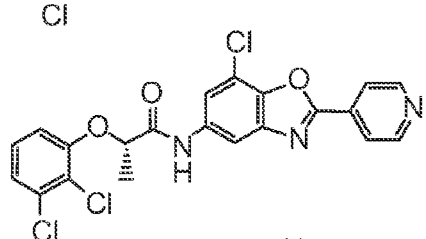 | 240 ± 90 | 600 ± 300 |
| 26 | 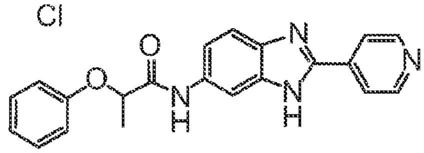 | >5000* | n.d. |
| 34 | 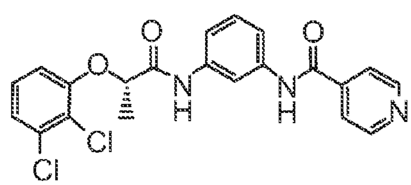 | >5000* | n.d. |

[a] n.d. = not determined. The asterisk indicates one determination.

(a)

(b)

| compd | substrate | mechanism | $K_{is}$ (nM) |
|---|---|---|---|
| 1 | IMP | NC | 58 ± 5 |
|   | NAD | C | 33 ± 8 |
| 63[b] | IMP | NC | 1.6 ± 0.7 |
|   | NAD | C | 0.9 ± 0.3 |
| 68 | IMP | NC | 210 ± 10 |
|   | NAD | C | 150 ± 30 |
| 72 | IMP | NC | 100 ± 20 |
|   | NAD | C | 40 ± 10 |

| connection | R₁ | R₂ | X | Y | $t_{1/2}$ (min) | |
|---|---|---|---|---|---|---|
| | | | | | +NADPH | −NADPH |
| 5 | 1-naphthyl | 4-Py | (S)-Me | O | 30 | 12 |
| 5 | 2,3-di-ClPh | 4-Py | (S)-Me | O | 9.0 | 11 |
| 5 | 2,3-di-ClPh | 5-thiazolyl | (S)-Me | O | 7.0 | 130[a] |
| 5 | Ph | 4-Py | (R)-Me | O | 43 | 130 |
| 5 | 2,3-di-ClPh | 4-Py | (R)-Me | NH | 25 | 110 |
| 5 | 2,3-di-ClPh | 4-Py | (S)-Me | NH | 44 | 27 |
| 5 | 1-naphthyl | 4-Py | (S)-Me | NH | 18 | 9 |
| 6 | 2,3-di-ClPh | 4-Py | (S)-Me | NH | 10 | |

FIG. 29

| EC$_{50}$ ($\mu$M) | | |
|---|---|---|
| Toxo/WT | Toxo/CpIMPDH | selectivity[b] |
| 1.3 ± 0.1[c] | 0.65 ± 0.03[c] | 2 |
| 9 ± 3 | 9 ± 3 | 1 |
| 3 ± 1 | 0.02 ± 0.02 | 150 |
| 3.0 ± 1.0 | 0.9 ± 0.4 | 3 |
| 7 ± 4 | 4 ± 2 | 2 |
| >25 | 0.5 ± 0.2 | >50 |
| 1.1 ± 0.4 | 0.5 ± 0.1 | 2 |
| 8 ± 2 | 0.22 ± 0.04 | 40 |
| 2.4 ± 0.3 | 0.20 ± 0.09[c] | 34 |
| 2.2 ± 0.6 | 0.4 ± 0.3 | 5 |
| 5 ± 2 | 0.3 ± 0.1 | 16 |
| 1.7 ± 0.6 | 0.8 ± 0.4 | 2 |
| 3 ± 1 | 0.19 ± 0.03 | 14 |
| 21 ± 6 | 0.7 ± 0.1 | 30 |
| 3.3 ± 0.5 | 0.2 ± 0.01 | 15 |
| 3.2 ± 0.8 | 0.30 ± 0.3 | 11 |
| 5 ± 4 | 2 ± 2 | 3 |
| 2.2 ± 0.8 | 0.3 ± 0.1 | 7 |
| 1.7 ± 0.7 | 1.0 ± 0.1 | 1.7 |
| 5 ± 3 | 2.5 ± 0.2 | 1.9 |
| 2.1 ± 0.5 | 0.4 ± 0.1 | 5 |
| 4 ± 2 | 0.02 ± 0.02 | 200 |

Figure 30

| Cmpd | Log P [a] | tPSA (Å²) [a] | Enzyme Inhibition IC$_{50}$ (nM) | T. gondii/CpIMPDH assay [e] | | C. parvum assay EC$_{50}$ (μM) | Mouse liver microsomal stability τ$_{1/2}$ (min) |
|---|---|---|---|---|---|---|---|
| | | | | EC$_{50}$ (nM) | Selectivity | | |
| P25 | 1.9 | 100 | 59 [b,d] | 380 [d] | >66 [d] | 12 [g,h] | ≥600 [k] |
| P32 | 2.3 | 117 | 6.7 [b,d] | 1900 [d] | >12 [d] | 6 [g,i] | 190 |
| P82 | 4.3 | 74 | 1.1 [b,d] | 10 [d] | 250 [d] | 15 [g]<br>8 [j]<br>7 [j]<br>9 [j] | 88 [d] |
| P83 | 4.6 | 63 | 2.9 [b,d] | 16 [d] | 86 [d] | 9 [j]<br>10 [j]<br>8 [j] | 33 [d] |
| P96 | 3.6 | 125 | 1.3 [b,d] | 6 [d] | 670 [d] | 8 [g,i] | 11 [d] |
| P131 | 3.7 | 141 | 18 [b,d] | 510 [d] | 20 [d] | 7 [g,i] | 120 [d] |

Figure 31

| Cmpd | Dose (mg/kg) | Average number of oocysts per 100 μL | | | | % Inhibition | P MW [c] | P TTest [f] | Exp. | Infection Protocol |
|---|---|---|---|---|---|---|---|---|---|---|
| | | Vehicle | n | Cmpd | n | | | | | |
| P25 [c,d] | 250 | 9400 ± 8900 | 9 | 8800 ± 11000 | 10 | 6 | 0.43 | 0.90 | 4 | A |
| P32 [c,d] | 250 | 9400 ± 8900 | 9 | 18,000 ± 10,000 | 10 | -91 | 0.13 | 0.068 | 4 | A |
| P82 | 250 | 5100 ± 2900 | 8 | 2300 ± 950 | 7 | 55 | 0.056 | 0.030 | 5 | A |
| P83 | 250 | 2100 ± 3300 | 8 | 1500 ± 670 | 8 | 29 | 0.43 | 0.55 | 2 | A |
| P96 | 250 | 5100 ± 2900 | 8 | 1400 ± 630 | 8 | 72 | 0.0074 | 0.0076 | 5 | A |
| | 250 | 3800 ± 3400 | 7 | 3000 ± 3600 | 10 | 21 | 0.46 | 0.64 | 3 | A |
| | 250 | 4100 ± 6200 | 10 | 1400 ± 980 | 10 | 66 | 0.045 | 0.2 | 6 | A |
| P131 | 250 | 2600 ± 1200 | 10 | 2400 ± 5100 | 9 | 4 | 0.0015 | 0.96 | 7 | A |
| | | | | 850 ± 580 [g] | 8 | 67 [g] | 0.0007 [g] | 0.00017 [g] | | |
| | 3×83 | 600 ± 960 | 9 | 21 ± 22 | 9 | 97 | 0.0004 | 0.091 | 8 | B |
| | 3×83 | 2200 ± 2600 | 11 | 24 ± 37 | 10 | 99 | 0.0001 | 0.021 | 9 | B |

Figure 32

| Compound | Mouse activity | Plasma | | | | |
|---|---|---|---|---|---|---|
| | | $C_{max}$ (μg/mL) | $T_{max}$ (hr) | $\tau_{1/2}$ (hr) | $AUC_{inf}$ (hr·μg/mL) | CL (mL/h·kg) |
| P82 | + | 9 (21 μM) | 0.3 | 12 | 41 | 6,100 |
| P83 | - | 22 (51 μM) | 1 | 4 | 79 | 3,100 |
| P82 ex P83 (*) | - | 3.6 (8.7 μM) | 2 | 3 | n.d. | n.d. |
| P96 | + | 5 (13 μM) | 0.3 | 8 | 15 | 17,000 |
| P131 | + | 4 (9.2 μM) | 1 | 4 | 13 | 20,000 |

Figure 33

| Cmpd | Cellular Uptake (nmol/4.2 cm$^2$) | | Intracellular Concentration $^a$ (μM) | | P (cm/sec) x 10$^5$ | | Efflux Ratio |
|---|---|---|---|---|---|---|---|
| | A->B | B->A | A->B | B->A | A->B | B->A | |
| P25 | 0.0021 ± 0.0002 | 0.0025 ± 0.0002 | 0.53 | 0.64 | 6 ± 1 | 9.6 ± 0.9 | 1.7 |
| P32 | 0.018 ± 0.002 | 0.031 ± 0.001 | 4.4 | 7.7 | 29 ± 5 | 60 ± 10 | 2.0 |
| P82 | 0.4 ± 0.1 | 0.15 ± 0.04 | 98 | 38 | 18 ± 3 | 11 ± 3 | 0.61 |
| P83 | 0.5 ± 0.2 | 0.43 ± 0.09 | 120 | 110 | 2.6 ± 0.6 | 1.4 ± 0.3 | 0.52 |
| P96 | 0.11 ± 0.04 | 0.1 ± 0.02 | 28 | 29 | 33 ± 5 | 28 ± 2 | 0.85 |
| P131 | 5 ± 2 | 7 ± 1 | 1300 | 1900 | 1.7 ± 0.1 | 1.2 ± 0.2 | 0.71 |

Figure 34

| Phylum | Vehicle | | P131 | |
|---|---|---|---|---|
| | Day 0 | Day 7 | Day 0 [a] | Day 7 |
| Bacteroidetes | 73 ± 3 | 84 ± 3 | 82 ± 4 | 78 ± 3 |
| Cyanobacteria | 0.01 ± 0.01 | 0.00 ± 0.00 | 0.00 ± 0.00 | 0.01 ± 0.01 |
| Firmicutes | 25 ± 3 | 8 ± 2 | 17 ± 4 | 12 ± 2 |
| Proteobacteria | 0.01 ± 0.01 | 0.00 ± 0.00 | 0.00 ± 0.00 | 0.01 ± 0.00 |
| Tenericutes | 0.5 ± 0.1 | 0.09 ± 0.03 | 0.19 ± 0.07 | 0.05 ± 0.02 |
| Verrucomicrobia | 0.08 ± 0.03 | 7 ± 1 | 0.00 ± 0.00 | 10 ± 2 |
| Bacteria_Other | 0.74 ± 0.09 | 0.58 ± 0.06 | 0.53 ± 0.08 | 0.80 ± 0.09 |

FIG. 41

| Exp. | Infection Protocol | Average number of oocysts/100 μL | | | | % Inhibition | P MW | P T-test |
|---|---|---|---|---|---|---|---|---|
| | | Vehicle | n | PRM | n | | | |
| 1ˢᵗ | A | 4500 ± 5200 | 10 | 1200 ± 700 | 9 | 73 | 0.18 | 0.038 |
| 2 | A | 2100 ± 3300 | 8 | 360 ± 240 | 3 | 83 | >0.05 | 0.084 |
| 3 | A | 3800 ± 3400 | 7 | 100 ± 60 | 5 | 97 | 0.0058 | 0.010 |
| 4 | A | 9400 ± 8900 | 9 | 60 ± 150 | 9 | 99 | 0.0004 | 0.0068 |
| 5 | A | 5100 ± 2900 | 8 | 170 ± 20 | 3 | 97 | ≤0.02 | 0.00093 |
| 6 | A | 2600 ± 1200 | 10 | 390 ± 250 | 4 | 82 | ≤0.02 | 0.00025 |
| 7 | B | 600 ± 960 | 10 | 70 ± 51 | 6 | 88 | 0.0041 | 0.059 |
| 8 | B | 2200 ± 2600 | 11 | 110 ± 100 | 5 | 95 | 0.0022 | 0.014 |

Figure 42
(a)
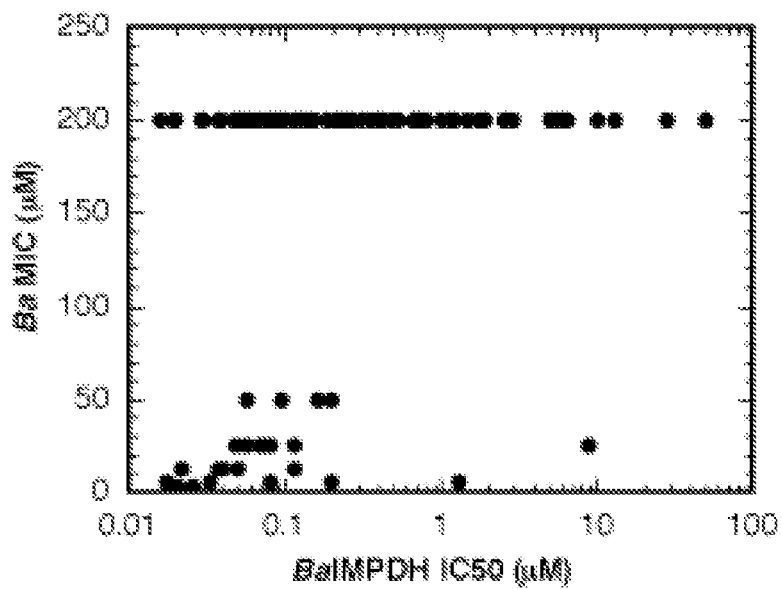
(b)
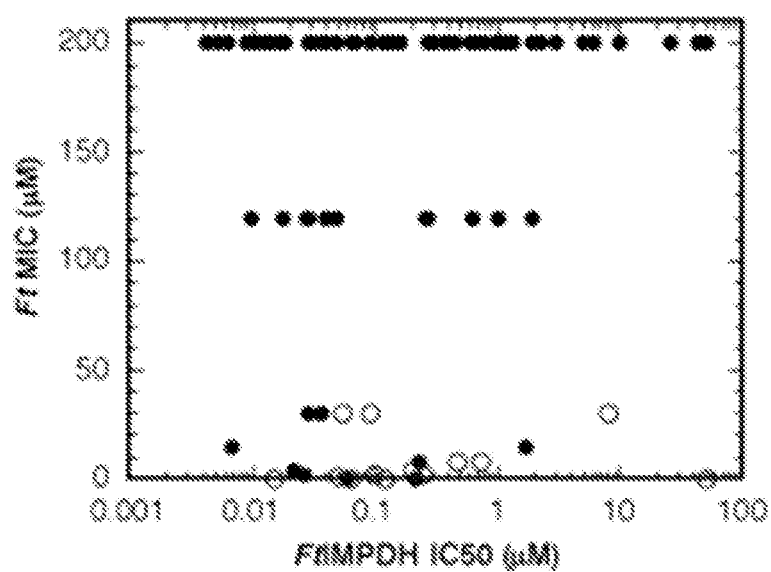

Figure 43

| Cmpd | MIC (μM) | | | | | | | | | | |
|---|---|---|---|---|---|---|---|---|---|---|---|
| | Ab | Ba | Bc | Bt | Cj | Clp | Ft | Hp | Lm | Mtb | Sa |
| # tested | 148 | 158 | 140 | 148 | 47 | 12 | 114 | 145 | 158 | 118 | 158 |
| # < 12 μM | 3 | 17** | 2 | 1 | 2* | 1 | 14 | 12** | 3 | 15** | 4 |
| D41 | | | | | | | 0.23 | | | | |
| D67 | | | | | | | 1.9 | | | | |
| D73 | | | | | | | 0.47 | | | | |
| D85 | | | | | | | 0.23 | 0.005 | | | |
| P27 | 12 | 6.3 | | | | | 7.5 | | | | |
| P37 | | 6.3 | | | | | | | | | |
| P41 | | | | | | | | | | 2.5 | |
| P47 | | 6.3 | 12 | | | | 3.8 | | 3.1 | | 12 |
| P52 | | 6.3 | | | | | | | 1.6 | | 12 |
| P67 | | | | | | | | | | 2.5, 5 | |
| P68 | | 3.1 | | | | | | | | | 12 |
| P70 | | 6.3 | | | < 50* | | | | | | |
| P90 | | | | | | | | 0.25 | | | |
| P94 | | | 3.1 | 12 | | | | | | | |
| P97 | | 3.1 | | | | | | | 12 | | |
| P126 | | 3 | | | | | | | | | |
| P127 | | | | | < 50* | | | | | | |
| Q21 | | | | | | | 0.94 | | | | |
| Q27 | | | | | | | 1.9 | 12 | | 10 | |
| Q32 | | | | | | | 0.47 | 12 | | | |
| Q33 | | | | | | | 0.94 | | | 5 | |
| Q41 | | | | | | | 0.23 | 12 | | | |
| Q46 | | | | | | 9 | 0.23 | | | 5 | |
| Q52 | | 12 | | | | | | | | | 12 |
| Q59 | 12 | | | | | | 1.9 | 25 | | 5 | |
| Q67 | 6.3 | 12 | | | | | 3.8 | | | 4 | |

Figure 44

| Code | Compounds | IC₅₀ (nM) |
|---|---|---|
| P140 | | >5000 |
| P141 | | 357 |
| P142 | | |
| P143 | | |
| P144 | | |
| P145 | | |
| P146 | | |

Figure 45
| Code | Compounds | IC$_{50}$ (nM) |
|---|---|---|
| Q76 | 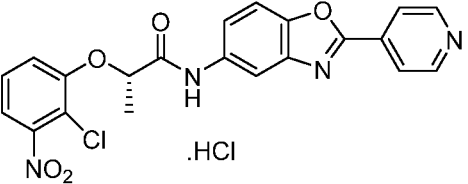 | -- |
| Q77 | 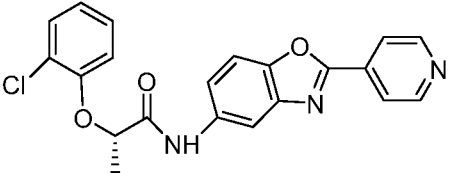 | |
| Q78 | 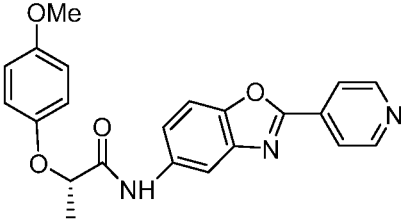 | |
| Q79 | 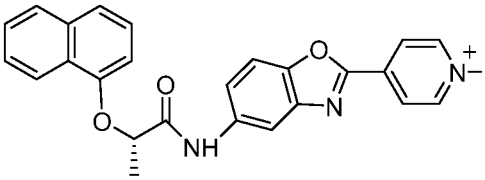 | |

# COMPOUNDS AND METHODS FOR TREATING MAMMALIAN GASTROINTESTINAL MICROBIAL INFECTIONS

RELATED APPLICATIONS

This application is the U.S. national phase of International Patent Application No. PCT/US13/055585, filed Aug. 19, 2013, which claims the benefit of priority to U.S. Provisional Patent Application Ser. No. 61/684,263, filed Aug. 17, 2012, the contents of which are hereby incorporated by reference.

GOVERNMENT SUPPORT

The invention was made with support provided by the National Institutes of Health (Grant Nos. U01 AI-075466 and 1R01AI093459); therefore, the government has certain rights in the invention.

BACKGROUND OF THE INVENTION

Organisms must synthesize nucleotides in order for their cells to divide and replicate. Nucleotide synthesis in mammals may be achieved through one of two pathways: the de novo synthesis pathway; or the salvage pathway. Different cell types use these pathways to differing extents.

Inosine-5'-monophosphate dehydrogenase (IMPDH; EC 1.1.1.205) is an enzyme involved in the biosynthesis of guanine nucleotides. IMPDH catalyzes the NAD-dependent oxidation of inosine-5'-monophosphate (IMP) to xanthosine-5'-monophosphate (XMP) [Jackson R. C. et. al., Nature, 256, pp. 331-333, (1975)]. Regardless of species, the reaction involves the random addition of substrates. A conserved active site Cys residue attacks the C2 position of IMP and hydride is transferred to NAD$^+$, producing NADH and the E-XMP* intermediate. NADH is released and a mobile flap folds into the vacant NADH site, E-XMP* hydrolyzes and XMP is released [W. Wang and L. Hedstrom, Biochemistry 36, pp. 8479-8483 (1997); J. Digits and L. Hedstrom, Biochemistry 38, pp. 2295-2306 (1999); Gan et al, Biochemistry 42, pp 847-863 (2003)]. The hydrolysis step is at least partially rate-limiting in most IMPDHs examined to date. The enzyme is unusual in that a large conformational change occurs in the middle of a catalytic cycle.

IMPDH is ubiquitous in eukaryotes, bacteria, archaebacteria, and protozoa [Y. Natsumeda & S. F. Carr, Ann. N.Y. Acad., 696, pp. 88-93 (1993)]. Two isoforms of human IMPDH, designated type I and type II, have been identified and sequenced [F. R Collart and E. Huberman, J. Biol. Chem., 263, pp. 15769-15772, (1988); Y. Natsumeda et al., J. Biol. Chem., 265, pp. 5292-5295, (1990)]. Type I has three isoforms derived from different mRNA splicing, with 514, 546 and 595 residues. Type II has 514 amino acids, and shares 84% sequence identity to the 514 isoform of Type I. Both IMPDH type I and type II form active tetramers in solution [Y. Yamada et al., Biochemistry, 27, pp. 2737-2745 (1988)].

Proliferation requires an expansion of the guanine nucleotide pool, so rapidly growing cells depend on IMPDH. Thus human IMPDHs are targets for anticancer chemotherapy [L. Che et al., Curr. Opin. Drug. Discov. Devel., 10, 403-12 92007); E. Olah et al., Adv. Enzyme. Regul., 46, 176-90 (2006)].

The activity of IMPDH is particularly important in B- and T-lymphocytes. These cells depend on the de novo, rather than salvage pathway to generate sufficient levels of nucleotides necessary to initiate a proliferative response to mitogen or antigen [A. C. Allison et. al., Lancet II, 1179, (1975) and A. C. Allison et al., Ciba Found. Symp., 48, 207, (1977)]. Thus, human IMPDHs are an attractive targets for selectively inhibiting the immune system without also inhibiting the proliferation of other cells.

Inhibitors of IMPDH are also known. U.S. Pat. No. 5,380,879 (incorporated by reference) and U.S. Pat. No. 5,444,072 (incorporated by reference) and PCT publications WO 94/01105 and WO 94/12184 describe mycophenolic acid (MPA) and some of its derivatives as potent, uncompetitive, reversible inhibitors of human IMPDH type I ($K_i$=33 nM) and type II ($K_i$=9 nM). MPA has been demonstrated to block the response of B- and T-cells to mitogen or antigen [A. C. Allison et. al., Ann. N.Y. Acad. Sci., 696, 63, (1993)].

Nucleoside analogs such as tiazofurin, ribavirin and mizoribine also inhibit IMPDH [L. Hedstrom, et. al. Biochemistry, 29, pp. 849-854 (1990); L. Hedstrom et al. Curr. Med. Chem. 1999, 6, 545-561]. These compounds require activation to either the adenine dinucleotide (tiazofurin) or monophosphate derivatives (ribavirin and mizoribine) that inhibit IMPDH. These activation pathways are often absent in the cell of interest. In addition, nucleoside analogs suffer from lack of selectivity and can be further metabolized to produce inhibitors of other enzymes. Therefore, nucleoside analogs are prone to toxic side effects.

Additionally, IMPDH has been shown to play a role in viral replication in some viral cell lines. [S. F. Carr, J. Biol. Chem., 268, pp. 27286-27290 (1993)]. Analogous to lymphocyte and tumor cell lines, the implication is that the de novo, rather than the salvage, pathway is critical in the process of viral replication.

IMPDH is also a promising target for antimicrobial chemotherapy. Microbial infections are now the second leading cause of death worldwide. Many commonly used antibiotics have been rendered ineffective by the upsurge of drug resistance, so there is an urgent need of new antimicrobial therapy. IMPDH2 is an essential gene in *Mycobacterium tuberculosis*, and deletion of IMPDH attenuates the virulence of many other bacteria. IMPDH inhibitors block the growth of *Helicobacter pylori, Staphylococcus aureus, Candida albicans, Pneumocystis carinii, Leishmania donovani, Trypanosoma brucei gambienese, Eimeria tenella, Plasmodium falciparum* and *Cryptosporidium parvum* in culture [L. Hedstrom et al., Curr. Med. Chem., 18, pp. 1909-1918 (2011)]. The prokaryotic IMPDHs share 30-40% sequence identity with the human enzyme, and have significantly different kinetic and functional properties. These observations indicate that specific inhibition of prokaryotic IMPDH can be achieved, and that such inhibitors are likely to have antibiotic activity. Curiously, *Cryptospordium* and several other eukaryotic organisms have prokaryote-like IMPDHs that appear to have been obtained via horizontal gene transfer. Eukaryotic organisms that contain a prokaryotic-like IMPDHs are also likely to be sensitive to prokaryotic IMPDH-specific inhibitors.

Cryptosporidiosis is a severe gastrointestinal disease caused by protozoan parasites of the genus *Cryptosporidium*. The most common causes of human disease are *C. parvum* and *C. hominis*, though disease can also result from *C. felis, C. meleagridis, C. canis,* and *C. muris* infection. Small children, pregnant women, the elderly, and immuno-compromised people (e.g., AIDS patients) are at risk of severe, chronic and often fatal infection [Carey, C. M., Lee, H., and Trevors, J. T., Water Res., 38, 818-62 (2004); and Fayer, R., Veterinary Parasitology, 126, 37-56 (2004)]. *Cryptosporidium* infection is a major cause of diarrhea and malnutrition in the developing world. The *Cryptosporidium* parasites produce spore-like oocysts that are highly resistant to water chlorination. Several large outbreaks in the U.S. have been linked to drinking and recreational water. Infection rates are extremely high, with disease manifest in 30% of exposed individuals and a 50-70% mortality rate among immuno-compromised individuals. Furthermore, there is a growing and credible concern that these organisms could be deliberately introduced into the water supply in an act of bioterrorism. Effective drugs are urgently needed for the management of cryptosporidiosis in AIDS patients and/or epidemic outbreaks. *Cryptospordum* parasites also cause significant disease in domestic livestock, especially calves, lambs, kids, foals, piglets and poultry.

All parasitic protozoa lack purine biosynthetic enzymes and must salvage purines from their hosts, making this pathway an extremely attractive target for developing anti-protozoal drugs. IMPDH is a key enzyme in the purine salvage pathway of *C. parvum* and general IMPDH inhibitors block parasite proliferation In vitro [N. N. Umejiego et al., J Biol Chem, 279 pp. 40320-40327 (2004); and B. Striepen et al, Proc Natl Acad Sci USA, 101 pp. 3154-9 (2004)]. The IMPDH protein of *C. hominis* is identical to that of *C. parvum*, as is the purine salvage pathway. As discussed above, IMPDH is a validated drug target in immunosuppressive, cancer and viral therapy, so the human enzymes are extremely well studied. *Cryptosporidium* appears to have obtained its IMPDH gene from a proteobacterium. Thus *C. parvum* IMPDH has very different structure and properties than the human enzymes. IMPDHs from many pathogenic bacteria have similar structures to *C. parvum* IMPDH [Gollapalli et al., Chem. Biol., 17, 1084-1091 (2010)]. There is a need for selective IMPDH inhibitors that can slow or block parasite and bacterial proliferation. The present invention fulfills this need and has other related advantages.

SUMMARY OF THE INVENTION

One aspect of the present invention relates to compounds and pharmaceutically acceptable salts thereof, which are useful as inhibitors of IMPDH. In certain embodiments, a compound of the invention selectively inhibits a parasitic IMPDH versus a host (e.g., mammalian) IMPDH. Further, the invention provides pharmaceutical compositions comprising one or more compounds of the invention. The invention also relates to methods of treating various parasitic and bacterial infections in mammals and birds. Moreover, the compounds may be used alone or in combination with other therapeutic or prophylactic agents, such as anti-virals, anti-inflammatory agents, antimicrobials and immunosuppressants.

BRIEF DESCRIPTION OF THE FIGURES

FIG. 1 depicts the correlation of compounds from Schemes 1-5 with the P Series numbering system.

FIG. 2 depicts P Series compounds and their $IC_{50}$ values against *C. parvum/C. hominis* IMPDH.

FIG. 5 (Table 3) depicts the results of structure activity relationship (SAR) studies of the urea portion of the P Series compounds with *C. parvum/C. hominis* IMPDH. a. One determination, b. n.d., not determined.

FIG. 7 (Table 5) depicts the stability of some P Series compounds (e.g., compounds depicted in FIGS. 1-6) in mouse liver microsomes and plasma. n.d., not determined.

FIG. 8 (Table 6) depicts antiparasitic activity of selected P Series compounds (e.g., compounds depicted in FIGS. 1-6). Assays were run as described in Sharling, L., et al. *PLoS Negl Trop Dis* 2010, 4 (8), e794. Unless otherwise stated all values are the average of three (3) independent determinations.

FIG. 9 depicts HPLC retention times and purities for various P Series compounds (e.g., compounds depicted in FIGS. 1-6). Instrument: Agilent 1100; Column: Zorbax® SB-C8 column, 30×4.6 mm, 3.5 µm; Injection volume: 5 µL; Sample concentration: 1-2 mg/mL in 100% acetonitrile; λ: 254 nm; Elution solvent: 5% acetonitrile and 95% water (both solvents contain 0.1% trifluoroacetic acid) with a total run time of 2.5 min.; Elution rate: 3.0 mL/min.

FIG. 10 depicts D Series compounds and their corresponding $IC_{50}$ values against *C. parvum/C. hominis* IMPDH.

FIG. 11 (Table 7) depicts a SAR of anilide and nathylide phthalazinone inhibitors in the D Series with *C. parvum/C. hominis* IMPDH. All values are an average of three independent determinations unless otherwise noted (* two determinations). ND, not determined.

FIG. 12 depicts a SAR of heterotricyclic anilide pthalazinone inhibitors with *C. parvum/C. hominis* IMPDH. All values are an average of three independent determinations unless otherwise stated. ND, not determined.

FIG. 13 (Table 8) depicts antiparasitic activity of selected D Series compounds. Values are the average and standard deviations of three independent determinations unless otherwise stated (* denotes average and range of two determinations). a. *T. gondii* RH (Toxo/WT) should be resistant to CpIMPDH inhibitors while *T. gondii*/CpIMPDH (Toxo/CpIMPDH) should be sensitive. b. Selectivity=$EC_{50}$ (Toxo/WT)/$EC_{50}$ (Toxo/CpIMPDH).

Figure 14:
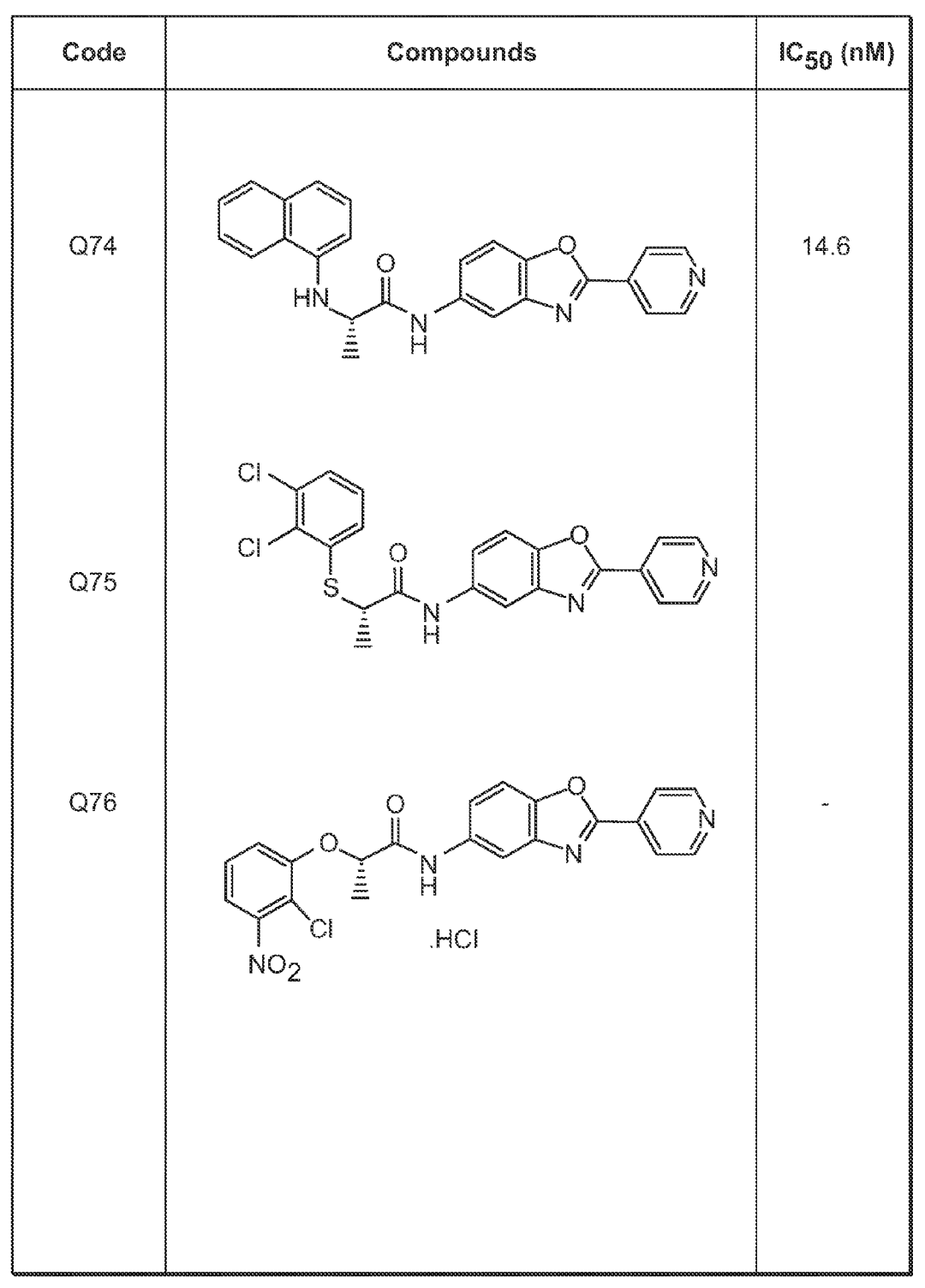

FIG. 14 depicts Q Series compounds and their corresponding $IC_{50}$ values against *C. parvum/C. hominis* IMPDH.

FIG. 34 tabulates the effects of vehicle and P131 on fecal microbiota. Mice (10 per group) were treated with single daily doses of vehicle or 250 mg/kg P131. Fecal samples were collected and amplicons of bacterial 16S rRNA gene were constructed, sequenced with 454 pyrosequencing and analyzed with the QIIME platform. The relative abundance of phyla is shown as the percentage and SEM of total reads. a. n=4; b. n=9.

FIG. 41 tabulates paromomycin controls for *C. parvum* infections of IL-12 knockout mice. Infection Protocol A was used unless otherwise noted. Infection protocol A: IL12 knockout mice were infected with 1000 oocysts on day 1. Mice were treated daily by oral gavage beginning 4 hours after infection. Feces were collected and counted on day 7 unless otherwise noted. Vehicle=5% DMSO/corn oil unless otherwise noted. PRM=paromomycin, 2000 mg/kg-d. Infection protocol B: IL-12 knockout mice were infected with 10,000 oocysts on day 1. Mice were treated three times daily by oral gavage beginning 4 hours after infection. Feces were collected and counted on day 4. Vehicle=5% DMSO/corn oil unless otherwise noted. PRM=paromomycin, 200 mg/kg-d. Significance was computed with the Mann Whitney nonparametric test using VassarStats and with a one tailed type 3 T-test (Microsoft Excel). a. Vehicle=20% PEG; b. Vehicle=10% PEG, DPI 6.

FIG. 42 depicts the correlation of antibacterial activity and enzyme inhibition. (a) *B. anthracis*. (b) *F. tularensis* Schu S4. Open circles denote compounds where potency does not change with deletion of the guaB gene.

Figure 3:
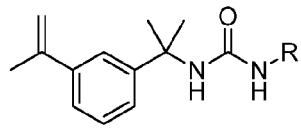
FIG. 3 (Table 1) depicts the results of structure activity relationship (SAR) studies of the anilide portion of the P Series compounds against *C. parvum/C. hominis* IMPDH. Assays as described in the methods section. No significant inhibition of human IMPDH type 2 was observed ($IC_{50} \geq 5$ µM). a. One determination. n.d., not determined FIG. 4 (Table 2) depicts the results of structure activity relationship (SAR) studies of the isopropenyl portion of the P Series compounds with *C. parvum/C. hominis* IMPDH. a. One determination, n.d., not determined.
Figure 6:
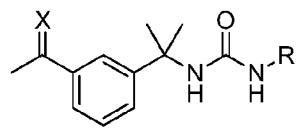
FIG. 6 (Table 4) depicts the results of structure activity relationship (SAR) studies of oxime and methyloxime compounds in the P Series with *C. parvum/C. hominis* IMPDH.
Figure 15:
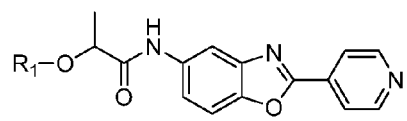
FIG. 15 (Table 9) depicts a SAR of the phenyl ring in Q Series compounds with *C. parvum/C. hominis* IMPDH. $IC_{50}$, inhibition of *C. parvum* IMPDH activity. $EC_{50}$, antiparasitic activity in a *Taxoplasma gondii* model of *Cryptosporidium* infection. WT, a *T. gondii* strain expressing endogenous *T. gondii* IMPDH that should be resistant to *C. parvum* IMPDH inhibitors; CpIMPDH, a *T. gondii* strain that relies on the expression of *C. parvum* IMPDH that should be sensitive to *C. parvum* IMPDH inhibitors; Sel, ratio of the values of $EC_{50}$.
Figure 16:
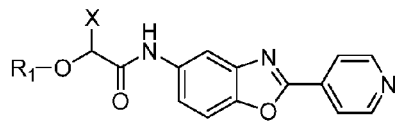
FIG. 16 (Table 10) depicts the effect in Q Series compounds of substitution on the carbon adjacent to the amide on inhibition of *C. parvum/C. hominis* IMPDH. $IC_{50}$, inhibition of *C. parvum* IMPDH activity. $EC_{50}$, antiparasitic activity in a *Taoxoplasma gondii* model of *Cryptosporidium* infection. WT, a *T. gondii* strain expressing endogenous *T. gondii* IMPDH that should be resistant to *C. parvum* IMPDH inhibitors; CpIMPDH, a *T. gondii* strain that relies on the expression of *C. parvum* IMPDH that should be sensitive to *C. parvum* IMPDH inhibitors; Sel, ratio of the values of $EC_{50}$.
Figure 17:
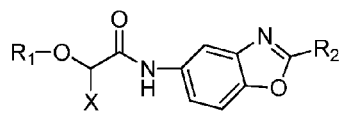
FIG. 17 (Table 11) depicts the optimization of Q Series compounds for inhibition of *C. parvum/C. hominis* IMPDH. $EC_{50}$, antiparasitic activity in a *Toxoplasma gondii* model of *Cryptosporidium* infection. W FIG. 33 tabulates urea CpIMPDH inhibitor permeability and uptake in Caco-2 TC7 cells. All compounds at 10 μM, pH 7.4 on both sides. Solid recovery >80% in all cases. a. Approximate intracellular concentration, assuming 4 μL of water for 1 mg of cellular protein.
Figure 18:
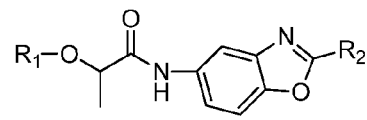
Figure 20:
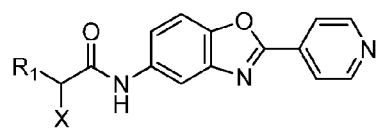
Figure 21:
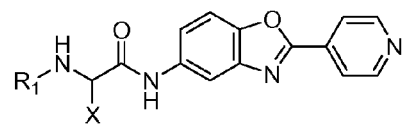

F production of NADH from NAD+), IMPDH radioassays (measuring enzymatic production of radiolabeled XMP from radiolabeled IMP or tritium release into water from 2-³H-IMP). [See C. Montero et al., Clinica Chimica Acta, 238, pp. 169-178 (1995)]. Additional assays known in the art can be used in ascertaining the degree of activity of an inventive compound as an IMPDH inhibitor. For example, activity of IMPDH I and IMPDH II can be measured following an adaptation of the method described in WO 97/40028. [See, additionally, U.S. Patent Application 2004/0102497 (incorporated by reference)].

Accordingly, in certain embodiments, the inventive compounds are capable of targeting and selectively inhibiting the IMPDH enzyme in bacteria. It is known that knocking out the IMPDH gene makes some bacteria avirulent, while has no effect on others. The effectiveness probably depends on which salvage pathways are operational in a given bacteria, and the environmental niche of the infection. It has been shown that IMPDHs from *Helicobacter pylori, Streptococcus pyogenes, Borrelia burgdorferi* are sensitive to inhibitors of *C. parvum* IMPDH, and that the growth of *H. pylori* can be blocked by *C. parvum* IMPDH inhibitors [Gollapalli et al, Chem. Biol., 17, 1084-1091 (2010)]. We have also shown IMPDHs from *Bacillus anthracis, Burkholderia mallei/pseudomallei, Listeria monocytogenes, Francisella tularensis, Acinetobacter baumannii, Staphylococcus aureus, Pseudomonas aeruginosa, Campylobacter jejuni* and *Clostridia perfringes* are inhibited by compounds that inhibit *C. parvum* IMPDH [Makowska-Gryska et al. Biochem. 2012, 51, 6148-6163]. We have also shown antibacterial activity of at least one *C. parvum* IMPDH inhibitor against *Ba. anthracis, F. tularensis, Sta. aureus, P. aeruginosa, C. perfringes, L. monocytogenes* and *Mycobacterium tuberculosis*. It is also expected that various *Campylobacter, Arcobacter, Bacteroides, Coxiella, Pseudomonas, Fusobacterium, Brucella, Burkholderia, Brachyspira, Clostridia, Neisseria, Mycobacterium,* or *Acinetobacter* organisms will be inhibited by the compounds described herein. Organisms belonging to these genera are responsible for illnesses such as ulcers and acid reflux (*H. pylori*), anthrax (*Ba. anthracis*), Lyme disease (*B. burgdorferi*), brucellosis (*Br. abortus*), infection (*S. pyogenes*), food poisoning (*Ca. jejuni* and *Ar. butzleri*), abscesses (*Bact. capillosis*), periodontitis (*F. nucleatum*), skin ulcers (*F. nucleatum*), Lemierre's syndrome (*F. nucleatum*), infection in cystic fibrosis (*Bu. cenocepacia*), pneumonia (*Str. pneumoniae*), botulism (*Cl. botulinum*), gonorrhea (*N. gonorrhoeae*), Q fever (*Co. burnetti*) tuberculosis (*M. tuberculosis*), leprosy (*M. leprae*), opportunistic infection (*Ps. aeruginosa*) and drug resistant infection (*A. baumannii*).

Further, in certain embodiments, the inventive compounds are capable of targeting and selectively inhibiting the IMPDH enzyme in protozoans, such as *Cryptosporidium, Entamoeba, Leishmania* and *Trypanosoma*. In certain embodiments, these compounds are capable of targeting and selectively inhibiting the IMPDH enzyme in *Cryptosporidium parvum/hominis* and other *Cryptosporidium* species.

Selected Compounds of the Invention

Phthalazinone Series

In certain embodiments, the invention relates to a compound, or a pharmaceutically acceptable salt or ester thereof, represented by Formula I:

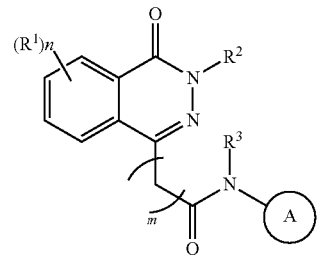

Formula I wherein, independently for each occurrence, $R^1$ is alkyl, alkenyl, alkynyl, cycloalkyl, heterocyclyl, haloalkyl, aralkyl, cycloalkyl, heterocyclyl, aryl, heteroaryl, heteroaralkyl, formyl, acyl, aracyl, heteroaracyl, carboxyl, alkoxycarbonyl, acyloxy, cyano, —OR', halide, —N(R')₂, azido, nitro, amido, isocyano, phosphonate, phosphinate, silyl, thio, alkylthio, sulfonate, sulfonyl, sulfonamido, or sulfhydryl;

wherein R' is hydrogen, alkyl, alkenyl, alkynyl, cycloalkyl, heterocyclyl, aryl, heteroaryl, acyl, aracyl, or heteroaracyl;

$R^2$ is hydrogen, alkyl, alkenyl, alkynyl, cycloalkyl, heterocyclyl, aryl, heteroaryl, acyl, aracyl, heteroaracyl sulfonate, sulfonyl, sulfonamido, formyl, carboxyl, alkoxycarbonyl, or acyloxy;

$R^3$ is hydrogen, alkyl, alkenyl, alkynyl, cycloalkyl, heterocyclyl, aryl, heteroaryl, acyl, aracyl, heteroaracyl sulfonate, sulfonyl, sulfonamido, formyl, carboxyl, alkoxycarbonyl, or acyloxy;

m is 0, 1, or 2;

n is 1-4; and

is alkyl, monocyclic or bicyclic cycloalkyl, monocyclic or bicyclic heterocyclyl, monocyclic or bicyclic aryl or monocyclic or bicyclic heteroaryl;

wherein any of the aforementioned alkyl, aryl, heteroaryl, or aralkyl may be substituted with one or more groups independently selected from the group consisting of halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, sulfhydryl, formyl, cyano, and isocyano.

In certain embodiments, the invention relates to any one of the aforementioned compounds, wherein $R^1$ is alkyl.

In certain embodiments, the invention relates to any one of the aforementioned compounds, wherein $R^1$ is halogen.

In certain embodiments, the invention relates to any one of the aforementioned compounds, wherein $R^1$ is OH or methoxy.

In certain embodiments, the invention relates to any one of the aforementioned compounds, wherein $R^2$ is hydrogen.

In certain embodiments, the invention relates to any one of the aforementioned compounds, wherein $R^2$ is alkyl.

In certain embodiments, the invention relates to any one of the aforementioned compounds, wherein $R^2$ is methyl, ethyl, n-propyl, i-propyl, n-butyl, s-butyl, i-butyl, or t-butyl.

In certain embodiments, the invention relates to any one of the aforementioned compounds, wherein $R^3$ is hydrogen.

In certain embodiments, the invention relates to any one of the aforementioned compounds, wherein m is 1.

In certain embodiments, the invention relates to any one of the aforementioned compounds, wherein n is 1.

In certain embodiments, the invention relates to any one of the aforementioned compounds, wherein n is 2.

In certain embodiments, the invention relates to any one of the aforementioned compounds, wherein

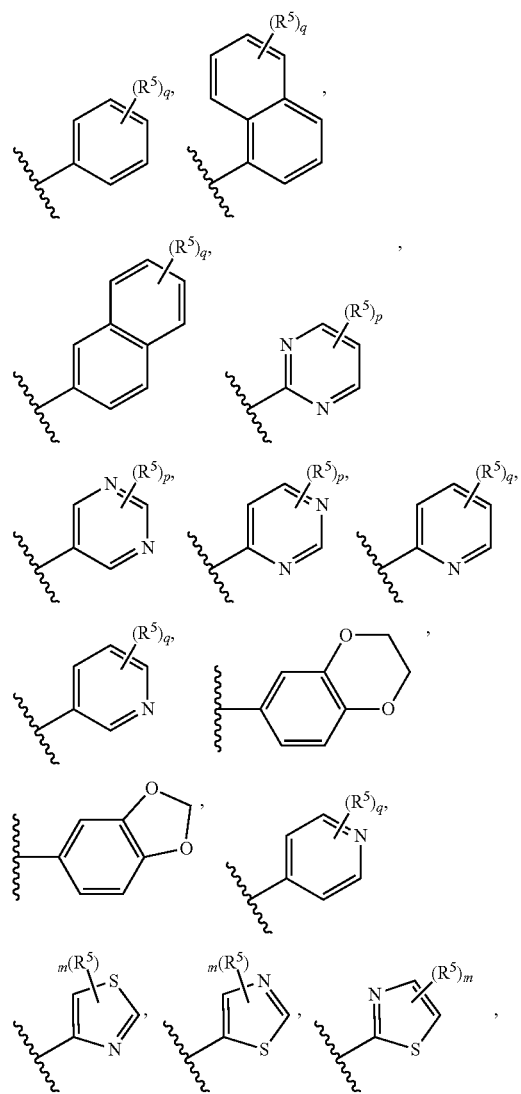

is alkyl, benzyl,

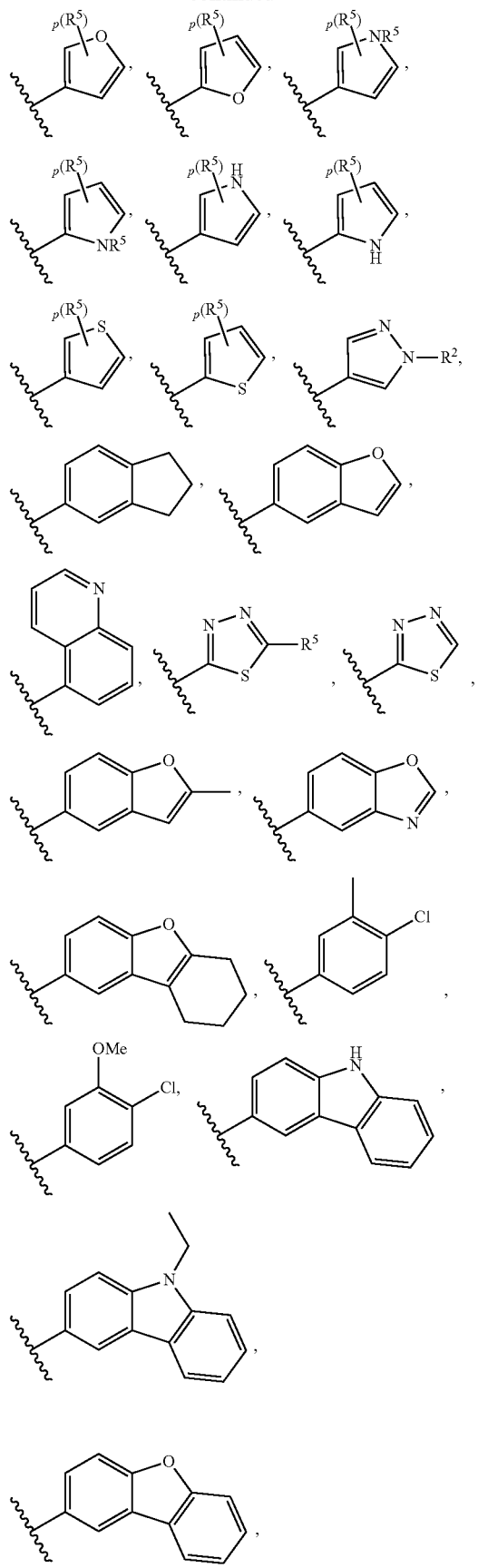

-continued

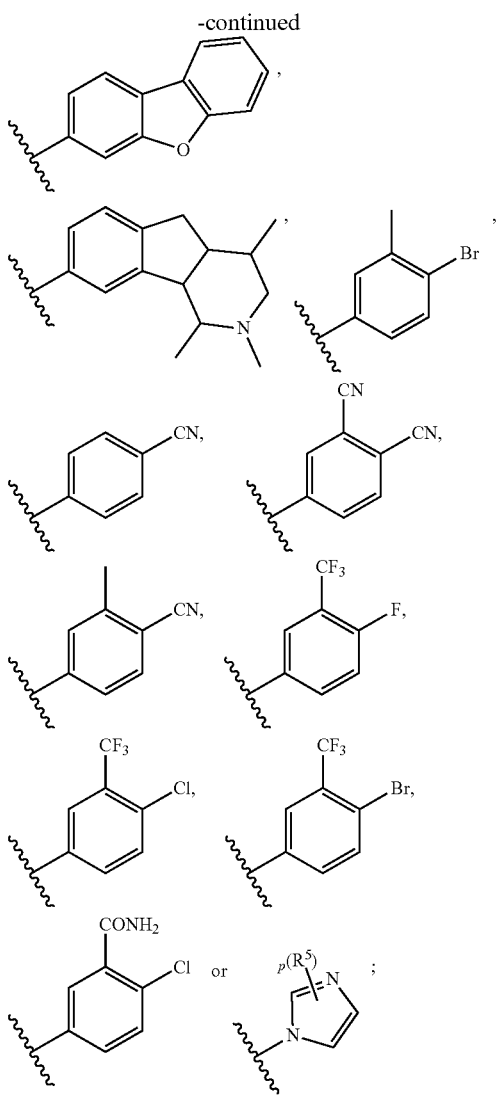

p is 0, 1, 2, or 3; q is 0, 1, 2, 3, or 4; and R⁵ is halo, azido, alkyl, haloalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, acyloxy, alkylthio, sulfonate, sulfonyl, sulfonamido, formyl, cyano, or isocyano.

In certain embodiments, the invention relates to any one of the aforementioned compounds, wherein n is 2 and R¹ is halogen.

In certain embodiments, the invention relates to any one of the aforementioned compounds, wherein

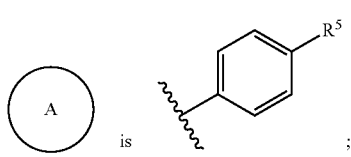

and R⁵ is amido, alkoxy, halo, haloalkyl, aryl, haloaryl, alkyl, hydroxy, alkylthio, sulfonyl, haloalkoxy, or cyano.

In certain embodiments, the invention relates to any one of the aforementioned compounds, wherein

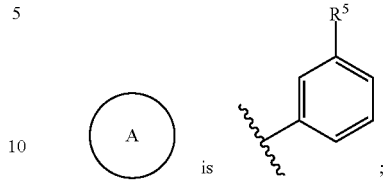

and R⁵ is alkoxy or halo.

In certain embodiments, the invention relates to any one of the aforementioned compounds, wherein

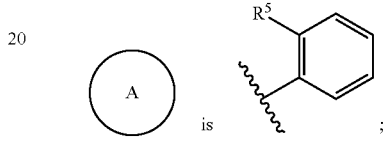

and R⁵ is halo.

In certain embodiments, the invention relates to any one of the aforementioned compounds, wherein

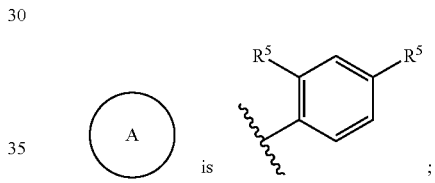

and R⁵ is halo or cyano.

In certain embodiments, the invention relates to any one of the aforementioned compounds, wherein

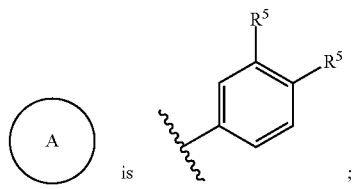

and R⁵ is amido, halo, or cyano.

In certain embodiments, the invention relates to any one of the aforementioned compounds, wherein

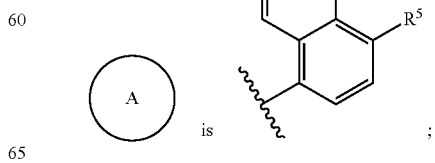

and R⁵ is halo.

In certain embodiments, the invention relates to any one of the aforementioned compounds, wherein

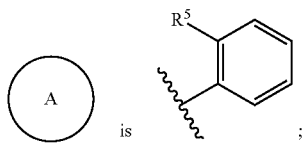

and R⁵ is amido.

In certain embodiments, the invention relates to a compound, or a pharmaceutically acceptable salt or ester thereof, represented by Formula II:

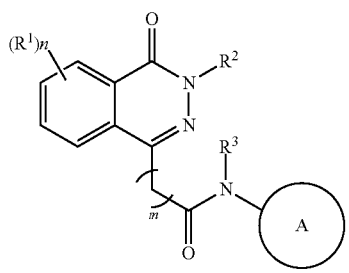

Formula II wherein, independently for each occurrence,
R¹ is hydrogen, alkyl, alkenyl, alkynyl, cycloalkyl, heterocyclyl, haloalkyl, aralkyl, cycloalkyl, heterocyclyl, aryl, heteroaryl, heteroaralkyl, formyl, acyl, aracyl, heteroaracyl, carboxyl, alkoxycarbonyl, acyloxy, cyano, —OR', halide, —N(R')₂, azido, nitro, amido, isocyano, phosphonate, phosphinate, silyl, thio, alkylthio, sulfonate, sulfonyl, sulfonamido, or sulfhydryl;
wherein R' is hydrogen, alkyl, alkenyl, alkynyl, cycloalkyl, heterocyclyl, aryl, heteroaryl, acyl, aracyl, or heteroaracyl;
R² is alkenyl, alkynyl, cycloalkyl, heterocyclyl, aryl, heteroaryl, acyl, aracyl, heteroaracyl sulfonate, sulfonyl, sulfonamido, formyl, carboxyl, alkoxycarbonyl, or acyloxy;
R³ is hydrogen, alkyl, alkenyl, alkynyl, cycloalkyl, heterocyclyl, aryl, heteroaryl, acyl, aracyl, heteroaracyl sulfonate, sulfonyl, sulfonamido, formyl, carboxyl, alkoxycarbonyl, or acyloxy;
m is 0, 1, or 2;
n is 1-4; and

is alkyl, monocyclic or bicyclic cycloalkyl, monocyclic or bicyclic heterocyclyl, monocyclic or bicyclic aryl or monocyclic or bicyclic heteroaryl;
wherein, any of the aforementioned alkyl, aryl, heteroaryl, or aralkyl may be substituted with one or more groups independently selected from the group consisting of halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, sulfhydryl, formyl, cyano, and isocyano.

In certain embodiments, the invention relates to any of the aforementioned compounds, wherein R¹ is hydrogen.

In certain embodiments, the invention relates to any one of the aforementioned compounds, wherein R¹ is alkyl.

In certain embodiments, the invention relates to any one of the aforementioned compounds, wherein R¹ is halogen.

In certain embodiments, the invention relates to any one of the aforementioned compounds, wherein R¹ is OH or methoxy.

In certain embodiments, the invention relates to any one of the aforementioned compounds, wherein R² is hydrogen.

In certain embodiments, the invention relates to any one of the aforementioned compounds, wherein R² is alkyl.

In certain embodiments, the invention relates to any one of the aforementioned compounds, wherein R² is methyl, ethyl, n-propyl, i-propyl, n-butyl, s-butyl, i-butyl, or t-butyl.

In certain embodiments, the invention relates to any one of the aforementioned compounds, wherein R³ is hydrogen.

In certain embodiments, the invention relates to any one of the aforementioned compounds, wherein m is 1.

In certain embodiments, the invention relates to any one of the aforementioned compounds, wherein n is 1.

In certain embodiments, the invention relates to any one of the aforementioned compounds, wherein n is 2.

In certain embodiments, the invention relates to any one of the aforementioned compounds, wherein

is alkyl, benzyl,

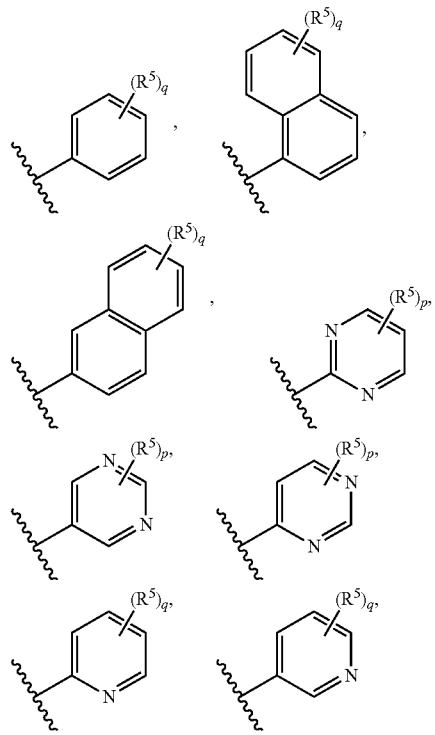

-continued

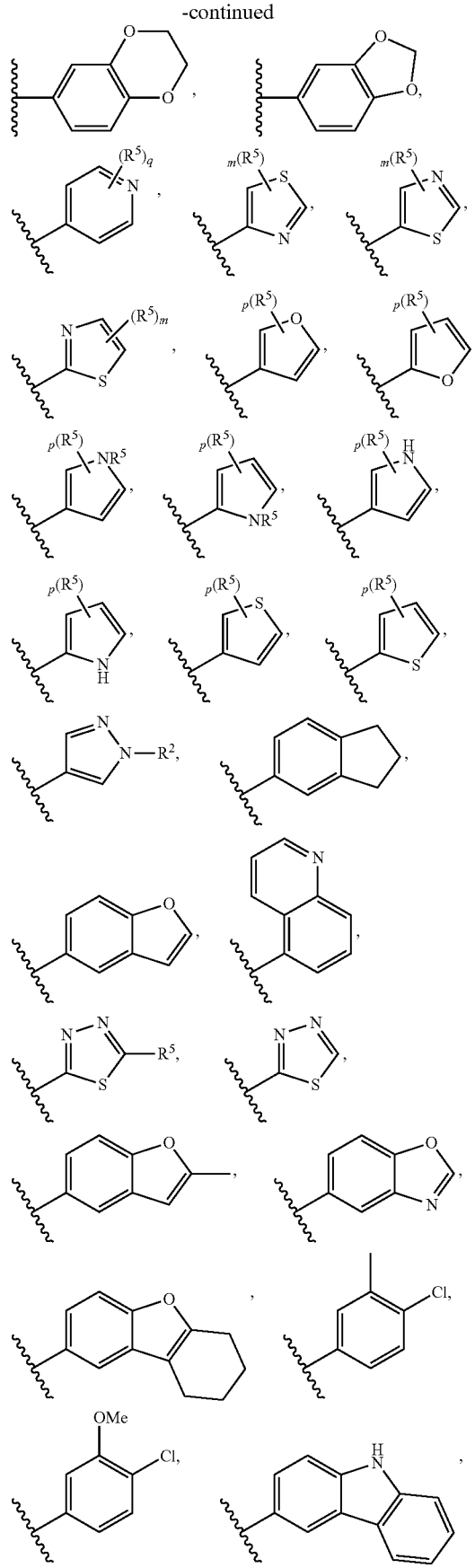

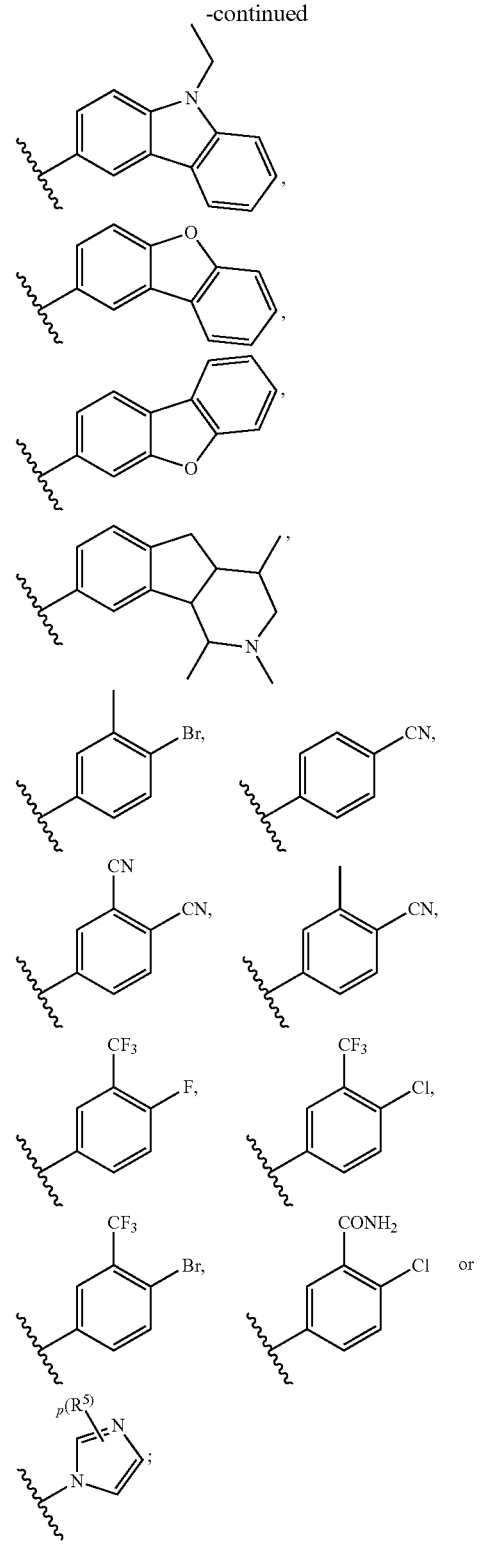

p is 0, 1, 2, or 3; q is 0, 1, 2, 3, or 4; and R⁵ is halo, azido, alkyl, haloalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, acyloxy, alkylthio, sulfonate, sulfonyl, sulfonamido, formyl, cyano, or isocyano.

In certain embodiments, the invention relates to any one of the aforementioned compounds, wherein n is 2 and R¹ is halogen.

In certain embodiments, the invention relates to any one of the aforementioned compounds, wherein

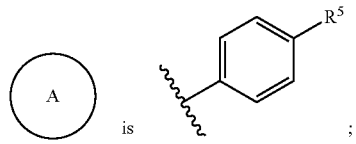

and R⁵ is amido, alkoxy, halo, haloalkyl, aryl, haloaryl, alkyl, hydroxy, alkylthio, sulfonyl, haloalkoxy, or cyano.

In certain embodiments, the invention relates to any one of the aforementioned compounds, wherein and R⁵ is alkoxy or halo.

In certain embodiments, the invention relates to any one of the aforementioned compounds, wherein and R⁵ is halo.

In certain embodiments, the invention relates to any one of the aforementioned compounds, wherein and R⁵ is halo or cyano.

In certain embodiments, the invention relates to any one of the aforementioned compounds, wherein and R⁵ is amido, halo, or cyano.

In certain embodiments, the invention relates to any one of the aforementioned compounds, wherein and R⁵ is halo.

In certain embodiments, the invention relates to any one of the aforementioned compounds, wherein and R⁵ is amido.

In certain embodiments, the invention relates to a compound, or a pharmaceutically acceptable salt or ester thereof, represented by Formula III:

Formula III wherein, independently for each occurrence,
R¹ is hydrogen, alkyl, alkenyl, alkynyl, cycloalkyl, heterocyclyl, haloalkyl, aralkyl, cycloalkyl, heterocyclyl, aryl, heteroaryl, heteroaralkyl, formyl, acyl, heteroaracyl, carboxyl, alkoxycarbonyl, acyloxy, cyano, —OR', halide, —N(R')₂, azido, nitro, amido, isocyano, phosphonate, phosphinate, silyl, thio, alkylthio, sulfonate, sulfonyl, sulfonamido, or sulfhydryl;
  wherein R' is hydrogen, alkyl, alkenyl, alkynyl, cycloalkyl, heterocyclyl, aryl, heteroaryl, acyl, aracyl, or heteroaracyl;
R² is hydrogen, is alkenyl, alkynyl, cycloalkyl, heterocycyl, aryl, heteroaryl, acyl, aracyl, heteroaracyl sulfonate, sulfonyl, sulfonamido, formyl, carboxyl, alkoxycarbonyl, or acyloxy;
R³ is alkyl, alkenyl, alkynyl, cycloalkyl, heterocyclyl, aryl, heteroaryl, acyl, aracyl, heteroaracyl sulfonate, sulfonyl, sulfonamido, formyl, carboxyl, alkoxycarbonyl, or acyloxy;
m is 0, 1, or 2;
n is 1-4; and is alkyl, monocyclic or bicyclic cycloalkyl, monocyclic or bicyclic heterocyclyl, monocyclic or bicyclic aryl or monocyclic or bicyclic heteroaryl;

wherein, any of the aforementioned alkyl, aryl, heteroaryl, or aralkyl may be substituted with one or more groups independently selected from the group consisting of halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, sulfhydryl formyl, cyano, and isocyano.

In certain embodiments, the invention relates to any one of the aforementioned compounds, wherein $R^1$ is hydrogen.

In certain embodiments, the invention relates to any one of the aforementioned compounds, wherein $R^1$ is alkyl.

In certain embodiments, the invention relates to any one of the aforementioned compounds, wherein $R^1$ is halogen.

In certain embodiments, the invention relates to any one of the aforementioned compounds, wherein $R^1$ is OH or methoxy.

In certain embodiments, the invention relates to any one of the aforementioned compounds, wherein $R^2$ is hydrogen.

In certain embodiments, the invention relates to any one of the aforementioned compounds, wherein $R^2$ is alkyl.

In certain embodiments, the invention relates to any one of the aforementioned compounds, wherein $R^2$ is methyl, ethyl, n-propyl, i-propyl, n-butyl, s-butyl, i-butyl, or t-butyl.

In certain embodiments, the invention relates to any one of the aforementioned compounds, wherein $R^3$ is alkyl.

In certain embodiments, the invention relates to any one of the aforementioned compounds, wherein m is 1.

In certain embodiments, the invention relates to any one of the aforementioned compounds, wherein n is 2.

In certain embodiments, the invention relates to any one of the aforementioned compounds, wherein

is alkyl, benzyl,

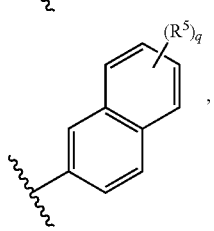

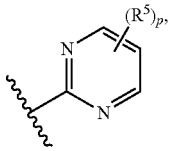

-continued

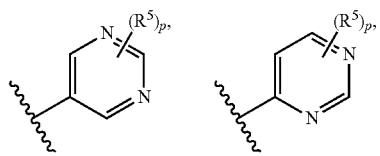

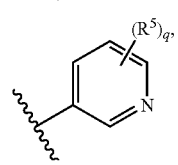

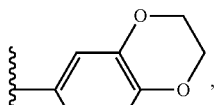

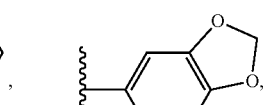

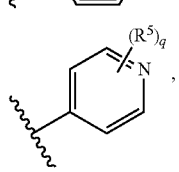

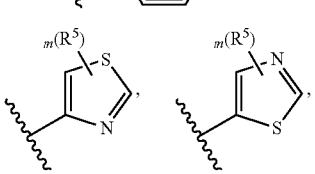

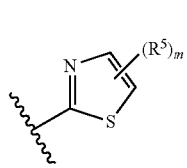

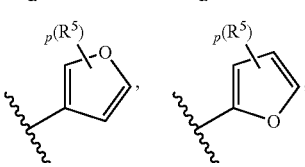

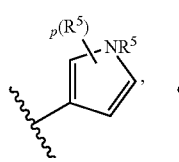

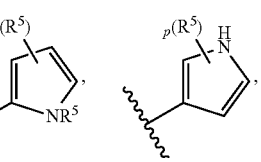

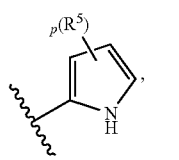

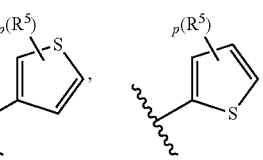

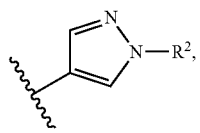

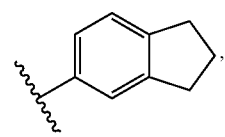

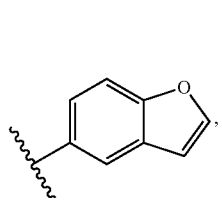

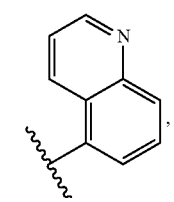

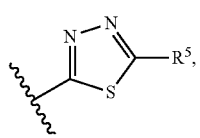

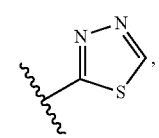

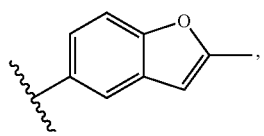

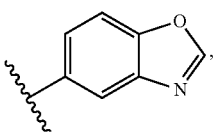

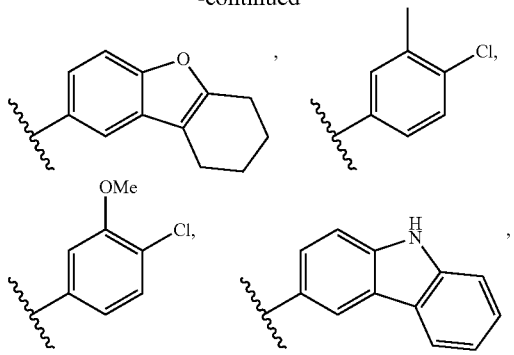

p is 0, 1, 2, or 3; q is 0, 1, 2, 3, or 4; and $R^5$ is halo, azido, alkyl, haloalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, acyloxy, alkylthio, sulfonate, sulfonyl, sulfonamido, formyl, cyano, or isocyano.

In certain embodiments, the invention relates to any one of the aforementioned compounds, wherein n is 2 and $R^1$ is halogen.

In certain embodiments, the invention relates to any one of the aforementioned compounds, wherein and $R^5$ is amido, alkoxy, halo, haloalkyl, aryl, haloaryl, alkyl, hydroxy, alkylthio, sulfonyl, haloalkoxy, or cyano.

In certain embodiments, the invention relates to any one of the aforementioned compounds, wherein and $R^5$ is alkoxy or halo.

In certain embodiments, the invention relates to any one of the aforementioned compounds, wherein and $R^5$ is halo.

In certain embodiments, the invention relates to any one of the aforementioned compounds, wherein and R[5] is halo or cyano.

In certain embodiments, the invention relates to any one of the aforementioned compounds, wherein

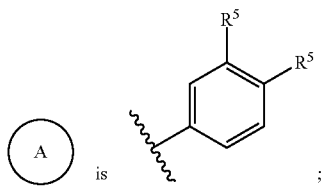

and R[5] is amido, halo, or cyano.

In certain embodiments, the invention relates to any one of the aforementioned compounds, wherein

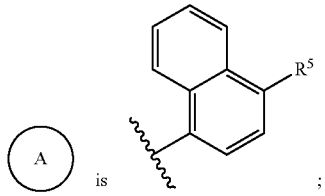

and R[5] is halo.

In certain embodiments, the invention relates to any one of the aforementioned compounds, wherein

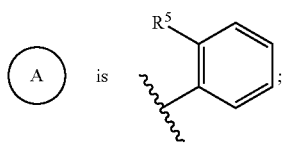

and R[5] is amido.

In certain embodiments, the invention relates to a compound, or a pharmaceutically acceptable salt or ester thereof, represented by Formula IV:

Formula IV

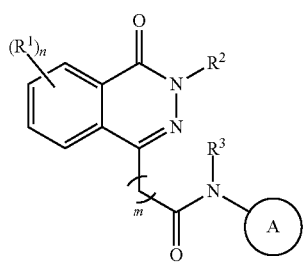

wherein, independently for each occurrence,

R[1] is alkyl, alkenyl, alkynyl, cycloalkyl, haloalkyl, aralkyl, cycloalkyl, heterocyclyl, aryl, heteroaryl, heteroaralkyl, formyl, acyl, aracyl, heteroaracyl, carboxyl, alkoxycarbonyl, acyloxy, cyano, —OR', halide, —N(R')$_2$, azido, nitro, amido, isocyano, phosphonate, phosphinate, silyl, thio, alkylthio, sulfonate, sulfonyl, sulfonamido, or sulfhydryl;

R' is hydrogen, alkyl, alkenyl, alkynyl, cycloalkyl, heterocyclyl, aryl, heteroaryl, acyl, aracyl, or heteroaracyl;

R[2] is hydrogen, alkyl, alkenyl, alkynyl, cycloalkyl, heterocyclyl, aryl, heteroaryl, acyl, aracyl, heteroaracyl sulfonate, sulfonyl, sulfonamido, formyl, carboxyl, alkoxycarbonyl, or acyloxy;

R[3] is hydrogen, alkyl, alkenyl, alkynyl, cycloalkyl, heterocyclyl, aryl, heteroaryl, acyl, aracyl, heteroaracyl sulfonate, sulfonyl, sulfonamido, formyl, carboxyl, alkoxycarbonyl, or acyloxy;

m is 0, 1, or 2;

n is 1-4; and

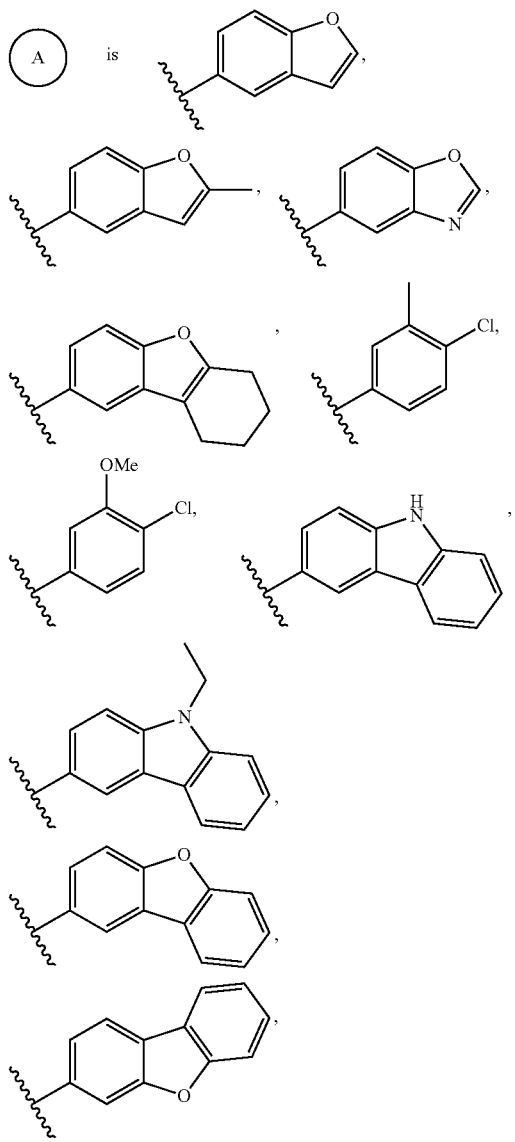

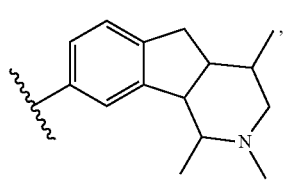

-continued

[chemical structures: 3-methyl-4-bromophenyl; 4-cyanophenyl; 3,4-dicyanophenyl; 3-methyl-4-cyanophenyl; 3-CF3-4-F-phenyl; 3-CF3-4-Cl-phenyl; 3-CF3-4-Br-phenyl; or 3-CONH2-4-Cl-phenyl;]

wherein any of the unsubstituted ring positions is optionally substituted with one or more groups independently selected from the group consisting of halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, sulfhydryl, formyl, cyano, and isocyano.

In certain embodiments, the invention relates to any one of the aforementioned compounds, wherein R¹ is alkyl.

In certain embodiments, the invention relates to any one of the aforementioned compounds, wherein R¹ is halogen.

In certain embodiments, the invention relates to any one of the aforementioned compounds, wherein R¹ is OH or methoxy.

In certain embodiments, the invention relates to any one of the aforementioned compounds, wherein R² is hydrogen.

In certain embodiments, the invention relates to any one of the aforementioned compounds, wherein R² is alkyl.

In certain embodiments, the invention relates to any one of the aforementioned compounds, wherein R² is methyl, ethyl, n-propyl, i-propyl, n-butyl, s-butyl, i-butyl, or t-butyl.

In certain embodiments, the invention relates to any one of the aforementioned compounds, wherein R³ is hydrogen.

In certain embodiments, the invention relates to any one of the aforementioned compounds, wherein R³ is alkyl.

In certain embodiments, the invention relates to any one of the aforementioned compounds, wherein m is 1.

In certain embodiments, the invention relates to any one of the aforementioned compounds, wherein n is 1.

In certain embodiments, the invention relates to any one of the aforementioned compounds, wherein n is 2.

In certain embodiments, the invention relates to any one of the aforementioned compounds, wherein

[circle labeled A]

is alkyl,

[chemical structures: benzofuran-2-yl; benzoxazol-2-yl; tetrahydrodibenzofuranyl; 3-methyl-4-chlorophenyl; 3-OMe-4-Cl-phenyl; carbazol-3-yl; N-ethylcarbazolyl; dibenzofuranyl; dibenzofuranyl (isomer); hexahydro-N-methyl fluoreno-pyridinyl; 3-methyl-4-bromophenyl; 4-cyanophenyl;]

-continued

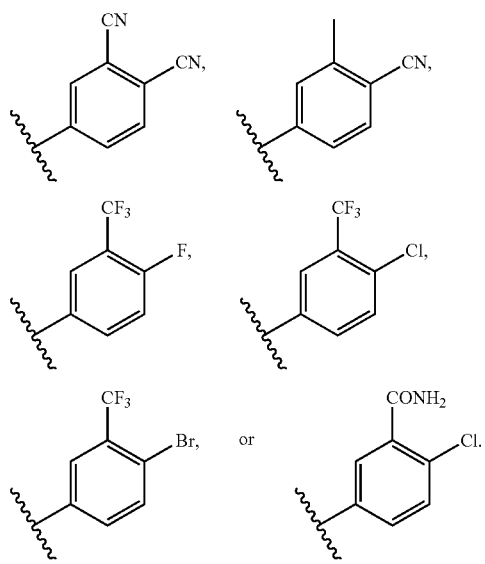

In certain embodiments, the invention relates to any one of the aforementioned compounds, wherein n is 2 and $R^1$ is halogen.

In certain embodiments, the invention relates to any one of the aforementioned compounds, wherein

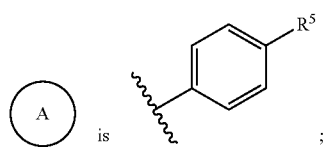

and $R^5$ is amido, alkoxy, halo, haloalkyl, aryl, haloaryl, alkyl, hydroxy, alkylthio, sulfonyl, haloalkoxy, or cyano.

In certain embodiments, the invention relates to any one of the aforementioned compounds, wherein

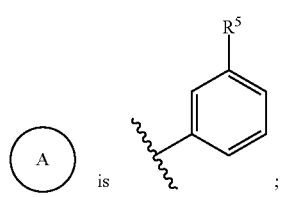

and $R^5$ is alkoxy or halo.

In certain embodiments, the invention relates to any one of the aforementioned compounds, wherein

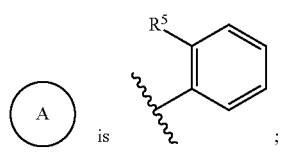

and $R^5$ is halo.

In certain embodiments, the invention relates to any one of the aforementioned compounds, wherein

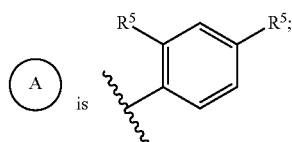

and $R^5$ is halo or cyano.

In certain embodiments, the invention relates to any one of the aforementioned compounds, wherein

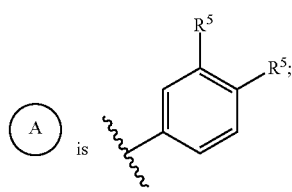

and $R^5$ is amido, halo, or cyano.

In certain embodiments, the invention relates to any one of the aforementioned compounds, wherein

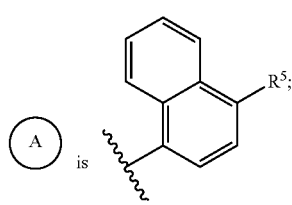

and $R^5$ is halo.

In certain embodiments, the invention relates to any one of the aforementioned compounds, wherein

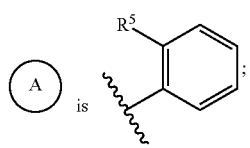

and $R^5$ is amido.

In certain embodiments, the invention relates to a compound, or a pharmaceutically acceptable salt or ester thereof, selected from the group consisting of

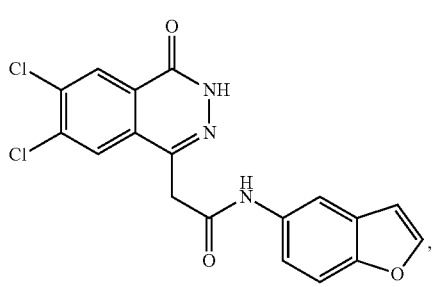

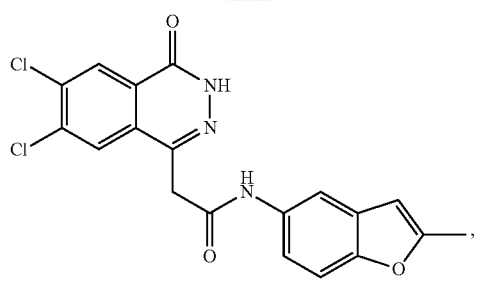
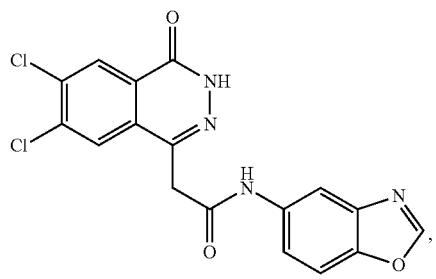
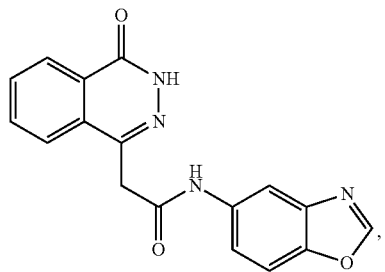
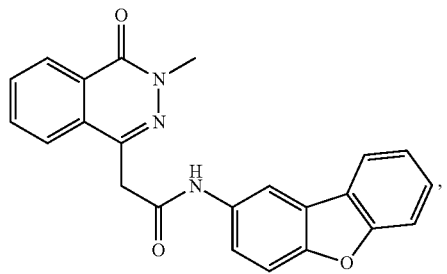
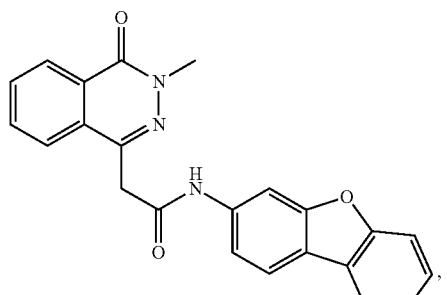
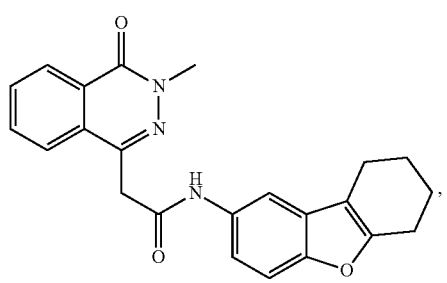
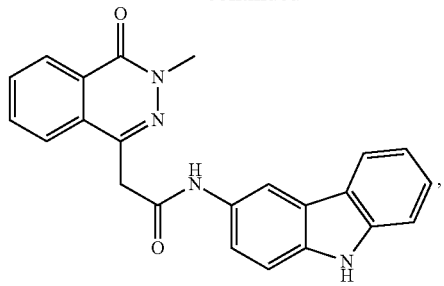
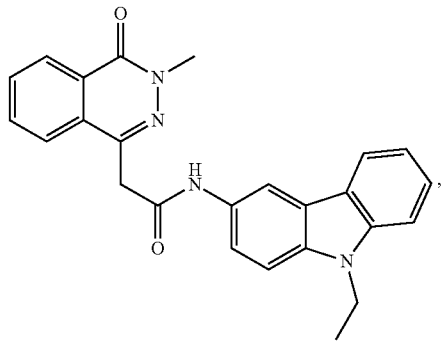
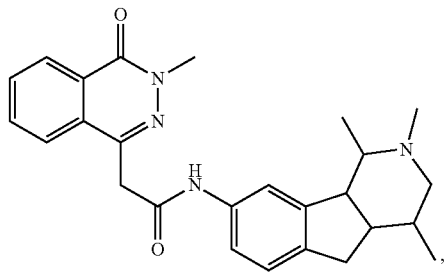
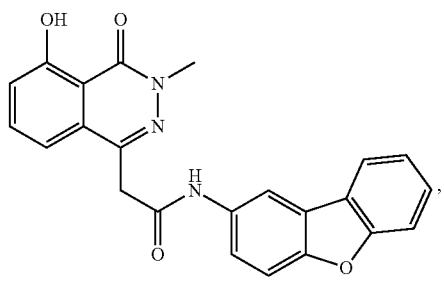
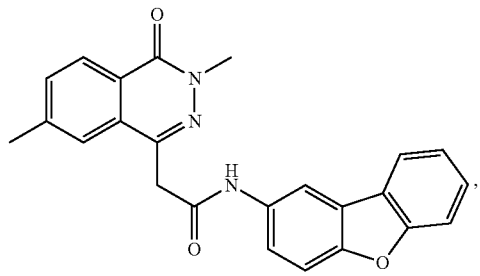
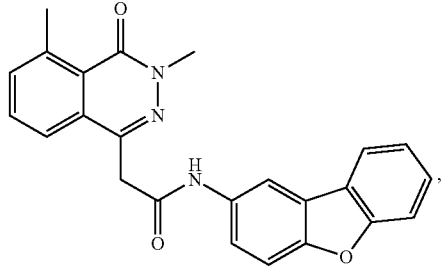

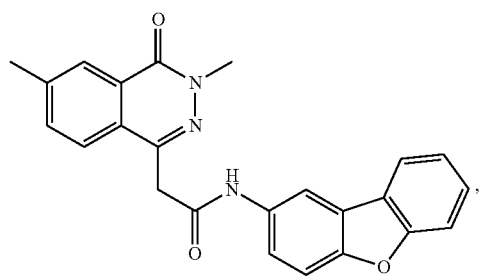
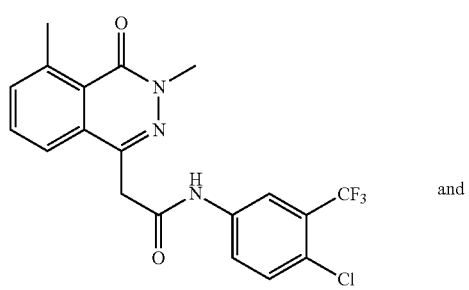
and
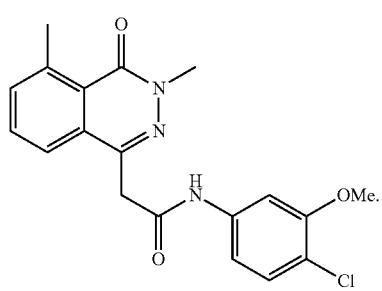 [SMILES: COc1cc(NC(=O)Cc2nn(C)c(=O)c3c(C)cccc23)ccc1Cl]
In certain embodiments, the invention relates to a compound, or a pharmaceutically acceptable salt or ester thereof, selected from the group consisting of
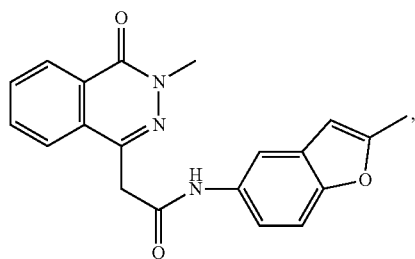
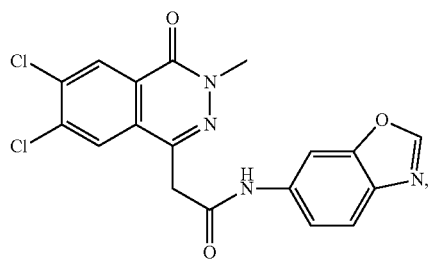
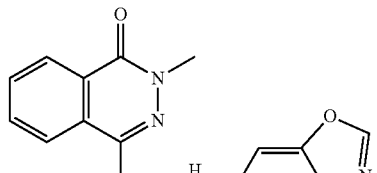
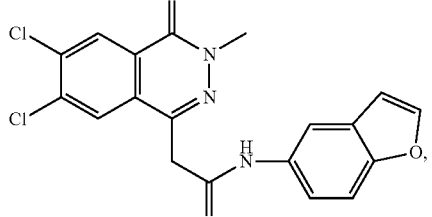
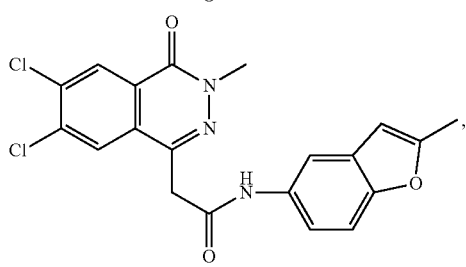
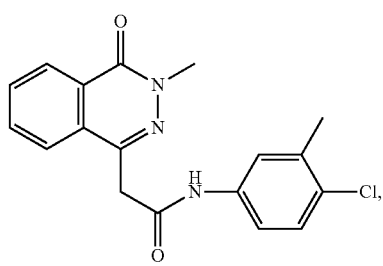
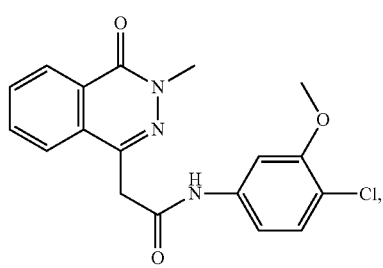
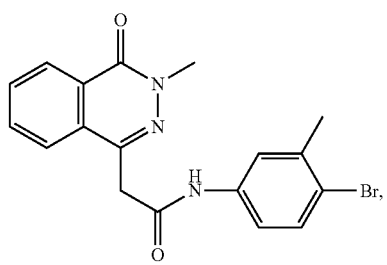

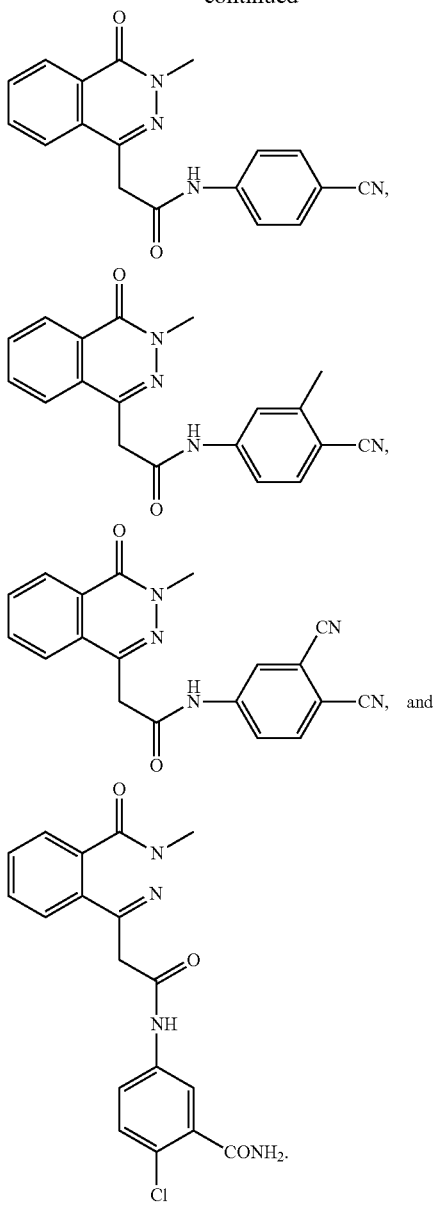

Urea Series

In certain embodiments, the invention relates to a compound, or a pharmaceutically acceptable salt or ester thereof, represented by Formula V:

Formula V

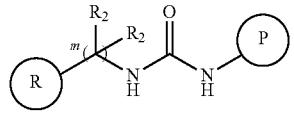

wherein, independently for each occurrence, m is 0, 1, or 2;

R² is cycloalkyl, heterocyclyl, aralkyl, heteroaralkyl, or two R² groups together form a non-aromatic ring containing 3 to 8 carbon atoms;

P is alkyl, monocyclic or bicyclic cycloalkyl, monocyclic or bicyclic heterocyclyl, monocyclic or bicyclic aryl or monocyclic or bicyclic heteroaryl; and R is alkyl, monocyclic or bicyclic cycloalkyl, monocyclic or bicyclic heterocyclyl, monocyclic or bicyclic aryl or monocyclic or bicyclic heteroaryl;

wherein any of the aforementioned alkyl, cycloalkyl, heterocyclyl aryl, heteroaryl, aralkyl, or heteroaralkyl may be substituted with one or more groups independently selected from the group consisting of of halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, sulfhydryl, formyl, cyano, and isocyano.

In certain embodiments, the invention relates to any one of the aforementioned compounds, wherein m is 0.

In certain embodiments, the invention relates to any one of the aforementioned compounds, wherein m is 1.

In certain embodiments, the invention relates to any one of the aforementioned compounds, wherein m is 1 or 2; and R² is cycloalkyl.

In certain embodiments, the invention relates to any one of the aforementioned compounds, wherein m is 1; and two R² groups together form a cyclopropyl ring.

In certain embodiments, the invention relates to any one of the aforementioned compounds, wherein P is alkyl,

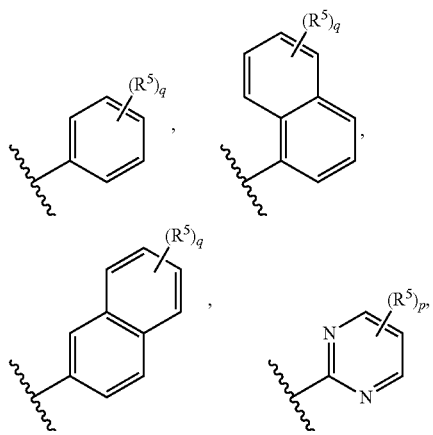

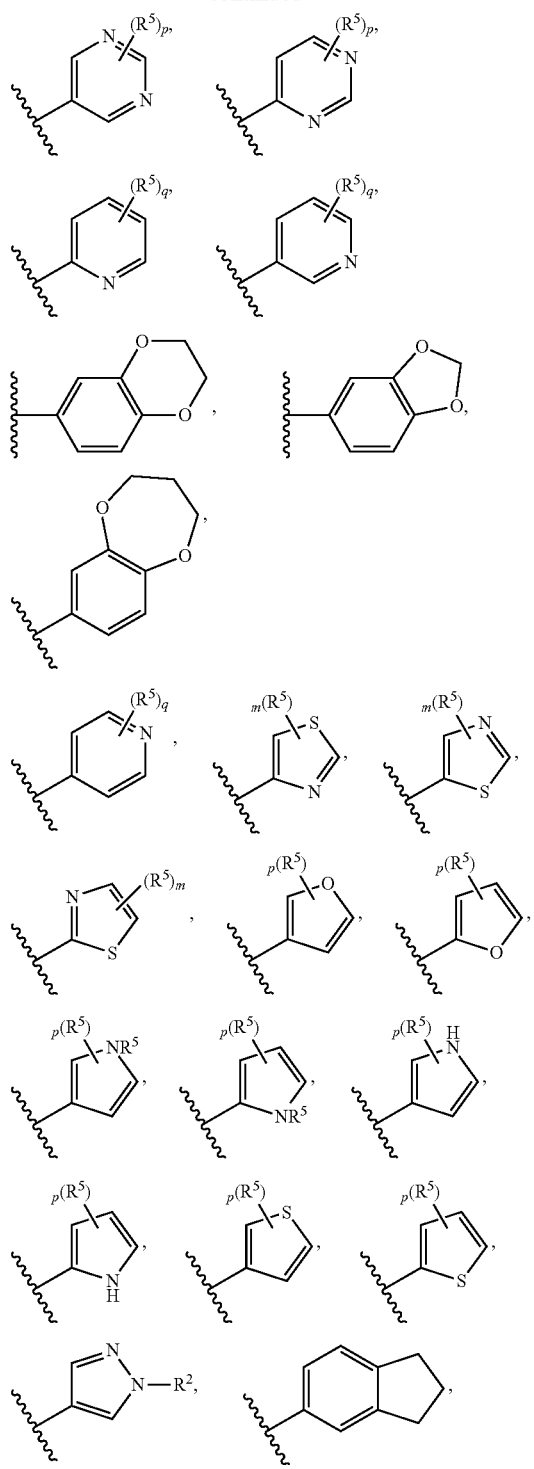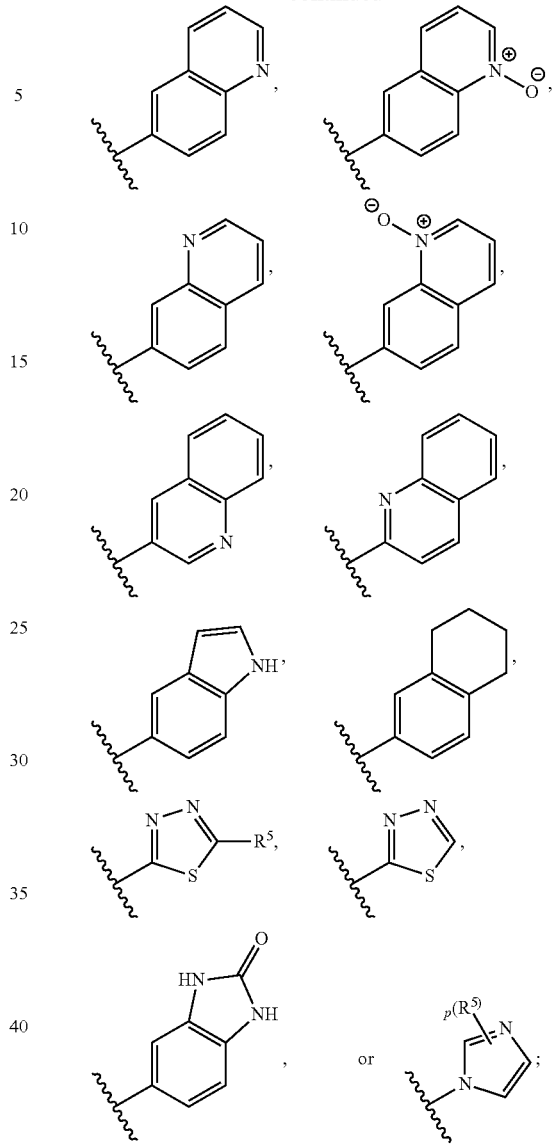

p is 0, 1, 2, or 3; q is 0, 1, 2, 3, or 4; and $R^5$ is halo, azido, alkyl, haloalkyl, hydroxyalkyl, aminoalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, carboxylic acid, acyloxy, alkylthio, sulfonate, sulfonyl, sulfonamido, formyl, cyano, or isocyano.

In certain embodiments, the invention relates to any one of the aforementioned compounds, wherein

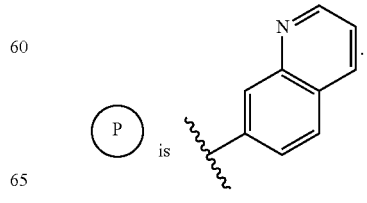

In certain embodiments, the invention relates to any one of the aforementioned compounds, wherein

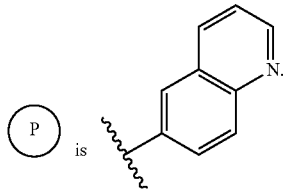

In certain embodiments, the invention relates to any one of the aforementioned compounds, wherein

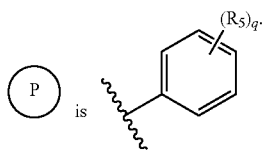

In certain embodiments, the invention relates to any one of the aforementioned compounds wherein

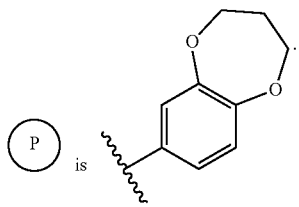

In certain embodiments, the invention relates to any one of the aforementioned compounds, wherein

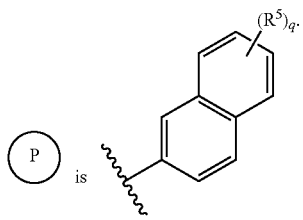

In certain embodiments, the invention relates to any one of the aforementioned compounds, wherein

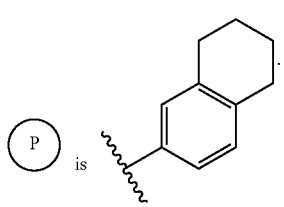

In certain embodiments, the invention relates to any one of the aforementioned compounds, wherein

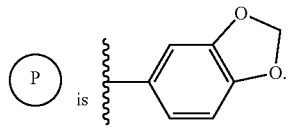

In certain embodiments, the invention relates to any one of the aforementioned compounds, wherein

is alkyl,

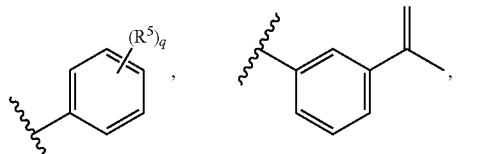

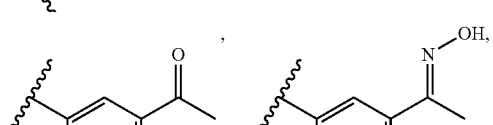

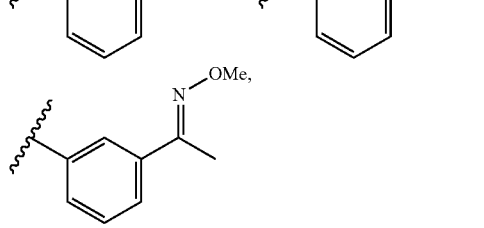

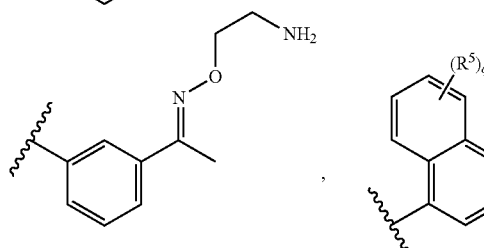

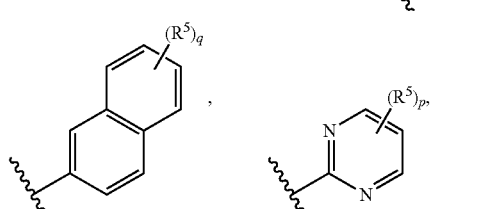

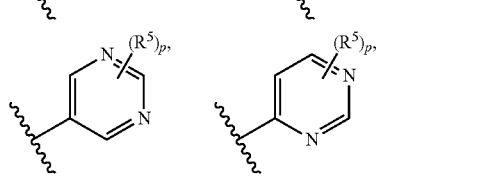

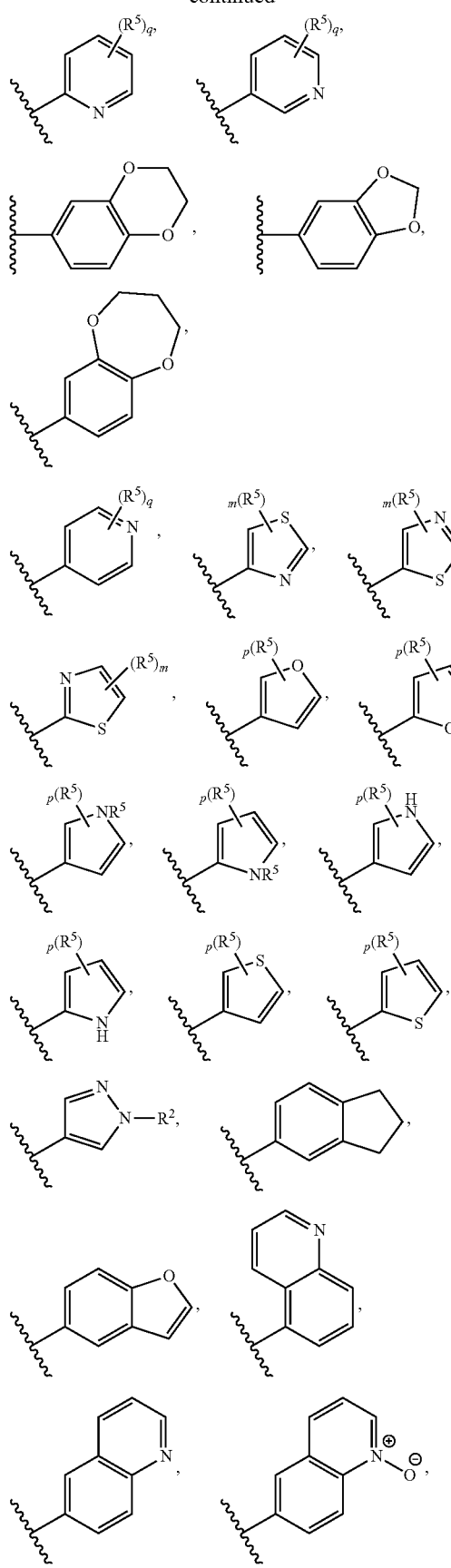
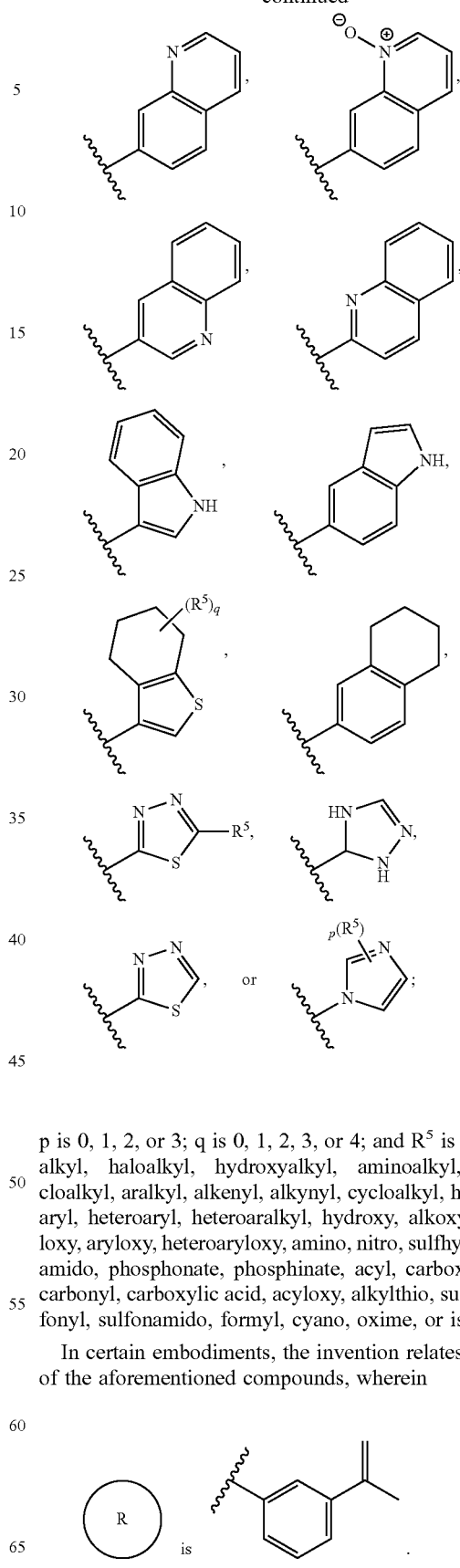

p is 0, 1, 2, or 3; q is 0, 1, 2, 3, or 4; and $R^5$ is halo, azido, alkyl, haloalkyl, hydroxyalkyl, aminoalkyl, heterocycloalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, carboxylic acid, acyloxy, alkylthio, sulfonate, sulfonyl, sulfonamido, formyl, cyano, oxime, or isocyano.

In certain embodiments, the invention relates to any one of the aforementioned compounds, wherein In certain embodiments, the invention relates to any one of the aforementioned compounds, wherein

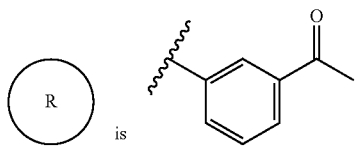 is .

In certain embodiments, the invention relates to any one of the aforementioned compounds, wherein

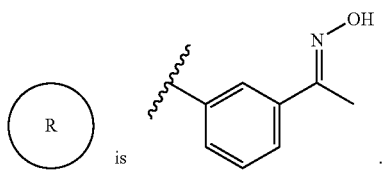 is .

In certain embodiments, the invention relates to any one of the aforementioned compounds, wherein

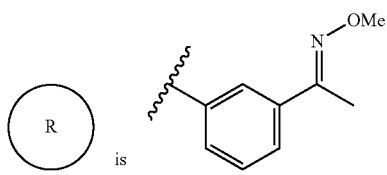 is .

In certain embodiments, the invention relates to any one of the aforementioned compounds, wherein

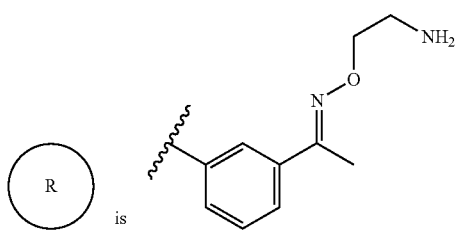 is .

In certain embodiments, the invention relates to any one of the aforementioned compounds, wherein

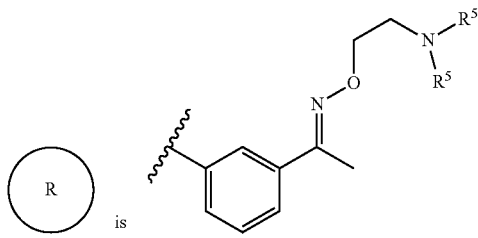 is .

In certain embodiments, the invention relates to any one of the aforementioned compounds, wherein

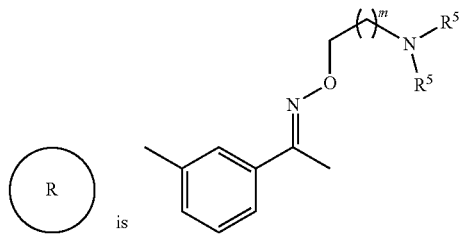 is .

In certain embodiments, the invention relates to any one of the aforementioned compounds, wherein

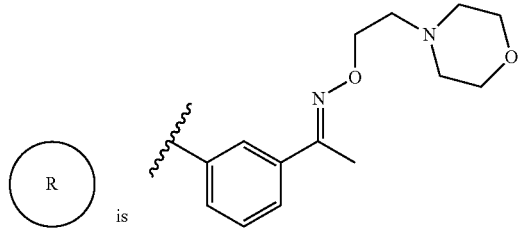 is .

In certain embodiments, the invention relates to any one of the aforementioned compounds wherein

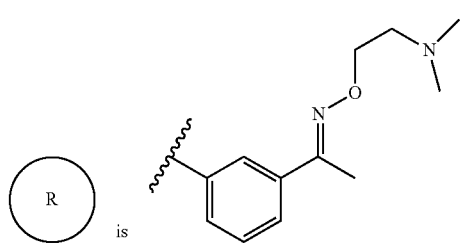 is .

In certain embodiments, the invention relates to a compound, or a pharmaceutically acceptable salt or ester thereof, represented by Formula VI:

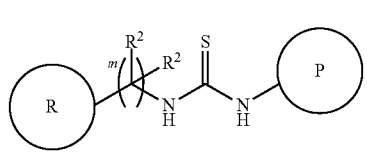

Formula VI wherein, independently for each occurrence,
m is 0, 1, or 2;
$R^2$ is hydrogen, alkyl, haloalkyl, alkoxyalkyl, alkylamino, alkylthio, cycloalkyl, heterocyclyl, aralkyl, heteroaralkyl, or two $R^2$ groups together form a non-aromatic ring containing 3 to 8 carbon atoms;

is alkyl, monocyclic or bicyclic cycloalkyl, monocyclic or bicyclic heterocyclyl, monocyclic or bicyclic aryl or monocyclic or bicyclic heteroaryl; and

is alkyl, monocyclic or bicyclic cycloalkyl, monocyclic or bicyclic heterocyclyl, monocyclic or bicyclic aryl or monocyclic or bicyclic heteroaryl;
wherein any of the aforementioned alkyl, cycloalkyl, heterocyclyl aryl, heteroaryl, aralkyl, or heteroaralkyl may be substituted with one or more groups independently selected from the group consisting of of halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, sulfhydryl, formyl, cyano, and isocyano.

In certain embodiments, the invention relates to any one of the aforementioned compounds, wherein m is 0.

In certain embodiments, the invention relates to any one of the aforementioned compounds, wherein m is 1.

In certain embodiments, the invention relates to any one of the aforementioned compounds, wherein m is 1 or 2; and $R^2$ is hydrogen.

In certain embodiments, the invention relates to any one of the aforementioned compounds, wherein m is 1 or 2; and $R^2$ is alkyl.

In certain embodiments, the invention relates to any one of the aforementioned compounds, wherein m is 1; and $R^2$ is methyl.

In certain embodiments, the invention relates to any one of the aforementioned compounds, wherein m is 1; and two $R^2$ groups together form a cyclopropyl ring.

In certain embodiments, the invention relates to any one of the aforementioned compounds, wherein

is alkyl,

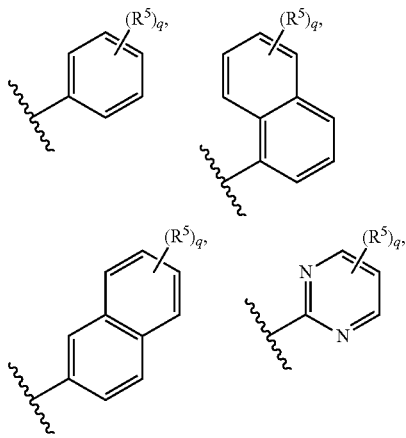

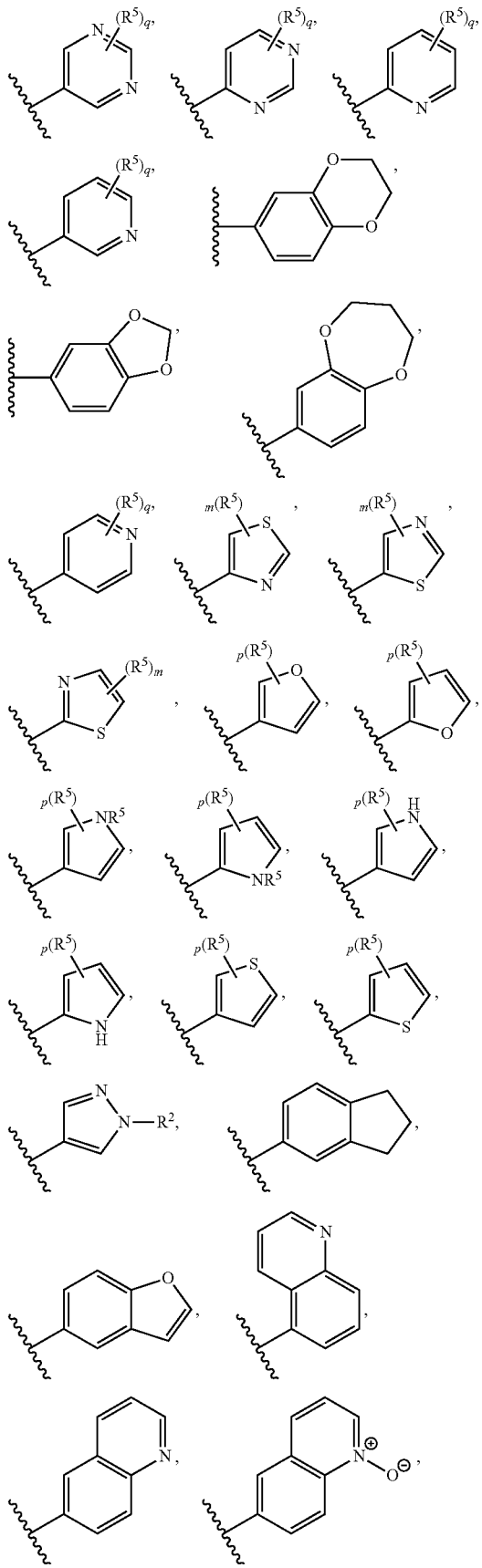

-continued

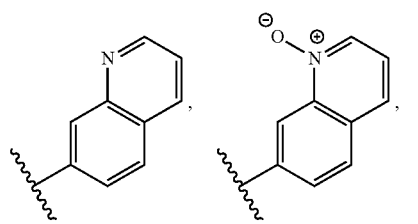

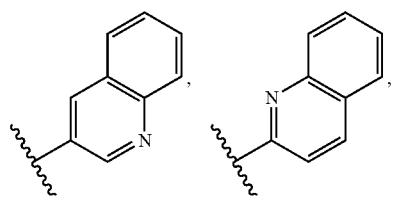

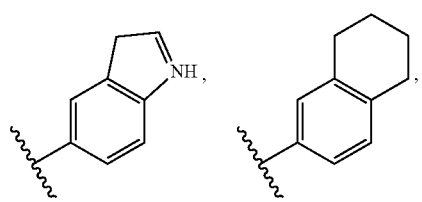

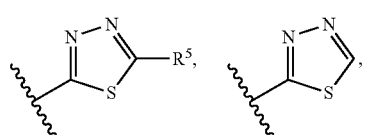

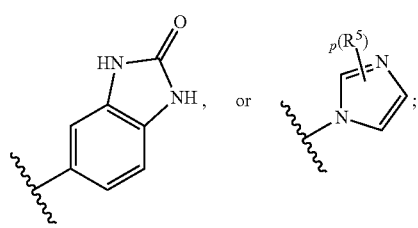

p is 0, 1, 2, or 3; q is 0, 1, 2, 3, or 4; and $R^5$ is halo, azido, alkyl, haloalkyl, hydroxyalkyl, aminoalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, carboxylic acid, acyloxy, alkylthio, sulfonate, sulfonyl, sulfonamido, formyl, cyano, or isocyano.

In certain embodiments, the invention relates to any one of the aforementioned compounds, wherein

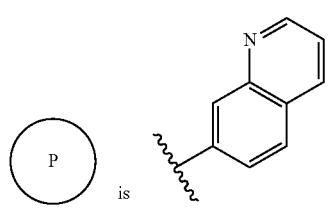

In certain embodiments, the invention relates to any one of the aforementioned compounds, wherein

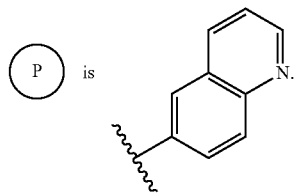

In certain embodiments, the invention relates to any one of the aforementioned compounds, wherein

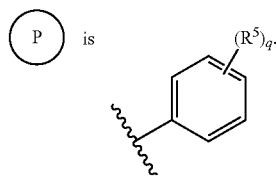

In certain embodiments, the invention relates to any one of the aforementioned compounds, wherein

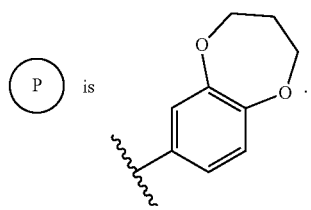

In certain embodiments, the invention relates to any one of the aforementioned compounds, wherein

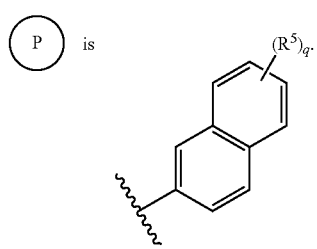

In certain embodiments, the invention relates to any one of the aforementioned compounds, wherein

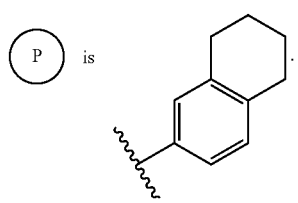

In certain embodiments, the invention relates to any one of the aforementioned compounds, wherein
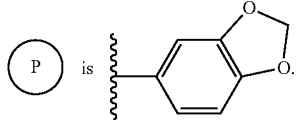 is
In certain embodiments, the invention relates to any one of the aforementioned compounds, wherein
is alkyl,
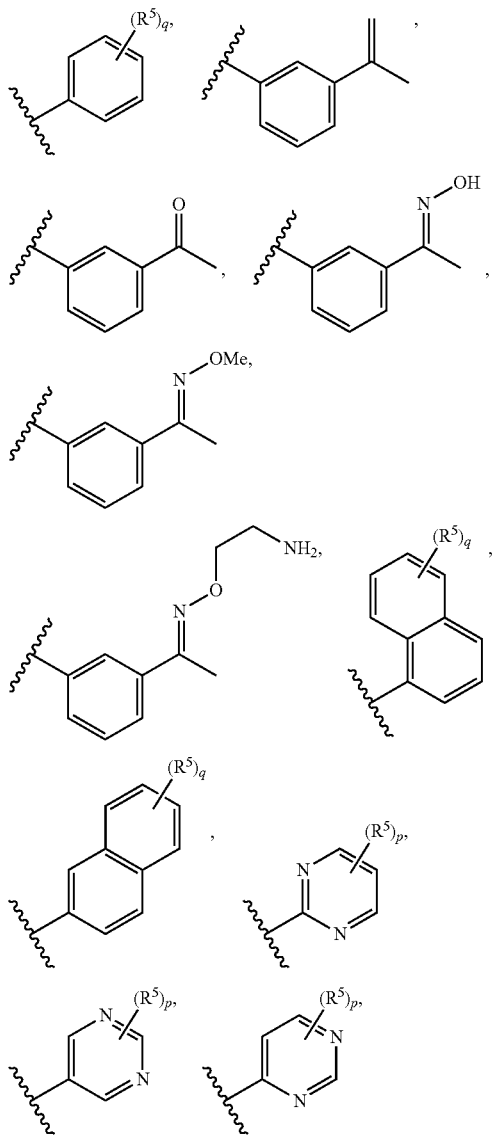
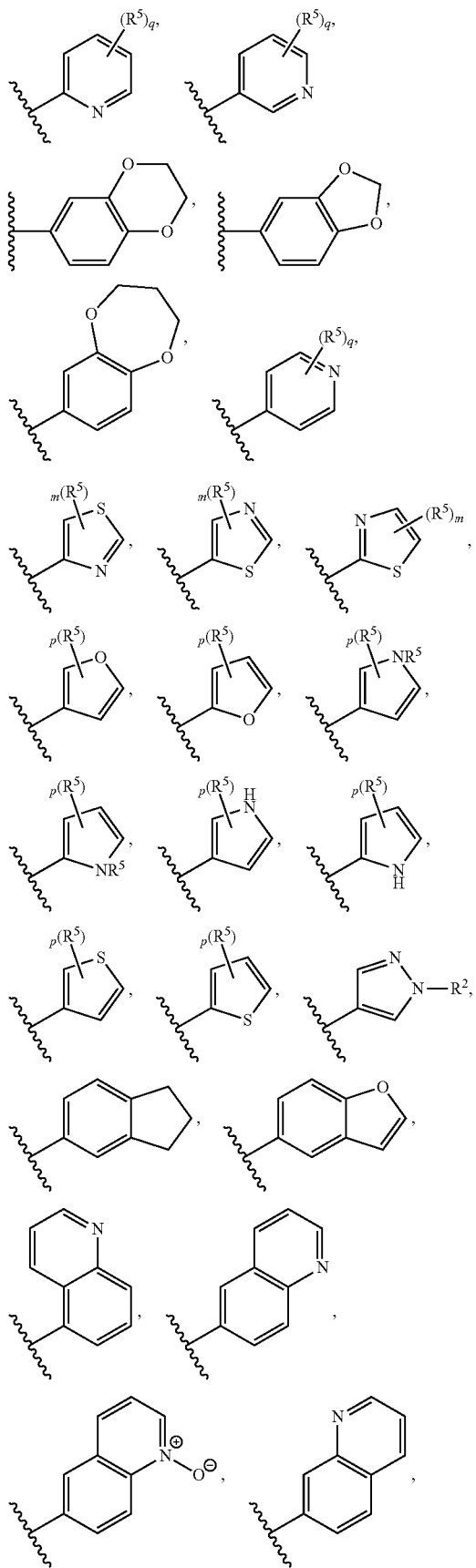

-continued

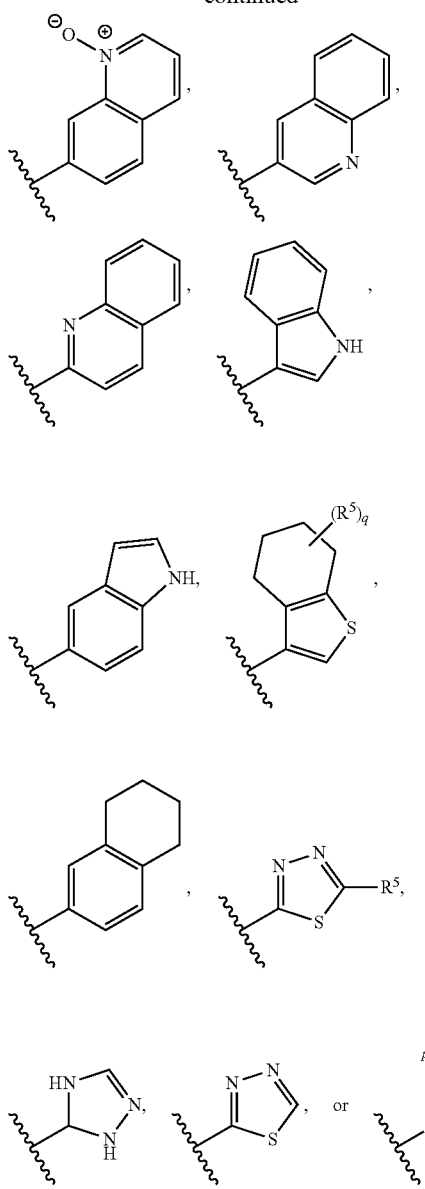

p is 0, 1, 2, or 3; q is 0, 1, 2, 3, or 4; and R⁵ is halo, azido, alkyl, haloalkyl, hydroxyalkyl, aminoalkyl, heterocycloalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, carboxylic acid, acyloxy, alkylthio, sulfonate, sulfonyl, sulfonamido, formyl, cyano, oxime, or isocyano.

In certain embodiments, the invention relates to any one of the aforementioned compounds, wherein

In certain embodiments, the invention relates to any one of the aforementioned compounds, wherein

In certain embodiments, the invention relates to any one of the aforementioned compounds, wherein (R) is [oxime with OH]

In certain embodiments, the invention relates to any one of the aforementioned compounds, wherein

In certain embodiments, the invention relates to any one of the aforementioned compounds, wherein (R) is [oxime ether with OCH₂CH₂NH₂]

In certain embodiments, the invention relates to any one of the aforementioned compounds, wherein (R) is [oxime ether with OCH₂CH₂N(R⁵)₂]

In certain embodiments, the invention relates to any one of the aforementioned compounds, wherein

 is 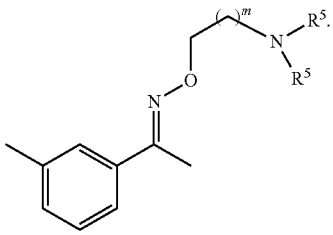

In certain embodiments, the invention relates to any one of the aforementioned compounds, wherein

 is 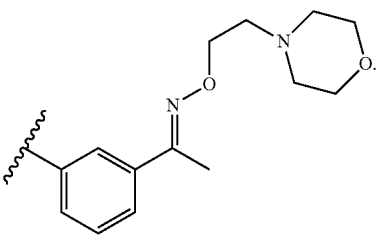

In certain embodiments, the invention relates to any one of the aforementioned compounds, wherein

 is 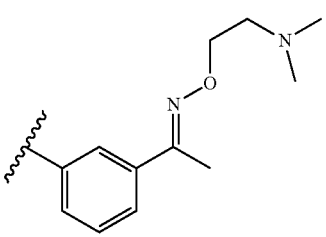.

In certain embodiments, the invention relates to a compound, or a pharmaceutically acceptable salt or ester thereof, represented by Formula VII:

Formula VII

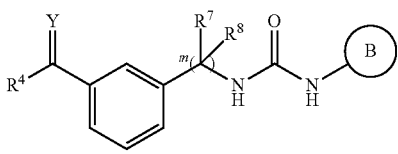

wherein, independently for each occurrence, m is 0, 1, or 2;

$R^4$ is hydrogen, $C_2$-$C_8$alkyl, alkenyl, alkynyl, cycloalkyl, heterocyclyl, aralkyl, heteroaralkyl, aryl, or heteroaryl;

Y is $C(R^6)_2$, O, S, NQ, or NOQ;

wherein $R^6$ is independently for each occurrence hydrogen, alkyl, alkenyl, alkynyl, cycloalkyl, heterocyclyl, aralkyl, heteroaralkyl, aryl, or heteroaryl, or two $R^6$ together form a ring containing 3 to 8 carbon atoms;

Q is hydrogen, alkyl, aminoalkyl, alkylaminoalkyl, arylaminoalkyl, alkenyl, alkynyl, cycloalkyl, heterocyclyl, heterocyclylalkyl, aralkyl, heteroaralkyl, aryl, or heteroaryl;

$R^7$ and $R^8$ are independently hydrogen, alkyl, cycloalkyl, aralkyl, heteroaralkyl, or $R^7$ and $R^8$ together form a ring containing 3 to 8 carbon atoms; and

is alkyl, monocyclic or bicyclic cycloalkyl, monocyclic or bicyclic heterocyclyl, monocyclic or bicyclic aryl or monocyclic or bicyclic heteroaryl;

wherein, any of the aforementioned alkyl, cycloalkyl, heterocyclyl aryl, heteroaryl, aralkyl, or heteroaralkyl may be substituted with one or more groups independently selected from the group consisting of halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, sulfhydryl, formyl, cyano, and isocyano.

In certain embodiments, the invention relates to any one of the aforementioned compounds, wherein m is 0.

In certain embodiments, the invention relates to any one of the aforementioned compounds, wherein m is 1.

In certain embodiments, the invention relates to any one of the aforementioned compounds, wherein m is 1 or 2; and $R^7$ and $R^8$ are hydrogen.

In certain embodiments, the invention relates to any one of the aforementioned compounds, wherein m is 1 or 2; and $R^7$ and $R^8$ are alkyl.

In certain embodiments, the invention relates to any one of the aforementioned compounds, wherein m is 1; and $R^7$ and $R^8$ are methyl.

In certain embodiments, the invention relates to any one of the aforementioned compounds, wherein m is 1; and two $R^2$ groups together form a cyclopropyl ring.

In certain embodiments, the invention relates to any one of the aforementioned compounds, wherein $R^4$ is hydrogen.

In certain embodiments, the invention relates to any one of the aforementioned compounds, wherein $R^4$ is methyl.

In certain embodiments, the invention relates to any one of the aforementioned compounds, wherein Y is $C(R')_2$ and both $R^6$ are hydrogen.

In certain embodiments, the invention relates to any one of the aforementioned compounds, wherein Y is O.

In certain embodiments, the invention relates to any one of the aforementioned compounds, wherein Y is NOH.

In certain embodiments, the invention relates to any one of the aforementioned compounds, wherein Y is NOMe.

In certain embodiments, the invention relates to any one of the aforementioned compounds, wherein Y is NO(t-Bu).

In certain embodiments, the invention relates to any one of the aforementioned compounds, wherein Y is $NO(CH_2CH_2NH_2)$.

In certain embodiments, the invention relates to any one of the aforementioned compounds, wherein Y is $NO(CH_2CH_2NHMe)$.

In certain embodiments, the invention relates to any one of the aforementioned compounds, wherein $R^4$ is methyl and Y is $C(R^6)_2$ and both $R^6$ are hydrogen.

In certain embodiments, the invention relates to any one of the aforementioned compounds, wherein $R^4$ is methyl and Y is O.

In certain embodiments, the invention relates to any one of the aforementioned compounds, wherein $R^4$ is methyl and Y is NOH.

In certain embodiments, the invention relates to any one of the aforementioned compounds, wherein $R^4$ is methyl and Y is NOMe.

In certain embodiments, the invention relates to any one of the aforementioned compounds, wherein $R^4$ is methyl and Y is NO(t-Bu).

In certain embodiments, the invention relates to any one of the aforementioned compounds, wherein $R^4$ is methyl and Y is $NO(CH_2CH_2NH_2)$.

In certain embodiments, the invention relates to any one of the aforementioned compounds, wherein $R^4$ is methyl and Y is $NO(CH_2CH_2NHMe)$.

In certain embodiments, the invention relates to any one of the aforementioned compounds wherein

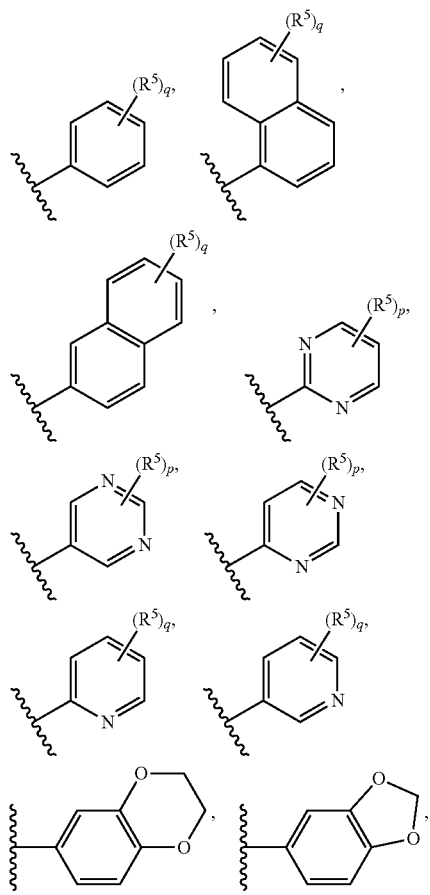

is alkyl,

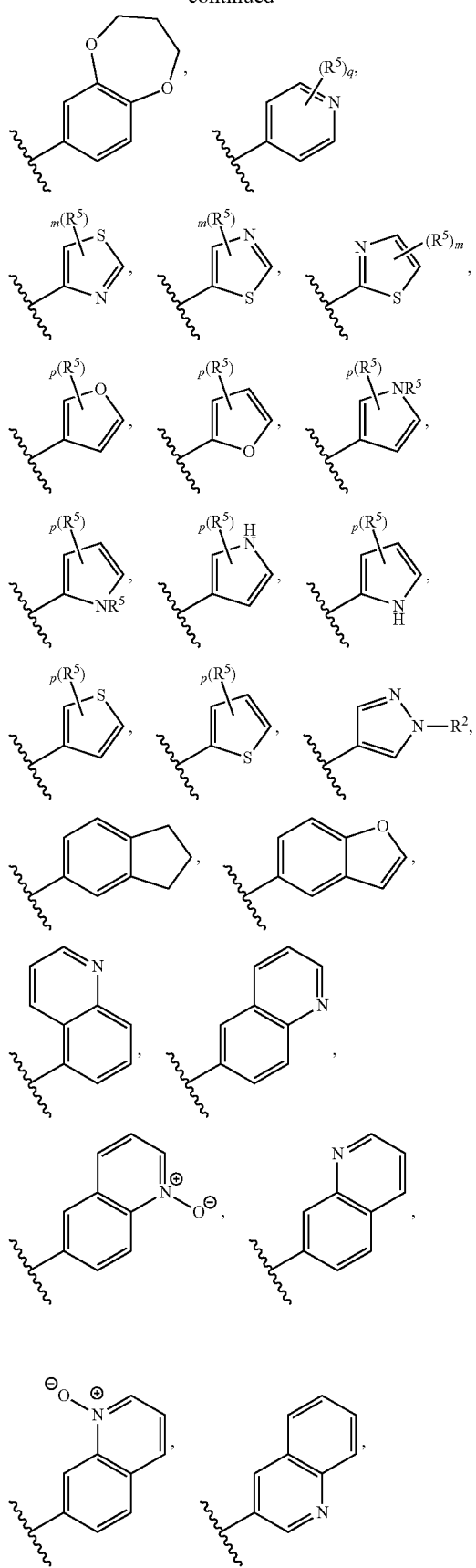

-continued

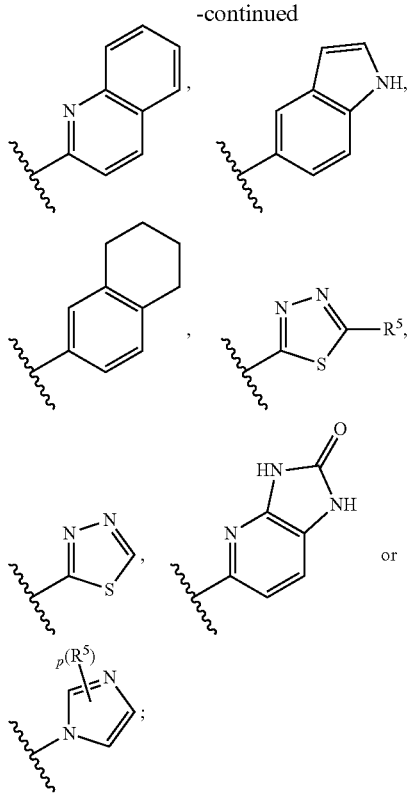

p is 0, 1, 2, or 3; q is 0, 1, 2, 3, or 4; and R⁵ is halo, azido, alkyl, haloalkyl, hydroxyalkyl, aminoalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, carboxylic acid, acyloxy, alkylthio, sulfonate, sulfonyl, sulfonamido, formyl, cyano, or isocyano.

In certain embodiments, the invention relates to any one of the aforementioned compounds, wherein

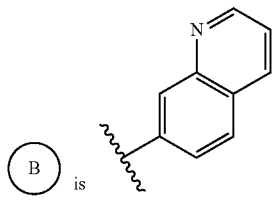

In certain embodiments, the invention relates to any one of the aforementioned compounds, wherein

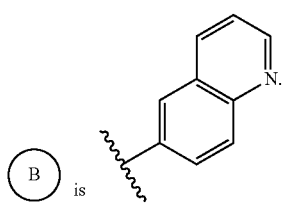

In certain embodiments, the invention relates to any one of the aforementioned compounds, wherein

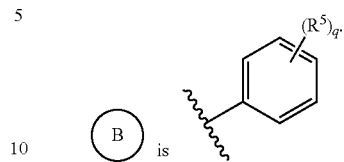

In certain embodiments, the invention relates to any one of the aforementioned compounds, wherein

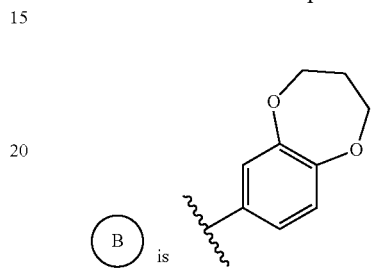

In certain embodiments, the invention relates to any one of the aforementioned compounds, wherein

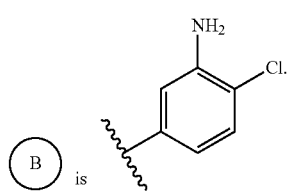

In certain embodiments, the invention relates to any one of the aforementioned compounds, wherein

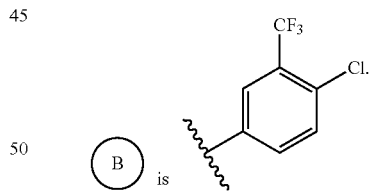

In certain embodiments, the invention relates to any one of the aforementioned compounds, wherein

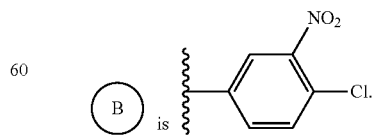

In certain embodiments, the invention relates to any one of the aforementioned compounds, wherein $R^4$ is methyl, Y is NO(t-Bu), and

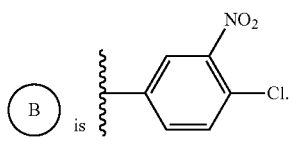 is 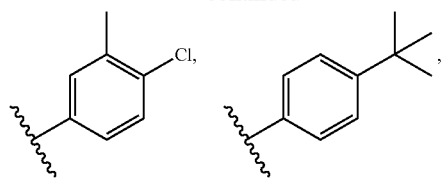

In certain embodiments, the invention relates to any one of the aforementioned compounds, wherein $R^4$ is methyl, Y is $NO(CH_2CH_2NH_2)$, and

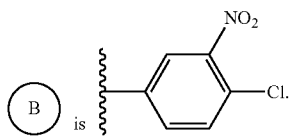 is 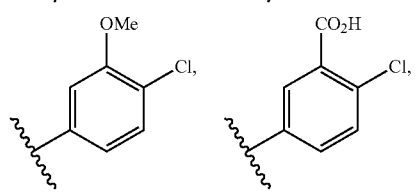

In certain embodiments, the invention relates to a compound, or a pharmaceutically acceptable salt or ester thereof, represented by Formula VIII:

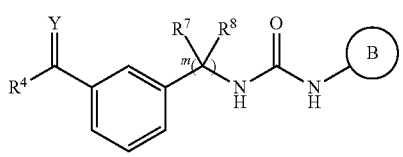

Formula VIII wherein, independently for each occurrence, m is 0, 1, or 2;

$R^4$ is hydrogen, alkyl, alkenyl, alkynyl, cycloalkyl, heterocyclyl, aralkyl, heteroaralkyl, aryl, or heteroaryl;

Y is $C(R^6)_2$, O, S, NQ, or NOQ
wherein $R^6$ is independently for each occurrence hydrogen, alkyl, alkenyl, alkynyl, cycloalkyl, heterocyclyl, aralkyl, heteroaralkyl, aryl, or heteroaryl, or $R^5$ and $R^6$ together form a ring containing 3 to 8 carbon atoms;

Q is hydrogen, alkyl, aminoalkyl, alkylaminoalkyl, arylaminoalkyl, alkenyl, alkynyl, cycloalkyl, heterocyclyl, heterocyclylalkyl, aralkyl, heteroaralkyl, aryl, or heteroaryl;

$R^7$ and $R^8$ are independently cycloalkyl, aralkyl, heteroaralkyl, or $R^7$ and $R^8$ together form a ring containing 3 to 8 carbon atoms;

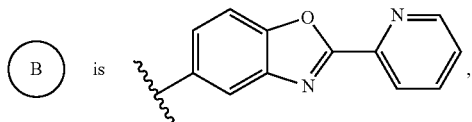

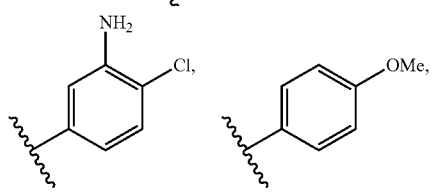

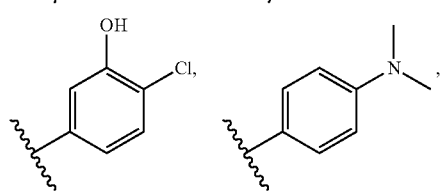

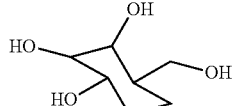

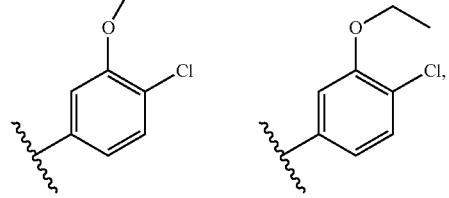

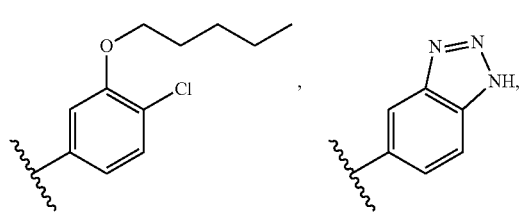

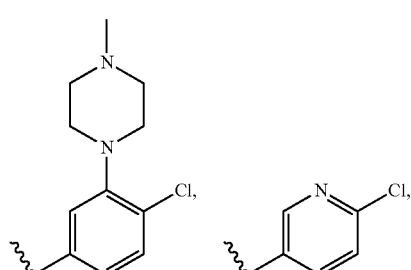

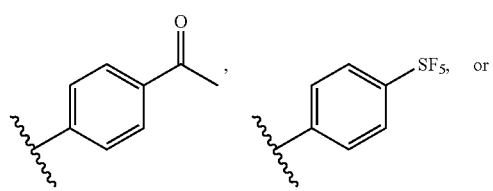 or

-continued

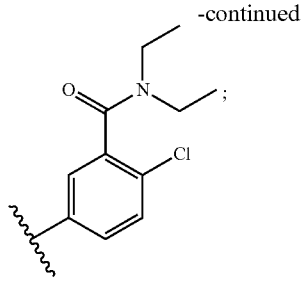

wherein any of the aforementioned alkyl, aryl, or heteroaryl may be substituted with one or more groups independently selected from the group consisting of halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, sulfhydryl, formyl, cyano, and isocyano.

In certain embodiments, the invention relates to any one of the aforementioned compounds, wherein m is 0.

In certain embodiments, the invention relates to any one of the aforementioned compounds, wherein m is 1.

In certain embodiments, the invention relates to any one of the aforementioned compounds, wherein m is 1 or 2; and $R^2$ is hydrogen.

In certain embodiments, the invention relates to any one of the aforementioned compounds, wherein m is 1 or 2; and $R^7$ and $R^8$ are alkyl.

In certain embodiments, the invention relates to any one of the aforementioned compounds, wherein m is 1; and $R^7$ and $R^8$ are methyl.

In certain embodiments, the invention relates to any one of the aforementioned compounds, wherein m is 1; and $R^7$ and $R^8$ together form a cyclopropyl ring.

In certain embodiments, the invention relates to any one of the aforementioned compounds, wherein $R^4$ is hydrogen.

In certain embodiments, the invention relates to any one of the aforementioned compounds, wherein $R^4$ is methyl.

In certain embodiments, the invention relates to any one of the aforementioned compounds, wherein Y is $C(R^6)_2$ and both $R^6$ are hydrogen.

In certain embodiments, the invention relates to any one of the aforementioned compounds, wherein Y is O.

In certain embodiments, the invention relates to any one of the aforementioned compounds, wherein Y is NOH.

In certain embodiments, the invention relates to any one of the aforementioned compounds, wherein Y is NOMe.

In certain embodiments, the invention relates to any one of the aforementioned compounds, wherein Y is NO(t-Bu).

In certain embodiments, the invention relates to any one of the aforementioned compounds, wherein Y is $NO(CH_2CH_2NH_2)$.

In certain embodiments, the invention relates to any one of the aforementioned compounds, wherein Y is $NO(CH_2CH_2NHMe)$.

In certain embodiments, the invention relates to any one of the aforementioned compounds, wherein $R^4$ is methyl and Y is $C(R^6)_2$ and both $R^6$ are hydrogen.

In certain embodiments, the invention relates to any one of the aforementioned compounds, wherein $R^4$ is methyl and Y is O.

In certain embodiments, the invention relates to any one of the aforementioned compounds, wherein $R^4$ is methyl and Y is NOH.

In certain embodiments, the invention relates to any one of the aforementioned compounds, wherein $R^4$ is methyl and Y is NOMe.

In certain embodiments, the invention relates to any one of the aforementioned compounds, wherein $R^4$ is methyl and Y is NO(t-Bu).

In certain embodiments, the invention relates to any one of the aforementioned compounds, wherein $R^4$ is methyl and Y is $NO(CH_2CH_2NH_2)$.

In certain embodiments, the invention relates to any one of the aforementioned compounds, wherein $R^4$ is methyl and Y is $NO(CH_2CH_2NHMe)$.

In certain embodiments, the invention relates to any one of the aforementioned compounds, wherein

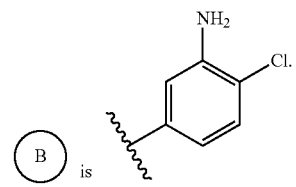

In certain embodiments, the invention relates to any one of the aforementioned compounds, wherein

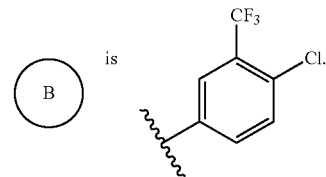

In certain embodiments, the invention relates to any one of the aforementioned compounds, wherein

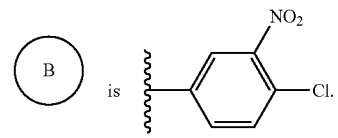

In certain embodiments, the invention relates to any one of the aforementioned compounds, wherein $R^4$ is methyl, Y is NO(t-Bu), and

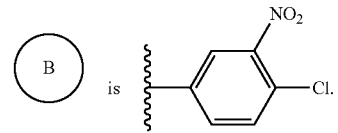

In certain embodiments, the invention relates to any one of the aforementioned compounds, wherein $R^4$ is methyl, Y is $NO(CH_2CH_2NH_2)$, and

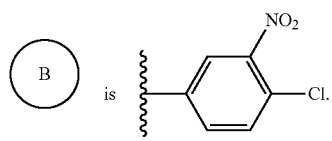
In certain embodiments, the invention relates to a compound, or a pharmaceutically acceptable salt or ester thereof, selected from the group consisting of
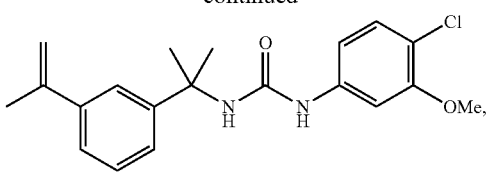
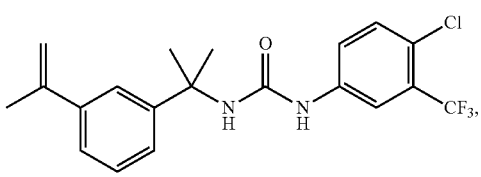
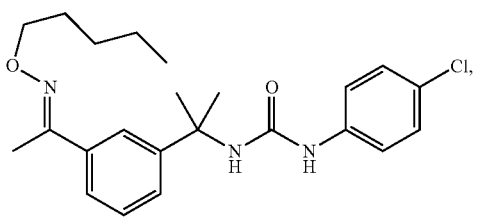
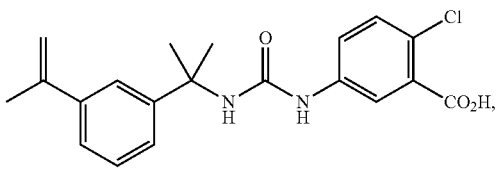
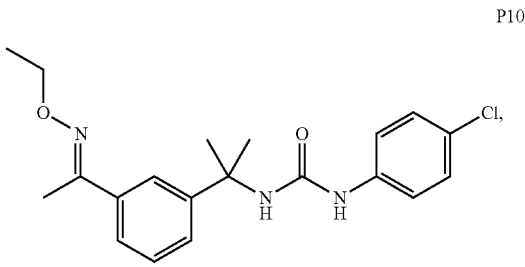
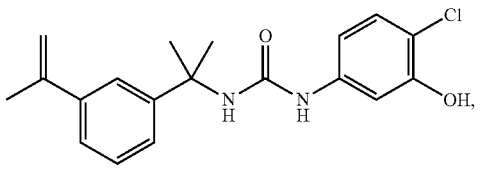
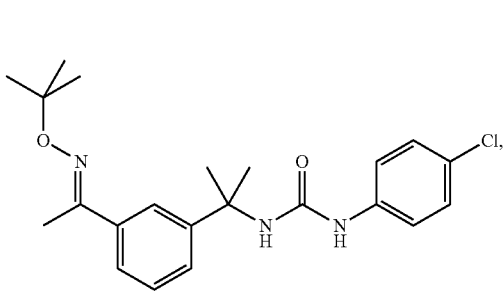
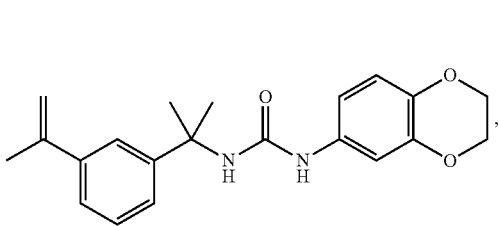

65
-continued
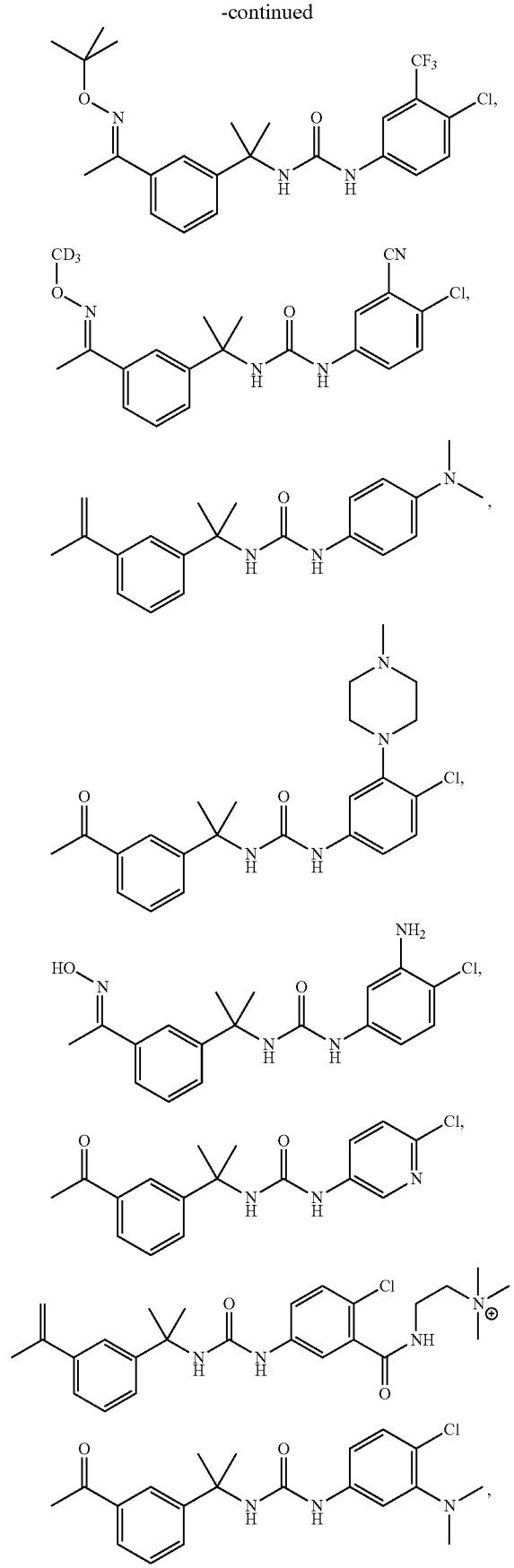
66
-continued
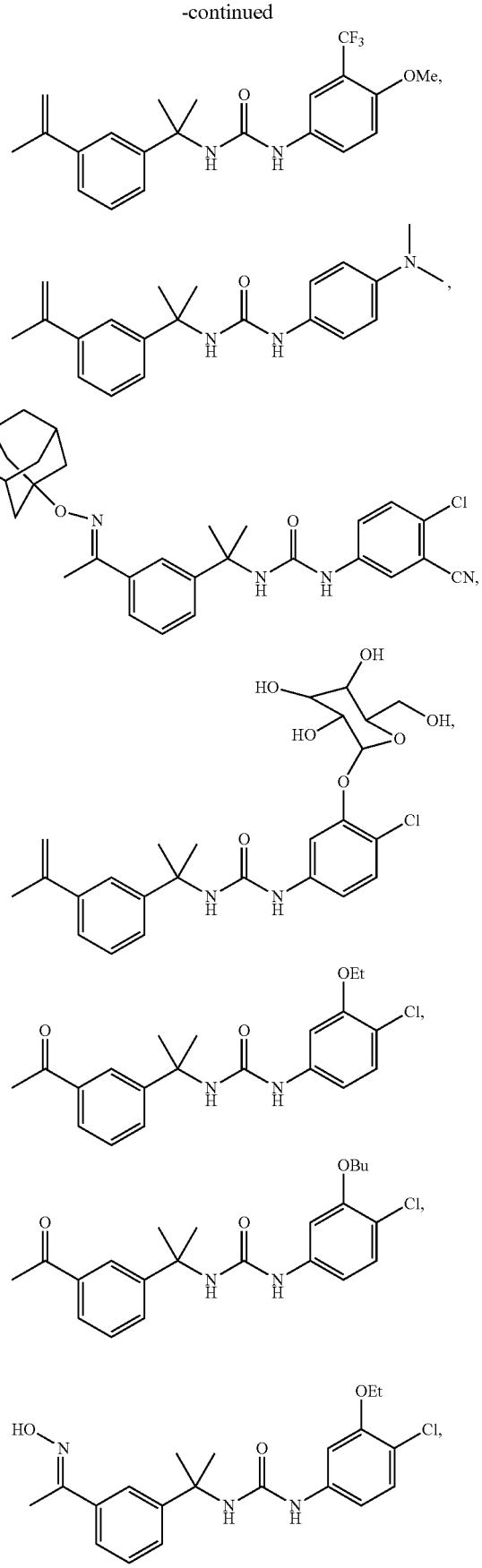

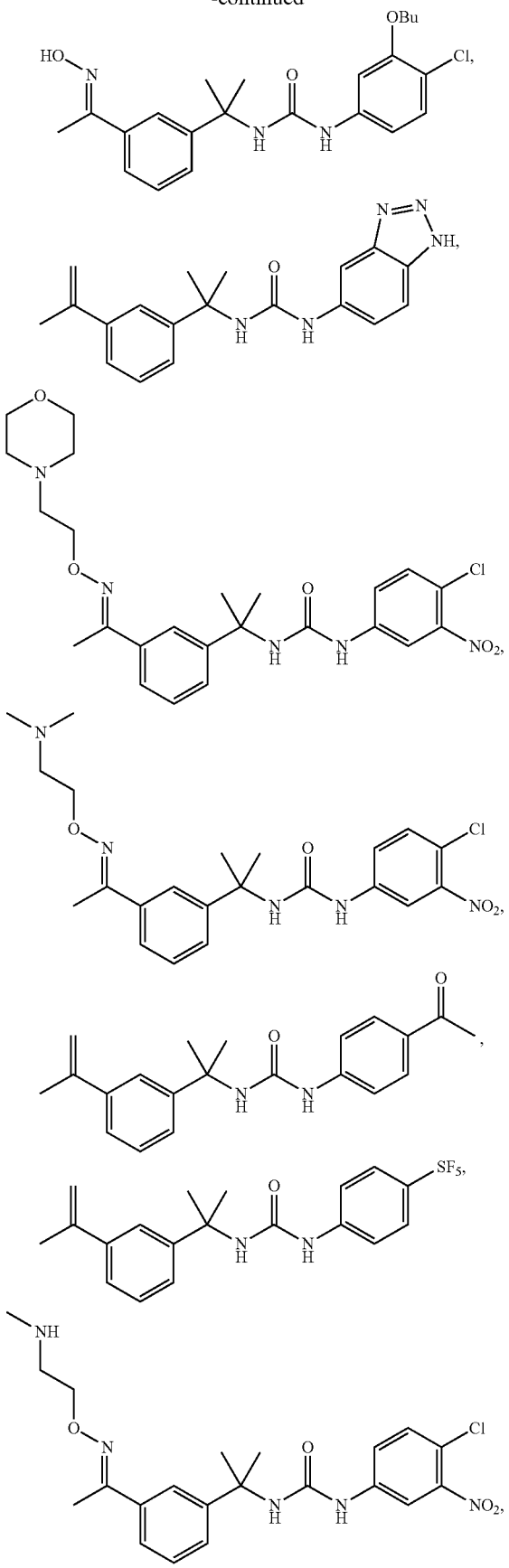

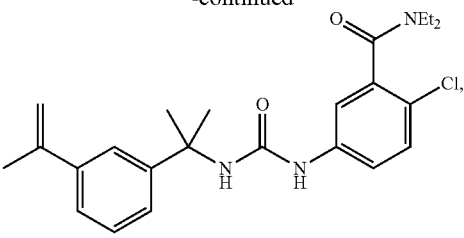

P127

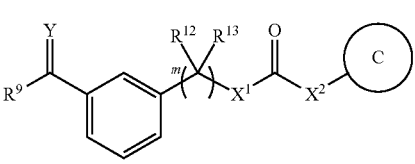

P131

In certain embodiments, the invention relates to a compound, or a pharmaceutically acceptable salt or ester thereof, represented by Formula IX:

$$R^9 \underset{Y}{\overset{\|}{C}} - \text{Ar} - (CR^{12}R^{13})_m - X^1 - \underset{O}{\overset{\|}{C}} - X^2 - C \qquad \text{Formula IX}$$

wherein, independently for each occurrence, m is 0, 1, or 2;

$R^9$ is hydrogen, alkyl, alkenyl, alkynyl, cycloalkyl, heterocyclyl, aralkyl, heteroaralkyl, aryl, or heteroaryl;

Y is $CH_2$, $C(R^{10})(R^{11})$ O, S, NQ, or NOQ;

wherein $R^{10}$ and $R^{11}$ are independently hydrogen, alkyl, alkenyl, alkynyl, cycloalkyl, heterocyclyl, aralkyl, heteroaralkyl, aryl, or heteroaryl, or $R^8$ and $R^9$ together form a ring containing 3 to 8 carbon atoms;

Q is hydrogen, alkyl, aminoalkyl, alkylaminoalkyl, arylaminoalkyl, alkenyl, alkynyl, cycloalkyl, heterocyclyl, heterocyclylalkyl, aralkyl, heteroaralkyl, aryl, or heteroaryl;

$R^{12}$ and $R^{13}$ are independently hydrogen, alkyl, cycloalkyl, aralkyl, heteroaralkyl, or $R^{12}$ and $R^{13}$ together form a ring containing 3 to 8 carbon atoms;

is alkyl, monocyclic or bicyclic cycloalkyl, monocyclic or bicyclic heterocyclyl, monocyclic or bicyclic aryl or monocyclic or bicyclic heteroaryl;

wherein any of the aforementioned alkyl, aryl, or heteroaryl may be substituted with one or more groups independently selected from the group consisting of halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, formyl, cyano, and isocyano; and $X^1$ and $X^2$ are independently O or NH, with the proviso that $X^1$ and $X^2$ cannot both be NH.

In certain embodiments, the invention relates to any one of the aforementioned compounds, wherein $X^1$ is O and $X^2$ is NH.

In certain embodiments, the invention relates to any one of the aforementioned compounds, wherein $X^1$ is NH and $X^2$ is O.

In certain embodiments, the invention relates to any one of the aforementioned compounds, wherein m is 0.

In certain embodiments, the invention relates to any one of the aforementioned compounds, wherein m is 1.

In certain embodiments, the invention relates to any one of the aforementioned compounds, wherein m is 1 or 2; and $R^{12}$ and $R^{13}$ are hydrogen.

In certain embodiments, the invention relates to any one of the aforementioned compounds, wherein m is 1 or 2; and $R^{12}$ and $R^{13}$ are alkyl.

In certain embodiments, the invention relates to any one of the aforementioned compounds, wherein m is 1; and $R^{12}$ and $R^{13}$ are methyl.

In certain embodiments, the invention relates to any one of the aforementioned compounds, wherein m is 1; and $R^{12}$ and $R^{13}$ together form a cyclopropyl ring.

In certain embodiments, the invention relates to any one of the aforementioned compounds, wherein $R^9$ is hydrogen.

In certain embodiments, the invention relates to any one of the aforementioned compounds, wherein $R^9$ is methyl.

In certain embodiments, the invention relates to any one of the aforementioned compounds, wherein Y is $C(R^{10})(R^{11})$ and $R^{10}$ and $R^{11}$ are hydrogen.

In certain embodiments, the invention relates to any one of the aforementioned compounds, wherein Y is O.

In certain embodiments, the invention relates to any one of the aforementioned compounds, wherein Y is NOH.

In certain embodiments, the invention relates to any one of the aforementioned compounds, wherein Y is NOMe.

In certain embodiments, the invention relates to any one of the aforementioned compounds, wherein Y is NO(t-Bu).

In certain embodiments, the invention relates to any one of the aforementioned compounds, wherein Y is $NO(CH_2CH_2NH_2)$.

In certain embodiments, the invention relates to any one of the aforementioned compounds, wherein Y is $NO(CH_2CH_2NHMe)$.

In certain embodiments, the invention relates to any one of the aforementioned compounds, wherein Y is $C(R^{10})(R^{11})$, $R^{10}$ and $R^{11}$ are hydrogen, and $R^{12}$ and $R^{13}$ are methyl.

In certain embodiments, the invention relates to any one of the aforementioned compounds, wherein $R^9$ is methyl and Y is $C(R^{10})(R^{11})$ and $R^{10}$ and $R^{11}$ are hydrogen.

In certain embodiments, the invention relates to any one of the aforementioned compounds, wherein $R^9$ is methyl and Y is O.

In certain embodiments, the invention relates to any one of the aforementioned compounds, wherein $R^9$ is methyl and Y is NOH.

In certain embodiments, the invention relates to any one of the aforementioned compounds, wherein $R^9$ is methyl and Y is NOMe.

In certain embodiments, the invention relates to any one of the aforementioned compounds, wherein $R^9$ is methyl and Y is NO(t-Bu).

In certain embodiments, the invention relates to any one of the aforementioned compounds, wherein $R^9$ is methyl and Y is $NO(CH_2CH_2NH_2)$.

In certain embodiments, the invention relates to any one of the aforementioned compounds, wherein R9 is methyl and Y is $NO(CH_2CH_2NHMe)$.

In certain embodiments, the invention relates to any one of the aforementioned compounds, wherein

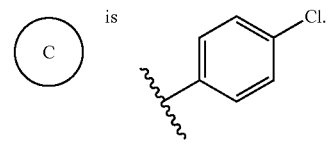

In certain embodiments, the invention relates to any one of the aforementioned compounds, wherein

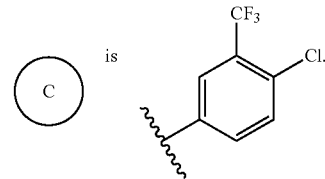

In certain embodiments, the invention relates to any one of the aforementioned compounds, wherein

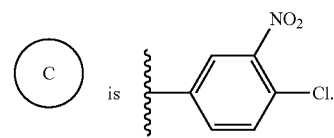

In certain embodiments, the invention relates to any one of the aforementioned compounds, wherein $R^4$ is methyl, Y is NO(t-Bu), and

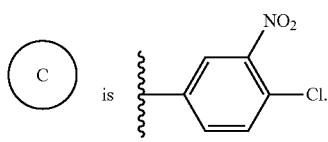

In certain embodiments, the invention relates to any one of the aforementioned compounds, wherein $R^4$ is methyl, Y is $NO(CH_2CH_2NH_2)$, and

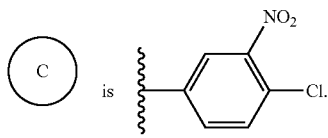

In certain embodiments, the invention relates to any one of the aforementioned compounds, wherein $R^9$ is methyl, Y is $C(R^{10})(R^{11})$, $R^{10}$ and $R^{11}$ are hydrogen, $X^1$ is O, and $X^2$ is NH.

In certain embodiments, the invention relates to any one of the aforementioned compounds, wherein $R^4$ is methyl, Y is $C(R^{10})(R^{11})$, $R^{10}$ and $R^{11}$ are hydrogen, $X^1$ is NH, and $X^2$ is O.

In certain embodiments, the invention relates to any one of the aforementioned compounds, wherein $R^9$ is methyl, Y is O, $X^1$ is O, and $X^2$ is NH.

In certain embodiments, the invention relates to any one of the aforementioned compounds, wherein $R^9$ is methyl, Y is O, $X^1$ is NH, and $X^2$ is O.

In certain embodiments, the invention relates to any one of the aforementioned compounds, wherein $R^9$ is methyl, Y is NOH, $X^1$ is NH, and $X^2$ is O.

In certain embodiments, the invention relates to any one of the aforementioned compounds, wherein $R^9$ is methyl, Y is NOH, $X^1$ is O, and $X^2$ is NH.

In certain embodiments, the invention relates to any one of the aforementioned compounds, wherein $R^9$ is methyl, Y is NOMe, $X^1$ is NH, and $X^2$ is O.

In certain embodiments, the invention relates to any one of the aforementioned compounds, wherein $R^9$ is methyl, Y is NOMe, $X^1$ is O, and $X^2$ is NH.

In certain embodiments, the invention relates to any one of the aforementioned compounds, wherein $R^9$ is methyl, Y is NO(t-Bu), $X^1$ is NH, and $X^2$ is O.

In certain embodiments, the invention relates to any one of the aforementioned compounds, wherein $R^9$ is methyl, Y is NO(t-Bu), $X^1$ is O, and $X^2$ is NH.

In certain embodiments, the invention relates to a compound, or a pharmaceutically acceptable salt or ester thereof, selected from the group consisting of

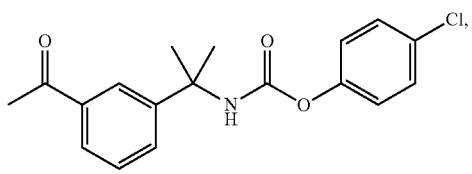

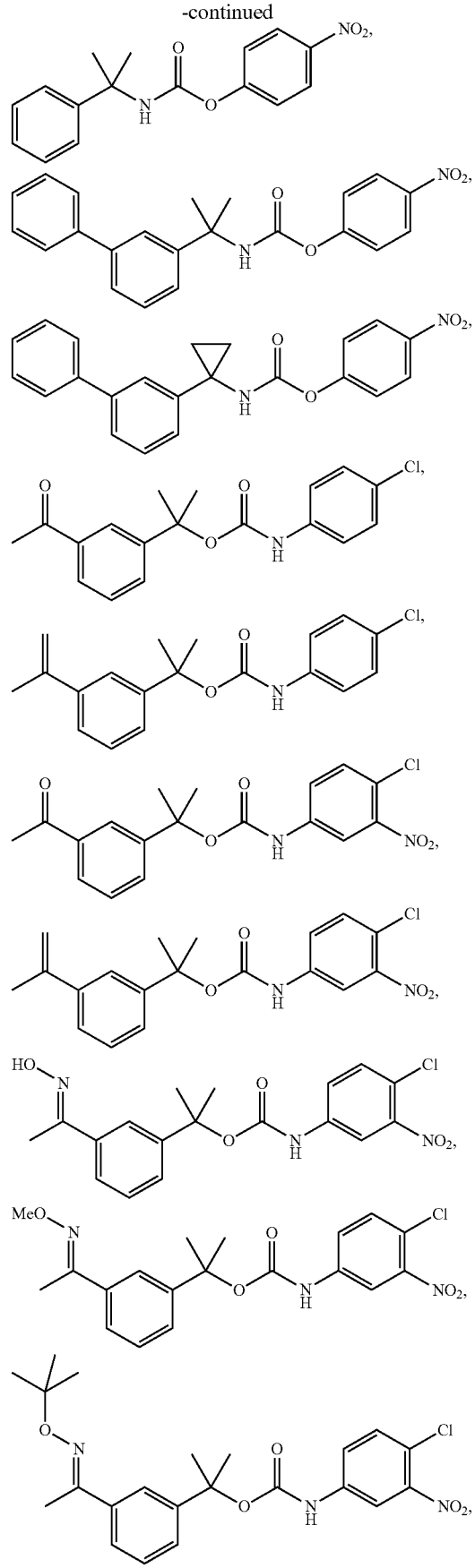

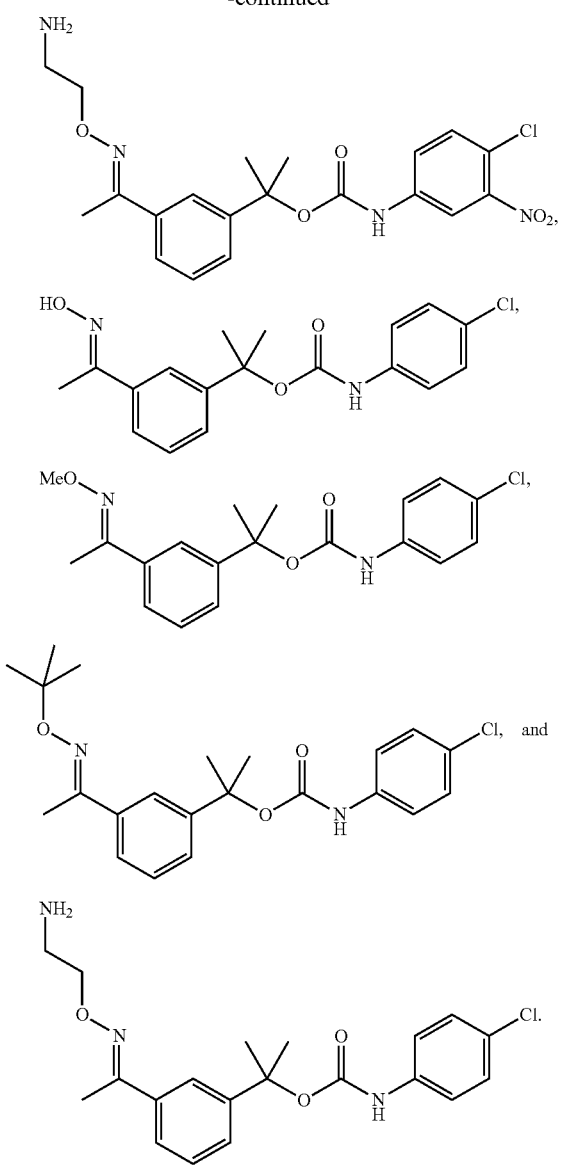
In certain embodiments, the invention relates to a compound, or a pharmaceutically acceptable salt or ester thereof, selected from the group consisting of
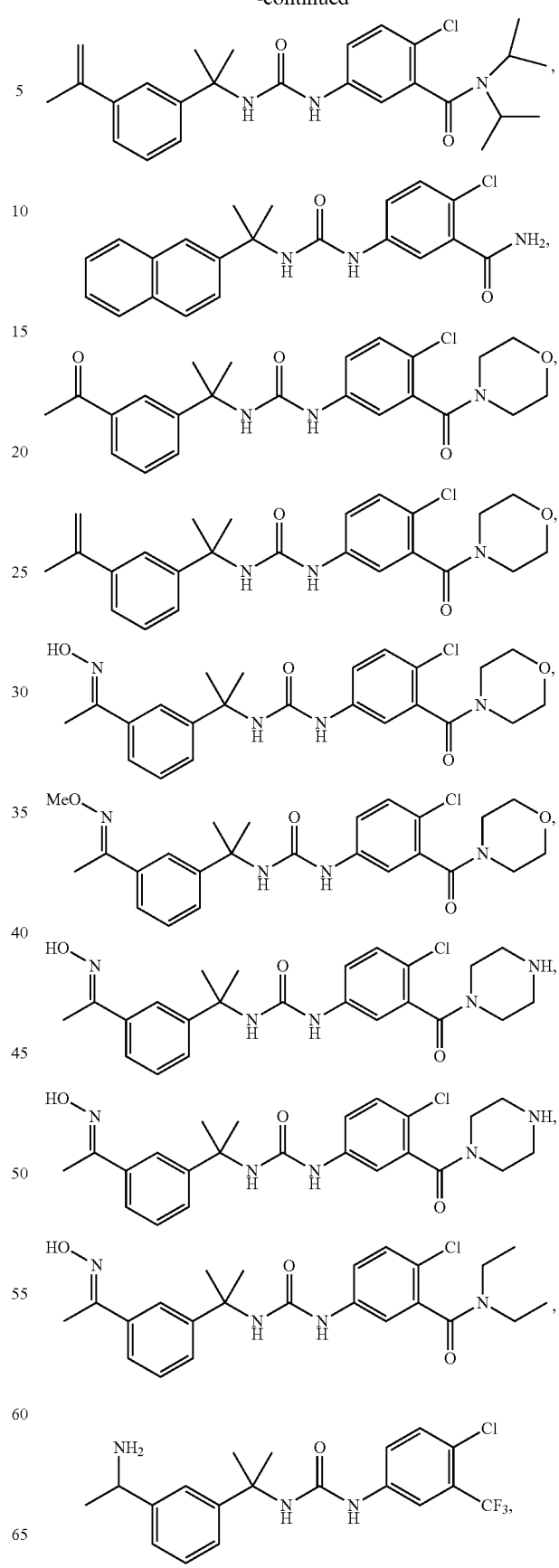

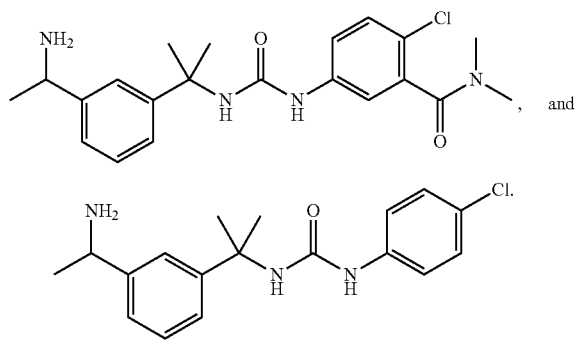

In certain embodiments, the invention relates to a compound, or a pharmaceutically acceptable salt or ester thereof, selected from the group consisting of

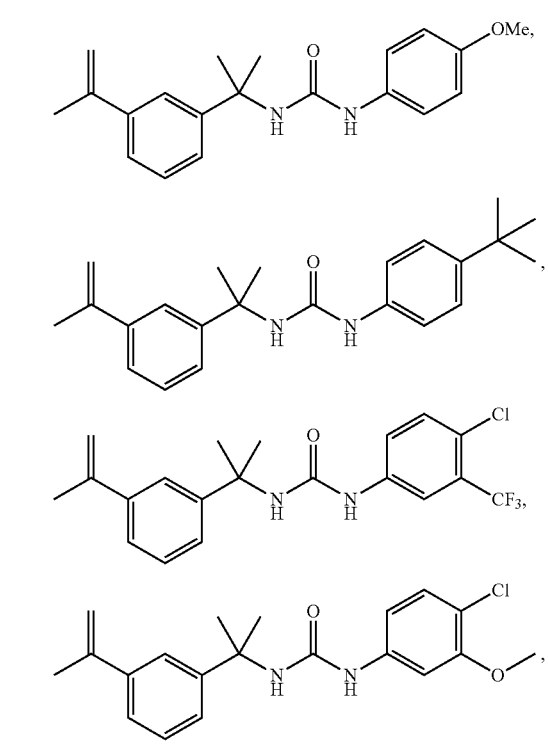

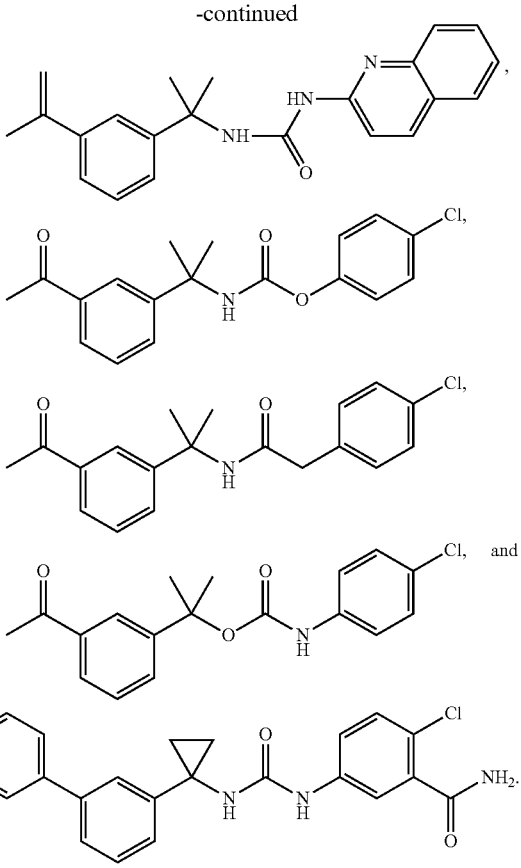

Benzoxazole Series

In certain embodiments, the invention relates to a compound, or a pharmaceutically acceptable salt or ester thereof, represented by Formula X:

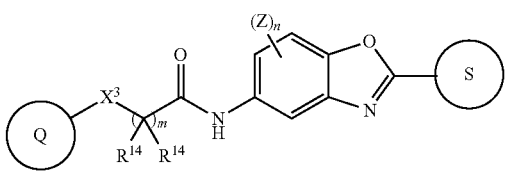

Formula X wherein, independently for each occurrence, $X^3$ is $C(R')_2$, S, or NR';
  wherein R' is hydrogen, halide, alkyl, alkenyl, alkynyl, cycloalkyl, heterocyclyl, aryl, heteroaryl, acyl, aracyl, or heteroaracyl;

m is 0, 1, or 2;

n is 0, 1, 2, or 3;

$R^{14}$ is hydrogen, alkyl, alkenyl, alkynyl, cycloalkyl, heterocyclyl, aryl, heteroaryl, acyl, aracyl, heteroaracyl sulfonate, sulfonyl, sulfonamido, formyl, carboxyl, alkoxycarbonyl, or acyloxy, or two $R^{14}$ groups taken together form a non-aromatic 3-8 membered ring, or two $R^{14}$ groups taken together form the side chain of a natural or non-natural D or L amino acid;

Z is hydrogen, halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, sulfhydryl, formyl, cyano, or isocyano;

is hydrogen, halogen, alkyl, alkenyl, alkynyl, aralkyl, heteroaralkyl, halogen, amino, amido, acyl, aracyl, heteroaracyl, alkoxy, hydroxyl, carboxyl, alkoxycarbonyl, acyloxy, silyl, alkylthio, sulfonate, sulfonyl, sulfonamido, sulfhydryl, formyl, cyano, isocyano, monocyclic or bicyclic cycloalkyl, monocyclic or bicyclic heterocyclyl, monocyclic or bicyclic aryl or monocyclic or bicyclic heteroaryl; and

is hydrogen, alkyl, monocyclic or bicyclic cycloalkyl, monocyclic or bicyclic heterocyclyl, monocyclic or bicyclic aryl or monocyclic or bicyclic heteroaryl;
  wherein, any of the aforementioned alkyl, aryl, or heteroaryl may be substituted with one or more groups independently selected from the group consisting of halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, sulfhydryl, formyl, cyano, and isocyano.

In certain embodiments, the invention relates to any one of the aforementioned compounds, wherein $X^3$ is $C(R')_2$.

In certain embodiments, the invention relates to any one of the aforementioned compounds, wherein $X^3$ is S.

In certain embodiments, the invention relates to any one of the aforementioned compounds, wherein $X^3$ is NR'.

In certain embodiments, the invention relates to any one of the aforementioned compounds, wherein $X^3$ is NR' and R' is hydrogen.

In certain embodiments, the invention relates to any one of the aforementioned compounds, wherein m is 0.

In certain embodiments, the invention relates to any one of the aforementioned compounds, wherein m is 1.

In certain embodiments, the invention relates to any one of the aforementioned compounds, wherein m is 1; and $R^{14}$ is hydrogen.

In certain embodiments, the invention relates to any one of the aforementioned compounds, wherein m is 1; and $R^{14}$ is alkyl.

In certain embodiments, the invention relates to any one of the aforementioned compounds, wherein m is 1, one $R^{14}$ is hydrogen, and one $R^{14}$ is alkyl.

In certain embodiments, the invention relates to any one of the aforementioned compounds, wherein m is 1; and two $R^{14}$ together form the side chain of a D or L natural or non-natural amino acid.

In certain embodiments, the invention relates to any one of the aforementioned compounds, wherein Z is halo.

In certain embodiments, the invention relates to any one of the aforementioned compounds, wherein Z is alkyl.

In certain embodiments, the invention relates to any one of the aforementioned compounds, wherein

is hydrogen, alkyl, amino, benzyl,

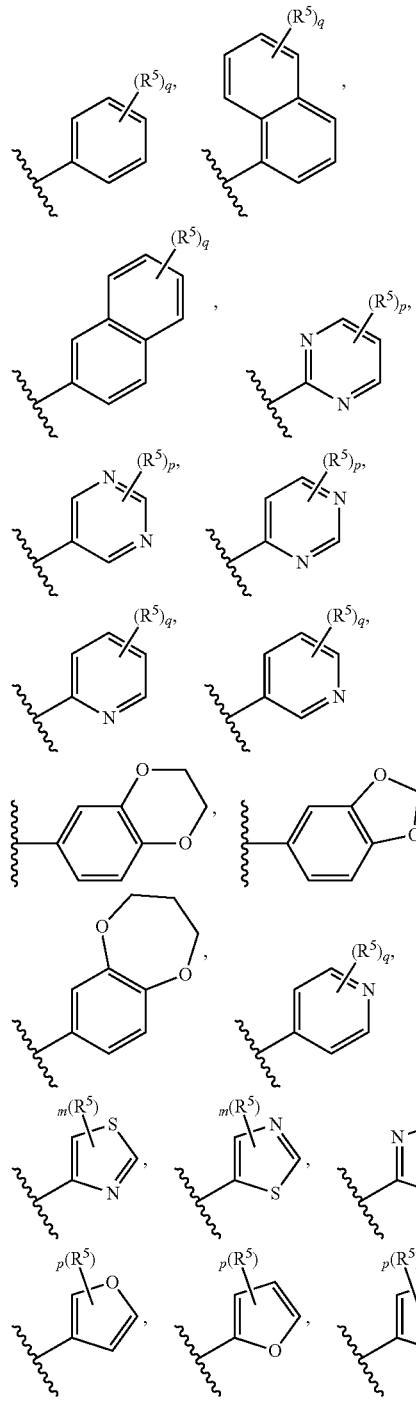

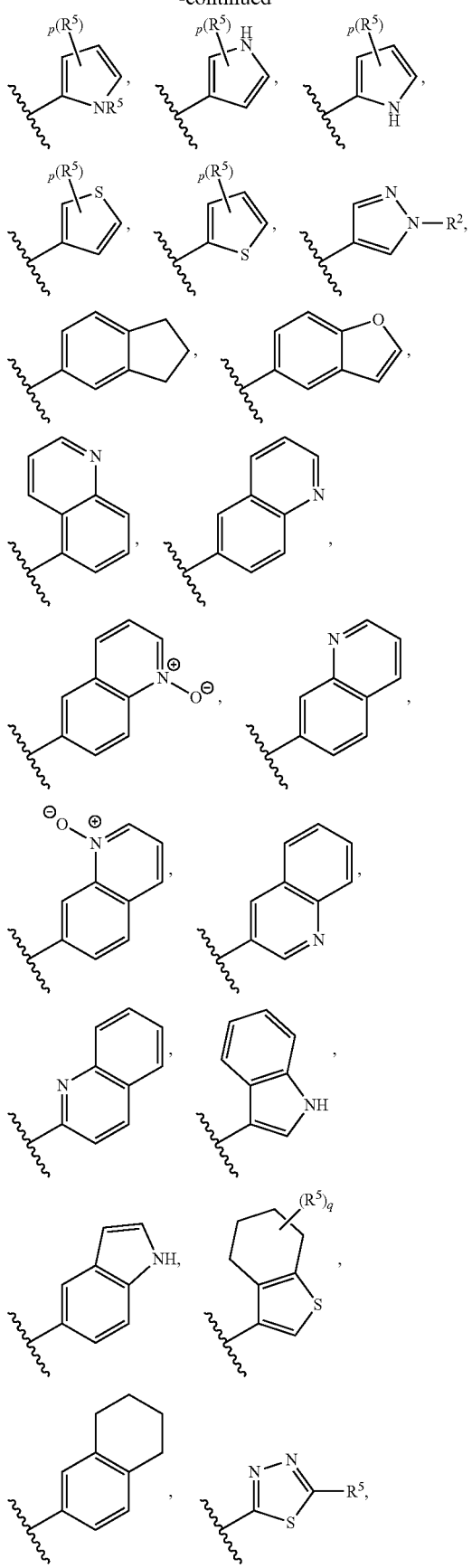

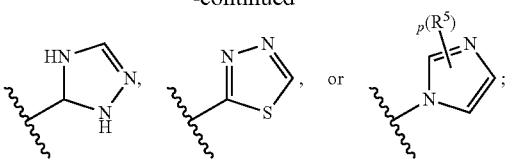

p is 0, 1, 2, or 3; q is 0, 1, 2, 3, or 4; and $R^5$ is halo, azido, alkyl, haloalkyl, hydroxyalkyl, aminoalkyl, heterocycloalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, carboxylic acid, acyloxy, alkylthio, sulfonate, sulfonyl, sulfonamido, formyl, cyano, oxime, or isocyano.

In certain embodiments, the invention relates to any one of the aforementioned compounds, wherein

is hydrogen.

In certain embodiments, the invention relates to any one of the aforementioned compounds, wherein

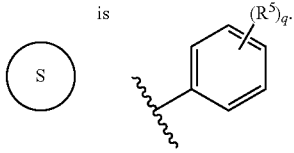

In certain embodiments, the invention relates to any one of the aforementioned compounds, wherein

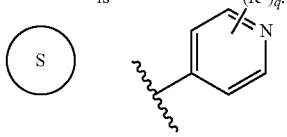

In certain embodiments, the invention relates to any one of the aforementioned compounds, wherein

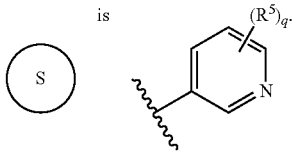

In certain embodiments, the invention relates to any one of the aforementioned compounds, wherein

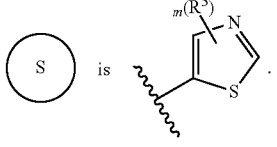

In certain embodiments, the invention relates to any one of the aforementioned compounds, wherein
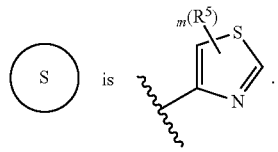
In certain embodiments, the invention relates to any one of the aforementioned compounds, wherein
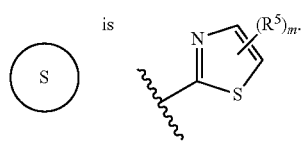
In certain embodiments, the invention relates to many one of the aforementioned compounds, wherein
is hydrogen, alkyl,
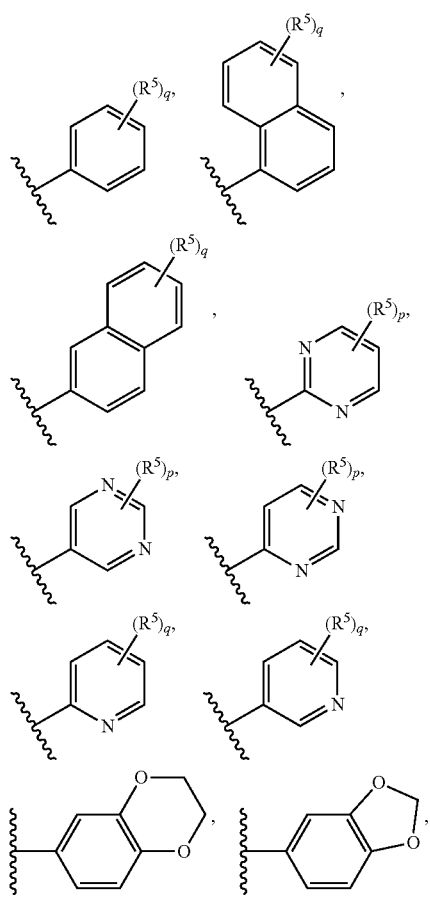
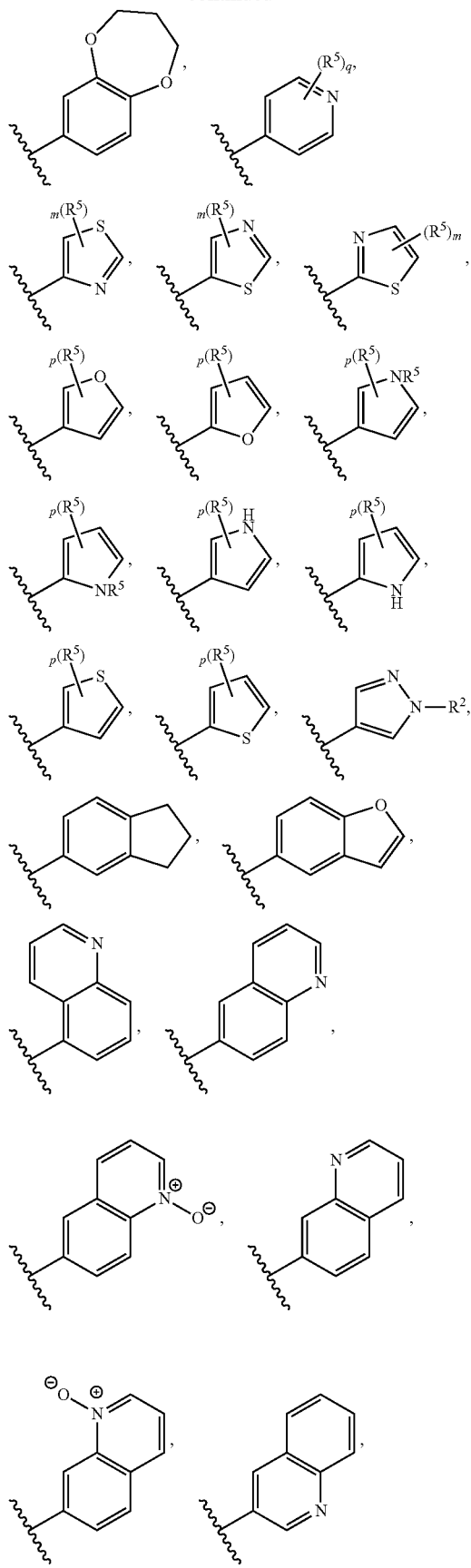

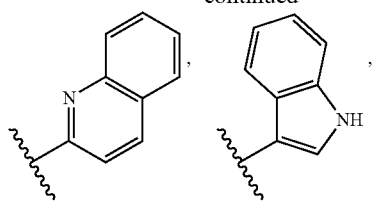

p is 0, 1, 2, or 3; q is 0, 1, 2, 3, or 4; and $R^5$ is halo, azido, alkyl, haloalkyl, hydroxyalkyl, aminoalkyl, heterocycloalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, carboxylic acid, acyloxy, alkylthio, sulfonate, sulfonyl, sulfonamido, formyl, cyano, oxime, or isocyano.

In certain embodiments, the invention relates to any one of the aforementioned compounds, wherein Q is hydrogen.

In certain embodiments, the invention relates to any one of the aforementioned compounds, wherein Q is alkyl.

In certain embodiments, the invention relates to any one of the aforementioned compounds, wherein Q is (phenyl with $(R^5)_q$).

In certain embodiments, the invention relates to any one of the aforementioned compounds, wherein Q is (naphthyl with $(R^5)_q$).

In certain embodiments, the invention relates to any one of the aforementioned compounds, wherein $X^3$ is NR', R' is hydrogen, m is 1, one $R^{14}$ is hydrogen, and one $R^{14}$ is methyl.

In certain embodiments, the invention relates to any one of the aforementioned compounds, wherein $X^3$ is NR', R' is hydrogen, m is 1, one $R^{14}$ is hydrogen, one $R^{14}$ is methyl and S is (thiazole with $m(R^5)$).

In certain embodiments, the invention relates to any one of the aforementioned compounds, wherein $X^3$ is NR', R' is hydrogen, m is 1, one $R^{14}$ is hydrogen, one $R^{14}$ is methyl and S is (pyridyl with $(R^5)_q$).

In certain embodiments, the invention relates to a compound, or a pharmaceutically acceptable salt or ester thereof, represented by Formula XI:

Formula XI

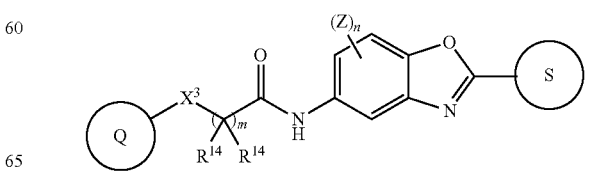

wherein, independently for each occurrence,

X³ is absent, O, C(R')₂, S, or NR';
  wherein R' is hydrogen, halide, alkyl, alkenyl, alkynyl, cycloalkyl, heterocyclyl, aryl, heteroaryl, acyl, aracyl, or heteroaracyl;

m is 0, 1, or 2;

n is 0, 1, 2, or 3;

R¹⁴ is alkenyl, alkynyl, cycloalkyl, heterocyclyl, aryl, heteroaryl, acyl, aracyl, heteroaracyl sulfonate, sulfonyl, sulfonamido, formyl, carboxyl, alkoxycarbonyl, or acyloxy, or two R¹⁴ groups taken together form a non-aromatic 3-8 membered ring, or two R¹⁴ groups taken together form the side chain of a natural or non-natural D or L amino acid, with the proviso that said side chain is neither glycine nor alanine;

Z is hydrogen, halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, sulfhydryl, formyl, cyano, or isocyano;

is hydrogen, halogen, alkyl, alkenyl, alkynyl, aralkyl, heteroaralkyl, halogen, amino, amido, acyl, aracyl, heteroaracyl, alkoxy, hydroxyl, carboxyl, alkoxycarbonyl, acyloxy, silyl, alkylthio, sulfonate, sulfonyl, sulfonamido, sulfhydryl, formyl, cyano, isocyano, monocyclic or bicyclic cycloalkyl, monocyclic or bicyclic heterocyclyl, monocyclic or bicyclic aryl or monocyclic or bicyclic heteroaryl; and

is hydrogen, alkyl, monocyclic or bicyclic cycloalkyl, monocyclic or bicyclic heterocyclyl, monocyclic or bicyclic aryl or monocyclic or bicyclic heteroaryl;
  wherein, any of the aforementioned alkyl, aryl, or heteroaryl may be substituted with one or more groups independently selected from the group consisting of halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, sulfhydryl, formyl, cyano, and isocyano.

In certain embodiments, the invention relates to any one of the aforementioned compounds, wherein X³ is absent.

In certain embodiments, the invention relates to any one of the aforementioned compounds, wherein X³ is O.

In certain embodiments, the invention relates to any one of the aforementioned compounds, wherein X³ is C(R')₂.

In certain embodiments, the invention relates to any one of the aforementioned compounds, wherein X³ is S.

In certain embodiments, the invention relates to any one of the aforementioned compounds, wherein X³ is NR'.

In certain embodiments, the invention relates to any one of the aforementioned compounds, wherein X³ is NR' and R' is hydrogen.

In certain embodiments, the invention relates to any one of the aforementioned compounds, wherein m is 0.

In certain embodiments, the invention relates to any one of the aforementioned compounds, wherein m is 1.

In certain embodiments, the invention relates to any one of the aforementioned compounds, wherein m is 1; and one R¹⁴ is alkenyl.

In certain embodiments, the invention relates to any one of the aforementioned compounds, wherein m is 1, one R¹⁴ is hydrogen, and one R¹⁴ is benzyl.

In certain embodiments, the invention relates to any one of the aforementioned compounds, wherein m is 1; and two R¹⁴ together form the side chain of a D or L natural or non-natural amino acid.

In certain embodiments, the invention relates to any one of the aforementioned compounds, wherein Z is hydrogen.

In certain embodiments, the invention relates to any one of the aforementioned compounds, wherein Z is halo.

In certain embodiments, the invention relates to any one of the aforementioned compounds, wherein Z is alkyl.

In certain embodiments, the invention relates to any one of the aforementioned compounds, wherein

is hydrogen, alkyl,

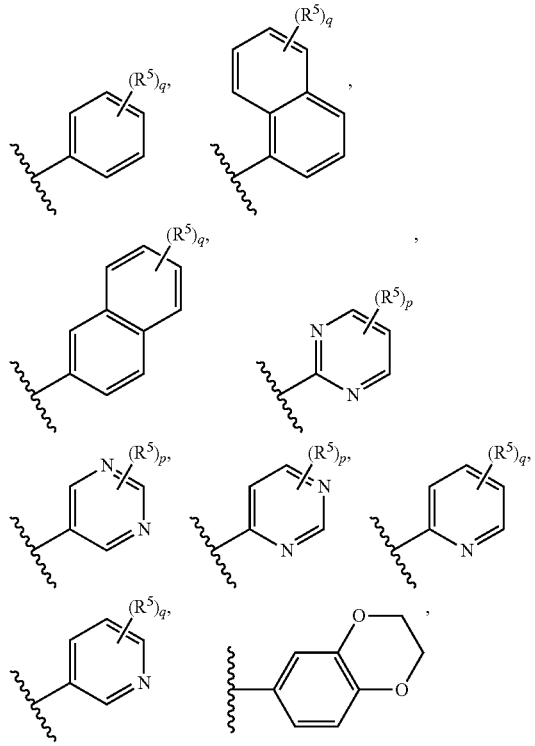

-continued

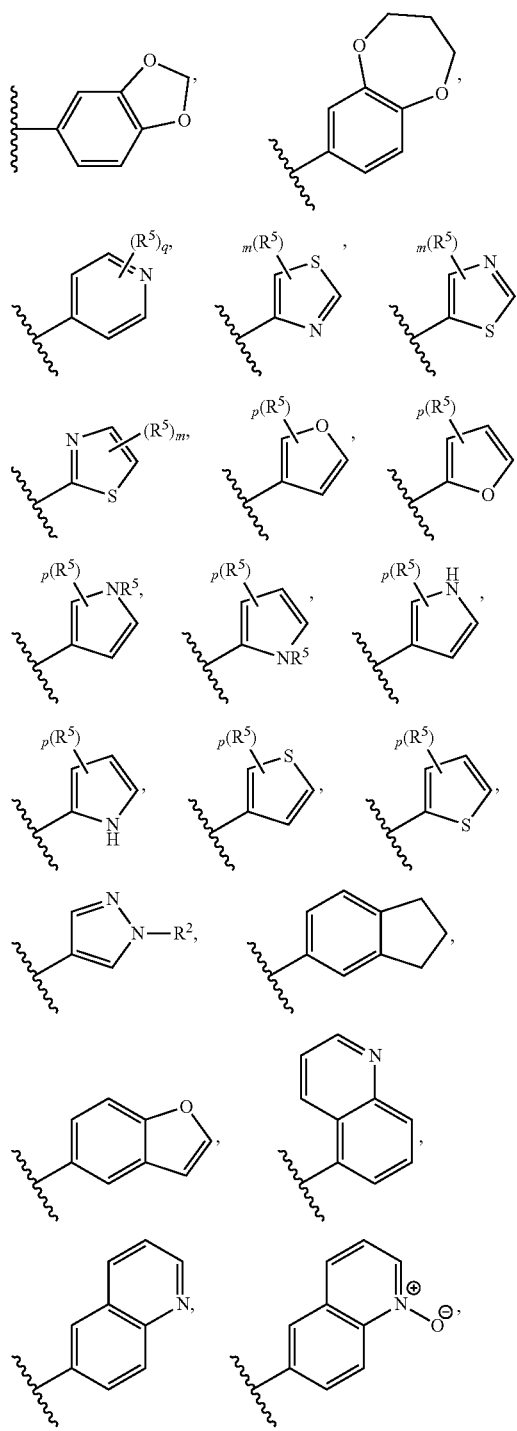

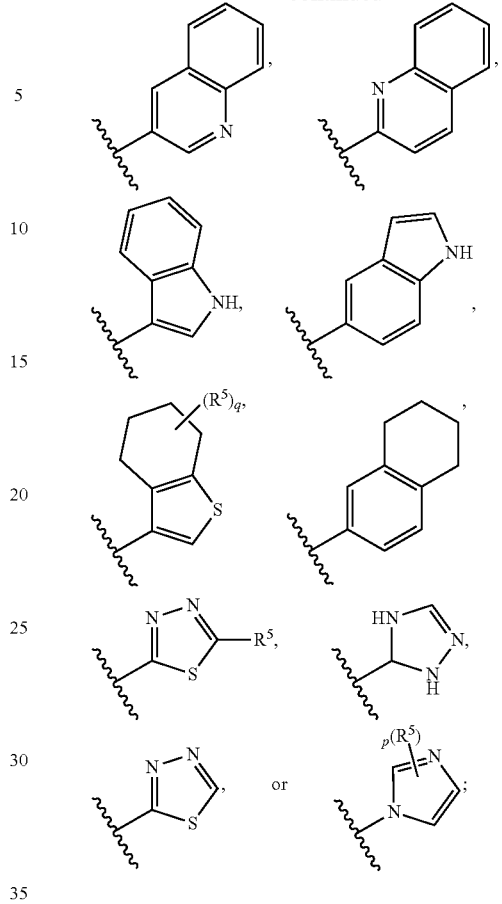

p is 0, 1, 2, or 3; q is 0, 1, 2, 3, or 4; and $R^5$ is halo, azido, alkyl, haloalkyl, hydroxyalkyl, aminoalkyl, heterocycloalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, carboxylic acid, acyloxy, alkylthio, sulfonate, sulfonyl, sulfonamido, formyl, cyano, oxime, or isocyano.

In certain embodiments, the invention relates to any one of the aforementioned compounds, where

is hydrogen.

In certain embodiments, the invention relates to any one of the aforementioned compounds, wherein

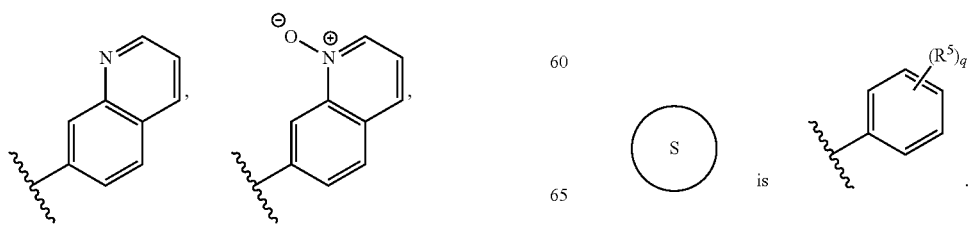

In certain embodiments, the invention relates to any one of the aforementioned compounds, wherein

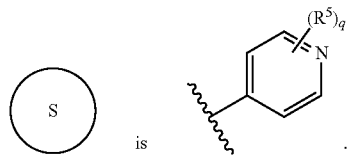 is 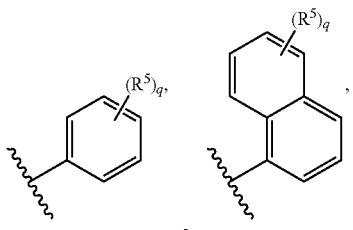.

In certain embodiments, the invention relates to any one of the aforementioned compounds, wherein

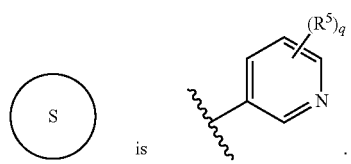 is .

In certain embodiments, the invention relates to any one of the aforementioned compounds, wherein

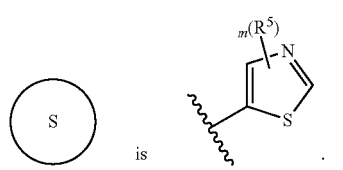 is .

In certain embodiments, the invention relates to any one of the aforementioned compounds, wherein

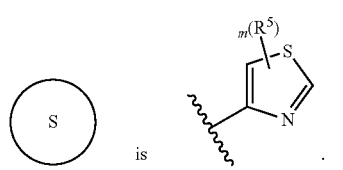 is .

In certain embodiments, the invention relates to any one of the aforementioned compounds, wherein

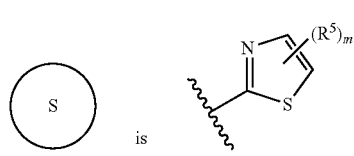 is .

In certain embodiments, the invention relates to any one of the aforementioned compounds, wherein

is hydrogen, alkyl,

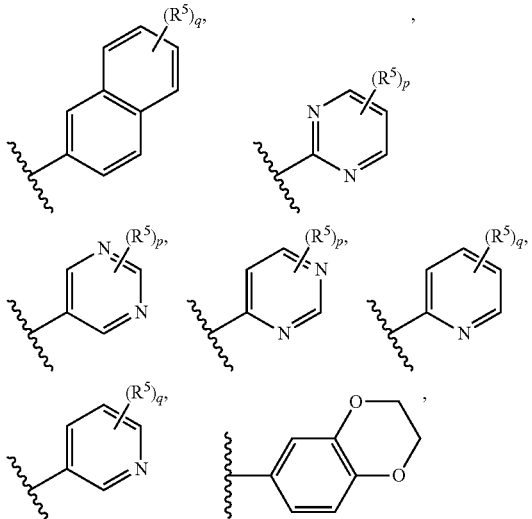
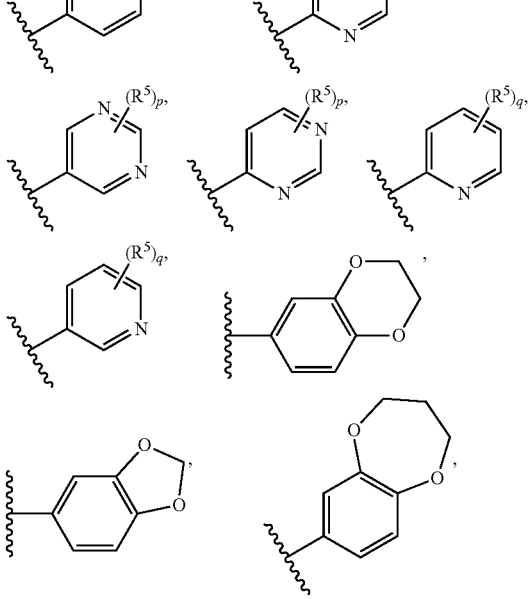
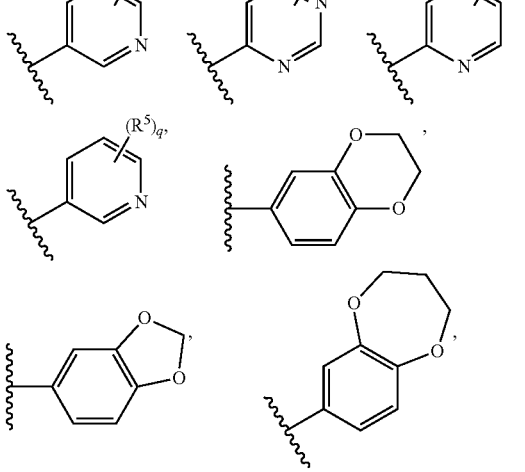
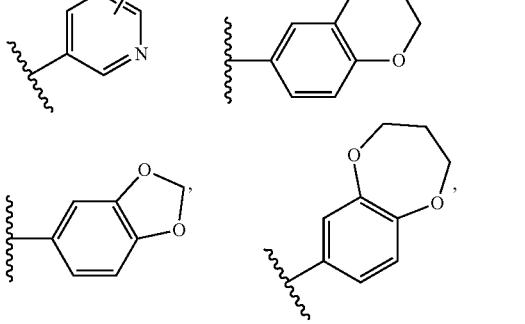
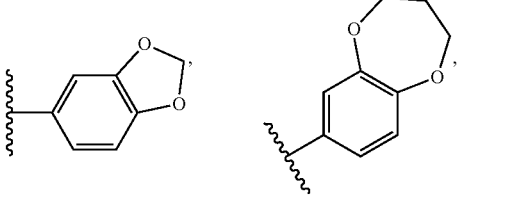

-continued

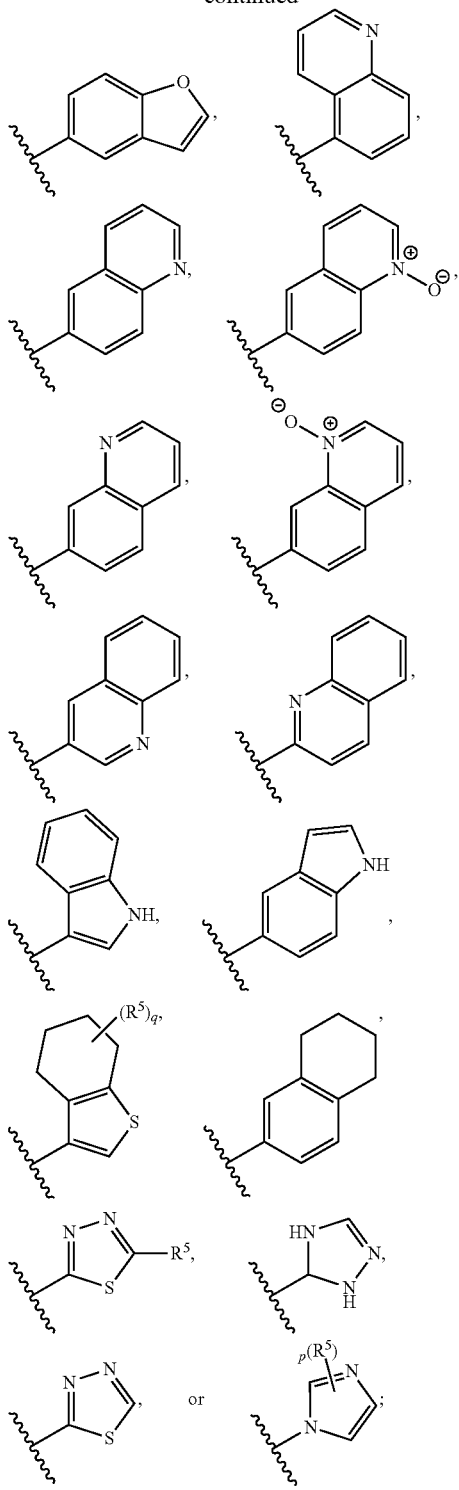

p is 0, 1, 2, or 3; q is 0, 1, 2, 3, or 4; and $R^5$ is halo, azido, alkyl, haloalkyl, hydroxyalkyl, aminoalkyl, heterocycloalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, carboxylic acid, acyloxy, alkylthio, sulfonate, sulfonyl, sulfonamido, formyl, cyano, oxime, or isocyano.

In certain embodiments, the invention relates to any one of the aforementioned compounds, wherein

is hydrogen.

In certain embodiments, the invention relates to any one of the aforementioned compounds, wherein

is alkyl.

In certain embodiments, the invention relates to any one of the aforementioned compounds, wherein

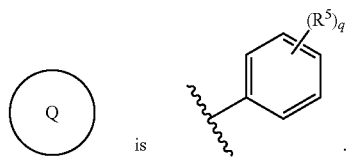

In certain embodiments, the invention relates to any one of the aforementioned compounds, wherein

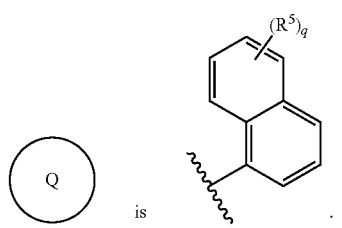

In certain embodiments, the invention relates to any one of the aforementioned compounds, wherein $X^3$ is NR', R' is hydrogen, m is 1, and the two $R^{14}$ together form the side chain of a D or L natural or non-natural amino acid, with the proviso that said side chain is neither glycine nor alanine.

In certain embodiments, the invention relates to any one of the aforementioned compounds, wherein $X^3$ is NR', R' is hydrogen, m is 1, one $R^{14}$ is hydrogen, one $R^{14}$ is benzyl and

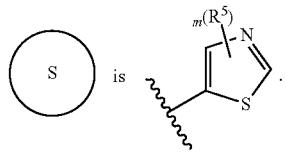

In certain embodiments, the invention relates to any one of the aforementioned compounds, wherein $X^3$ is NR', R' is hydrogen, m is 1, the two $R^{14}$ together form the side chain of a D or L natural or non-natural amino acid, with the proviso that said side chain is neither glycine nor alanine, and

 is 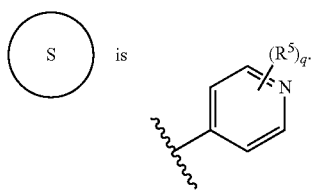

In certain embodiments, the invention relates to a compound, or a pharmaceutically acceptable salt or ester thereof, represented by Formula XII:

Formula XII

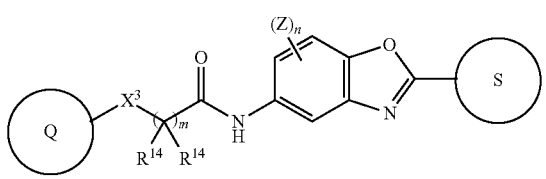

wherein, independently for each occurrence, $X^3$ is absent, O, $C(R')_2$, S, or NR';
  wherein R' is hydrogen, halide, alkyl, alkenyl, alkynyl, cycloalkyl, heterocyclyl, aryl, heteroaryl, acyl, aracyl, or heteroaracyl;

m is 0, 1, or 2;

n is 0, 1, 2, or 3;

$R^{14}$ is hydrogen, alkyl, alkenyl, alkynyl, cycloalkyl, heterocyclyl, aryl, heteroaryl, acyl, aracyl, heteroaracyl sulfonate, sulfonyl, sulfonamido, formyl, carboxyl, alkoxycarbonyl, or acyloxy, or two $R^{14}$ groups taken together form a non-aromatic 3-8 membered ring, or two $R^{14}$ groups taken together form the side chain of a natural or non-natural D or L amino acid;

Z is halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, sulfhydryl, formyl, cyano, or isocyano;

is hydrogen, alkyl, alkenyl, alkynyl, aralkyl, heteroaralkyl, halogen, amino, amido, acyl, aracyl, heteroaracyl, alkoxy, hydroxyl, carboxyl, alkoxycarbonyl, acyloxy, silyl, alkylthio, sulfonate, sulfonyl, sulfonamido, sulfhydryl, formyl, cyano, isocyano, monocyclic or bicyclic cycloalkyl, bicyclic heterocyclyl, bicyclic aryl or bicyclic heteroaryl; and

Q is hydrogen, alkyl, monocyclic or bicyclic cycloalkyl, monocyclic or bicyclic heterocyclyl, monocyclic or bicyclic aryl or monocyclic or bicyclic heteroaryl;

wherein, any of the aforementioned alkyl, aryl, or heteroaryl may be substituted with one or more groups independently selected from the group consisting of halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, sulfhydryl, formyl, cyano, and isocyano.

In certain embodiments, the invention relates to any one of the aforementioned compounds, wherein $X^3$ is absent.

In certain embodiments, the invention relates to any one of the aforementioned compounds, wherein $X^3$ is O.

In certain embodiments, the invention relates to any one of the aforementioned compounds, wherein $X^3$ is $C(R')_2$.

In certain embodiments, the invention relates to any one of the aforementioned compounds, wherein $X^3$ is S.

In certain embodiments, the invention relates to any one of the aforementioned compounds, wherein $X^3$ is NR'.

In certain embodiments, the invention relates to any one of the aforementioned compounds, wherein $X^3$ is NR' and R' is hydrogen.

In certain embodiments, the invention relates to any one of the aforementioned compounds, wherein m is 0.

In certain embodiments, the invention relates to any one of the aforementioned compounds, wherein m is 1.

In certain embodiments, the invention relates to any one of the aforementioned compounds, wherein m is 1; and one $R^{14}$ is alkenyl.

In certain embodiments, the invention relates to any one of the aforementioned compounds, wherein m is 1, one $R^{14}$ is hydrogen, and one $R^{14}$ is methyl.

In certain embodiments, the invention relates to any one of the aforementioned compounds, wherein m is 1; and two $R^{14}$ together form the side chain of a D or L natural or non-natural amino acid.

In certain embodiments, the invention relates to any one of the aforementioned compounds, wherein Z is halo.

In certain embodiments, the invention relates to any one of the aforementioned compounds, wherein Z is alkyl.

In certain embodiments, the invention relates to any one of the aforementioned compounds, wherein

is hydrogen, alkyl,

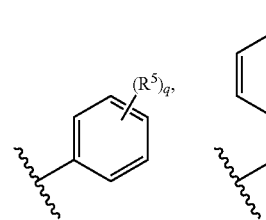

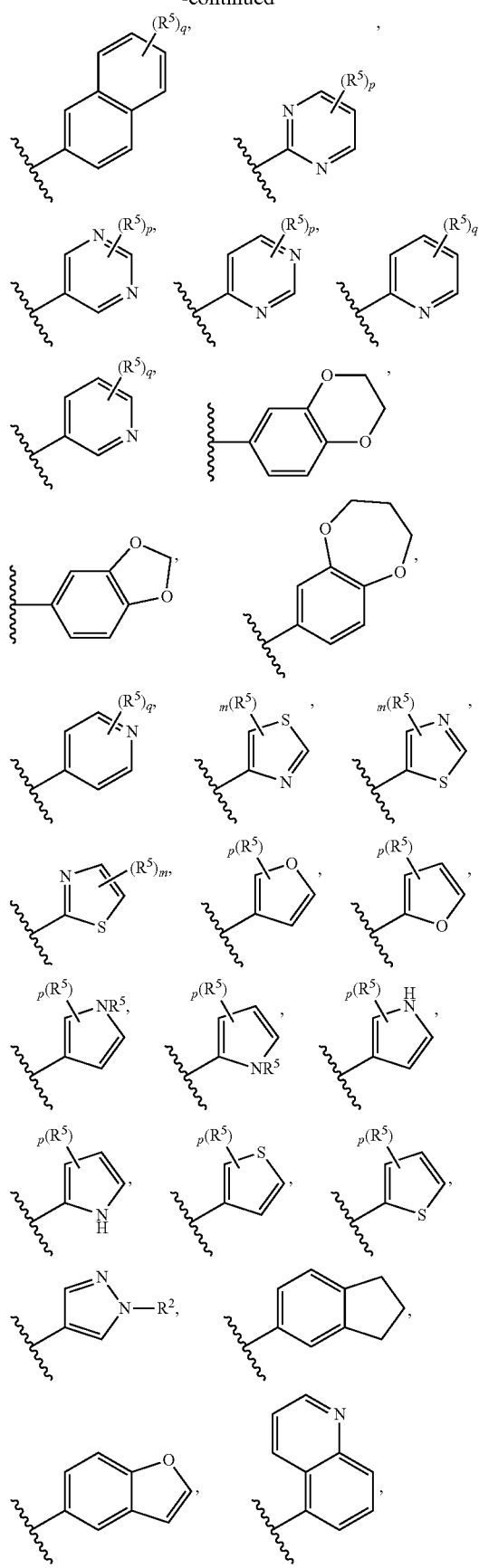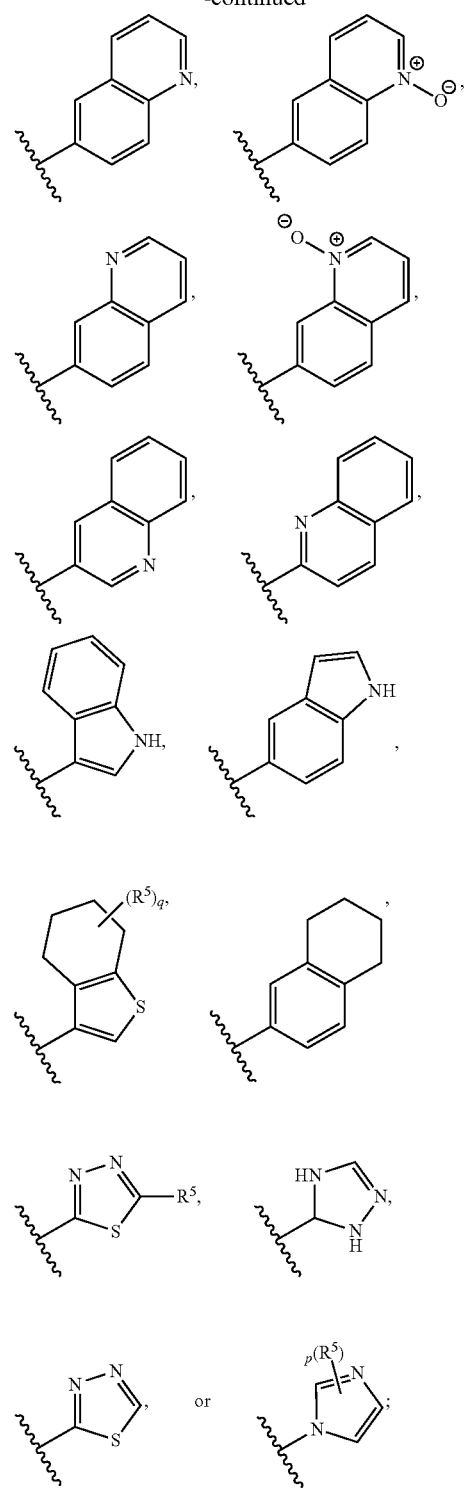

p is 0, 1, 2, or 3; q is 0, 1, 2, 3, or 4; and $R^5$ is halo, azido, alkyl, haloalkyl, hydroxyalkyl, aminoalkyl, heterocycloalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, carboxylic acid, acyloxy, alkylthio, sulfonate, sulfonyl, sulfonamido, formyl, cyano, oxime, or isocyano.

In certain embodiments, the invention relates to any one of the aforementioned compounds, wherein

is hydrogen.

In certain embodiments, the invention relates to any one of the aforementioned compounds, wherein

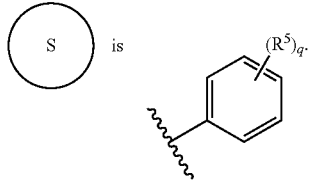

In certain embodiments, the invention relates to any one of the aforementioned compounds, wherein

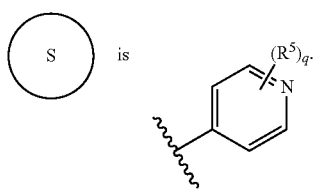

In certain embodiments, the invention relates to any one of the aforementioned compounds, wherein

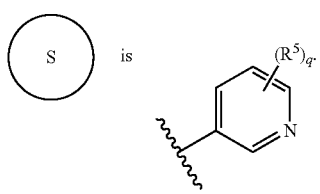

In certain embodiments, the invention relates to any one of the aforementioned compounds, where

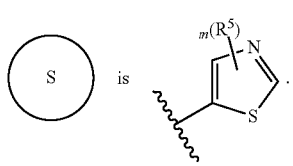

In certain embodiments, the invention relates to any one of the aforementioned compounds, wherein

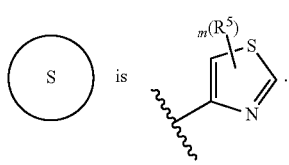

In certain embodiments, the invention relates to any one of the aforementioned compounds, wherein

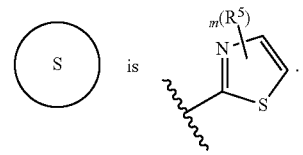

In certain embodiments, the invention relates to any one of the aforementioned compounds, wherein

is hydrogen, alkyl,

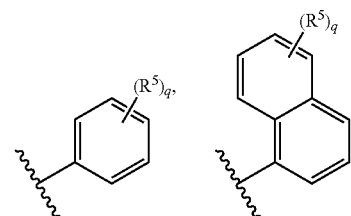
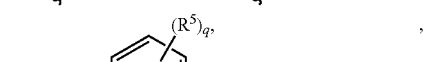
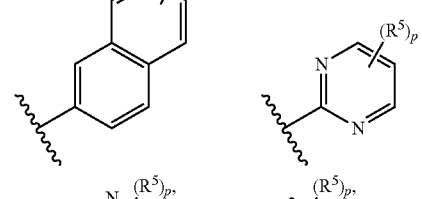
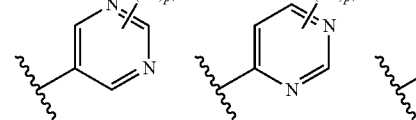
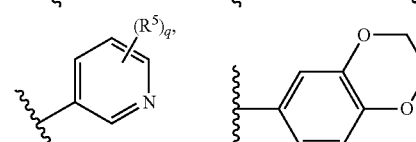
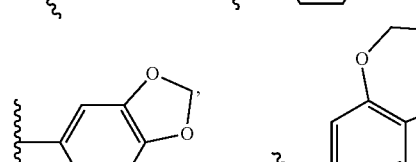
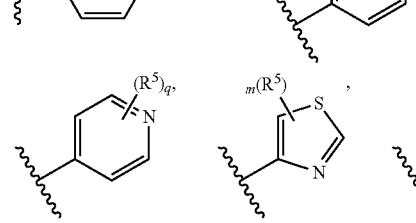

-continued

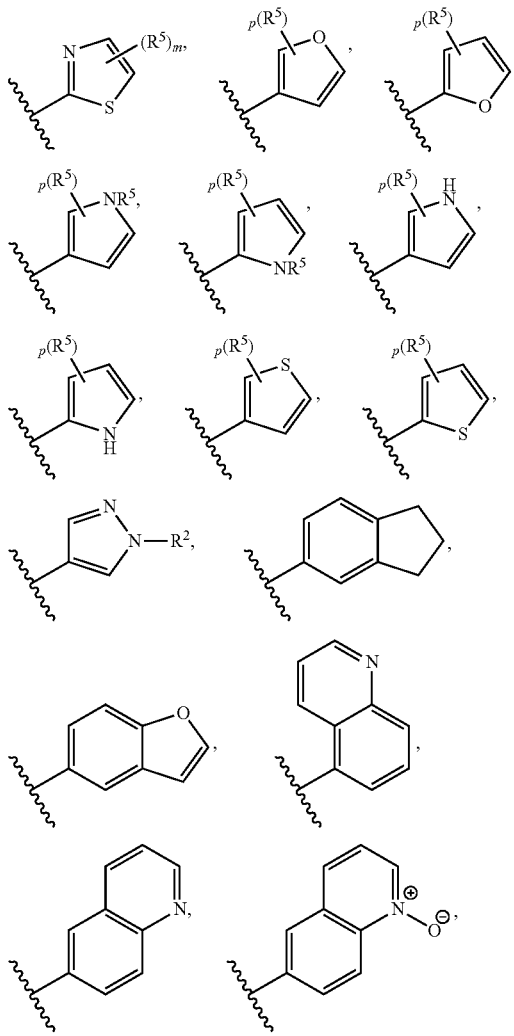
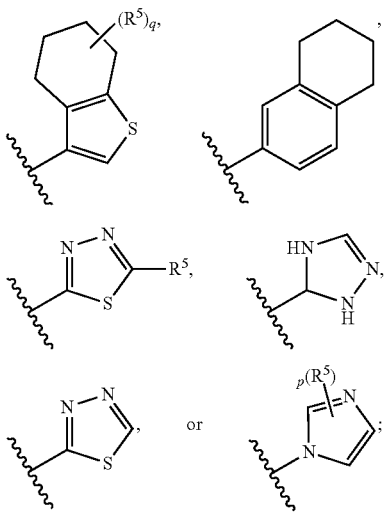

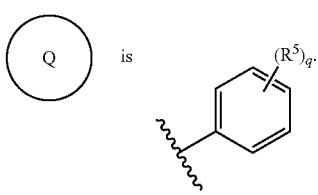

p is 0, 1, 2, or 3; q is 0, 1, 2, 3, or 4; and $R^5$ is halo, azido, alkyl, haloalkyl, hydroxyalkyl, aminoalkyl, heterocycloalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, carboxylic acid, acyloxy, alkylthio, sulfonate, sulfonyl, sulfonamido, formyl, cyano, oxime, or isocyano.

In certain embodiments, the invention relates to any one of the aforementioned compounds, wherein is hydrogen.

In certain embodiments, the invention relates to any one of the aforementioned compounds, wherein is alkyl.

In certain embodiments, the invention relates to any one of the aforementioned compounds, wherein In certain embodiments, the invention relates to any one of the aforementioned compounds, wherein

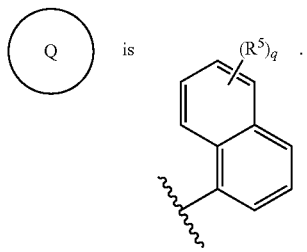

In certain embodiments, the invention relates to any one of the aforementioned compounds, wherein $X^3$ is O, m is 1, one $R^{14}$ is hydrogen, and one $R^{14}$ is methyl.

In certain embodiments, the invention relates to any one of the aforementioned compounds, wherein $X^3$ is O, m is 1, one $R^{14}$ is hydrogen, one $R^{14}$ is methyl and

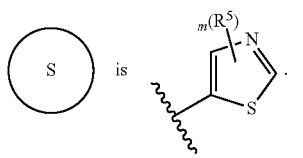

In certain embodiments, the invention relates to any one of the aforementioned compounds, wherein $X^3$ is O, wherein m is 1, one $R^{14}$ is hydrogen, one $R^{14}$ is methyl and

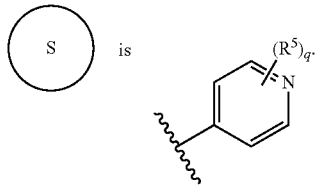

In certain embodiments, the invention relates to a compound, or a pharmaceutically acceptable salt or ester thereof, represented by Formula XIII:

Formula XIII

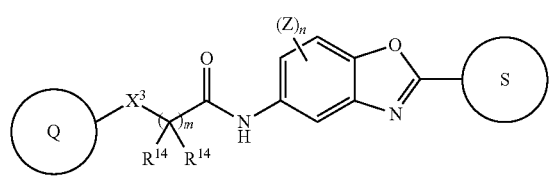

wherein, independently for each occurrence,
$X^3$ is absent, O, $C(R')_2$, S, or NR';
  wherein R' is hydrogen, halide, alkyl, alkenyl, alkynyl, cycloalkyl, heterocyclyl, aryl, heteroaryl, acyl, aracyl, or heteroaracyl;
m is 0, 1, or 2;
n is 0, 1, 2, or 3;
$R^{14}$ is hydrogen, alkyl, alkenyl, alkynyl, cycloalkyl, heterocyclyl, aryl, heteroaryl, acyl, aracyl, heteroaracyl sulfonate, sulfonyl, sulfonamido, formyl, carboxyl, alkoxycarbonyl, or acyloxy, or two $R^{14}$ groups taken together form a non-aromatic 3-8 membered ring, or two $R^{14}$ groups taken together form the side chain of a natural or non-natural D or L amino acid;
Z is hydrogen, halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, sulfhydryl, formyl, cyano, or isocyano;

is hydrogen, alkyl, alkenyl, alkynyl, aralkyl, heteroaralkyl, halogen, amino, amido, acyl, aracyl, heteroaracyl, alkoxy, hydroxyl, carboxyl, alkoxycarbonyl, acyloxy, silyl, alkylthio, sulfonate, sulfonyl, sulfonamido, sulfhydryl, formyl, cyano, isocyano, monocyclic or bicyclic cycloalkyl, monocyclic or bicyclic heterocyclyl, monocyclic or bicyclic aryl or monocyclic or bicyclic heteroaryl; and

is monocyclic or bicyclic cycloalkyl, monocyclic or bicyclic heterocyclyl, or monocyclic or bicyclic heteroaryl;
wherein, any of the aforementioned alkyl, aryl, or heteroaryl may be substituted with one or more groups independently selected from the group consisting of halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, sulfhydryl, formyl, cyano, and isocyano.

In certain embodiments, the invention relates to any one of the aforementioned compounds, wherein $X^3$ is absent.

In certain embodiments, the invention relates to any one of the aforementioned compounds, wherein $X^3$ is O.

In certain embodiments, the invention relates to any one of the aforementioned compounds, wherein $X^3$ is $C(R')_2$.

In certain embodiments, the invention relates to any one of the aforementioned compounds, wherein $X^3$ is S.

In certain embodiments, the invention relates to any one of the aforementioned compounds, wherein $X^3$ is NR'.

In certain embodiments, the invention relates to any one of the aforementioned compounds, wherein $X^3$ is NR' and R' is hydrogen.

In certain embodiments, the invention relates to any one of the aforementioned compounds, wherein m is 0.

In certain embodiments, the invention relates to any one of the aforementioned compounds, wherein m is 1.

In certain embodiments, the invention relates to any one of the aforementioned compounds, wherein m is 1; and one $R^{14}$ is alkenyl.

In certain embodiments, the invention relates to any one of the aforementioned compounds, wherein m is 1, one $R^{14}$ is hydrogen, and one $R^{14}$ is methyl.

In certain embodiments, the invention relates to any one of the aforementioned compounds, wherein m is 1; and two $R^{14}$ together form the side chain of a D or L natural or non-natural amino acid.

In certain embodiments, the invention relates to any one of the aforementioned compounds, wherein Z is hydrogen.

In certain embodiments, the invention relates to any one of the aforementioned compounds, wherein Z is halo.

In certain embodiments, the invention relates to any one of the aforementioned compounds, wherein

is hydrogen, alkyl,

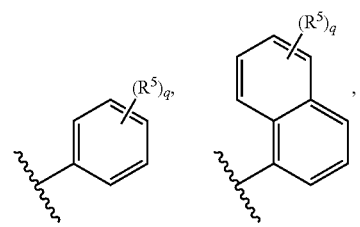
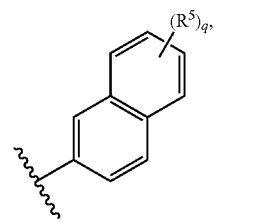
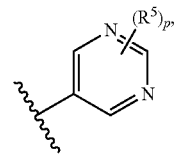
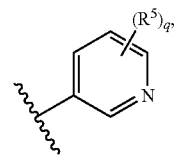
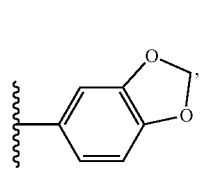
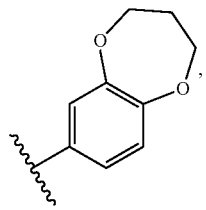

-continued

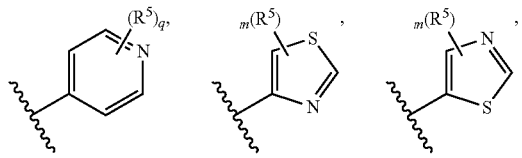
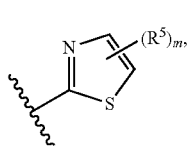
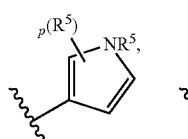
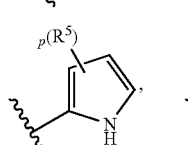
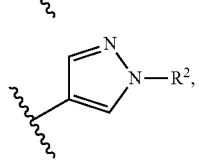
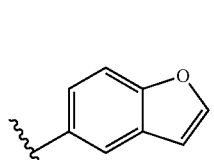
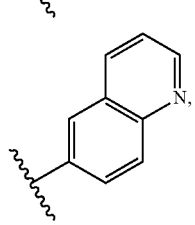
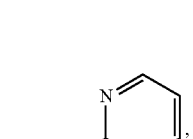
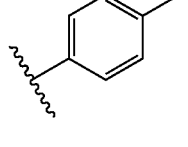
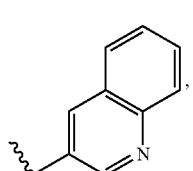

-continued

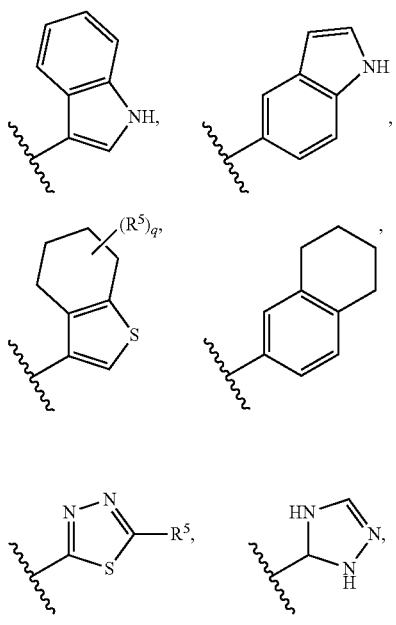

p is 0, 1, 2, or 3; q is 0, 1, 2, 3, or 4; and R⁵ is halo, azido, alkyl, haloalkyl, hydroxyalkyl, aminoalkyl, heterocycloalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, carboxylic acid, acyloxy, alkylthio, sulfonate, sulfonyl, sulfonamido, formyl, cyano, oxime, or isocyano.

In certain embodiments, the invention relates to any one of the aforementioned compounds, wherein

is hydrogen.

In certain embodiments, the invention relates to any one of the aforementioned compounds, wherein

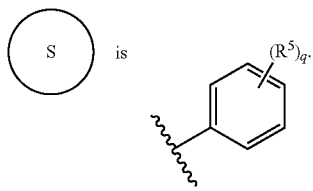

In certain embodiments, the invention relates to any one of the aforementioned compounds, wherein

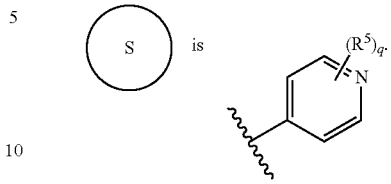

In certain embodiments, the invention relates to any one of the aforementioned compounds, wherein

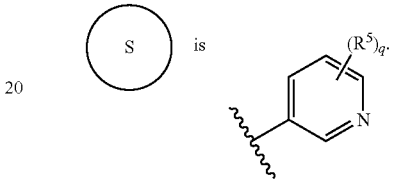

In certain embodiments, the invention relates to any one of the aforementioned compounds, wherein

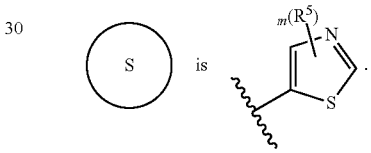

In certain embodiments, the invention relates to any one of the aforementioned compounds, wherein

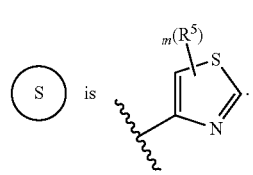

In certain embodiments, the invention relates to any one of the aforementioned compounds, wherein

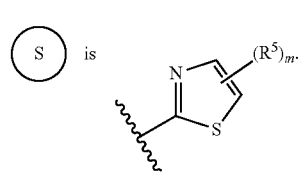

In certain embodiments, the invention relates to any one of the aforementioned compounds, wherein

is hydrogen, alkyl,

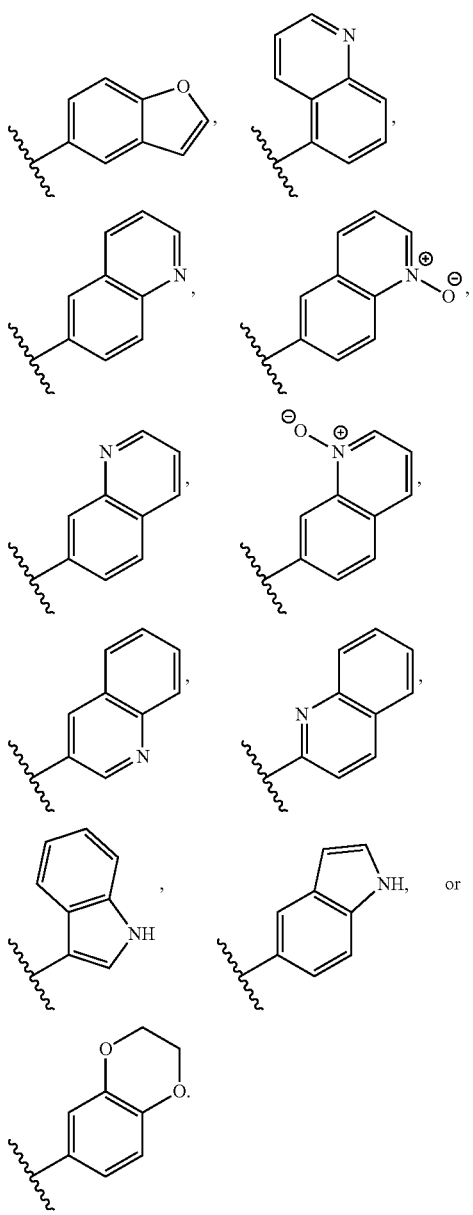

In certain embodiments, the invention relates to any one of the aforementioned compounds, wherein

is hydrogen.

In certain embodiments, the invention relates to any one of the aforementioned compounds, wherein

is alkyl.

In certain embodiments, the invention relates to any one of the aforementioned compounds, wherein $X^3$ is O, m is 1, one $R^{14}$ is hydrogen, and one $R^{14}$ is methyl.

In certain embodiments, the invention relates to any one of the aforementioned compounds, wherein $X^3$ is O, m is 1, one $R^{14}$ is hydrogen, one $R^{14}$ is methyl and

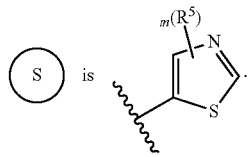

In certain embodiments, the invention relates to any one of the aforementioned compounds, wherein $X^3$ is O, m is 1, one $R^{14}$ is hydrogen, one $R^{14}$ is methyl and

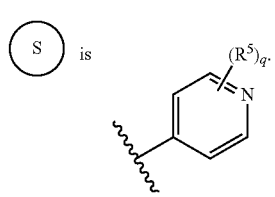

In certain embodiments, the invention relates to a compound, or a pharmaceutically acceptable salt or ester thereof, represented by Formula XIV:

Formula XIV

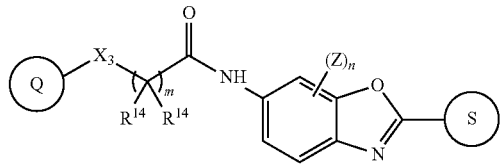

wherein, independently for each occurrence, $X^3$ is absent, O, C(R')$_2$, S, or NR';
wherein R' is hydrogen, halide, alkyl, alkenyl, alkynyl, cycloalkyl, heterocyclyl, aryl, heteroaryl, acyl, aracyl, or heteroaracyl;

m is 0, 1, or 2;

n is 0, 1, 2, or 3;

$R^{14}$ is hydrogen, alkyl, alkenyl, alkynyl, cycloalkyl, heterocyclyl, aryl, heteroaryl, acyl, aracyl, heteroaracyl sulfonate, sulfonyl, sulfonamido, formyl, carboxyl, alkoxycarbonyl, or acyloxy, or two $R^{14}$ groups taken together form a non-aromatic 3-8 membered ring, or two $R^{14}$ groups taken together form the side chain of a natural or non-natural D or L amino acid;

Z is hydrogen, halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, sulfhydryl, formyl, cyano, or isocyano;

(S) is hydrogen, alkyl, alkenyl, alkynyl, aralkyl, heteroaralkyl, halogen, amino, amido, acyl, aracyl, heteroaracyl, alkoxy, hydroxyl, carboxyl, alkoxycarbonyl, acyloxy, silyl, alkylthio, sulfonate, sulfonyl, sulfonamido, sulfhydryl, formyl, cyano, isocyano, monocyclic or bicyclic cycloalkyl, monocyclic or bicyclic heterocyclyl, monocyclic or bicyclic aryl or monocyclic or bicyclic heteroaryl; and (Q) is hydrogen, alkyl, monocyclic or bicyclic cycloalkyl, monocyclic or bicyclic heterocyclyl, monocyclic or bicyclic aryl or monocyclic or bicyclic heteroaryl;
wherein, any of the aforementioned alkyl, aryl, or heteroaryl may be substituted with one or more groups independently selected from the group consisting of halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, sulfhydryl, formyl, cyano, and isocyano.

In certain embodiments, the invention relates to any one of the aforementioned compounds, wherein $X^3$ is absent.

In certain embodiments, the invention relates to any one of the aforementioned compounds, wherein $X^3$ is O.

In certain embodiments, the invention relates to any one of the aforementioned compounds, wherein $X^3$ is $C(R')_2$.

In certain embodiments, the invention relates to any one of the aforementioned compounds, wherein $X^3$ is S.

In certain embodiments, the invention relates to any one of the aforementioned compounds, wherein $X^3$ is NR'.

In certain embodiments, the invention relates to any one of the aforementioned compounds, wherein $X^3$ is NR' and R' is hydrogen.

In certain embodiments, the invention relates to any one of the aforementioned compounds, wherein m is 0.

In certain embodiments, the invention relates to any one of the aforementioned compounds, wherein m is 1.

In certain embodiments, the invention relates to any one of the aforementioned compounds, wherein m is 1, one $R^{14}$ is hydrogen, and one $R^{14}$ is methyl.

In certain embodiments, the invention relates to any one of the aforementioned compounds, wherein m is 1; and one $R^{14}$ is alkenyl.

In certain embodiments, the invention relates to any one of the aforementioned compounds, wherein m is 1, one $R^{14}$ is hydrogen, and one $R^{14}$ is benzyl.

In certain embodiments, the invention relates to any one of the aforementioned compounds, wherein m is 1; and two $R^{14}$ together form the side chain of a D or L natural or non-natural amino acid.

In certain embodiments, the invention relates to any one of the aforementioned compounds, wherein Z is hydrogen.

In certain embodiments, the invention relates to any one of the aforementioned compounds, wherein Z is halo.

In certain embodiments, the invention relates to any one of the aforementioned compounds, wherein Z is alkyl.

In certain embodiments, the invention relates to any one of the aforementioned compounds, wherein (S) is hydrogen, alkyl,

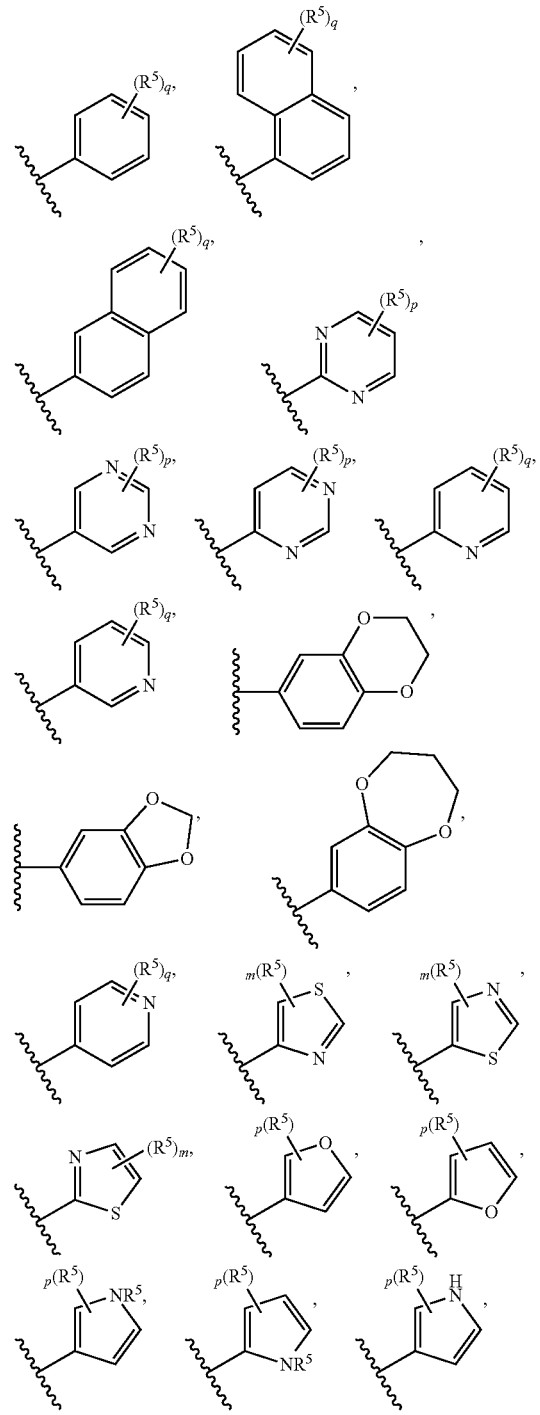

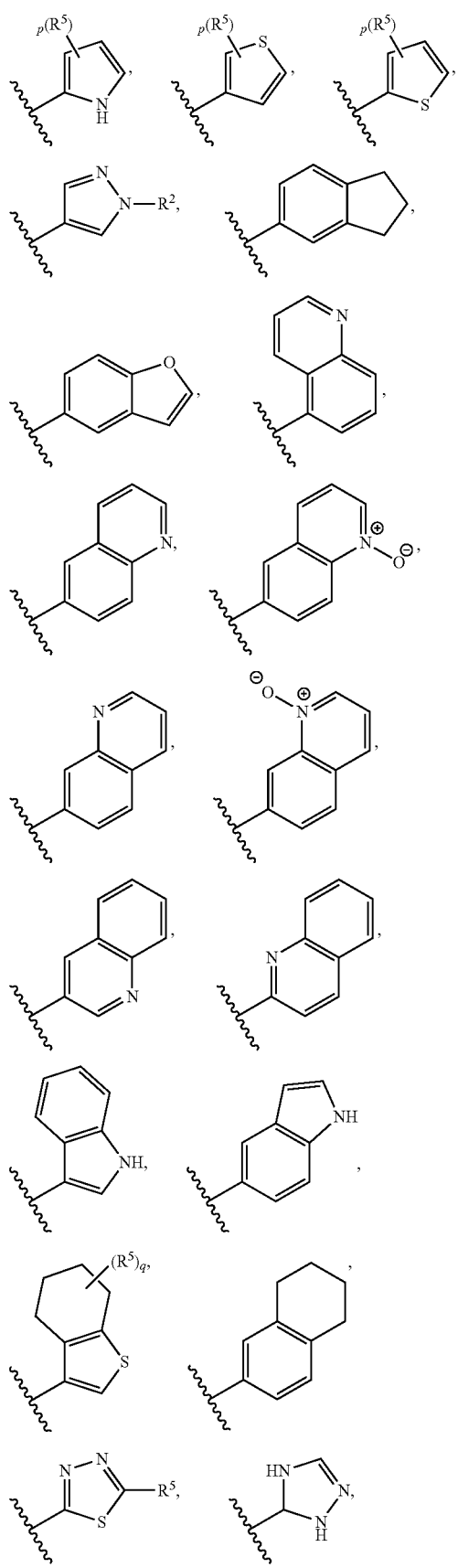

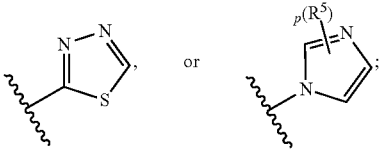

p is 0, 1, 2, or 3; q is 0, 1, 2, 3, or 4; and $R^5$ is halo, azido, alkyl, haloalkyl, hydroxyalkyl, aminoalkyl, heterocycloalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, carboxylic acid, acyloxy, alkylthio, sulfonate, sulfonyl, sulfonamido, formyl, cyano, oxime, or isocyano.

In certain embodiments, the invention relates to any one of the aforementioned compounds, wherein

is hydrogen.

In certain embodiments, the invention relates to any one of the aforementioned compounds, wherein

 is 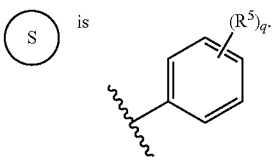

In certain embodiments, the invention relates to any one of the aforementioned compounds, wherein

 is 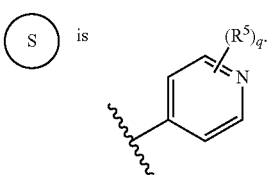

In certain embodiments, the invention relates to any one of the aforementioned compounds, wherein

 is 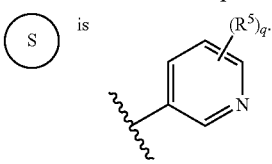

In certain embodiments, the invention relates to any one of the aforementioned compounds, wherein

 is 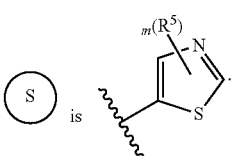

In certain embodiments, the invention relates to any one of the aforementioned compounds, wherein
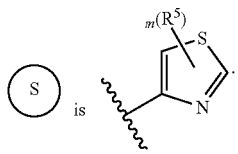
In certain embodiments, the invention relates to any one of the aforementioned compounds, wherein
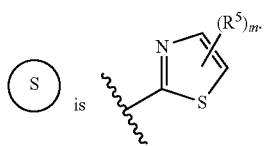
In certain embodiments, the invention relates to any one of the aforementioned compounds, wherein
is hydrogen, alkyl,
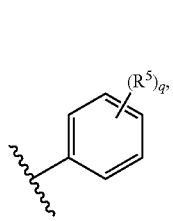 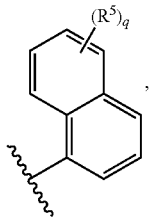
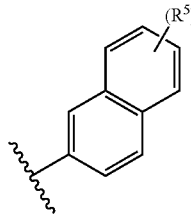 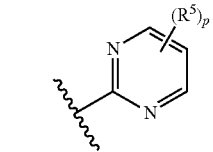
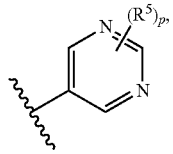 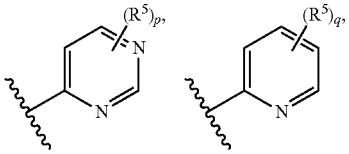
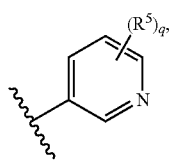 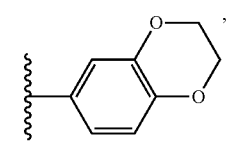
-continued
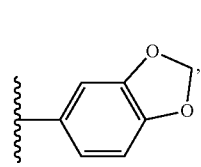 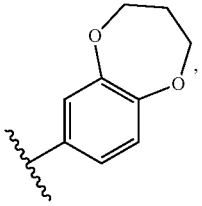
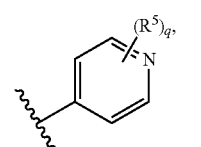 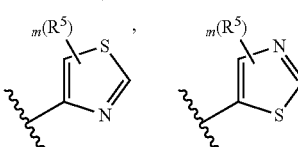
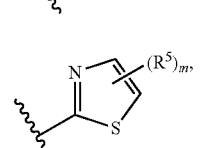 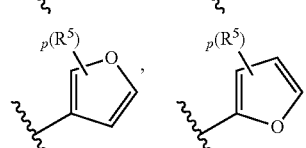
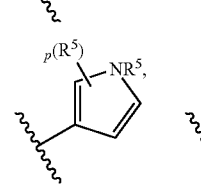 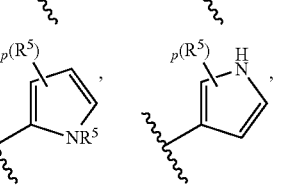
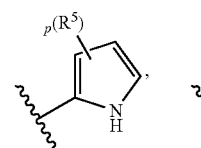 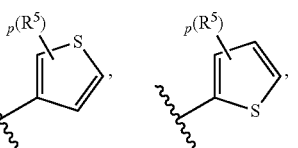
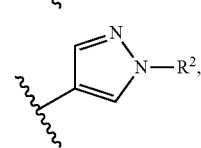 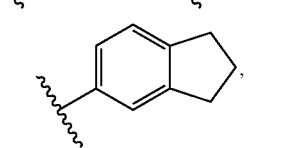
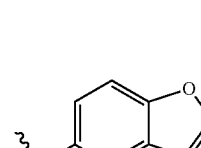 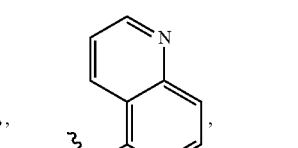
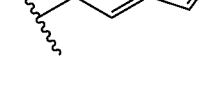 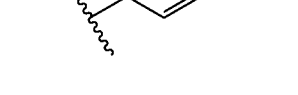
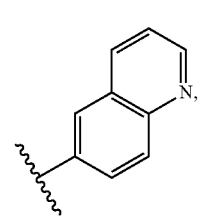 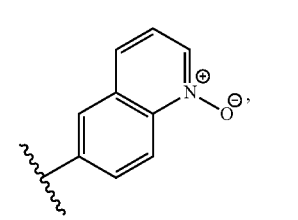
 
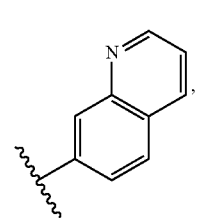 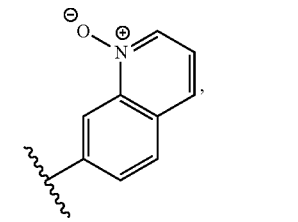

-continued

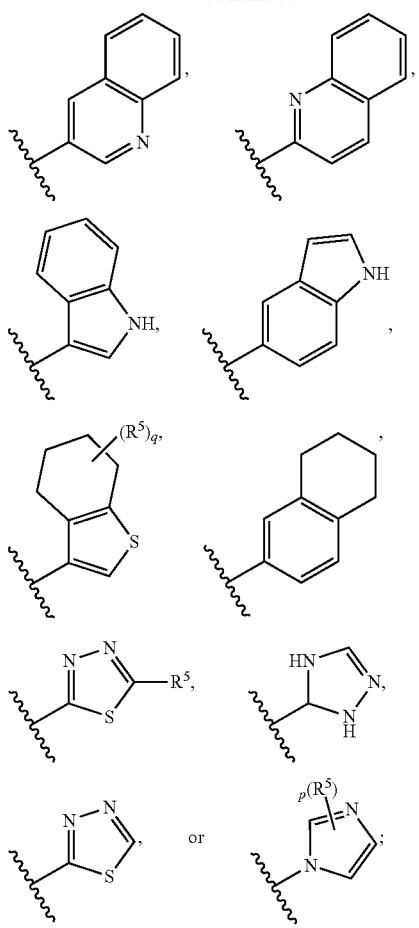

p is 0, 1, 2, or 3; q is 0, 1, 2, 3, or 4; and $R^5$ is halo, azido, alkyl, haloalkyl, hydroxyalkyl, aminoalkyl, heterocycloalkyl, aralkyl, alkenyl, alkynyl, cycloalkyl, heterocyclyl, aryl, heteroaryl, heteroaralkyl, hydroxy, alkoxy, haloalkyloxy, aryloxy, heteroaryloxy, amino, nitro, sulfhydryl, imino, amido, phosphonate, phosphinate, acyl, carboxyl, alkoxycarbonyl, carboxylic acid, acyloxy, alkylthio, sulfonate, sulfonyl, sulfonamido, formyl, cyano, oxime, or isocyano.

In certain embodiments, the invention relates to any one of the aforementioned compounds, wherein

is hydrogen.

In certain embodiments, the invention relates to any one of the aforementioned compounds, wherein

is alkyl.

In certain embodiments, the invention relates to any one of the aforementioned compounds, wherein

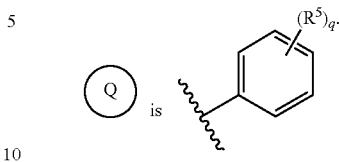

In certain embodiments, the invention relates to any one of the aforementioned compounds, wherein

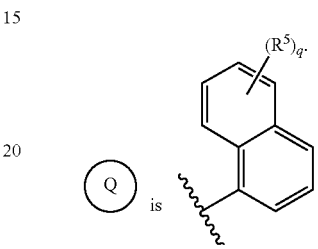

In certain embodiments, the invention relates to any one of the aforementioned compounds, wherein $X^3$ is NR', R' is hydrogen, m is 1, and the two $R^{14}$ together form the side chain of a D or L natural or non-natural amino acid, with the proviso that said side chain is neither glycine nor alanine.

In certain embodiments, the invention relates to any one of the aforementioned compounds, wherein $X^3$ is NR', R' is hydrogen, m is 1, one $R^{14}$ is hydrogen, one $R^{14}$ is benzyl and

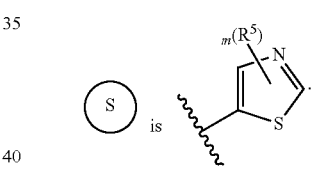

In certain embodiments, the invention relates to any one of the aforementioned compounds, wherein $X^3$ is NR', R' is hydrogen, m is 1, the two $R^{14}$ together form the side chain of a D or L natural or non-natural amino acid, with the proviso that said side chain is neither glycine nor alanine, and

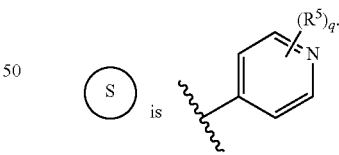

In certain embodiments, the invention relates to a compound, or a pharmaceutically acceptable salt or ester thereof, selected from the group consisting of

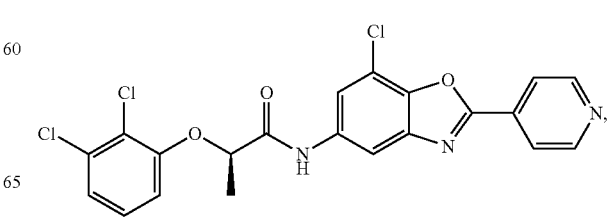

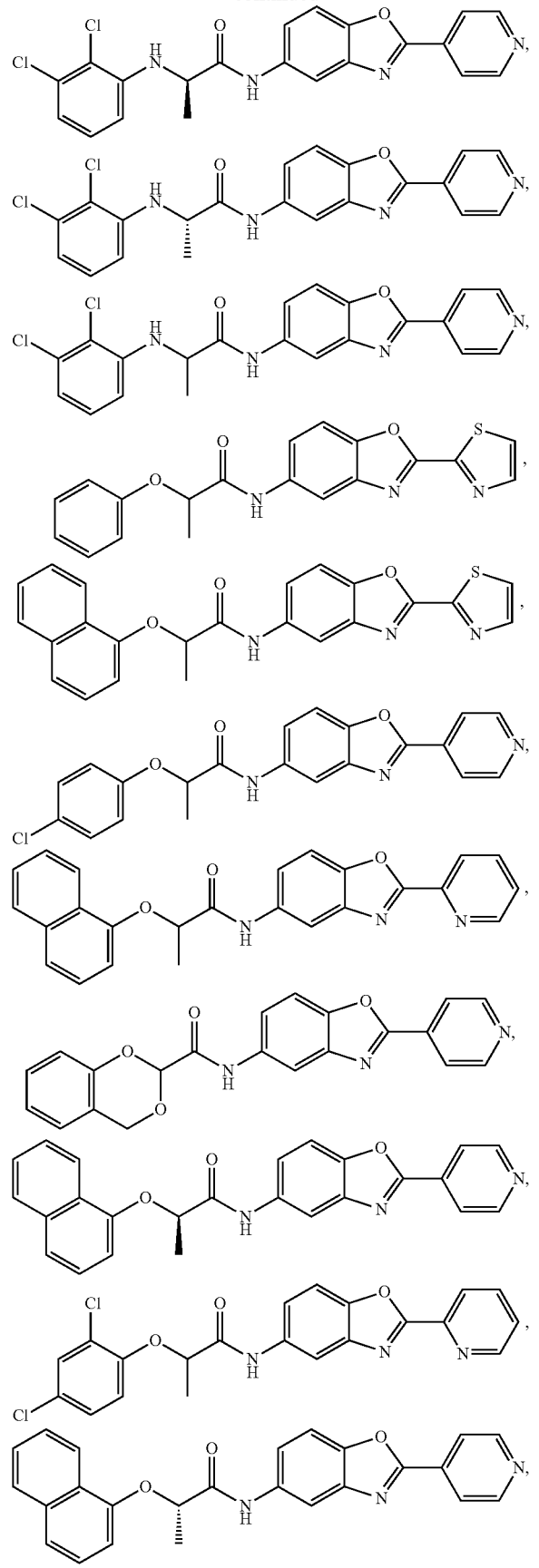
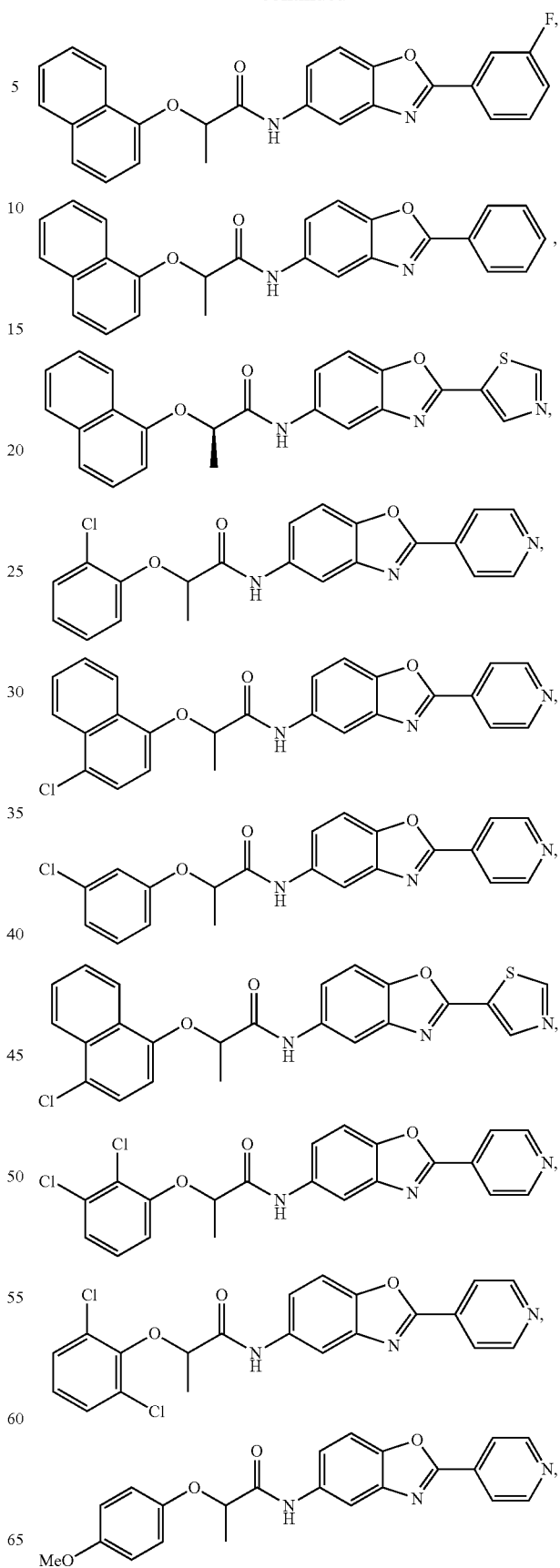

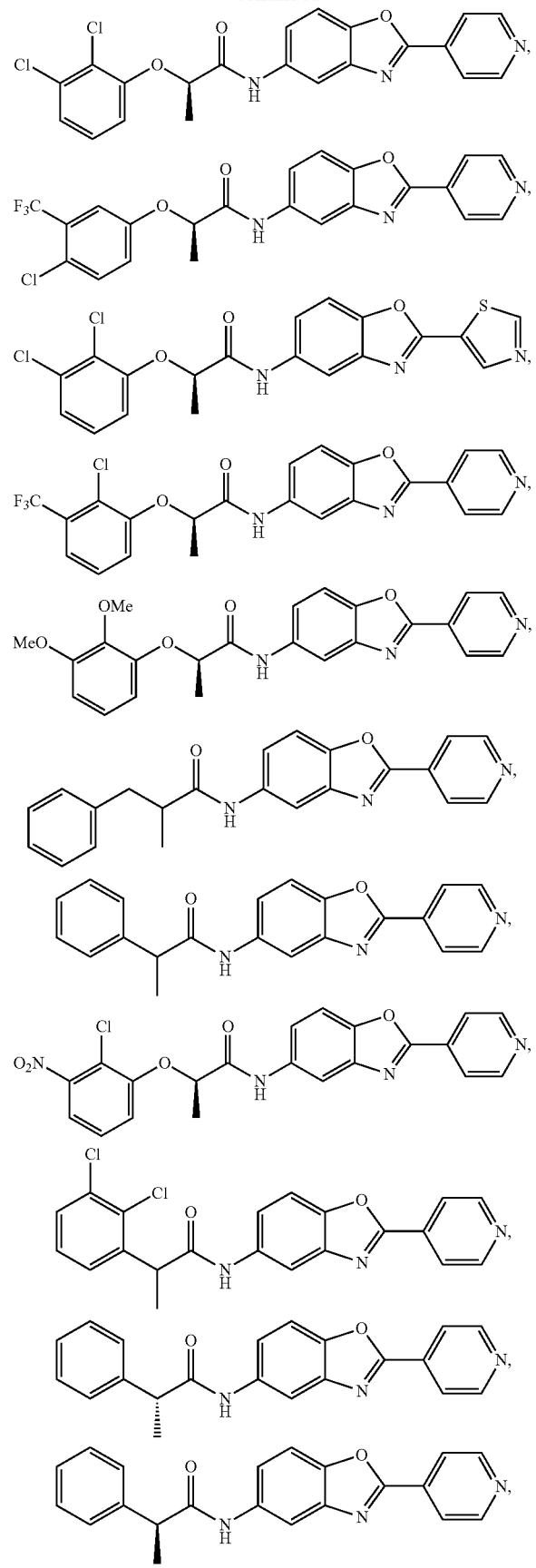
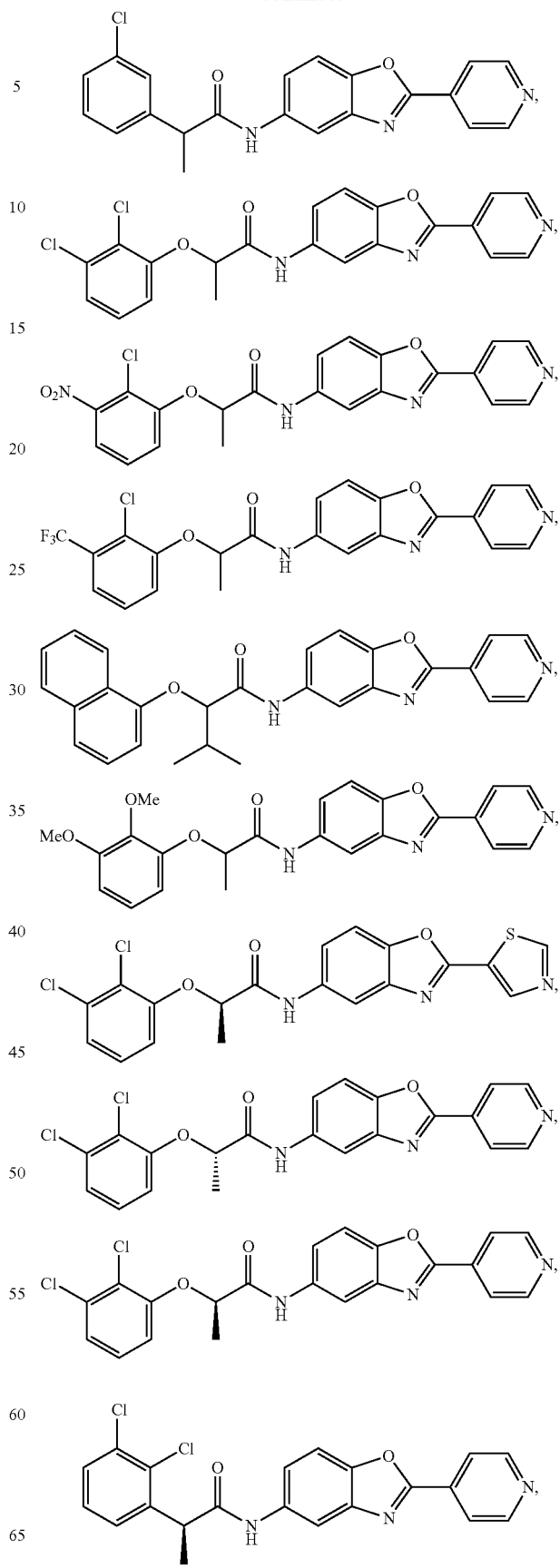

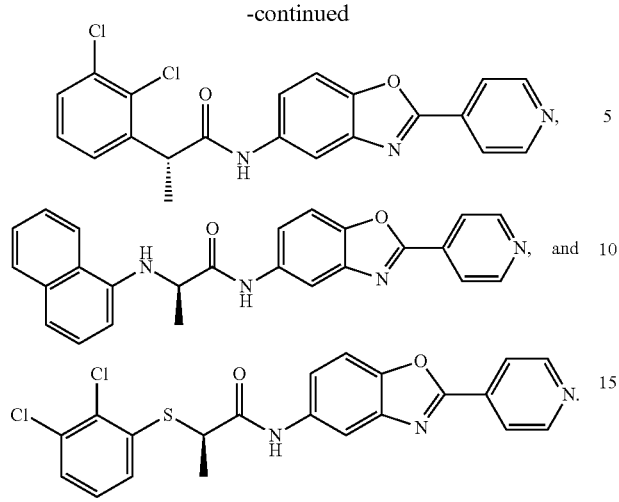
In certain embodiments, the invention relates to a compound, or a pharmaceutically acceptable salt or ester thereof, selected from the group consisting of
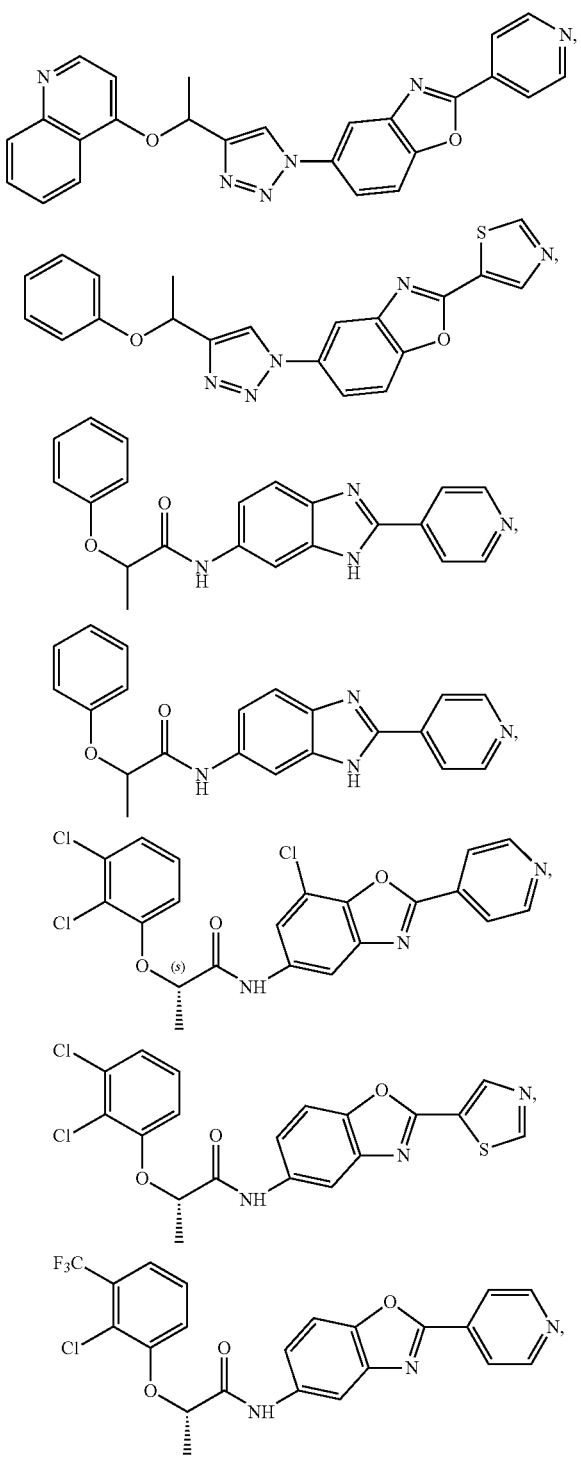
In certain embodiments, the invention relates to a compound, or a pharmaceutically acceptable salt or ester thereof, selected from the group consisting of
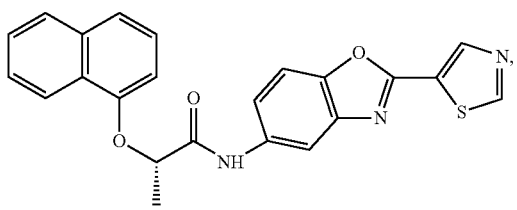

-continued

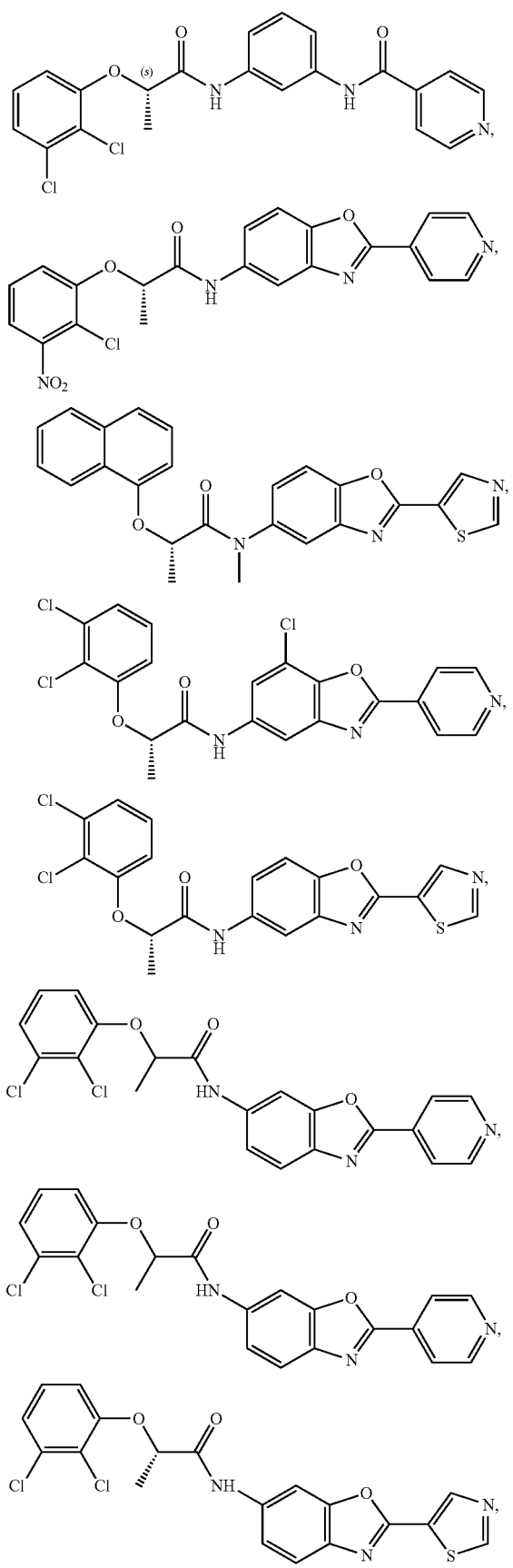

-continued

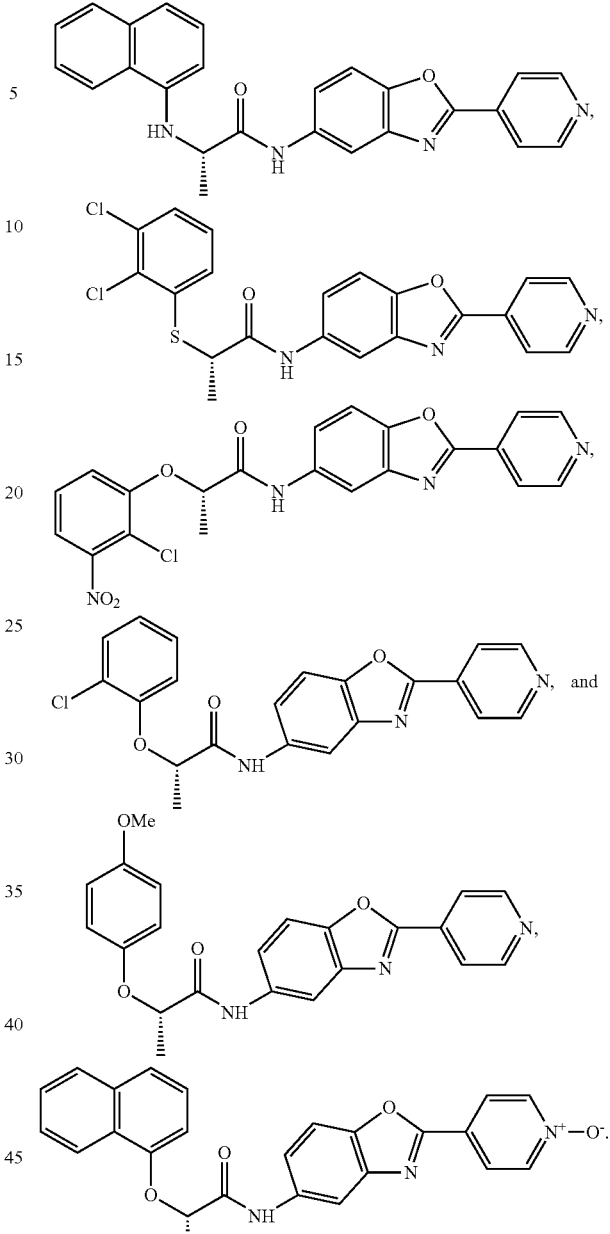

General Considerations for Compounds of the Invention

When stereochemistry is not specifically indicated, the compounds of the invention may contain one or more asymmetric carbon atoms and thus may occur as racemates and racemic mixtures, single enantiomers, diastereomeric mixtures and individual diastereomers. All such isomeric forms of these compounds are included in the present invention, unless expressly excluded. Each stereogenic carbon may be of the R or S configuration.

In addition, the compounds of the invention described above may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Pharmaceutical Compositions of the Invention

In certain embodiments, the invention relates to a pharmaceutical composition, comprising a pharmaceutically acceptable carrier, adjuvant, or vehicle; and any one of the aforementioned compounds.

In certain embodiments, the invention relates to any one of the aforementioned compositions, further comprising an antimicrobial agent.

In certain embodiments, the invention relates to any one of the aforementioned compositions, further comprising an antibiotic or antiprotozoal agent.

In certain embodiments, the invention relates to any one of the aforementioned compositions, further comprising an antibiotic agent selected from the group consisting of vancomycin, metronidazole, amoxicillin, ciprofloxacin, doxycycline, gentamicin and clindamycin.

In certain embodiments, the invention relates to any one of the aforementioned compositions, further comprising an antiprotozoal agent selected from the group consisting of eflornmithine, furazolidone, melarsoprol, metronidazole, omidazole, paromomycin sulfate, pentamidine, pyrimethamine, and tinidazole.

In certain embodiments, the invention relates to any one of the aforementioned compositions, further comprising an immunosuppression agent.

In certain embodiments, the invention relates to any one of the aforementioned compositions, further comprising an immunosuppression agent selected from the group consisting of cyclosporin A, FK506, rapamycin, leflunomide, deoxyspergualin, prednisone, azathioprine, mycophenolate mofetil, OKT3, ATAG, interferon and mizoribine.

In certain embodiments, the invention relates to any one of the aforementioned compositions, further comprising an anti-cancer agent.

In certain embodiments, the invention relates to any one of the aforementioned compositions, further comprising an anti-cancer agent selected from the group consisting of cis-platin, actinomycin D, doxorubicin, vincristine, vinblastine, etoposide, amsacrine, mitoxantrone, tenipaside, taxol, colchicine, cyclosporin A, phenothiazines, interferon and thioxantheres.

In certain embodiments, the invention relates to any one of the aforementioned compositions, further comprising an anti-viral agent.

In certain embodiments, the invention relates to any one of the aforementioned compositions, further comprising an anti-viral agent selected from the group consisting of cytovene, ganciclovir, trisodium phosphonoformate, Ribavirin, d4T, ddI, AZT, and acyclovir.

In certain embodiments, the invention relates to any one of the aforementioned compositions, further comprising an anti-vascular hyperproliferative agent.

In certain embodiments, the invention relates to any one of the aforementioned compositions, further comprising an anti-vascular hyperproliferative selected from the group consisting of HMG Co-A reductase inhibitors such as lovastatin, thromboxane A2 synthetase inhibitors, eicosapentanoic acid, ciprostene, trapidil, ACE inhibitors, low molecular weight heparin, mycophenolic acid, rapamycin and 5-(3'-pyridinylmethyl)benzofuran-2-carboxylate.

The compounds of the invention are defined to include pharmaceutically acceptable salts thereof. A "pharmaceutically acceptable salt" means any pharmaceutically acceptable salt, which, upon administration to a recipient, is capable of providing (directly or indirectly) a compound of this invention. Pharmaceutically acceptable salts of the compounds of the invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium), alkaline earth metal (e.g., magnesium), and ammonium salts. This invention also envisions the quaternization of any basic nitrogen-containing groups of the compounds disclosed herein. Water or oil-soluble or dispersible products may be obtained by such quaternization.

In certain embodiments, the invention relates to a pharmaceutical composition, wherein the pharmaceutical composition comprises any one of the aforementioned compounds or a pharmaceutically acceptable salt or ester thereof; an additional agent selected from the group consisting of an immunosuppressant, an anti-cancer agent, an anti-viral agent, antiinflammatory agent, antibiotic, and an anti-vascular hyperproliferation compound; and any pharmaceutically acceptable carrier, adjuvant or vehicle. In certain embodiments, the invention relates to any one of the aforementioned pharmaceutical compositions, wherein the pharmaceutical composition comprises any one of the aforementioned compounds or a pharmaceutically acceptable salt or ester thereof; and a pharmaceutically acceptable carrier, adjuvant or vehicle. In certain embodiments, the invention relates to any one of the aforementioned pharmaceutical compositions, wherein the pharmaceutical composition optionally comprises an additional agent selected from the group consisting of an immunosuppressant, an anti-cancer agent, an anti-viral agent, antiinflammatory agent, antibiotic, and an anti-vascular hyperproliferation compound.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of the invention include, but are not limited to, ion exchangers, alumina, aluminum stearate, lecithin, self-emulsifying drug delivery systems (SEDDS) such as d.alpha.-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of any one of the aforementioned compounds.

The pharmaceutical compositions of the invention may be administered orally, parenterally, by inhalation spray, topically, rectally, nasally, buccally, vaginally or via an implanted reservoir. The pharmaceutical compositions of the invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as those described in Pharmacopeia Helvetica, Ph. Helv., or a similar alcohol, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of the invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried con starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of the invention may also be administered in the form of suppositories for rectal administration. These compositions can be prepared by mixing a compound of the invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of the invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of the invention include, but are not limited to, mineral oil, liquid petroleum, white petroleum, propylene glycol, polyoxy-ethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of the invention may also be topically applied to the lower intestinal tract by rectal suppository formulation or in a suitable enema formulation. Topically-transdermal patches are also included in this invention.

The pharmaceutical compositions of the invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 1000 mg/kg body weight per day, or between about 0.5 and about 75 mg/kg body weight per day, of the IMPDH inhibitory compounds described herein are useful in a monotherapy and/or in combination therapy for the prevention and treatment of IMPDH-mediated disease or infection. Typically, the pharmaceutical compositions of the invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Such preparations contain from about 20% to about 80% active compound.

When the compositions of the invention comprise a combination of an IMPDH inhibitor of the invention and one or more additional therapeutic or prophylactic agents, both the IMPDH inhibitor and the additional agent should be present at dosage levels of between about 10 to 100%, or between about 10 to 80% of the dosage normally administered in a monotherapy regimen. The additional agents may be administered separately, as part of a multiple dose regimen, from the compounds of this invention. Alternatively, those agents may be part of a single dosage form, mixed together with the compounds of the invention in a single composition.

Upon improvement of a patient's condition, a maintenance dose of a compound, composition or combination of the invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

In certain embodiments, the invention relates to a pharmaceutical composition for treatment or prevention of a protozoan infection, comprising a pharmaceutically acceptable carrier, adjuvant or vehicle and at least one of the aforementioned compounds, or a pharmaceutically acceptable salt or ester thereof.

In certain embodiments, the invention relates to any one of the aforementioned pharmaceutical compositions, wherein said protozoan infection is caused by a protozoan selected from the group consisting of the genera *Cryptosporidium*, *Entamoeba*, *Leishmania* and *Trypanosoma*.

In certain embodiments, the invention relates to any one of the aforementioned pharmaceutical compositions, wherein said protozoan infection is caused by a protozoan selected from the genus *Cryptosporidium*.

In certain embodiments, the invention relates to any one of the aforementioned pharmaceutical compositions, wherein said protozoan infection is caused by *Cryptosporidium parvum* and/or *C. hominis*.

In certain embodiments, the invention relates to any one of the aforementioned pharmaceutical compositions, wherein the pharmaceutical composition further comprises an antimicrobial agent, such as an antibiotic or antiprotozoal agent. Examples of antibiotic agents include, but are not limited to, vancomycin, metronidazole, amoxicillin, ciprofloxacin, doxycycline, gentamicin and clindamycin. Examples of antiprotozoal agents include, but are not limited to, eflornithine, furazolidone, melarsoprol, metronidazole, omidazole, paromomycin sulfate, pentamidine, pyrimethamine, and tinidazole.

In certain embodiments, the invention relates to any one of the aforementioned pharmaceutical compositions, wherein the pharmaceutical composition is used for treatment or prevention of an IMPDH-mediated disease, and comprises a pharmaceutically acceptable carrier, adjuvant or vehicle and at least one aforementioned compound.

In certain embodiments, the invention relates to any one of the aforementioned pharmaceutical compositions, further comprising an immunosuppression agent. Examples of additional immunosuppression agents include, but are not limited to, cyclosporin A, FK506, rapamycin, leflunomide, deoxyspergualin, prednisone, azathioprine, mycophenolate mofetil, OKT3, ATAG, interferon, and mizoribine.

In certain embodiments, the invention relates to any one of the aforementioned pharmaceutical compositions, further comprising an anti-cancer agent. Examples of anti-cancer agents include, but are not limited to, cis-platin, actinomycin D, doxorubicin, vincristine, vinblastine, etoposide, amsacrine, mitoxantrone, tenipaside, taxol, colchicine, cyclosporin A, phenothiazines, interferon, and thioxantheres.

In certain embodiments, the invention relates to any one of the aforementioned pharmaceutical compositions, further comprising an anti-viral agent. Examples of anti-viral agents include, but are not limited to, cytovene, ganciclovir, trisodium phosphonoformate, Ribavirin, d4T, ddI, AZT, and acyclovir.

In certain embodiments, the invention relates to any one of the aforementioned pharmaceutical compositions, further comprising an anti-vascular hyperproliferative agent. Examples of anti-vascular hyperproliferative agents include, but are not limited to, HMG Co-A reductase inhibitors such as lovastatin, thromboxane A2 synthetase inhibitors, eicosapentanoic acid, ciprostene, trapidil, ACE inhibitors, low molecular weight heparin, mycophenolic acid, rapamycin, and 5-(3'-pyridinylmethyl)benzofuran-2-carboxylate.

Selected Methods of the Invention

In certain embodiments, the invention relates to a method of killing or inhibiting the growth of a microbe, comprising the step of contacting said microbe with an effective amount of any one of the aforementioned compounds.

In certain embodiments, the invention relates to any one of the aforementioned methods, wherein said microbe is a protozoan or bacterium.

In certain embodiments, the invention relates to any one of the aforementioned methods, wherein said microbe is a protozoan or a bacterium selected from the group consisting of the genera *Acinetobacter*, *Arcobacter*, *Bacillus*, *Bacteroides*, *Borrelia*, *Brucella*, *Burkholderia*, *Campylobacter*, *Clostridia*, *Coxiella*, *Cryptosporidium*, *Entamoeba*, *Enterococcus*, *Erysipelothrix*, *Francisella*, *Fusobacterium*, *Helicobacter*, *Lactobacillus*, *Leishmania*, *Listeria*, *Mycobacterium*, *Neisseria*, *Pseudomonas*, *Staphylococcus*, *Streptococcus*, and *Trypanosoma*.

In certain embodiments, the invention relates to any one of the aforementioned methods, wherein said microbe is a protozoan or a bacterium selected from the group consisting of *Acinetobacter baumannii*, *Bacillus anthracis*, *Burkholderia cenocepacia*, *B. thailandensis*, *Campylobacter jejuni*, *Francisella tularensis*, *Helicobacter pylori*, *Staphylococcus aureus*, *Listeria monocytogenes*, and *Mycobacterium tuberculosis*.

In certain embodiments, the invention relates to any one of the aforementioned methods, wherein said microbe is a protozoan or a bacterium selected from the group consisting of *Acinetobacter baumannii* ATCC 17961, *Bacillus anthracis* Sterne 7702, *Burkholderia cenocepacia* K56-2, *B. thailandensis* E264, *Campylobacter jejuni* 81-176, *Francisella tularensis* Schu S4, *Helicobacter pylori*, *Staphylococcus aureus* NCTC 8325, *Listeria monocytogenes* 10403S, and *Mycobacterium tuberculosis* H37Rv.

In certain embodiments, the invention relates to any one of the aforementioned methods, wherein said microbe is a protozoan; and said protozoan is selected from the group consisting of the genera *Cryptosporidium*, *Entamoeba*, *Leishmania* and *Trypanosoma*.

In certain embodiments, the invention relates to any one of the aforementioned methods, wherein said protozoan is selected from the genus *Cryptosporidium*.

In certain embodiments, the invention relates to any one of the aforementioned methods, wherein said protozoan is *Cryptosporidium parvum* and/or *Cryptosporidium hominis*.

In certain embodiments, the invention relates to any one of the aforementioned methods, wherein said microbe is a bacterium; and said bacterium is selected from the group consisting of the genera *Acinetobacter, Arcobacter, Bacillus, Bacteroides, Borrelia, Brucella, Burkholderia, Brachyspira, Campylobacter, Clostridia, Coxiella, Enterococcus, Erysipelothrix, Francisella, Fusobacterium, Helicobacter, Lactobacillus, Listeria, Mycobacterium, Neisseria, Pseudomonas, Staphylococcus* and *Streptococcus*.

In certain embodiments, the invention relates to a method of treating or preventing a microbial infection in a mammal, comprising the step of administering to a mammal in need thereof a therapeutically effective amount of any one of the aforementioned compounds.

In certain embodiments, the invention relates to a method of treating or preventing a parasitic infection in a mammal comprising the step of administering to a mammal in need thereof a therapeutically effective amount of any one of the aforementioned compounds.

In certain embodiments, the invention relates to any one of the aforementioned methods, wherein said microbial infection is caused by a protozoan or bacterium.

In certain embodiments, the invention relates to any one of the aforementioned methods, wherein said microbial infection is caused by a protozoan or a bacterium selected from the group consisting of the genera *Cryptosporidium, Entamoeba, Leishmania, Trypanosoma, Acinetobacter, Arcobacter, Bacillus, Bacteroides, Borrelia, Brucella, Burkholderia, Brachyspira, Campylobacter, Clostridia, Coxiella, Enterococcus, Erysipelothrix, Francisella, Fusobacterium, Helicobacter, Lactobacillus, Listeria, Mycobacterium, Neisseria, Pseudomonas, Staphylococcus* and *Streptococcus*.

In certain embodiments, the invention relates to any one of the aforementioned methods, wherein said microbial infection is caused by a protozoan; and said protozoan is selected from the group consisting of the genera *Cryptosporidium, Entamoeba, Leishmania* and *Trypanosoma*.

In certain embodiments, the invention relates to any one of the aforementioned methods, wherein said protozoan is selected from the genus *Cryptosporidium*.

In certain embodiments, the invention relates to any one of the aforementioned methods, wherein said microbial infection is caused by *Cryptosporidium parvum* or *Cryptosporidium hominis* or both.

In certain embodiments, the invention relates to any one of the aforementioned methods, wherein said microbe is a bacterium; and said bacterium is selected from the group consisting of the genera *Acinetobacter, Arcobacter, Bacillus, Bacteroides, Borrelia, Brucella, Burkholderia, Brachyspira, Campylobacter, Clostridia, Coxiella, Enterococcus, Erysipelothrix, Francisella, Fusobacterium, Helicobacter, Lactobacillus, Listeria, Mycobacterium, Neisseria, Pseudomonas, Staphylococcus* and *Streptococcus*.

In certain embodiments, the invention relates to any one of the aforementioned methods, further comprising the step of co-administering to a mammal or bird in need thereof a therapeutically effective amount of an antimicrobial agent. In certain embodiments, the infection is in a mammal. In certain embodiments, the infection is in a bird.

In certain embodiments, the invention relates to any one of the aforementioned methods, wherein said antimicrobial agent is an antibiotic. In certain embodiments, the invention relates to any one of the aforementioned methods, wherein said antimicrobial agent is an antibiotic. In certain embodiments, the invention relates to any one of the aforementioned methods, wherein said antibiotic agent is selected from the group consisting of vancomycin, metronidazole, amoxicillin, ciprofloxacin, doxycycline, gentamicin, and clindamycin.

In certain embodiments, the invention relates to any one of the aforementioned methods, wherein said antimicrobial agent is an antiparasitic. In certain embodiments, the invention relates to any one of the aforementioned methods, wherein said antiparasitic agent is selected from the group consisting of eflomithine, furazolidone, melarsoprol, metronidazole, omidazole, paromomycin sulfate, pentamidine, pyrimethamine, and tinidazole.

DEFINITIONS

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 80 or fewer carbon atoms in its backbone (e.g., $C_1$-$C_{80}$ for straight chain, $C_3$-$C_{80}$ for branched chain), and alternatively, about 30 or fewer. Likewise, cycloalkyls have from about 3 to about 10 carbon atoms in their ring structure, and alternatively about 5, 6 or 7 carbons in the ring structure. As used herein, "fluoroalkyl" denotes an alkyl where one or more hydrogens have been replaced with fluorines.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, alkylthio, sulfonyl, sulfonamido, ketone, aldehyde, ester, heterocyclyl, aromatic or heteroaromatic moieties, trifluoromethyl, cyano, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted aryl, respectively. For example, the names 1,2-dimethylbenzene and ortho-dimethylbenzene are synonymous.

The terms "heterocyclyl", "heteroaryl", or "heterocylic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, alkylthio, sulfonyl, ketone, aldehyde, ester, a heterocyclyl, an aromatic or heteroaromatic moiety, trifluoromethyl, cyano, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, alkylthio, sulfonyl, ketone, aldehyde, ester, a heterocyclyl, an aromatic or heteroaromatic moiety, trifluoromethyl, cyano, or the like.

The term "carbocycle" is art-recognized and refers to an aromatic or non-aromatic ring in which each atom of the ring is carbon.

The terms "monocyclic," "bicyclic," or "tricyclic" ring systems refers to 5 or 6 member monocyclic rings, 8, 9 and 10 membered bicyclic ring structures, and 11, 12, 13 and 14 membered tricyclic ring structures, wherein each bond in each ring may be possess any degree of saturation that is chemically feasible. When such structures contain substituents, those substituents may be at any position of the ring system, unless otherwise specified. As specified, such ring systems may optionally comprise up to 4 heteroatoms selected from N, O or S. Those heteroatoms may replace any carbon atoms in these ring systems as long as the resulting compound is chemically stable.

The term "monocyclic" ring system, as used herein, includes saturated, partially unsaturated and fully unsaturated ring structures. The term "bicyclic" ring system, as used herein, includes systems wherein each ring is independently saturated, partially unsaturated and fully unsaturated. Examples of monocyclic and bicyclic ring systems useful in the compounds of the invention include, but are not limited to, cyclopentane, cyclopentene, indane, indene, cyclohexane, cyclohexene, cyclohexadiene, benzene, tetrahydronaphthalene, decahydronaphthalene, naphthalene, pyridine, piperidine, pyridazine, pyrimidine, pyrazine, 1,2,3-triazine, 1,2,4-triazine, 1,3,5-triazine, 1,2,3,4-tetrazine, 1,2,4,5-tetrazine, 1,2,3,4-tetrahydroquinoline, quinoline, 1,2,3,4-tetrahydroisoquinoline, isoquinoline, cinnoline, phthalazine, quinazoline, quinoxaline, 1,5-naphthyridine, 1,6-naphthyridine, 1,7-naphthyridine, 1,8-naphthyridine, 2,6-naphthyridine, 2,7-naphthyridine, pteridine, acridine, phenazine, 1,10-phenatroline, dibenzopyrans, 1-benzopyrans, phenothiazine, phenoxazine, thianthrene, dibenzo-p-dioxin, phenoxathiin, phenoxthionine, morpholine, thiomorpholine, tetrahydropyran, pyran, benzopyran, 1,4-dioxane, 1,3-dioxane, dihyropyridine, dihydropyran, 1-pyrindine, quinuclidine, triazolopyridine, β-carboline, indolizine, quinolizidine, tetrahydronaphtheridine, diazaphenanthrenes, thiopyran, tetrahydrothiopyran, benzodioxane, furan, benzofuran, tetrahydrofuran, pyrrole, indole, thiophene, benzothiopene, carbazole, pyrrolidine, pyrazole, isoxazole, isothiazole, imidazole, oxazole, thiazole, 1,2,3-triazole, 1,2,4-triazole, 1,2,3-oxadiazole, 1,2,4-oxadiazole, 1,3,4 oxadiazole, 1,2,5-oxadiazole, 1,2,3-thiadiazole, 1,2,4-thiadiazole, 1,3,4-thiadiazole, 1,2,5 thiadiazole, tetrazole, benzothiazole, benzoxazole, benzotriazole, benzimidazole, benzopyrazole, benzisothiazole, benzisoxazole and purine.

Additional monocyclic and bicyclic structures falling within the above description may be found in A. R. Katritzky, and C. W. Rees, eds. "Comprehensive Heterocyclic Chemistry: Structure, Reactions, Synthesis and Use of Heterocyclic Compounds, Vol. 1-8," Pergamon Press, NY (1984), the disclosure of which is herein incorporated by reference.

It should be understood that heterocycles may be attached to the rest of the compound by any atom of the heterocycle which results in the creation of a stable structure.

The term "ring atom", as used herein, refers to a backbone atom that makes up the ring. Such ring atoms are selected from C, N, O or S and are bound to 2 or 3 other such ring atoms (3 in the case of certain ring atoms in a bicyclic ring system). The term "ring atom" does not include hydrogen.

The term "nitro" is art-recognized and refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2^-$. "Halide" designates the corresponding anion of the halogens, and "pseudohalide" has the definition set forth on page 560 of "Advanced Inorganic Chemistry" by Cotton and Wilkinson, that is, for example, monovalent anionic groups sufficiently electronegative to exhibit a positive Hammett sigma value at least equaling that of a halide (e.g., CN, OCN, SCN, SeCN, TeCN, N$_3$, and C(CN)$_3$).

The terms "amine" and "amino" are art-recognized and refer to both unsubstituted and substituted amines, e.g., a moiety that may be represented by the general formulas:

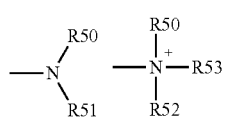

wherein R50, R51, R52 and R53 each independently represent a hydrogen, an alkyl, an alkenyl, —(CH$_2$)$_m$—R61, or R50 and R51 or R52, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

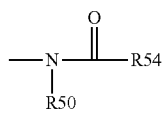

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

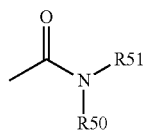

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carboxyl" is art recognized and includes such moieties as may be represented by the general formulas:

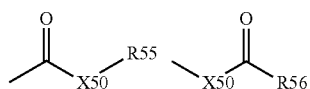

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester." Where X50 is an oxygen, and R55 is as defined above, the moiety is referred to herein as a carboxyl group, and particularly when R55 is a hydrogen, the formula represents a "carboxylic acid." Where X50 is an oxygen, and R56 is hydrogen, the formula represents a "formate." In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to —O(C═O)NRR', where R and R' are independently H, aliphatic groups, aryl groups or heteroaryl groups.

The term "oxo" refers to a carbonyl oxygen (═O).

The terms "oxime" and "oxime ether" are art-recognized and refer to moieties that may be represented by the general formula:

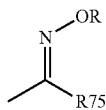

wherein R75 is hydrogen, alkyl, cycloalkyl, alkenyl, alkynyl, aryl, aralkyl, or —(CH$_2$)$_m$—R61. The moiety is an "oxime" when R is H; and it is an "oxime ether" when R is alkyl, cycloalkyl, alkenyl, alkynyl, aryl, aralkyl, or —(CH$_2$)$_m$—R61.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

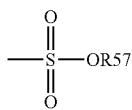

in which R57 is an electron pair, hydrogen, alkyl, cycloalkyl, or aryl.

The term "sulfate" is art recognized and includes a moiety that may be represented by the general formula:

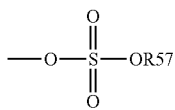

in which R57 is as defined above.

The term "sulfonamido" is art recognized and includes a moiety that may be represented by the general formula:

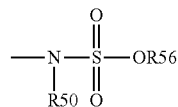

in which R50 and R56 are as defined above.

The term "sulfamoyl" is art-recognized and refers to a moiety that may be represented by the general formula:

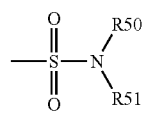

in which R50 and R51 are as defined above.

The term "sulfonyl" is art-recognized and refers to a moiety that may be represented by the general formula:

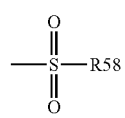

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

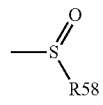

in which R58 is defined above.

The term "phosphoryl" is art-recognized and may in general be represented by the formula:

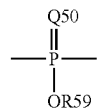

wherein Q50 represents S or O, and R59 represents hydrogen, a lower alkyl or an aryl. When used to substitute, e.g., an alkyl, the phosphoryl group of the phosphorylalkyl may be represented by the general formulas:

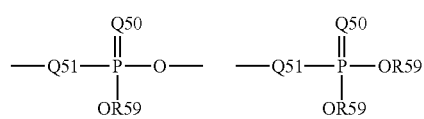

wherein Q50 and R59, each independently, are defined above, and Q51 represents O, S or N. When Q50 is S, the phosphoryl moiety is a "phosphorothioate."

The term "phosphoramidite" is art-recognized and may be represented in the general formulas:

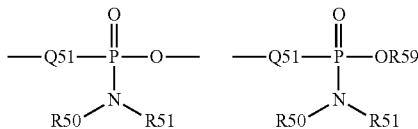

wherein Q51, R50, R51 and R59 are as defined above.

The term "phosphonamidite" is art-recognized and may be represented in the general formulas:

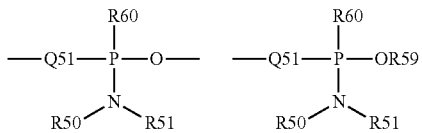

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The definition of each expression, e.g., alkyl, m, n, and the like, when it occurs more than once in any structure, is intended to be independent of its definition elsewhere in the same structure.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, "Handbook of Chemistry and Physics", 67th Ed., 1986-87, inside cover.

The term "treating" as used herein refers to the alleviation of symptoms of a particular disorder in a patient or the improvement of an ascertainable measurement associated with a particular disorder. As used herein, the term "patient" refers to a mammal, including a human.

While several embodiments of the present invention are described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

EXEMPLIFICATION

The invention now being generally described, it will be more readily understood by reference to the following examples which are included merely for purposes of illustration of certain aspects and embodiments of the present invention, and are not intended to limit the invention.

Abbreviations: Cp: *Cryptosporidium parvum*, BSA: bovine serum albumin, DCM: dichloromethane, DIPEA: diisopropylethylamine, hTERT: human telomerase reverse transcriptase, HTS: high throughput screening, IMP: inosine 5'-monophosphate, IMPDH: inosine 5'-monophosphate dehydrogenase, LAH: lithium aluminum hydride, NAD$^+$: nicotinamide-adenine dinucleotide, N.D.: not determined, SAR: structure-activity relationship, p-TSA: p-toluenesulfonic acid, TEA: triethylamine, THF: tetrahydrofuran, Toxo: *Toxoplasma*, WT: wild-type, XMP: xanthosine 5'-monophosphate.

Biological Assays.

Determination of IC$_{50}$ Values.

Inhibition of recombinant CpIMPDH, purified from *E. coli*, was assessed by monitoring the production of NADH by fluorescence at varying inhibitor concentrations (25 pM-5 µM). IMPDH was incubated with inhibitor for 5 min at room temperature prior to addition of substrates. The following conditions were used: 50 mM Tris-HCl, pH 8.0, 100 mM KCl, 3 mM EDTA, 1 mM dithiothreitol (assay buffer) at 25° C., 10 nM CpIMPDH, 300 µM NAD and 150 µM IMP. To characterize the non-specific binding of inhibitors, assays were also carried out in the presence of 0.05% BSA (fatty acid free). IC$_{50}$ values were calculated for each inhibitor according to Equation 1 using the SigmaPlot program (SPSS, Inc.):

$$v_i = v_o/(1+[I]/IC_{50}) \quad \text{(Eq. 1)}$$

where $v_i$ is initial velocity in the presence of inhibitor (I) and $v_o$ is the initial velocity in the absence of inhibitor. Inhibition at each inhibitor concentration was measured in quadruplicate and averaged; this value was used as $v_i$. The IC$_{50}$ values were determined three times; the average and standard deviations are reported.

Determination of Antiparastic Activity.

Antiparasitic activity was tested by monitoring the growth of a of *T. gondii* strain (Toxo/CpIMPDH) that relies on CpIMPDH. Wild-type *T. gondii* (Toxo/WT) relies on a eukaryotic IMPDH that should be resistant to CpIMPDH inhibitors. Both parasites express yellow fluorescent protein, which allows growth to be easily monitored. Parasites were cultured on hTERT immortalized human foreskin fibroblasts cells in 96 well plates and fluorescence was measured daily with a SpectraMax M22/M2e (Molecular Devices) plate reader (Ex 485, Em 530) for 6-7 days. Growth inhibition was calculated on a day within the exponential growth phase (see Sharling, L.; Liu, X.; Gollapalli, D. R.; Maurya, S. K.; Hedstrom, L.; Striepen, B., "A Screening Pipeline for Antiparasitic Agents Targeting *Cryptospordium* Inosine Monophosphate Dehydrogenase" *PLoS Negl Trop Dis* 2010, 4 (8), e794.

Stability Assays.

Mouse microsomal and plasma stability experiments were performed by Cyprotex Discovery (Watertown, Mass.).

Chemistry Materials and Methods.

Unless otherwise noted, all reagents and solvents were purchased from commercial sources and used without further purification. All reactions were performed under nitrogen atmosphere unless otherwise noted. The NMR spectra were obtained using a 400 MHz spectrometer. All $^1$H NMR spectra are reported in δ units ppm and are reference to tetramethylsilane (TMS) if conducted in CDCl$_3$ or to the central line of the quintet at 2.49 ppm for samples in DMSO-d$_6$. All chemical shift values are also reported with multiplicity, coupling constants and proton count. All $^{13}$C NMR spectra are reported in δ units ppm and are reference to the central line of the triplet at 77.23 ppm if conducted in CDCl$_3$ or to the central line of the septet at 39.5 ppm for samples in DMSO-d$_4$. Coupling constants (J values) are reported in hertz. Column chromatography was carried out on SILICYCLE SiliaFlash silica gel F60 (40-63 µm, mesh 230-400). High-resolution mass spectra were obtained using a Q-Tof Ultima mass spectrometer (University of Illinois Urbana-Champaign, Urbana, Ill. 61801). All melting points were taken in glass capillary tubes and are uncorrected. Chemical purity was determined using an HPLC instrument equipped with a quaternary pump and a Zorbax® SB-C8 column (30×4.6 mm, 3.5 µm). UV absorption was monitored at λ=254 nm. The injection volume was 5 µL. HPLC gradient went from 5% acetonitrile and 95% water to 95% acetonitrile and 5% water (both solvents contain 0.1% trifluoroacetic acid) over 1.9 min with a total run time of 2.5 min and a flow rate of 3.0 mL/min.

Synthesis of P Series Compounds and Examples

Scheme 1.

7 R = H
8 R = Me
9 R = CH$_2$CH$_2$NH$_2$ d, e or f

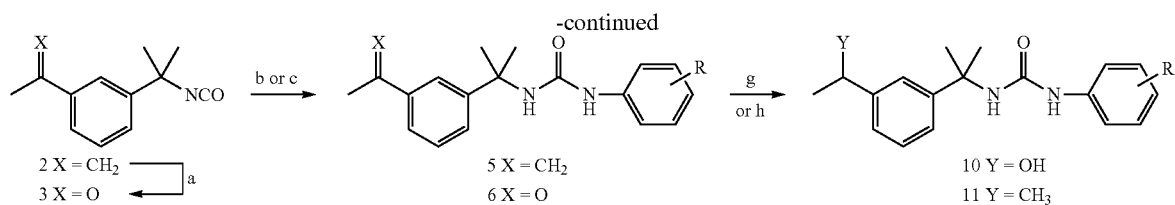

*Reagents and conditions: (a) (i) O₃, DCM, −78° C.; (ii) Me₂S, 10 h, 58%; (b) DCM,R — PhNH₂ (4), 2-4 h, 70-85%; (c) THF, R — PhNH₂ (4), 6 h, 70° C., 70-75%; (d) NH₂OH•HCl, pyridine, 2 h, 90° C., 80-85%; (e) NH₂OMe•HCl, pyridine, 2 h, 90° C., 60-85%; (f) (i) NaH, THF, 0° C., 30 min; (ii) Cl(CH₂)₂NH₂•HCl, rt, 10 h, 53%; (g) LAH, THF, 1 h, 0° C., 74%; (h) H₂/Pd — C, MeOH, 1 h, 90%.

Scheme 2.

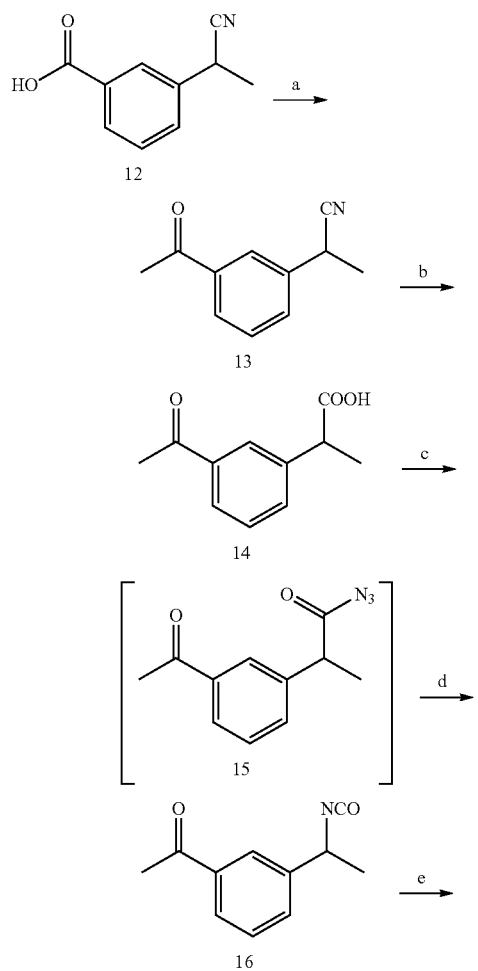

Scheme 3.

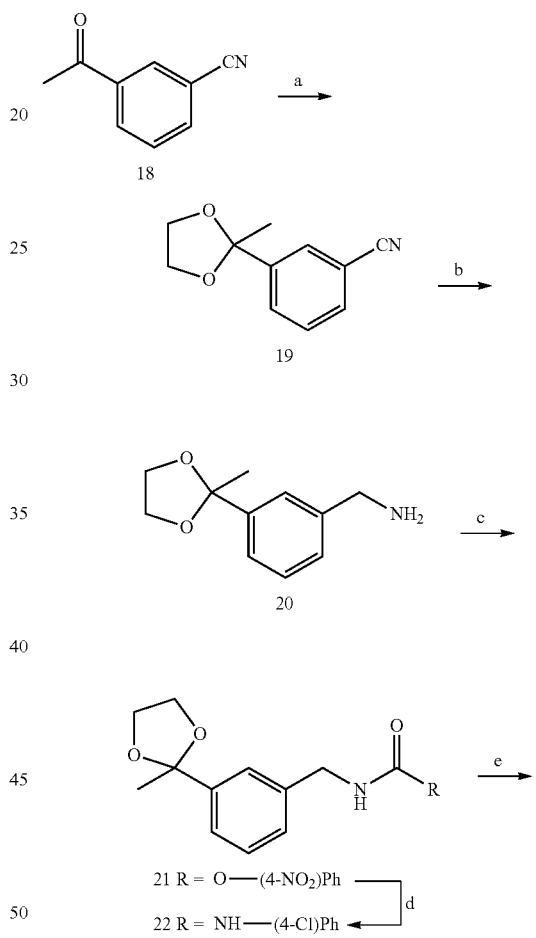

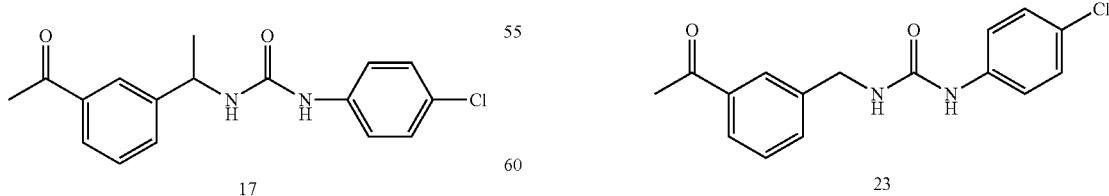

*Reagents and conditions (a) (i) SOCl₂, reflux, 2 h; (ii) Meldrum's acid, pyridine, DCM, 0-5° C., 2 h; iii) AcOH, H₂O, reflux, 4 h, 28%; (b) Conc. HCl, 1,4-dioxane, reflux, 2 h, 78%; (c) (i) SOCl₂, reflux; (ii) NaN₃, DCM; (d) benzene, reflux, 1.5 h, 92%; (e) 4-Cl-PhNH₂, THF, reflux, 6 h, 70%.

*Reagents and conditions (a) (CH₂OH)₂, p-TSA, benzene, 4 h, 110° C., Dean-Stark, 76%; (b) LAH, ether, 0° C., 1.5 h, 60%; (c) DIPEA, 4-NO₂—PhOCOCl, DCM/THF (1:1), rt, 24 h, 82%; (d) 4-Cl—PhNH₂, DCM, rt, 10 h, 71%; (e) 2N HCl, THF, rt, 2 h, 91%.

Scheme 4.

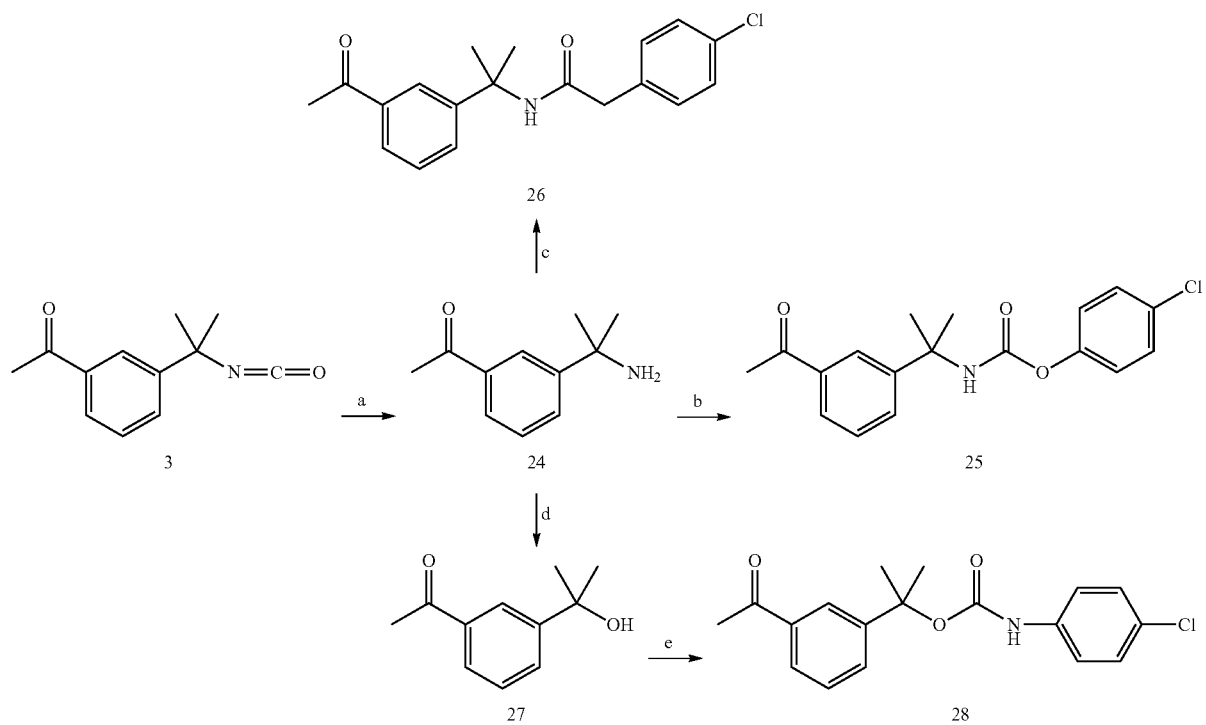

Reagents and conditions (a) 8N HCl, 70° C., 3 h, 55%; (b) 4-ClPhOCOCl, DIPEA, DCM/THF, rt, 24 h, 81%; (c) 4-Cl—PhCH₂COCl, DCM, 0° C. to rt, 80%; (d) (i) ClSO₃H, CHCl₃, 0° C. (ii) KNO₂ (iii) Water, pH = 2.8, 30%; (e) TEA, benzene, 4-Cl—Ph—NCO, 70° C., 3 h, 62%.

Scheme 5.

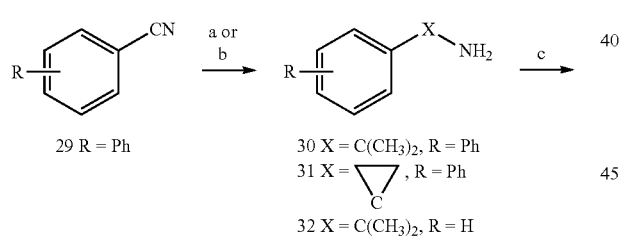

29 R = Ph

30 X = C(CH₃)₂, R = Ph
31 X = ▽C, R = Ph
32 X = C(CH₃)₂, R = H

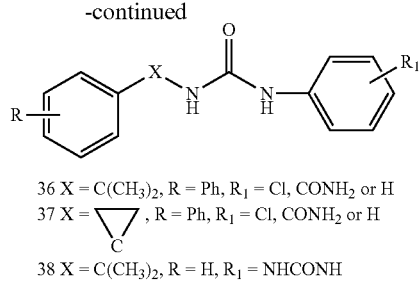

36 X = C(CH₃)₂, R = Ph, R₁ = Cl, CONH₂ or H
37 X = ▽C, R = Ph, R₁ = Cl, CONH₂ or H
38 X = C(CH₃)₂, R = H, R₁ = NHCONH

Reagents and conditions (a) (i) 3 equiv. CH₃MgBr, ether, rt, 30 min; (ii) Ti(i-PrO)₄, 10 h, 57%; (b) (i) 2 equiv. EtMgBr, Ti(i-PrO)₄, -78° C. to rt, 1 h; (ii) 2 equiv. BF₃•OEt₂, 1 h, 52%; (c) 4-NO₂PhOCOCl, DIPEA, DCM/THF, 10 h; (d) 4-Cl—PhNH₂, TEA, DCM, rt, 10 h, 71%.

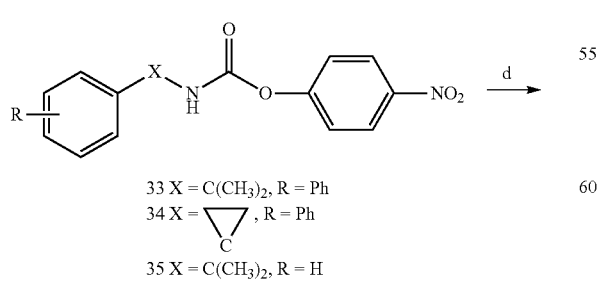

33 X = C(CH₃)₂, R = Ph
34 X = ▽C, R = Ph
35 X = C(CH₃)₂, R = H

Example 1

General procedure for the preparation of urea derivatives 5: Exemplified for the preparation of 1-(4-chlorophenyl)-3-(2-(3-(prop-1-en-2-yl)phenyl)propan-2-yl)urea (5b)

Synthesis of 3-acetyl-α,α-dimethylbenzyl isocyanate (3)

A solution of 3-isopropenyl-α, α-dimethyl benzyl isocyanate (2.04 g, 10.14 mmol) in dichloromethane (40 mL) was cooled to −78° C. and then treated with dry ozone in oxygen until a blue color persist. Excess ozone was flushed off with oxygen. Dimethyl sulfide (0.74 mL, 10.14 mmol) was added to the reaction mixture, which was then stirred overnight at room temperature. Excess Me$_2$S was removed by evaporated on a water bath placed inside a fume hood. Water (30 mL) was added to the reaction mixture, which was then extracted with dichloromethane. The combined organic layers were washed with brine (30 mL) and dried over anhydrous MgSO$_4$. The mixture was filtered and the filtrate concentrated. The residue was purified by silica gel column chromatography using ethylacetate/hexane (1:10) as an eluent to furnish 5b (1.19 g, 58%). $^1$H NMR (CDCl$_3$, 400 MHz) δ 1.76 (s, 6H), 2.63 (s, 3H), 7.47 (t, J=8 Hz, 1H), 7.67 (dd, J$_1$=7.6 Hz, J$_2$=2 Hz, 1H), 7.86 (dt, J$_1$=7.6 Hz, J$_2$=1.2 Hz, 1H), 8.04 (t, J=2 Hz, 1H); $^{13}$C NMR (CDCl$_3$, 100 MHz) δ 26.9, 33.2, 60.9, 124.2, 127.6, 129.0, 129.4, 137.4, 146.6, 198.1.

1-(4-chlorophenyl)-3-(2-(3-(prop-1-en-2-yl)phenyl)propan-2-yl)urea (5b)

To a solution of 3-isopropenyl α, α-dimethylbenzyl isocyanate 2 (473 mg, 2.35 mmol) in dichloromethane (6 mL) at 0° C. was added 4-chloroaniline (300 mg, 2.35 mmol) in dichloromethane (3 mL). The reaction was stirred until complete consumption of starting materials. The precipitated product was collected by filtration and washed with dichloromethane to give 5b (852 mg, 80%). mp 234-236° C. Yield 80%; $^1$H NMR (DMSO-d$_6$, 400 MHz) δ 1.58 (s, 6H), 2.08 (s, 3H), 5.06 (s, 1H), 5.36 (s, 1H), 6.64 (s, 1H), 7.20 (d, J=6.4 Hz, 2H), 7.23-7.32 (m, 5H), 7.47 (s, 1H), 8.55 (s, 1H); $^{13}$C NMR (DMSO-d$_6$, 100 MHz) δ 22.24, 30.30, 55.0, 113.06, 119.50, 122.35, 123.69, 124.86, 124.95, 128.65, 129.09, 140.11, 140.73, 143.60, 148.95, 154.53; ESI-HRMS for C$_9$H$_{22}$N$_2$OCl (M+H)$^+$ calcd. 329.1421. found 329.1418.

1-Phenyl-3-(2-(3-(prop-1-en-2-yl)phenyl)propan-2-yl)urea (5a)

mp 188-190° C.; Yield 81%; $^1$H NMR (DMSO-d, 400 MHz) δ 1.58 (s, 6H), 2.08 (s, 3H), 5.06 (s, 1H), 5.36 (s, 1H), 6.59 (s, 1H), 6.83 (t, J=7.2 Hz, 1H), 7.15 (t, J=8 Hz, 2H), 7.24-7.31 (m, 5H), 7.47 (s, 1H), 8.39 (s, 1H); $^{13}$C NMR (DMSO-d$_6$, 100 MHz) δ 22.25, 30.39, 54.97, 113.05, 118.00, 121.55, 122.36, 123.65, 124.87, 128.64, 129.28, 140.70, 141.12, 143.62, 149.11, 154.71; ESI-HRMS for C$_{19}$H$_{23}$N$_2$O (M+H)$^+$ calcd. 295.1810. found 389.1815.

1-(4-Bromophenyl)-3-(2-(3-(prop-1-en-2-yl)phenyl)propan-2-yl)urea (5c)

Yield 78%; $^1$H NMR (DMSO-d$_6$, 400 MHz) δ 1.61 (s, 6H), 2.10 (s, 3H), 5.08 (s, 1H), 5.38 (s, 1H), 6.66 (s, 1H), 7.28-7.35 (m, 5H), 7.49 (s, 1H), 8.57 (s, 1H); $^{13}$C NMR (DMSO-d$_6$, 100 MHz) δ 22.23, 30.29, 55.07, 112.76, 113.06, 119.96, 122.35, 123.70, 124.85, 128.65, 131.97, 140.53, 140.74, 143.62, 148.94, 154.50; ESI-HRMS for C$_{19}$H$_{22}$N$_2$OBr (M+H)$^+$ calcd. 373.0915. found 373.0915.

1-(3-Chlorophenyl-3-(2-(3-(prop-1-en-2-yl)phenyl)propan-2-yl)urea (5d)

Yield 83%; $^1$H NMR (DMSO-d$_6$, 400 MHz) δ 1.59 (s, 6H), 2.09 (s, 3H), 5.07 (s, 1H), 5.37 (s, 1H), 6.70 (s, 1H), 6.89 (d, J=7.6 Hz, 1H), 7.05 (d, J=7.6 Hz 1H), 7.19 (t, J=8 Hz, 1H), 7.28-7.30 (m, 3H), 7.48 (s, 1H), 7.60 (s, 1H), 8.63 (s, 1H); $^{13}$C NMR (DMSO-d$_6$, 100 MHz) δ 22.23, 30.26, 55.08, 113.08, 116.41, 117.32, 121.15, 122.32, 123.71, 124.83, 128.67, 130.88, 133.78, 140.74, 142.63, 143.60, 148.88, 154.44; ESI-HRMS for C$_{19}$H$_{22}$N$_2$OCl (M+H)$^+$ calcd. 329.1421. found 329.1430.

1-(2-Chlorophenyl)-3-(2-(3-(prop-1-en-2-yl)phenyl)propan-2-yl)urea (5e)

Yield 65%; $^1$H NMR (DMSO-d$_6$, 400 MHz) δ 1.62 (s, 6H), 2.1 (s, 3H), 5.08 (s, 1H), 5.38 (s, 1H), 6.91 (t, J=7.2 Hz, 1H), 7.16 (t, J=8.8 Hz, 1H), 7.30-7.32 (m, 3H), 7.37 (dd, 1H, J=7.2 Hz, J2=3.2 Hz), 7.49-7.52 (m, 2H), 8.02 (dd, J=7.8 Hz, J$_2$=2 Hz), 8.09 (d, J=2 Hz, 1H); $^{13}$C NMR (DMSO-d$_6$, 100 MHz) δ 22.22, 30.29, 55.17, 113.06, 121.08, 121.50, 122.32, 122.86, 123.69, 124.86, 127.99, 128.68, 129.67, 137.38, 140.71, 143.59, 148.92, 154.22; ESI-HRMS for C$_{19}$H$_{22}$N$_2$OCl (M+H)$^+$ calcd. 329.1421. found 329.1430.

1-(4-Methoyphenyl)-3-(2-(3-(prop-1-en-2-yl)propan-2-yl)phenyl)propan-2-yl)urea (5f)

Yield 85%; $^1$H NMR (DMSO-d, 400 MHz) δ 1.59 (s, 6H), 2.10 (s, 3H), 3.66 (s, 3H), 5.08 (s, 1H), 5.37 (s, 1H, 6.50 (s, 1H), 6.77 (d, J=8.4 Hz, 2H), 7.20 (d, J=8.4 Hz, 2H), 7.29-7.31 (m, 3H), 7.49 (s, 1H), 8.22 (s, 1H); $^{13}$C NMR (DMSO-d, 100 MHz) δ 22.23, 30.46, 54.92, 55.74, 113.01, 114.47, 119.64, 122.36, 123.60, 124.88, 128.61, 134.28, 140.67, 143.63, 149.25, 154.40, 154.95; ESI-HRMS for C$_{20}$H$_{25}$N$_2$O$_2$ (M+H)$^+$ calcd. 325.1916. found 325.1919.

1-(4-(tert-Butyl)phenyl)-3-(2-(3-(prop-1-en-2-yl)phenyl)propan-2-yl)urea (5g)

Yield 87%; $^1$H NMR (DMSO-d$_6$, 400 MHz) δ 1.20 (s, 9H), 1.58 (s, 6H), 2.09 (s, 3H), 5.06 (s, 1H), 5.36 (s, 1H), 6.54 (s, 1H), 7.15-7.19 (m, 4H), 7.27-7.30 (m, 3H), 7.48 (s, 1H), 8.31 (s, 1H); $^{13}$C NMR (DMSO-d$_6$, 100 MHz) δ 22.25, 30.45, 31.93, 34.42, 54.95, 113.02, 117.88, 122.37, 123.62, 124.87, 125.84, 128.62, 138.52, 140.70, 143.63, 143.79, 149.19, 154.82; ESI-HRMS for C$_{23}$H$_{31}$N$_2$O (M+H)$^+$ calcd. 351.2436. found 3512433.

1-(3,4-Dichlorophenyl)-3-(2-(3-(prop-1-en-2-yl)phenyl)propan-2-yl)urea (5h)

mp 198-200° C. Yield 80%; $^1$H NMR (DMSO-d, 400 MHz) δ 1.61 (s, 6H), 2.10 (s, 3H), 5.09 (s, 1H), 5.38 (s, 1H), 6.79 (s, 1H), 7.13 (t, J=4.8 Hz, 1H), 7.31-7.34 (m, 3H), 7.42 (d, J=7.6 Hz, 1H), 7.49 (s, 1H), 7.79 (s, 1H), 8.79 (s, 1H); $^{13}$C NMR (DMSO-d$_4$, 100 MHz) δ 22.23, 30.21, 55.14, 113.03, 118.13, 118.95, 122.31, 123.75, 124.82, 128.69, 131.07, 131.58, 140.76, 141.31, 141.34, 143.58, 148.79, 154.33; ESI-HRMS for C$_{19}$H$_{21}$N$_2$OCl$_2$ (M+H)$^+$ calcd. 363.1031. found 363.1029.

1-(4-Chloro-3-(trifluoromethyl)phenyl)-3-(2-(3-(prop-1-en-2-yl)phenyl)propan-2-yl)urea (5i)

Yield 82%; $^1$H NMR (DMSO-d$_6$, 400 MHz) δ 1.61 (s, 6H), 2.10 (s, 3H), 5.09 (s, 1H), 5.38 (s, 1H), 6.81 (s, 1H), 7.30-7.33 (m, 3H), 7.42-7.44 (m, 1H), 7.49-7.53 (m, 2H), 8.01 (s, 1H); $^{13}$C NMR (DMSO-d$_6$, 100 MHz) δ 22.22, 30.22, 55.20, 113.11, 116.35, 116.40, 121.90, 122.12, 122.30, 122.78, 123.77, 124.81, 128.70, 132.50, 140.66, 140.78, 143.58, 148.73, 154.36; ESI-HRMS for C$_{20}$H$_{21}$OClF$_3$ (M+H)$^+$ calcd. 397.1295. found 397.1296.

1-(4-Chlor-3-methoxyphenyl)-3-(2-(3-(prop-1-en-2-yl)phenyl)propan-2-yl)urea (5j)

Yield 89%: $^1$H NMR (DMSO-d$_6$, 400 MHz) δ 1.59 (s, 6H), 2.09 (s, 3H), 3.73 (s, 3H), 5.07 (s, 1H), 5.37 (s, 1H), 6.66 (s, 1H), 6.72 (d, J=8.8 Hz, 1H), 7.18 (d, J=8.8 Hz, 1H), 7.28-7.32 (m, 4H), 7.48 (s, 1H), 8.59 (s, 1H); $^{13}$C NMR (DMSO-d$_6$, 100 MHz) δ 22.23, 30.34, 55.03, 56.28, 102.50, 110.59, 112.95, 113.10, 122.33, 123.72, 124.85, 128.70, 130.16, 140.75, 141.47, 143.59, 148.97, 154.53, 155.10; ESI-HRMS for $C_{20}H_{24}N_2O_2Cl$ (M+H)$^+$ calcd. 359.1529. found 359.1532.

2-Chloro-5-(2-(3-(prop-1-en-2-yl)phenyl)propan-2-yl)ureido)benzamide (5k)

Yield 72%; $^1$H NMR (DMSO-d$_6$, 400 MHz) δ 1.57 (s, 6H), 2.06 (s, 3H), 5.04 (s, 1H), 5.34 (s, 1H), 6.65 (s, 1H), 7.22-7.27 (m, 5H), 7.44-7.48 (m, 3H), 7.75 (s, 1H), 8.61 (s, 1H); $^{13}$C NMR (DMSO-d$_6$, 100 MHz) δ 22.23, 30.27, 55.08, 113.08, 117.61, 119.67, 121.36, 122.31, 123.71, 124.82, 128.66, 130.33, 137.89, 139.95, 140.73, 143.59, 148.89, 154.45, 168.85; ESI-HRMS for $C_{20}H_{23}N_3O_2Cl$ (M+H)$^+$ calcd. 372.1479. found 372.1485.

2-Chloro-N-methyl-5-(3-(2-(3-(prop-1-en-2-yl)phenyl)propan-2-yl)ureido)benzamide (5l)

Yield 72%; $^1$H NMR (CDCl$_3$, 400 MHz) δ 1.64 (s, 6H), 2.17 (s, 3H), 2.89 (d, J=4.8 Hz, 3H), 5.05 (s, 1H), 5.32 (s, 1H), 5.97 (s, 1H,), 6.61 (d, J=4.4 Hz, 1H), 7.10-7.13 (m, 2H), 7.27-7.31 (m, 2H), 7.49-7.51 (m, 3H), 7.81 (s, 1H); $^{13}$C NMR (DMSO-d$_6$, 100 MHz) δ 22.25, 26.56, 30.26, 55.08, 113.09, 117.76, 119.75, 121.57, 122.31, 123.71, 124.82, 128.66, 130.32, 137.80, 140.01, 140.74, 143.59, 148.90, 167.41, 189.22; ESI-HRMS for $C_{21}H_{25}N_3O_2Cl$ (M+H)$^+$ cacld. 386.1635. found 386.1639.

2-Chloro-N,N-dimethyl-5-(3-(2-(3-(prop-1-en-2-yl)phenyl)propan-2-yl)ureido)benzamide (5m)

Yield 72%; $^1$H NMR (CDCl$_3$, 400 MHz) δ 1.66 (s, 6H), 2.13 (s, 3H), 2.86 (s, 3H), 3.07 (s, 3H), 5.05 (s, 1H), 5.33 (s, 1H), 6.02 (s, 18,), 6.88 (d, J=2.4 Hz, 1H), 7.11 (d, J=8.8 Hz, 2H), 7.25-7.35 (m, 4H), 7.50 (s, 1H), 8.01 (s, 1H); $^{13}$C NMR (CDCl$_3$, 100 MHz) δ 22.17, 29.89, 30.16, 34.94, 38.49, 55.13, 112.51, 116.93, 120.92, 121.29, 122.18, 123.81, 124.24, 128.33, 129.97, 135.15, 139.83, 141.27, 143.81, 147.93, 154.48, 169.80; ESI-HRMS for $C_{22}H_{27}N_3O_2Cl$ (M+H)$^+$ calcd. 400.1792. found 400.1787.

1-(2,3-Dihydrobenzo[b][1,4]dioxin-6-yl)-3-(2-(3-(prop-1-en-2-yl)phenyl)propan-2-yl)urea (5n)

Yield 75%; $^1$H NMR (DMSO-d$_6$, 400 MHz) δ 1.59 (s, 6H), 2.10 (s, 3H), 4.15 (d, J=7.6 Hz, 4H), 5.08 (s, 1H), 5.37 (s, 1H), 6.50 (s, 1H), 6.67 (d, J=8.4 Hz, 2H), 6.97 (s, 1H), 7.29-7.31 (m, 3H), 7.49 (s, 18), 8.22 (s, 1H); $^{13}$C NMR (DMSO-d$_6$, 100 MHz) δ22.22, 30.42, 54.93, 64.44, 64.82, 107.22, 111.36, 113.0, 117.31, 122.35, 123.60, 124.85, 128.60, 134.89, 138.31, 140.68, 143.62, 143.65, 149.17, 154.81; ESI-HRMS for $C_{21}H_{25}N_2O_3$ (M+H)$^+$ calcd. 353.1865. found 353.186.

1-(Naphthalen-2-yl)-3-(2-(3-(prop-1-en-2-yl)phenyl)propan-2-yl)urea (5o)

mp 201-203° C.; Yield 75%; $^1$H NMR (DMSO-d, 400 MHz) δ 1.64 (s, 6H), 2.11 (s, 3H), 5.08 (s, 1H), 5.39 (s, 1H), 6.72 (s, 1H), 7.27-7.39 (m, 6H), 7.53 (d, J=1.2 Hz, 1H), 7.68 (d, J=8 Hz, 1H), 7.75 (d, J=8.4 Hz, 2H), 7.98 (s, 1H), 8.64 (s, 18); $^{13}$C NMR (DMSO-d$_6$, 100 MHz) δ 22.23, 30.35, 55.04, 112.83, 113.06, 119.92, 122.37, 123.69, 124.12, 124.90, 126.85, 127.38, 128.01, 128.67, 128.89, 129.29, 134.49, 138.73, 140.75, 143.63, 149.09, 154.78; ESI-HRMS for $C_{23}H_{25}N_2O$ (M+H)$^+$ calcd. 345.1967. found 345.1964.

1-(Naphthalen-1-yl)-3-(2-(3-(prop-1-en-2-yl)phenyl-propan-2-yl)urea (5p)

mp 206-208° C.; Yield 75%; $^1$H NMR (DMSO-d, 400 MHz) δ 1.66 (s, 6H), 2.10 (s, 3H), 5.08 (s, 1H), 5.39 (s, 1H), 7.13 (s, 1H), 7.29-7.38 (m, 4H), 7.50-7.55 (m, 4H), 7.90 (d, J=7.6 Hz, 1H), 7.87 (d, J=8 Hz, 1H), 8.10 (d, J=8.4 Hz, 18), 8.54 (s, 1H); $^{13}$C NMR (DMSO-d$_6$, 100 MHz) δ 22.24, 30.42, 55.16, 113.05, 116.51, 121.79, 122.40, 123.68, 124.92, 125.80, 126.01, 126.36, 126.52, 128.68, 129.06, 134.33, 135.77, 140.74, 143.61, 149.15, 155.02; ESI-HRMS for $C_{23}H_{25}N_2O$ (M+H)$^+$ calcd. 345.1967. found 345.1976.

1-(2-(3-(Prop-1-en-2-yl)phenyl)propan-2-yl)-3-(quinolin-6-yl)urea (5q)

Yield 81%; $^1$H NMR (DMSO-d$_6$, 400 MHz) δ 1.65 (s, 6H), 2.11 (s, 3H), 5.08 (s, 1H), 5.39 (s, 1H), 7.10 (s, 1H), 7.29-7.37 (m, 2H), 7.54 (s, 1H), 7.67-7.74 (m, 2H), 8.04 (d, J=9.2 Hz, 1H), 8.27 (d, J=2 Hz, 1H), 8.33 (s, 1H), 8.57 (d, J=8.4 Hz, 1H), 8.87 (d, J=4 Hz, 1H), 9.39 (s, 1H); $^{13}$C NMR (DMSO-d$_6$, 100 MHz) δ 22.25, 30.31, 55.14, 112.04, 113.07, 122.37, 122.45, 123.68, 124.87, 125.70, 125.75, 128.65, 130.06, 138.77, 138.79, 140.72, 140.75, 143.58, 145.04, 148.96, 154.68; ESI-HRMS for $C_{22}H_{24}N_3O$ (M+H)$^+$ calcd. 346.1919. found 346.1925.

1-(2-(3-(Prop-1-en-2-yl)phenyl)propan-2-yl)-3-(quinolin-7-yl)urea (5r)

Yield 72%; $^1$H NMR (DMSO-dc 400 MHz) δ 1.64 (s, 6H), 2.11 (s, 3H), 5.08 (s, 1H), 5.39 (s, 114), 6.79 (s, 1H), 7.28-7.37 (m, 4H), 7.47-7.53 (m, 2H), 7.80 (d, J=8.8 Hz, 1H), 8.03 (d, J=2 Hz, 1H), 8.18 (d, J=8.4 Hz, 1H), 8.75 (dd, $J_1$=4.4 Hz, $J_2$=1.6 Hz, 1H), 8.85 (s, 1H); $^{13}$C NMR (DMSO-d$_6$, 100 MHz) δ 22.23, 30.30, 55.16, 113.09, 113.66, 119.69, 120.23, 122.37, 123.73, 124.88, 128.69, 128.98, 136.03, 140.77, 142.06, 143.61, 148.92, 149.48, 151.27, 154.55; ESI-HRMS for $C_{22}H_{24}N_3O$ (M+H)$^+$ calcd. 346.1919. found 346.1915.

1-(2-(prop-1-en-2-yl)phenyl)propan-2-yl)-3-(quinolin-3-yl)urea (5r)

Yield 69%; $^1$H NMR (DMSO-d$_6$, 400 MHz) δ 1.65 (s, 6H), 2.11 (s, 3H), 5.09 (s, 1H), 5.39 (s, 1H), 6.88 (s, 1H), 7.31-7.38 (m, 3H), 7.49-7.55 (m, 3H), 7.79 (d, J=7.2 Hz, 1H), 7.88 (d, J=7.4 Hz, 1H), 8.41 (s, 1H), 8.66 (d, J=2.4 Hz, 1H), 8.91 (s, 1H); $^{13}$C NMR (DMSO-d$_6$, 100 MHz) δ 22.24, 30.25, 55.17, 113.11, 119.44, 122.35, 123.75, 124.89, 127.27, 127.49, 127.81, 128.71, 128.90, 129.10, 134.88, 140.77, 143.60, 143.82, 144.47, 148.88, 154.72; ESI-HRMS for $C_{22}H_{24}N_3O$ (M+H)$^+$ calcd. 346.1919. found 346.1924.

1-(2-(3-(prop-1-en-2-yl)phenyl)propan-2-yl)-3-(quinolin-2-yl)urea (5t)

mp 126-128° C.; Yield 75%; $^1$H NMR (CDCl$_3$, 400 MHz) δ 1.90 (s, 6H), 2.13 (s, 3H), 5.05 (s, 1H), 5.37 (s, 1H), 6.54

(d, J=8.8 Hz, 1H), 7.25-7.38 (m, 3H), 7.48 (d, J=7.6 Hz, 1H), 7.57-7.67 (m, 4H), 7.83 (d, J=8.8 Hz, 1H), 9.69 (s, 1H), 10.92 (s, 1H); $^{13}$C NMR (CDCl$_3$, 100 MHz) δ22.20, 30.11, 55.62, 113.19, 114.22, 122.47, 123.95, 124.71, 124.84, 124.89, 126.57, 128.42, 128.82, 130.71, 139.03, 140.94, 143.57, 145.55, 148.65, 153.54, 154.10; ESI-HRMS for C$_{22}$H$_{24}$N$_3$O (M+H)$^+$ calcd. 346.1919. found 346.1917.

1-(4-Chlorophenyl)-1-methyl-3-(2-(3-(prop-1-en-2-yl)phenyl)propan-2-yl)urea (5u)

Yield 56%; $^1$H NMR (DMSO-d$_6$, 400 MHz) δ 1.50 (s, 6H), 2.06 (s, 3H), 3.11 (s, 3H), 5.04 (s, 1H), 5.32 (s, 1H), 6.11 (s, 1H), 7.21-7.25 (m, 5H), 7.34-7.40 (m, 3H); $^{13}$C NMR (DMSO-d, 100 MHz) δ 22.25, 30.28, 37.49, 55.72, 112.90, 122.26, 123.40, 124.81, 127.92, 128.49, 129.50, 129.58, 140.54, 143.64, 144.18, 149.37, 156.06; ESI-HRMS for C$_{20}$H$_{24}$N$_2$OCl (M+H)$^+$ calcd. 343.1577. found 343.1570.

Example 2

General procedure for the preparation of urea derivatives 6: Exemplified for the preparation of 5-(3-(2-(3-acetylphenyl)propan-2-yl)ureido-2-chlorobenzamide (6b)

To a solution of 3-acetyl α, α dimethyl isocyanate 3 (118 mg, 0.584 mmol) in THF at room temperature was added 5-amino-2-chlorobenzamide (100 mg, 0.584 mmol). The reaction was heated to 70° C. for 6 h. Volatiles were removed under reduced pressure and the residue was purified by column chromatography using methanol/chloroform as eluent to obtain urea derivative 6b (156 mg, 72%). $^1$H NMR (DMSO-d, 400 MHz) δ 1.61 (s, 6H), 2.58 (s, 3H), 6.80 (s, 1H), 7.26 (s, 2H), 7.45-7.52 (m, 3H), 7.66 (d, J=7.2 Hz, 1H), 7.79-7.83 (nm, 2H), 7.94 (s, 1H), 8.68 (s, 1H); $^{13}$C NMR (DMSO-d, 100 MHz) δ 27.44, 30.19, 54.89, 117.63, 119.72, 121.43, 124.57, 127.12, 129.11, 130.42, 137.24, 137.89, 139.87, 149.54, 154.40, 168.87, 198.76; ESI-HRMS for C$_{25}$H$_{16}$N$_3$O (M+H)$^+$ calcd. 374.1293. found 374.1283.

1-(2-(3-Acetylphenyl)propan-2-yl)-3-(4-chloro-3-(trifluoromethyl)phenyl)urea (6a)

Yield 69%; $^1$H NMR (DMSO-d$_6$, 400 MHz) δ 1.62 (s, 6H), 2.51 (s, 3H), 6.91 (s, 1H), 7.42-7.53 (m, 3H), 7.68 (d, J=7.2 Hz, 1H), 7.84 (d, J=7.2 Hz, 1H), 7.95 (s, 18), 8.01 (s, 1H), 8.95 (s, 1H); $^{13}$C NMR (DMSO-d$_6$, 100 MHz) δ 27.45, 30.14, 54.99, 116.36, 116.41, 116.47, 121.96, 122.83, 124.56, 127.17, 129.15, 130.42, 132.50, 137.28, 140.58, 149.37, 154.31, 198.71; ESI-HRMS for C$_{19}$H$_{19}$N$_2$O$_2$ClF$_3$ (M+H)$^+$ calcd. 399.1087. found 399.1089.

Example 3

General procedure for the preparation of oxime derivatives 7: Exemplified for the preparation of (E)-2-chloro-5-(3-(2-(3-(1-(hydroxyimino)ethyl)phenol)propan-2-yl)ureido)benzamide (7c)

Hydroxylamine hydrochloride (25 mg, 0.362 mmol) was added to a solution of 56 (100 mg, 0.302 mmol) in 3 mL of pyridine. The reaction solution was heated to 90° C. for 2 hours. The reaction was allowed to cool to room temperature and then the pyridine was removed by evaporation under reduced pressure. The resulting residue was dissolved in methanol and purified by column chromatography eluting with methanol/chloroform to obtained 7c (88 mg, 85%). $^1$H NMR (DMSO-d$_6$, 400 MHz) δ 1.54 (s, 6H), 2.11 (s, 3H), 6.67 (s, 1H), 7.20-7.49 (m, 7H), 7.67 (s, 1H), 7.76 (s, 1H), 8.62 (s, 1H), 11.13 (s, 1H); $^{13}$C NMR (DMSO-d$_6$, 100 MHz) δ 12.42, 30.27, 54.98, 117.59, 119.67, 121.38, 122.44, 124.21, 125.87, 128.76, 130.35, 137.33, 137.90, 139.96, 148.95, 153.79, 154.39, 168.90; ESI-HRMS for C$_{19}$H$_{22}$N$_4$O$_3$Cl (M+H)$^+$ calcd. 389.1380. found 389.1384.

(E)-1-(4-Chloro-3-(trifluoromethyl)phenyl)-3-(2-(3-(1-(hydroxyimino)ethyl)phenyl)propan-2-yl)urea (7a)

mp 194-196° C.; Yield 71%; $^1$H NMR (DMSO-d$_6$, 400 MHz) δ 1.61 (s, 6H), 2.15 (s, 3H), 6.82 (s, 1H), 7.34 (d, J=8 Hz, 1H), 7.39-7.46 (m, 3H), 7.52 (d, J=9.2 Hz, 1H), 7.70 (s, 1H), 8.01 (s, 1H), 8.91 (s, 1H), 11.17 (bs, 1H); $^{13}$C NMR (DMSO-d$_6$, 100 MHz) δ 12.39, 30.19, 55.07, 116.31, 116.37, 116.42, 121.91, 122.44, 122.76, 124.25, 125.84, 128.78, 132.50, 137.36, 140.64, 149.77, 153.74, 154.29; ESI-HRMS for C$_{19}$H$_{20}$N$_3$O$_2$ClF$_3$ (M+H)$^+$ calcd. 414.1196. found 414.1191.

(E)-1-(4-Chloro-3-nitrophenyl-3-(2-(3-(1-(hydroxyimino)ethyl)phenyl)propan-2-yl)urea (7b)

mp 183-185° C.; Yield 80%; $^1$H NMR (DMSO-d$_6$, 400 MHz) δ 1.62 (s, 6H), 2.16 (s, 3H), 6.91 (s, 1H), 7.35 (t, J=8.0 Hz, 1H), 7.35 (t, J=8.0 Hz, 1H), 7.41-7.47 (m, 3H), 7.58 (d, J=8.8 Hz, 1H), 7.71 (s, 1H), 8.22 (d, J=2.4 Hz, 1H), 9.04 (s, 1H), 11.18 (s, 1H); 13C NMR (DMSO-d$_6$, 100 MHz) δ 12.4, 30.13, 55.12, 113.84, 116.26, 122.42, 122.86, 124.27, 125.84, 128.79, 132.28, 137.36, 141.11, 148.14, 148.67, 153.74, 154.12; ESI-HRMS for C$_{18}$H$_{20}$N$_4$O$_4$Cl (M+H)$^+$ calcd. 391.1173. found 391.1172.

(E)-1-(2-(3-(1-(Hydroxyimino)ethyl)phenyl)propan-2-yl)-3-(naphthalen-2-yl)urea (7d)

Yield 85%; $^1$H NMR (DMSO-d$_6$, 400 MHz) δ 1.69 (s, 6H), 2.21 (s, 3H), 6.81 (s, 1H), 7.35-7.50 (m, 6H), 7.72-7.80 (m, 4H), 8.05 (s, 1H), 8.70 (s, 1H), 11.22 (s, 1H); $^{13}$C NMR (DMSO-d$_6$, 100 MHz) δ 12.40, 30.32, 54.90, 112.75, 119.86, 122.49, 124.11, 124.16, 125.93, 126.85, 127.37, 128.00, 128.74, 128.90, 129.26, 134.48, 137.32, 138.70, 149.12, 153.77, 154.66; ESI-HRMS for C$_{22}$H$_{24}$N$_3$O$_2$ (M+H)$^+$ calcd. 362.1869. found 362.1872.

(E)-1-(2-(3-(1-(Hydroxyimino)ethyl)phenyl)propan-2-yl)-3-(quinolin-7-yl)urea (7e)

mp 164-166° C.; Yield 85%; $^1$H NMR (pyridine-d$_6$, 400 MHz) δ 1.68 (s, 6H), 2.28 (s, 3H), 6.99-7.02 (m, 2H), 7.25 (t, J=8 Hz, 1H), 7.53-7.62 (m, 3H), 7.88 (t, J=9.6 Hz, 2H), 8.16 (s, 1H), 8.63 (s, 1H), 8.77 (d, J=1.6 Hz, 1H), 9.54 (s, 1H); $^{13}$C NMR (DMSO-d$_6$, 100 MHz) δ 12.41, 30.29, 55.03, 113.61, 119.70, 120.20, 122.50, 123.78, 124.22, 125.93, 128.77, 129.01, 136.04, 137.35, 142.06, 148.97, 149.4, 151.29, 153.77, 154.47; ESI-HRMS for C$_{21}$H$_{23}$N$_4$O$_2$ (M+H)$^+$ calcd. 363.1821. found 363.1825.

Example 4

General procedure for the preparation of alkoxy oxime derivatives 8: Exemplified for the preparation of (E)-2-chloro-5-(3-(2-(3-(1-(methoxyimino)ethyl)phenyl)propan-2-yl)ureido)benzamide (8b)

Methoxyamine hydrochloride (30 mg, 0.362 mmol) was added to a solution of 6b (100 mg, 0.302 mmol) in 3 mL of pyridine. The reaction solution was heated to 90° C. for 2 h and then the pyridine was removed by evaporation under reduced pressure. The residue was dissolved in methanol and purified by column chromatography eluting with methanol/chloroform to obtained 8b (99 mg, 82%). $^1$H NMR (CDCl$_3$, 400 MHz) δ 1.55 (s, 6H), 2.12 (s, 3H), 3.91 (s, 3H), 6.18 (s, 1H), 6.59 (s, 1H), 6.86 (s, 1H), 7.06 (d, J=8.8 Hz, 1H), 7.15 (s, 1H), 7.25 (d, J=6.8 Hz, 1H), 7.33 (d, J=7.6 Hz, 1H), 7.37 (d, J=7.6 Hz, 2H), 7.67 (1H, s), 7.97 (s, 1H); $^{13}$C NMR (CDCl$_3$, 100 MHz) δ 13.29, 30.23, 54.97, 62.17, 117.68, 119.75, 121.42, 122.77, 124.49, 126.46, 128.83, 130.33, 136.30, 137.89, 139.93, 149.10, 154.43, 155.037, 168.88; ESI-HRMS for C$_{20}$H$_{24}$N$_4$O$_3$Cl (M+H)$^+$ calcd. 403.1537. found 403.1532.

(E)-1-(4-Chloro-3-(trifluoromethyl)phenyl)-3-(2-(3-(1-(methoxyimino)ethyl)phenyl)propan-2-yl)urea (8a)

$^1$H NMR (DMSO-d$_6$, 400 MHz) δ 1.62 (s, 6H), 2.1 (s, 3H), 3.90 (s. 3H), 6.84 (s, 1H), 7.36 (dd, J$_1$=7.6 Hz, J$_2$=1.6 Hz, 1H), 7.43-7.48 (m, 3H), 7.52 (dd, J$_1$=8.8 Hz, J$_2$=1.6 Hz), 7.67 (s, 1H), 8.01 (s. 1H), 8.93 (s, 1H); $^{13}$C NMR (DMSO-d$_6$, 100 MHz) δ 12.80, 29.86, 55.30, 62.04, 117.77, 117.82, 117.88, 122.29, 122.87, 124.88, 124.93, 125.63, 128.82, 131.77, 136.96, 137.96, 147.31, 154.63, 154.91; ESI-HRMS for C$_{20}$H$_{22}$N$_3$O$_2$F$_3$Cl (M+H)$^+$ calcd. 428.1353. found 428.1353.

(E)-1-(2-(3-(1-(Methoxyimino)ethyl)phenyl)propan-2-yl)-3-(naphthalen-2-yl)urea (8c)

Yield 58%; $^1$H NMR (DMSO-d$_6$, 400 MHz) δ 1.65 (s, 6H) 2.19 (s, 3H), 3.90 (s, 3H), 6.78 (s, 1H), 7.30-7.42 (4H, m), 7.48 (d, J=7.2 Hz, 2H), 7.68-7.72 (m, 2H), 7.76 (d, J=8.4 Hz, 2H), 8.00 (s, 1H), 8.67 (s, 1H); $^{13}$C NMR (DMSO-d$_6$, 100 MHz) δ 13.30, 30.30, 54.91, 62.16, 112.8, 119.9, 122.8, 124.1, 124.4, 126.5, 126.8, 127.3, 128.0, 128.83, 128.89, 129.28, 134.47, 136.29, 138.68, 149.28, 154.71, 155.06; ESI-HRMS for C$_{23}$H$_2$N$_3$O$_2$ (M+H)$^+$ calcd. 376.2025. found. 376.2026.

Preparation of (E)-1-(2-(3-(1-((2-aminoethoxy)imino)ethyl)phenyl)propan-2-yl)-3-(4 chloro-3-nitrophenyl)urea (9)

(E)-1-(4-Chloro-3-nitrophenyl)-3-(2-(3-(1-(hydroxyimino)ethyl)phenyl)propan-2-yl)urea (7b, 100 mg, 0.25 mmol) in 3 mL dry DMF was added drop wise at 0° C. to sodium hydride dispersion in mineral oil (15.3 mg, 0.50 mmol). The resulting mixture was stirred at 0° C. for 30 min. 2-Chloroethylamine hydrochloride (29.6 mg, 0.25 mmol) in 2 mL DMF was added and the reaction mixture was stirred at room temperature for 2 h and then the volatiles were removed under reduced pressure. The residue was dissolved in a minimal amount of methanol and purified by column chromatography using methanol/chloroform to obtained 9 (49 mg, 46%) $^1$H NMR (DMSO-d$_6$, 400 MHz) δ 1.61 (s, 6H), 2.19 (s, 3H), 2.79 (t, J=5.6 Hz, 2H), 4.05 (t, J=5.6 Hz, 2H), 6.95 (s, 1H), 7.34 (t, J=7.6 Hz, 1H), 7.42-7.47 (m, 3H), 7.56 (d, J=8.8 Hz, 1H), 7.65 (s, 1H), 8.20 (d, J=2 Hz, 1H), 9 (s, 1H); $^{13}$C NMR (DMSO-d$_6$, 100 MHz) δ 13.3, 30.1, 41.6, 55.4, 76.6, 113.8, 116.2, 122.7, 122.9, 124.5, 126.3, 128.8, 132.2, 136.5, 141.1, 148.1, 148.8, 154.2, 154.9; ESI-HRMS for C$_{20}$H$_{24}$Cl N$_5$O$_4$ (M+H)$^+$ calcd. 434.1595. found. 434.1595.

1-(4-chlorophenyl)-3-(2-(3-(1-hydroxyethyl)phenyl)propan-2-yl)urea (10)

A solution of 1-(2-(3-acetylphenyl)propan-2-yl)-3-(4-chlorophenyl)urea (25 mg, 0.07 mmol) in THF was cooled in an ice bath to 0° C. Lithium aluminum hydride solution (2 M in THF, 0.8 equiv) was added drop wise over 5 min and then the reaction was continued for approximately 1 h at 0° C. until starting material disappeared. The reaction was carefully quenched with a solution of sodium sulfate. The reaction mixture was filtered through a sintered funnel and the supernatant washed with dichloromethane. Combined organic fractions were concentrated under reduced pressure. The residue was purified by column chromatography using chloroform-methanol as a eluent to give 10 (19 mg, 74%). $^1$H NMR (DMSO-d$_6$, 400 MHz) δ 1.25 (d, J=6 Hz, 3H), 1.54 (s, 6H), 4.64 (pent, J=4.4 Hz, 1H), 5.09 (d, J=4 Hz, 1H), 6.56 (s, 1H), 7.11-7.19 (m, 5H), 7.28 (s, 1H), 7.31 (d, J=9.2 Hz, 1H), 8.51 (s, 1H); $^{13}$C NMR (DMSO-d$_6$, 100 MHz) δ 26.78, 30.33, 30.44, 55.06, 68.94, 119.47, 122.42, 123.70, 124.88, 128.28, 129.10, 140.18, 147.68, 148.65, 154.48; ESI-HRMS for C$_{18}$H$_{22}$N$_2$O$_2$Cl (M+H)$^+$ calcd. 333.1370. found 333.1378.

1-(2-(3-Isopropylphenyl)propan-2-yl)-3-(naphthale-2-yl)urea (11)

A solution of 1-(naphthalen-2-yl)-3-(2-(3-(prop-1-en-2-yl)phenyl)propan-2-yl)urea (5o, 25 mg, 0.072 mmol) in methanol (3 mL) containing a catalytic amount of 10% Pd/C. was placed under an atmosphere of hydrogen. After 1h the reaction mixture was filtered through a short silica gel column and concentrated to give 11 (24 mg, 98%). $^1$H NMR (DMSO-d$_6$, 400 MHz) δ 1.17 (d, J=4.4 Hz, 6H), 1.60 (s, 6H), 2.84 (hept, J=6.8 Hz, 1H), 6.66 (s, 1H), 7.03-7.36 (m, 7H), 7.66 (d, J=8 Hz, 1H), 7.75 (d, J=8 Hz, 2H); $^{13}$C NMR (DMSO-d, 100 MHz) 524.69, 30.42, 34.26, 55.09, 122.75, 118.22, 119.91, 123.01, 123.58, 124.08, 124.31, 126.84, 127.36, 128.01, 128.59, 128.87, 129.25, 134.49, 138.80, 149.00, 154.78; ESI-HRMS for C$_{23}$H$_{27}$N$_2$O (M+H)$^+$ calcd. 347.2123. found 347.2126.

2-(3-Acetylphenyl)propanenitrile (13)

Thionyl chloride (10 mL) was added at 0° C. to 3-(l-cyanoethyl)benzoic acid (12, 500 mg, 2.85 mmol). The reaction mixture was heated at 80° C. for 2 h. The excess thionyl chloride was removed to give 3-(l-cyanoethyl)benzoyl chloride, which was used without further purification.

Next, to a solution of Meldrum's acid (408 mg, 2.84 mmol) in dichloromethane (15 mL) at 0° C. was added pyridine (0.457 mL, 5.68 mmol). The resulting mixture was stirred for 15 min and then 3-(1-cyanoethyl)benzoyl chloride (482.5 mg, 2.5 mmol) was added. The reaction mixture was stirred at 0° C. for 30 min and then for 1 h at room temperature. The reaction mixture was diluted with dichloromethane and washed with 1 N HCl. The organic layer was dried over anhydrous magnesium sulfate, filtered and concentrated under reduced pressure. The crude product was dissolved in AcOH—H$_2$O (1:2) and heated at reflux for 4 h. The reaction mixture was diluted with water and extracted with ethyl acetate (3×30 mL). The combined organic extracts were washed with NaHCO$_3$ solution and brine, then dried over anhydrous magnesium sulfate, filtered and concentrated. The residue was purified by column chromatography using hexane-ethyl acetate (9:1) as eluent to give 13 (138 mg, 28%). $^1$H NMR (CDCl$_3$, 400 MHz) δ 1.68 (d, J=7.2 Hz 3H), 2.63 (s, 3H), 3.99 (q, J=7.2 Hz, 1H), 6.60 (d, J=7.6 Hz, 1H), 7.53 (d, J=2.8 Hz, 1H), 7.60 (d, J=7.2 Hz, 1H), 7.91 (t, J=2 Hz, 1H), 7.94 (s, 1H).

2-(3-Acetylphenyl) propanoic acid (14)

To a solution of 13 (100 mg, 0.57 mmol) in 2 mL of 1,4-dioxane was added conc. HCl (1.5 mL) and then the resulting mixture was refluxed for 5 h. After the mixture was allowed to cool to room temperature, the volatiles were removed under reduced pressure. The residue was diluted with water (10 mL) and extracted with dichloromethane (3×10 mL). The organic extracts were combined, washed with brine (2×10 mL), dried over anhydrous magnesium sulfate, filtered and concentrated to give 14 as a white solid (86 mg, 78% yield). $^1$H NMR (CDCl$_3$, 400 MHz) δ 1.57 (d, J=7.2 Hz, 3H), 2.38 (s, 3H), 3.83 (q, J=7.2 Hz, 1H), 7.42-7.50 (m, 2H), 7.61 (d, J=7.6 Hz, 1H), 7.75 (s, 1H).

2-(3-Acetylphenyl)propanoyl azide (15)

Thionyl chloride (2 mL) was added to 14 (86 mg, 0.40 mmol) at 0° C. The mixture was then heated at 80° C. for 2 h. The reaction mixture was concentrated under reduced pressure. The resulting acid chloride was used without further purification.

A solution of the acid chloride (84 mg, 0.40 mmol) in 3 mL dry acetone was added to a solution of sodium azide (325 mg, 5 mmol) in 2 mL of water at 0° C. over 10 min. The reaction mixture was stirred for 2 h at 25° C., and then poured into ice and extracted with ether (2×10 mL). The organic extracts were combined, washed with brine, dried over anhydrous MgSO$_4$, filtered and concentrated to give acyl azide 15, which was used without further purification.

1-(3-(1-Isocyanatoethyl)phenyl) ethanone (16)

Acyl azide 15 (80 mg, 0.42 mmol) was refluxed in benzene (5 mL) of 1.5 h and then the solvent was removed under vacuum to give isocyanate 16 in quantitative yield, which was used without further purification.

1-(1-(3-Acetylphenyl)ethyl)-3-(4-chlorophenyl)urea (17)

Compound 17 (71%) was prepared following the general procedure for 6. $^1$H NMR (DMSO-d$_6$, 400 MHz) δ 1.35 (d, J=6.8 Hz, 3H), 2.55 (s, 3H), 4.95 (pent, J=6.8 Hz, 1H), 5.68 (d, J=7.2 Hz, 1H), 7.12-7.17 (m, 4H), 7.32-7.36 (m, 2H), 7.44 (d, J=8.0 Hz, 1H), 7.76 (d, J=7.6 Hz, 1H), 7.84 (s, 1H); $^{13}$C NMR (DMSO-d$_6$, 100 MHz) δ 23.20, 26.97, 49.77, 120.94, 124.96, 127.84, 128.14, 129.14, 129.16, 131.40, 137.47, 137.58, 145.23, 155.23, 199.09; ESI-HRMS for C$_{17}$H$_{18}$N$_2$O$_2$Cl (M+H)$^+$ calcd. 317.1057. found 317.1060.

3-(2-Methyl-1, 3-dioxolan-2-yl)benzonitrile (19)

To the mixture of ethylene glycol (0.22 mL, 4 mmol), 3-acetylbenzonitrile 18 (300 mg, 2.04 mmol) and benzene (10 mL) in a Dean-Stark apparatus was added a catalytic amount of p-TSA (0.1 equiv). The reaction mixture was heated at 110° C. for 4 h. The benzene was removed under reduced pressure and the residue was purified by column chromatography using ethylacetate-hexane as an eluent to give 19 (293 mg, 76%). $^1$H NMR (CDCl$_3$, 400 MHz) δ 2.62 (s, 4H), 7.59 (t, J=7.6 Hz, 1H), 7.82 (d, J=7.6 Hz, 1H)), 8.15 (d, J=8 Hz, 1H), 8.21 (s, 1H).

3-(2-Methyl-1,3-dioxolan-2-yl)phenylmethanamine (20)

A solution of cyano ketal 19 (290 mg, 1.53 mmol) in dry THF (10 mL) was cooled to 0° C. under a nitrogen atmosphere. Then a solution of 2 M lithium aluminum hydride (3 mmol) in THF was added over a 10-min period. The reaction mixture was stirred for 1.5 h and then ethyl acetate was added followed by slow addition of water to decompose the excess LAH. The reaction mixture was concentrated under reduced pressure. The residue was dissolved in chloroform, washed with brine, dried over anhydrous MgSO$_4$, filtered and concentrated. The residue was purified by column chromatography using chloroform and methanol as an eluent to give 20 (176 mg, yield 60%). $^1$H NMR (CDCl$_3$, 400 MHz) δ 1.66 (s, 3H), 3.79 (t, J=6 Hz, 2H), 3.88 (s, 2H), 4.04 (t, J=6 Hz, 2H), 7.24-7.42 (m, 4H).

4-Nitrophenyl 3-(2-methyl-1,3-dioxolan-2-yl)benzylcarbamate (21)

To a solution of benzylamine 20 (176 mg, 0.911 mmol) and N,N-diisopropylethylamine (313 μL, 1.8 mmol) in 4 mL of 1:1 CH$_2$Cl$_2$/THF was added a solution of 4-nitrophenyl-chloroformate (366 mg, 1.82 mmol) in 2 mL of 1:1 CH$_2$Cl$_2$/THF. After stirring the reaction mixture at room temperature for 24 h, it was diluted with dichloromethane and washed sequentially with saturated NaHCO$_3$, water and brine. The organic layer was dried over anhydrous MgSO$_4$, filtered and concentrated. The residue was purified by column chromatography eluting with ethylacetate/hexane to give 21 (267 mg, 82%).

1-(4-Chlorophenyl)-3-(3-(2-methyl-1,3-dioxolan-2-yl)benzyl)urea (22)

4-Nitrophenyl-N-benzylcarbamate 21 (267 mg, 0.767 mmol) was added to a solution of 4-chloroaniline (97 mg, 0.767 mmol) and triethylamine in dichloromethane (5 mL). The mixture was stirred at room temperature until starting materials were consumed. The reaction mixture was then diluted with dichloromethane (50 mL) and washed with aq. NaOH, water and brine. The organic layer was dried over anhydrous MgSO$_4$, filtered and concentrated The residue was purified by column chromatography eluting with methanol/chloroform to give 22 (165 mg, 71%). $^1$H NMR (CDCl$_3$, 400 MHz) δ 1.58 (s, 3H), 3.71 (t, J=6.8 Hz, 2H), 3.99 (t, J=6.8 Hz, 2H), 4.36 (d, J=5.6 Hz, 2H), 6.78 (s, 1H), 7.16-7.18 (m, 4H), 7.23-7.26 (m, 1H), 7.35 (d, J=5.6 Hz, 2H).

1-(3-Acetylbenzyl)-3-(4-chlorophenyl) urea (23)

A 2N HCl solution was added to a solution of 22 (165 mg, 0.479 mmol) in THF (2 mL). The mixture was refluxed for several hours until the starting materials were consumed. The reaction mixture was allowed to cool to room temperature, quenched with solid NaHCO$_3$, and then the volatiles were removed under reduced pressure. The residue was diluted with ethyl acetate and then washed with water. The organic layer was dried over anhydrous MgSO$_4$, filtered and concentrated. The residue was purified by chromatography to give 23 (144 mg, 100%) $^1$H NMR (DMSO-d, 400 MHz) δ 4.44 (d, J=5.6 Hz, 2H), 5.37 (t, J=3.7 Hz, 1H), 6.83 (s, 1H), 7.20-7.26 (5H, m), 7.40 (t, J=7.6 Hz, 1H), 7.50 (d, J=7.2 Hz, 1H), 7.82 (d, J=7.6 Hz, 1H), 7.85 (s, 1H); $^{13}$C NMR (DMSO-d$_6$, 100 MHz) δ 27.45, 43.13, 119.85, 125.21, 127.11, 127.59, 129.13, 129.37, 132.61, 137.49, 140.07, 141.68, 155.73, 198.58; ESI-HRMS for $C_{16}H_{16}N_2O_2Cl$ (M+H)$^+$ calcd. 303.0900. found 303.0907.

3-Acetyl-α, α-dimethylbenzylamine (24)

3-Acetyl-α, α-dimethylbenzyl isocyanate 3 (1000 mg, 4.92 mmol) in 8N HCl (30 mL) were refluxed for 30 min. The reaction mixture was cooled to 0° C. and then washed with diethyl ether. The aqueous portion was neutralized with a 10% NaOH solution and extracted with diethyl ether (3×20 mL). The combined organic layers were washed with brine, dried over anhydrous MgSO$_4$, filtered and concentrated. The residue was purified by chromatography eluting with methanol/chloroform to give 24 as a yellow oil (478 mg, 55%). $^1$H NMR (CDCl$_3$, 400 MHz) δ 1.57 (s, 6H), 2.61 (s, 3H), 3.72 (s, 2H), 7.43 (t, J=7.6 Hz, 1H), 7.75 (d, J=7.6 Hz, 1H), 7.82 (d, J=7.6 Hz, 1H), 8.14 (s, 1H).

4-Chlorophenyl (2-(3-acetylphenyl)propan-2-yl) carbamate (25)

4-Chlorophenyl chloroformate (317 μL, 2.24 mmol) in dichloromethane (2 mL) was added to a mixture of 3-acetyl-α, α-dimethylbenzylamine 24 and diisopropylethylamine (390 μL, 2.24 mmol). The reaction mixture was stirred for 2 h. It was then diluted with dichloromethane, washed with 1 N HCl, and then brine. The organic layer was dried over anhydrous magnesium sulfate, filtered and concentrated. The residue was purified by column chromatography using hexane/ethyl acetate as eluent to give 25 (594 mg, 81%). $^1$H NMR (CDCl$_3$, 400 MHz) δ 1.73 (s, 6H), 2.60 (s, 3H), 5.65 (s, 1H), 7.02 (d, J=8.4 Hz, 1H), 7.25 (d, J=6 Hz, 2H), 7.44 (t, J=8 Hz, 1H), 7.65 (d, J=7.6 Hz, 1H), 7.82 (d, J=7.6 Hz, 1H), 8.07 (1H, s); $^{13}$C NMR (DMSO-d, 100 MHz) δ 27.45, 29.79, 55.50, 124.23, 124.55, 127.31, 129.28, 129.55, 129.79, 130.39, 137.30, 148.70, 150.32, 152.97, 198.64; ESI-HRMS for $C_{18}H_{19}NO_3Cl$ (M+H)$^+$ calcd. 332.1053. found 332.1059.

N-(2-(3-Acetylphenyl)propan-2-yl)-2-(4-chlorophenyl)acetamide (26)

4-Chlorophenylacetylchloride (106 mg, 0.56 mmol) in dichloromethane was added to a solution of 3-acetyl-α, α-dimethylbenzylamine 24 (100 mg, 0.56 mmol) and triethylamine (120 μL, 0.86 mmol) in dichloromethane over a period of 5 to 10 min at 0° C. The reaction mixture was stirred at room temperature for 2 h. The mixture was diluted with dichloromethane (20 mL) and washed with 1 N HCl, water and brine. The organic layer was dried over anhydrous MgSO$_4$, filtered and concentrated. The residue was purified by column chromatography using hexane/ethyl acetate as eluent to give 26 (146 mg, 80%). $^1$H NMR (CDCl$_3$, 400 MHz) δ 1.61 (s, 6H), 2.53 (s, 3H), 3.46 (s, 2H), 5.68 (s, 1H), 7.19 (d, J=7.2 Hz, 2H), 7.30-7.38 (m, 3H), 7.46 (d, J=8 Hz, 1H), 7.75 (d, J=7.2 Hz, 1H), 7.87 (s, 1H); $^{13}$C NMR (DMSO-d$_6$ 100 MHz) δ 27.26, 29.89, 42.54, 55.34, 124.71, 126.76, 128.74, 128.98, 130.23, 131.45, 131.63, 136.22, 137.19, 148.96, 169.54, 198.59; ESI-HRMS for $C_{19}H_{21}NO_2Cl$ (M+H)$^+$ calcd. 330.1261. found 330.1270.

3-Acetyl-α, α-dimethylbenzylalcohol (27)

A solution of 3-acetyl-α α-dimethylbenzylamine (500 mg, 2.82 mmol) in chloroform was cooled to 0° C. Chlorosulfonic acid (109 mg, 0.94 mmol) was added drop wise over a period of 15 min. During this time a white precipitate formed. Stirring was continued for another 10 min. The reaction mixture was filtered to yield the corresponding substituted N-benzylsulfonic acid (253 mg, 70% with respect to chlorosulfonic acid), which was used without further purification.

The N-benzylsulfonic acid (169 mg, 0.658 mmol) was suspended in 2 mL of water and then KNO$_2$ (168 mg, 1.97 mmol, 3 equiv) was added. An almost clear solution was immediately formed. To this solution was added 2 mL sulfate buffer (pH=2.8) and the resulting mixture was stirred for 2 hours. The reaction mixture was diluted with 4 mL water and extracted with ethyl acetate (3×10 mL). The combined organic layers were washed with water. The organic layer was dried over anhydrous MgSO$_4$, filtered and concentrated. The residue was purified by column chromatography eluting with ethyl acetate/hexane to obtained 26 (26 mg, 30%). $^1$H NMR (CDCl$_3$, 400 MHz) δ 1.55 (s, 6H), 2.55 (s, 3H), 7.37 (t, J=8 Hz, 1H), 7.66 (d, J=7.2 Hz, 1H), 7.76 (d, J=7.6 Hz, 1H), 8.04 (s, 1H). $^{13}$C NMR (CDCl$_3$, 400 MHz) δ 26.9, 31.9, 72.5, 124.4, 126.9, 128.6, 129.6, 137.1, 150.0, 198.8.

2-(3-Acetylphenyl) propan-2-yl (4-chlorophenyl) carbamate (28)

To a solution of 3-acetyl-α, α-dimethylbenzylalcohol (27, 21 mg, 0.117 mmol) in 2 mL dry benzene was added 4-chlorophenyl isocyante, followed by 17 μL triethyamine. The reaction mixture was heated to 70° C. for 3 h. The reaction mixture was allowed to cool to room temperature and then diluted with ethyl acetate (20 mL), washed with 1 N HCl, brine and water. The organic layer was dried over anhydrous magnesium sulfate, filtered and evaporated. The residue was purified by column chromatography eluting with ethyl acetate/hexane yielding 28 (23 mg, 62%). $^1$H NMR (CDCl$_3$, 400 MHz) δ 1.84 (s, 6H), 2.60 (s, 3H), 6.71 (s, 1H), 7.20 (d, J=8.8 Hz, 2H), 7.27 (d, J=8.4 Hz, 2H), 7.45 (t, J=8.0 Hz), 7.62 (d, J=7.6 Hz, 1H), 7.84 (d, J=7.6 Hz, 1H), 8.02 (s, 1H); $^{13}$C NMR (CDCl$_3$, 100 MHz) δ 26.96, 29.08, 81.73, 119.8, 127.74, 128.90, 129.15, 129.26, 129.92, 136.67, 137.39, 146.71, 151.89, 198.29; ESI-HRMS for $C_{18}H_{18}ClNO_3$ (M+Na)+ calcd. 354.0873. found 354.0872.

5-(3-(1-([1,1'-Biphenyl]-3-yl)cyclopropyl)ureido)-2-chlorobenzamide (37)

Prepared following the same procedure as 22. Yield 62%; $^1$H NMR (DMSO-d$_6$, 400 MHz) δ 1.23 (t, 2H, J=6.8 Hz), 1.30 (t, 2H, J=8 Hz), 7.22 (d, J=7.2 Hz, 2H), 7.28 (d, J=8.8 Hz, 1H), 7.35-7.47 (m, 5H), 7.53 (t, J=2.4 Hz, 2H), 7.61 (d, J=7.6 Hz, 2H), 7.80 (s, 1H), 8.70 (s, 1H), 8.70 (s, 1H); $^{13}$C NMR (DMSO-d$_6$, 100 MHz) δ 19.2, 34.9, 118.1, 121.6, 123.7, 124.6, 124.8, 127.0, 127.4, 128.0, 129.3, 129.5, 130.3, 137.8, 139.8, 140.7, 141.1, 145.5, 155.5, 168.8; ESI-HRMS for $C_{23}H_{20}N_3O_2Cl$ (M+H)$^+$ calcd. 406.1322. found 406.1323.

Synthesis of Q Series Compounds

Scheme 1: General procedure for the synthesis of Benzoxazole derivatives

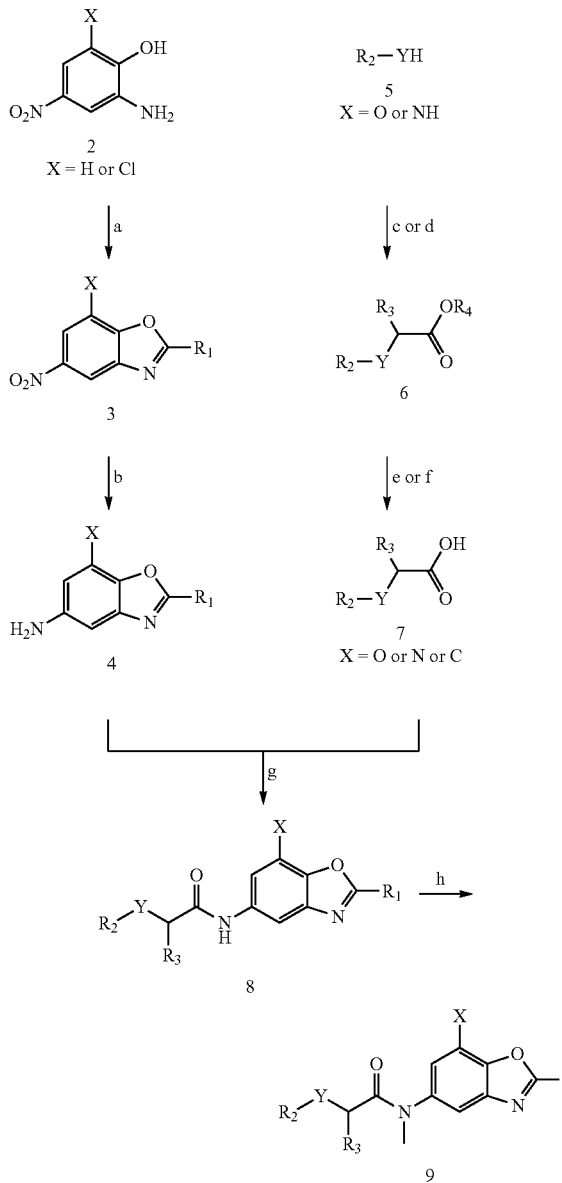

$R_1$ = Pyridyl, Thiazole, Pyrimidine, Phenyl, pyrrole
$R_2$ = substituted-Ph, Naphthyl.
$R_3$ = Methyl, isopropyl.
$R_4$ = Me, Et Reagents and conditions: (a) $R_1$—CHO, $O_2$, DarcoKB, xylene, 120° C., 6 h, 70-80% (b) $H_2$, 10% Pd—C, EtOAc, 1 atm, 6 h, 80-86% (c) $R_3$CHBrCOOR$_4$, $K_2CO_3$, DMF, rt, 5 h, 85-92% (d) (R) or (S) $R_3$CH(OH)COOR$_4$, 0° C., PPh$_3$, 10 min, DEAD, rt, 12 h, 75-84% (e) 3M NaOH, THF:H$_2$O (2:1), 80° C., 3 h, 85-95% (f) 3N HCl, THF, 70° C., 6 h, 60-70% (g) 0° C., EDCl•HCl, DMF, rt, 12 h, 63-79% (h) MeI, NaH, THF, 0° C.-rt, 1.5 h, 48%.

Scheme 2: General procedure for the synthesis of secondary chiral amines of Benzoxazole derivatives:

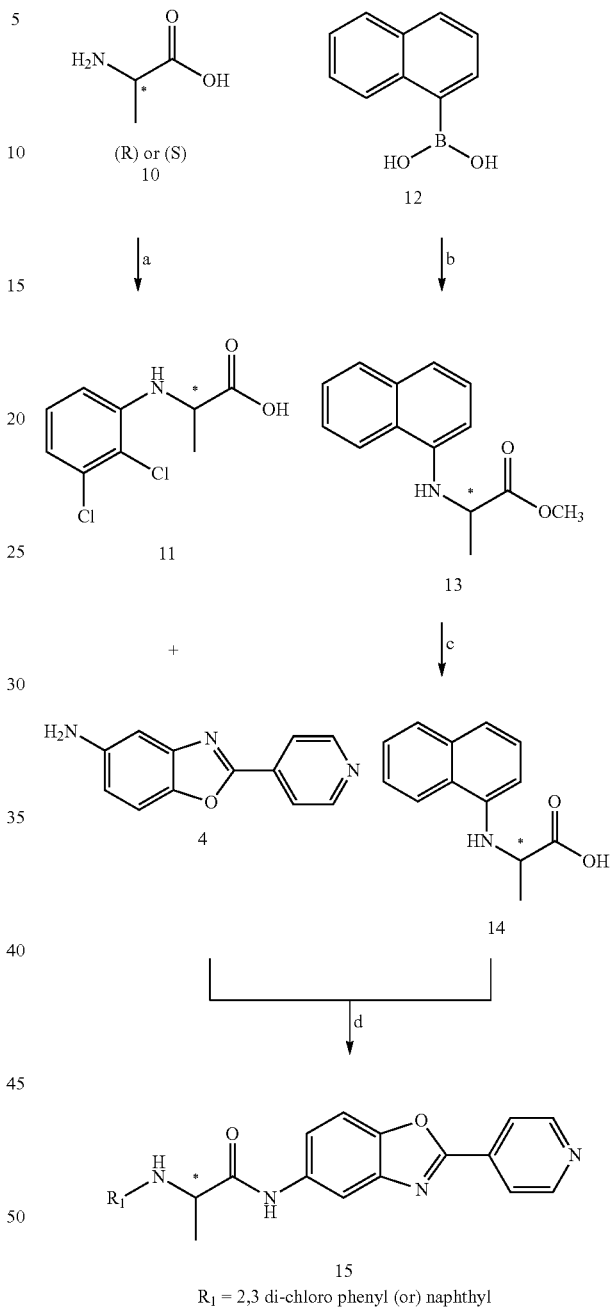

$R_1$ = 2,3 di-chloro phenyl (or) naphthyl

Reagents and conditions: (a) 2,3-di-chloro iodobenzene, $Cs_2CO_3$, CuI, DMF, 90° C., 48 h, 57% (b) L-alanine methyl ester hydrochloride, Cu(OAc)$_2$, DCM, TEA, 4A° molecular sieves, 34% (c) 1M NaOH, EtOH, rt, 67% (d) EDCl•HCl, DMF, rt, 12 h, 60-70%.

Scheme 3: Synthesis of Benzoxazole derivative without ether oxygen:

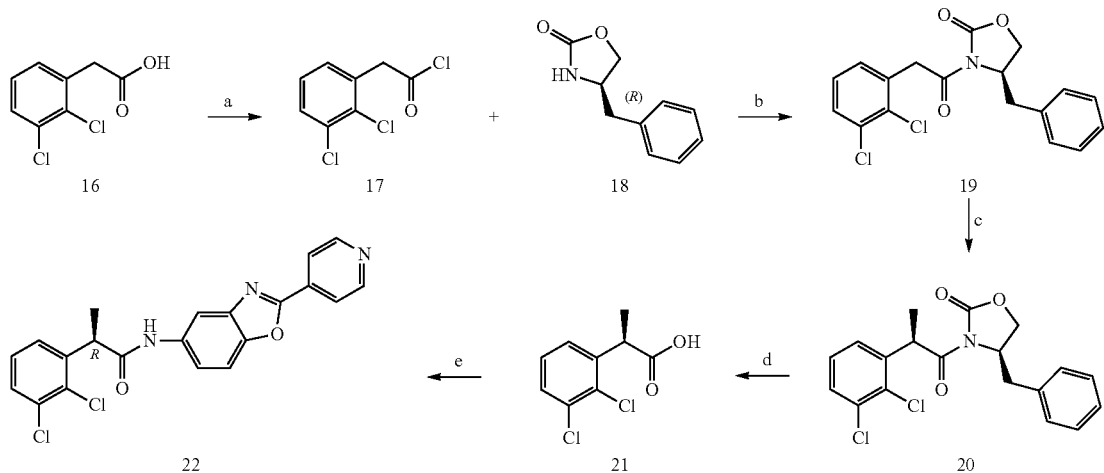

Reagents and conditions: (a) SOCl₂, 90° C., 2 h, (b) n-BuLi (2.5M), THF, -78° C. to 0° C.,
1 h, 80% (C) ((CH₃)₃Si)₂N•Na in THF, 1 h, -78° C., 77% (ii) MeI, THF, 2 h, -78° C. (iii) rt,
4 h (d) Li—O—O—Li, THF, H₂O, 0° C., 1 h, 87% (e) EDCl•HCl, DMF, rt, 12 h, 70%.

Scheme 4: General procedure for the synthesis of Benzimidazole derivatives

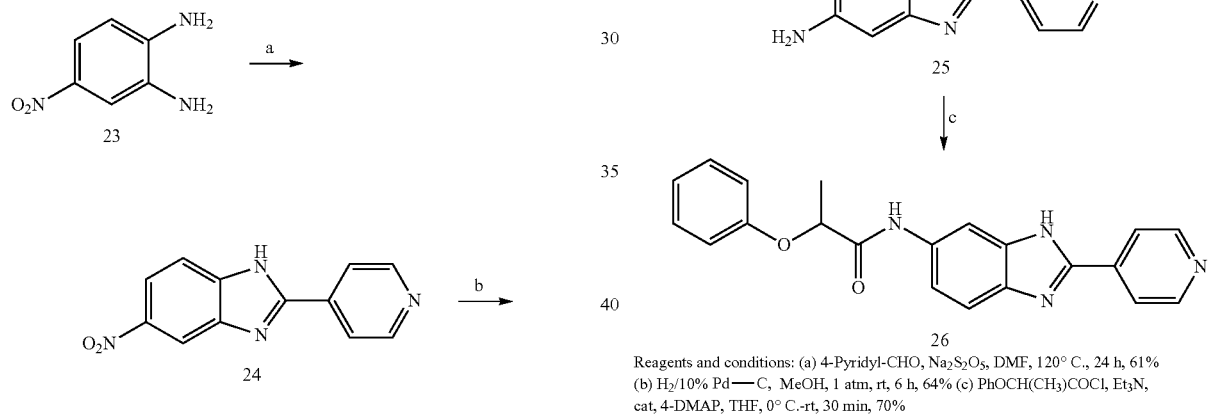

Reagents and conditions: (a) 4-Pyridyl-CHO, Na₂S₂O₅, DMF, 120° C., 24 h, 61%
(b) H₂/10% Pd—C, MeOH, 1 atm, rt, 6 h, 64% (c) PhOCH(CH₃)COCl, Et₃N,
cat, 4-DMAP, THF, 0° C.-rt, 30 min, 70%

Scheme 5: General procedure for the synthesis of amide bioisosters of triazole derivatives

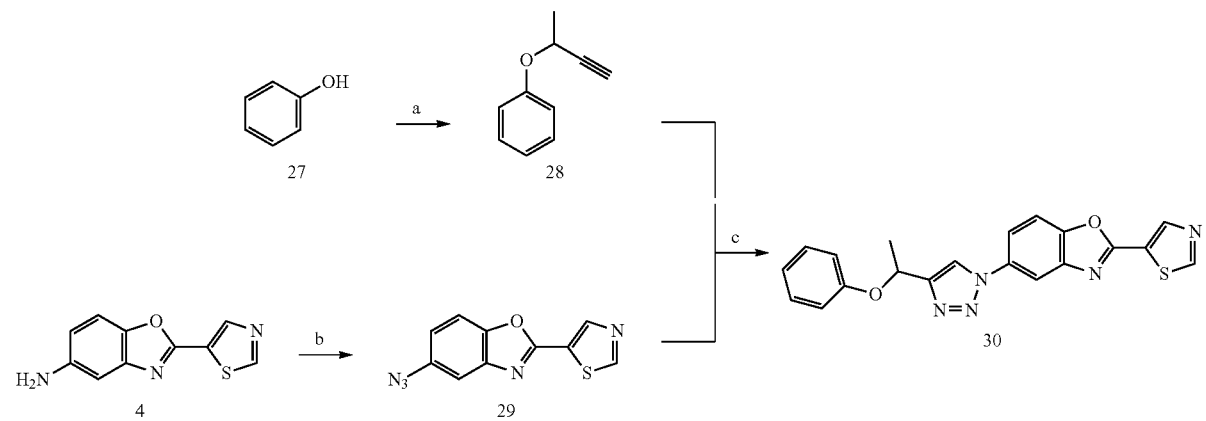

Reagents and conditions: (a) CH₃CH(OH)C≡CH, 0° C., PPh₃, 10 min, DEAD, THF, 70° C.,
20 h, 69% (b) NaNO₂, HCl, H₂O, NaN₃, -5° C.-0° C., 1.5 h, 89% (c) CH₃CN, DIPEA, CuI, rt,
40 min, 84%.

Scheme 6: General procedure for the synthesis of open ring amide derivatives

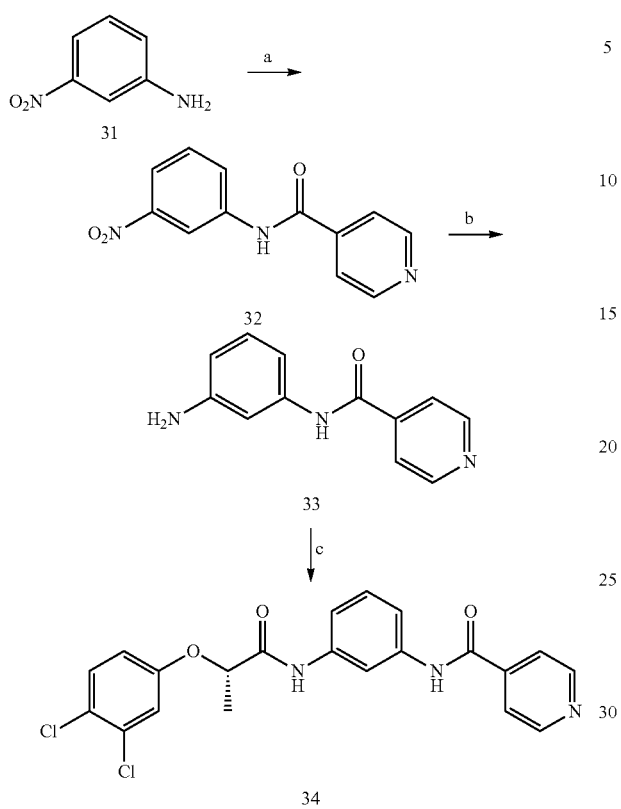

Reagents and conditions: (a) 4-PyCO₂H, 0° C., EDCl•HCl, DCM, rt, 12 h, 68% (b) H₂/10% Pd—C (1 atm), MeOH, rt, 6 h, 65% (c) 0° C., (S)- 2, 3-di-Cl—PhOCH(CH₃)COOH, EDCl•HCl, DCM, rt, 12 h, 63%.

Scheme 7: General procedure for the synthesis of amide derivatives

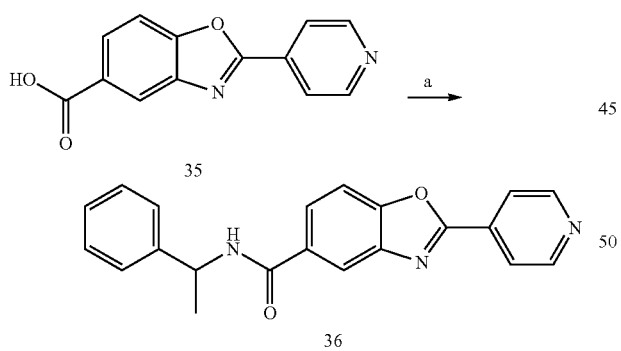

Reagents and conditions: (a) α-methyl benzyl amine, EDCl•HCl, DMF, rt, 12 h, 71%.

Scheme 8: General procedure for the synthesis of regioisomer of Benzoxazole derivatives

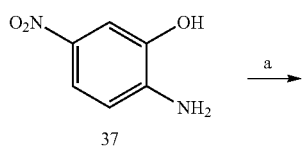

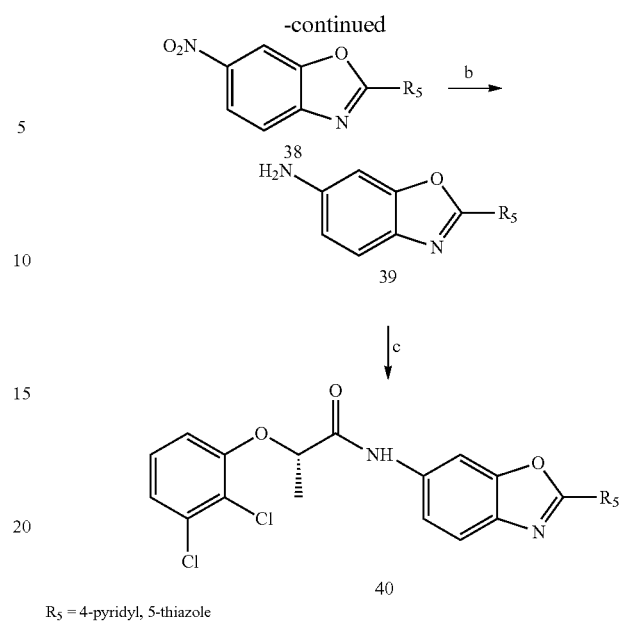

$R_5$ = 4-pyridyl, 5-thiazole

Reagents and conditions: (a) $R_5$—CHO, O₂, DarcoKB, xylene, 120° C., 6 h, 75% (b) H₂/10% Pd—C, EtOAc, 1 atm, 6 h, 85% (c) 0° C., (S)-2, 3-di-Cl—PhOCH(CH₃)COOH, EDCl•HCl, DMF, rt, 12 h, 76%.

Example 5

General procedure for the preparation of 5-nitro-2-Aryl-benzo[d] oxazole (3). Exemplified for 5-nitro-2-(pyridine-4-yl) benzo [d] oxazole (3, $R_1$=4-Pyridyl, X=H)

To a solution of 2-amino-4-nitrophenol 2 (500 mg, 3.24 mmol) in anhydrous xylene (10 mL) was added 4-pyridine carboxaldehyde (347 mg, 3.23 mmol) and Darco KB (600 mg) placed in a 100 mL three-necked flask under an oxygen atmosphere and stirred at 120° C. for 4 h. The reaction mixture was filtered by using celite. Then the filtrate was concentrated. The product was purified by silica gel column chromatography using a mixture of ethyl acetate/n-hexane (50:50) to give 5-nitro-2-(pyridine-4-yl) benzo [d]oxazole 3 (600 mg, 77%) as a yellow solid. ¹H NMR (CDCl₃, 400 MHz) δ 7.76 (d, J=9.2 Hz, 1H), 8.11 (d, J=6 Hz, 2H), 8.40 (d, $J_1$=12 Hz, $J_2$=2.4 Hz, 1H), 8.73 (d, J=2 Hz, 1H), 8.89 (d, J=6 Hz, 2H).

Example 6

General procedure for the Synthesis of 5-amino-2-Aryl-benzo [d] oxazole (4). Exemplified for 5-amino-2-(pyridine-4-yl) benzo[d]oxazole (4, $R_1$=4-Pyridyl, X=H)

To a solution of 5-nitro-2-(pyridine-4-yl) benzo[d]oxazole 3 (600 mg, 2.48 mmol) in ethyl acetate/MeOH (10 mL) was added catalytic amount of 10% Pd—C under hydrogen atmosphere and stirred it for 6 h at room temperature and filtered by flash column chromatography (100% ethyl acetate) to afford 5-amino-2-(pyridine-4-yl) benzo[d] oxazole 4 (450 mg, 86%) as a yellow solid. ¹H NMR (CDCl₃, 400 MHz) δ 6.78 (dd, $J_1$=12 Hz, $J_2$=2.4 Hz, 1H), 7.07 (d, J=2 Hz, 1H), 7.40 (d, J=4.8 Hz, 1H), 8.05 (dd, $J_1$=8 Hz, $J_2$=1.6 Hz, 2H), 8.79 (dd, $J_1$=4 Hz, $J_2$=1.6 Hz, 2H), 3.78 (s, 2H).

Example 7

General procedure for synthesis of racemic propionic acid derivative 7. Exemplified for 2-(2,3-dichlorophenoxy) propanoic acid (7, $R_2$=2, 3-di-Cl-ph, $R_3$=Me. Y=O)

To a solution of 2, 3-dichloro phenol 5 (200 mg, 1.22 mmol) in anhydrous DMF (15 mL) was added $K_2CO_3$ (505 mg, 3.66 mmol) and ethyl-2-bromopropanoate (287.1 mg, 1.58 mmol). The mixture was heated at 70° C. for 3 h under $N_2$ atmosphere and then diluted with water (50 mL) and extract with ethyl acetate (3×50 mL). The organic layers were collected and washed with brine solution, dried over anhydrous $MgSO_4$, filtered and concentrated in vacuo, and isolated by silica gel column chromatography by using mixture ethyl acetate/n-hexane (5:90) to give 2-(2, 3-dichlorophenoxy) propanoate 6 ($R_4$=Et)(290 mg, 1.2 mmol, 90%) as a color less liquid. The ester (290 mg, 1.60 mmol) was dissolved in THF: $H_2O$ (2:1), and then 3N NaOH (132 mg, 3.3 mmol) was added, refluxed at 80° C. for 3 h. Then cool the reaction mixture and added 1N HCl to a $P^H$ ~7 and then extracted with DCM. The organic layers were dried over $MgSO_4$, filtered, concentrated under vacuum, and isolated by using silica gel column chromatography using a mixture of ethyl acetate/n-hexane (60:40) to afford 2-(2, 3-dichlorophenoxy) propanoic acid 7 (270 mg, 95%) as a white solid.

Example 8

General procedure for the synthesis of chiral (R&S) versions of 2-(substituted phenoxy, 1-naphthalenyloxy propanoic/butanoic acids (7) via Mitsonobu reaction. Exemplified for (S)-2-(2, 3-dichlorophenoxy) propanoic acid ($R_2$=2, 3-di-Cl-ph, $R_3$=(S) Me, Y=O)

A compound of 2, 3-dichlorophenol 5 (150 mg, 0.92 mmol) was dissolved in anhydrous DCM (6 mL) under $N_2$ atmosphere and then added Methyl (R)-(+)-2-(4-hydroxyphenoxy)propionate (143.7 mg, 1.38 mmol). At 0° C., $PPh_3$ (289.4 mg, 1.10 mmol) was added portions wise and stirred it for 10 minutes. After that DEAD (240 mg, 1.37 mmol) was added slowly, stirred it for 24 h at room temperature. The corresponding mixture was extracted with DCM and brine solution. The organic layers were collected and dried over $MgSO_4$, filtered and concentrated. Crude product was isolated by column on silica using ethyl acetate/n-hexane (5:90) to yielded (S)-2-(2, 3-dichlorophenoxy) propanoate 6 ($R_4$=Me) (180 mg, 0.76 mmol, 83%) as a colour less liquid. To this ester (180 mg, 0.72 mmol) was hydrolysed by THF: 3 N HCl (2:8), refluxed at 70° C. for 6 h. The reaction mixture was cooled to room temperature then extracted with DCM and washed with brine solution. Organic layers were dried on anhydrous $MgSO_4$, filtered, concentrated and purified by silica gel column chromatography using ethyl acetate/n-hexane (60:40) to afford (S)-2-(2, 3-dichlorophenoxy) propanoic acid 7 (110 mg, 62%) as a white solid. $^1$H NMR ($CDCl_3$, 400 MHz) δ 1.51 (d, J=7.2 Hz, 3H), 4.27 (q, J=7.2 Hz, 1H), 7.16-7.24 (nm 2H), 7.37 (dd, J, =3.6 Hz, $J_2$=1.6 Hz, 1H).

Example 9

General procedure for the preparation of Benzoxazole derivatives (8). Exemplified for (S)-2-(2,3-dichlorophenoxy)-N-(2-(pyridin-4-yl)benzo[d]oxazol-5-yl)propanamide (Q36, $R_1$=4-pyridyl, $R_2$=2, 3-dichlorophenyl, $R_3$=(S)-Me, Y=O, X=H)

To a solution of compound 5-amino-2-(pyridine-4-yl) benzo [d]oxazole 4 (266.7 mg, 1.27 mmol) and 2-(2,3-dichlorophenoxy)propanoic acid 7 ($R_2$=2,3-di-Cl-Ph, $R_3$=Me) (300 mg, 1.27 mmol) were dissolved in anhydrous DMF (5 mL) under $N_2$ atmosphere, cooled to 0° C. and added EDCI.HCl (489.6 mg, 2.55 mmol) stirred it for 12 h at room temperature. Volatiles were removed under reduced pressure and extracted the residue with dichloromethane. Organic layer washed with sodium bicarbonate and brine solution. Collected the organic layers and dried over anhydrous $MgSO_4$, filtered, concentrated and isolated by flash column chromatography using ethylacetate/n-hexane solvent system (50:50) to give compound 8 (390 mg, 72%) as a white solid. $^1$H NMR ($CDCl_3$, 400 MHz) δ 1.76 (d, J=6.8 Hz, 3H), 4.90 (q, J=6.8 Hz, 1H), 6.93 (dd, J, =7.2 Hz, $J_2$=2.4 Hz, 1H), 7.17-7.23 (m, 2H), 7.56-7.61 (m, 2H), 8.06 (dd, $J_1$=4 Hz, $J_2$=1.6 Hz, 2H), 8.17 (s, 1H), 8.81-8.83 (m, 3H); $^{13}$C NMR ($CDCl_3$, 100 MHz) δ 18.6, 76.9, 111.2, 112.1, 113.2, 119.2, 121.2, 122.9, 124.3, 128.1, 134.3, 134.5, 134.7, 142.4, 148.0, 150.9, 153.7, 161.8, 169.2; ESI-HRMS for $C_{21}H_{16}N_3O_3Cl_2$ $(M+H)^+$ calcd. 428.0569. found 428.0568, Chiral purity (% ee >98, $t_R$=12.84 min).

(S)—N-methyl-2-(naphthalen-1-yloxy)-N-(2-(thiazol-5-yl)benzo[d]oxazol-5-yl)propanamide (9) (Q56, $R_1$=thiazole, $R_2$=1-naphthyl, $R_3$=(S)-Me, Y=O, X=H)

A solution of Q26 (30 mg, 0.072 mmol) in 2 mL dry THF was added drop wise to sodium hydride (60% in mineral oil, 1.89 mg, 0.079 mmol) in anhydrous THF (3 mL) under $N_2$ atmosphere at 0° C., and stirred for 30 min. at room temperature. The mixture was cooled to 0° C. and added MeI (11.2 mg, 0.079 mmol), stirred for 1 h at room temperature. The resulting mixture was quenched and extracted with DCM, washed with brine solution. Organic layer was dried over anhydrous MgSO4, filtered, volatiles were removed under reduced pressure purified by column chromatography on silica using ethyl acetate/n-hexane (40:60) to yield Q56 (15 mg, 48%) as a white solid. $^1$H NMR ($CDCl_3$, 400 MHz) δ 1.62 (d, J=6.4 Hz, 3H), 3.34 (s, 3H), 4.92 (q, J=6.4 Hz, 1H), 6.49 (d, J=7.6 Hz, 1H), 7.03 (d, J=8.4 Hz, 1H), 7.19-7.39 (m, 6H), 7.69 (d, J=8 Hz, 1H), 7.90 (d, J=8.4 Hz, 1H), 8.61 (s, 1H), 8.61 (s, 1H), 8.98 (s, 1H); $^{13}$C NMR ($CDCl_3$, 100 MHz) δ 18.7, 39.0, 72.6, 105.9, 111.4, 119.0, 121.3, 122.3, 125.2, 125.29, 125.3, 125.5, 126.0, 126.5, 127.4, 134.7, 140.0, 142.6, 146.0, 149.7, 153.0, 156.9, 158.4, 171.3; ESI-HRMS for $C_{24}H_{20}N_3O_3S$ $(M+H)^+$ calcd. 430.1225. found 430.1222, Chiral purity (% ee >99, $t_R$=12.27 min).

2-(2-chlorophenoxy)-N-(2-(pyridine-4-yl) benzo[d]oxazol-5-yl) propanamide ($R_1$=4-Pyridyl, X=H, $R_2$=2-Cl-Ph, $R_3$=Me, Y=O, Q27)

The general procedure for compound 8 was followed condensing 2-(2-chlorophenoxy) propanoic acid (7) with compound 4 to afforded title compound Q27 (71%) as white solid. $^1$H NMR ($CDCl_3$, 400 MHz) δ 1.77 (d, J=6.4 Hz, 3H), 4.90 (q, J=6.8 Hz, 1H), 7.02 (t, J=7.6 Hz, 2H), 7.25-7.29 (m, 1H), 7.45 (d, J=8 Hz, 1H), 7.57 (d, J=8.4 Hz, 1H), 7.64 (dd, $J_1$=8 Hz, $J_2$=2 Hz, 1H), 8.06 (d, J=5.2 Hz, 2H), 8.17 (s, 1H), 8.82 (d, J=4.4 Hz, 2H), 8.95 (s, 1H); $^{13}$C NMR (CDCl$_3$, 100 MHz) δ 18.7, 76.8, 111.1, 111.9, 115.6, 119.2, 121.1, 123.5, 123.8, 128.4, 130.8, 134.3, 134.9, 142.3, 147.9, 150.9, 152.4, 161.7, 169.5; ESI-HRMS for $C_{21}H_{17}N_3O_3Cl$ (M+H)$^+$ calcd. 394.0958 found 394.0961.

2-(4-chlorophenoxy)-N-(2-(pyridine-4-yl) benzo [d]oxazol-5-yl) propanamide ($R_1$=4-Pyridyl, X=H, $R_2$=4-Cl-Ph, $R_3$=Me, Y=O, Q18)

The general procedure for compound 8 was followed condensing 2-(4-chlorophenoxy) propanoic acid (7) with 4 to afforded title compound Q18 (72%) as white solid. $^1$H NMR (CDCl$_3$, 400 MHz) δ 1.69 (d, J=6.8 Hz, 3H), 4.79 (q, J=6.8 Hz, 1H), 6.94 (d, J=8.8 Hz, 2H), 7.30 (d, J=8.4 Hz, 2H), 7.51-7.58 (m, 2H), 8.08 (dd, $J_1$=10 Hz, $J_2$=2 Hz, 3H), 8.29 (s, 1H), 8.82 (d=4.8 Hz, 2H); $^{13}$C NMR (CDCl$_3$, 100 MHz) δ 18.8, 76.0, 111.2, 112.5, 117.3, 119.5, 121.2, 127.8, 130.1, 134.3, 134.5, 142.4, 148.1, 150.9, 155.3, 161.8, 170.1; ESI-HRMS for $C_{21}H_{17}N_3O_3Cl$ (M+H)$^+$ calcd. 394.0958 found 394.0961.

2-(4-methoxyphenoxy)-N-(2-(pyridine-4-yl) benzo [d]oxazol-5-yl) propanamide ($R_1$=4-Pyridyl, X=H, $R_2$=4-OMePh, $R_3$=Me, Y=O, Q33)

The general procedure for compound 8 was followed by condensing 2-(4-methoxyphenoxy) propanoic acid (7) with compound 4 to afford title compound Q33 (73%) as a white solid. $^1$H NMR (CDCl$_3$, 400 MHz) δ 1.66 (d, J=6.8 Hz, 3H), 3.78 (s, 3H), 4.72 (q, J=6.8 Hz, 1H), 6.86 (d, J=9.2 Hz, 2H), 6.94 (d, J=9.2 Hz, 2H), 7.56 (s, 2H), 8.07 (d, J=6 Hz, 2H), 8.11 (s, 1H), 8.44 (s, 1H), 8.81 (d, J=6 Hz, 2H); 13C NMR (CDCl$_3$, 100 MHz) δ 18.8, 55.8, 76.6, 94.6, 111.1, 112.3, 115.1, 117.4, 119.5, 121.2, 134.3, 134.7, 142.4, 148.0, 150.9, 155.2, 161.7, 170.8; ESI-HRMS for $C_{22}H_{20}N_3O_4$ (M+H)$^+$ calcd. 390.1454 found 390.1457.

2-phenoxy-N-(2-(pyridine-4-yl) benzo [d]oxazol-5-yl) propanamide ($R_1$=4-Pyridyl, X=H, $R_2$=Ph, $R_3$=Me, Y=O, Q9)

The general procedure for compound 8 was followed condensing 2-phenoxypropanoic acid propanoic acid (compound 7) with compound 4 to afforded title compound Q9 (63%) as a white solid. $^1$H NMR (CDCl$_3$, 400 MHz) δ 1.69 (d, J=6.4 Hz, 3H), 4.84 (q, J=6.4 Hz, 1H), 7.07-6.99 (m, 3H), 7.34 (t, J=8 Hz, 2H), 7.54 (t, J=8.4 Hz, 2H), 8.08 (d, J=13.6 Hz, 3H), 8.42 (s, 1H), 8.82 (s, 2H); 13C NMR (CDCl$_3$, 100 MHz) δ 18.9, 75.6, 111.1, 112.4, 115.9, 119.6, 120.5, 121.2, 121.2, 121.3, 122.7, 128.1, 130.1, 134.3, 134.6, 142.4, 148.0, 150.9, 156.8, 161.7, 170.6; ESI-HRMS for $C_{21}H_{18}N_3O_3$ (M+H)$^+$ calcd. 360.1348. found 360.1350.

2-(3-chlorophenoxy)-N-(2-(pyridine-4-yl) benzo[d] oxazol-5-yl) propanamide($R_1$=4-Pyridyl, X=H, $R_2$=3-Cl-Ph, $R_3$=Me, Y=O, Q28)

The general procedure for compound 8 was followed condensing 2-(3-chloro phenoxypropanoic acid (7) with compound 4 to afforded title compound (73%) as white solid. $^1$H NMR (CDCl$_3$, 400 MHz) δ 1.68 (d, J=6.8 Hz, 3H), 4.82 (q, J=6.8 Hz, 1H), 6.86-6.89 (m, 1H), 7.02 (d, J=7.6 Hz, 2H), 7.23-7.27 (m, 1H), 7.51-7.57 (m, 2H), 8.05 (d, J=5.2 Hz, 2H), 8.09 (s, 1H), 8.37 (s, 1H), 8.81 (s, 2H); $^{13}$C NMR (CDCl$_3$, 100 MHz) δ 18.7, 75.8, 111.1, 112.5, 113.8, 116.8, 119.6, 121.2, 123.0, 130.9, 134.2, 134.5, 135.5, 142.4, 148.1, 150.9, 157.4, 161.7, 170.0; ESI-HRMS for $C_{21}H_{17}N_3O_3Cl$ (M+H)$^+$ calcd. 394.0958. found 394.0959.

2-(2, 3-dichlorophenoxy)-N-(2-(pyridine-4-yl) benzo [d]oxazol-5-yl) propanamide ($R_1$=4-Pyridyl, X=H, $R_2$=2,3-di-Ph, $R_3$=Me, Y=O, Q32)

The general procedure for compound 8 was followed condensing 2-(2,3-dichloro phenoxypropanoic acid (7) with compound 4 to afforded title Q32 as white solid yielded 71%. $^1$H NMR (CDCl$_3$, 400 MHz) δ 1.77 (d, J=6.8 Hz, 3H), 4.91 (q, J=6.8 Hz, 1H), 6.93 (dd, J=6.6 Hz, $J_2$=2.8 Hz, 1H), 7.20-7.23 (m, 2H), 7.60 (d, J=1.2 Hz, 2H), 8.08 (d, J=4.4 Hz, 2H), 8.18 (s, 1H), 8.83 (s, 3H); $^{13}$C NMR (CDCl$_3$, 100 MHz) δ 18.3, 76.6, 111.0, 111.8, 113.0, 119.0, 120.9, 122.7, 124.1, 127.8, 134.1, 134.3, 134.5, 142.2, 147.8, 150.7, 153.5, 161.5, 168.9; ESI-HRMS for $C_{21}H_{16}N_3O_3Cl_2$ (M+H)$^+$ calcd. 428.0569. found 428.0569.

2-(2, 6-dichlorophenoxy)-N-(2-(pyridine-4-yl) benzo[d]oxazol-5-yl) propanamide ($R_1$=4-Pyridyl, X=H, $R_2$=2,6-dichlorophenyl, $R_3$=Me, Y=O, Q34)

The general procedure for compound 8 was followed condensing 2-(2,6-dichloro-phenoxypropanoic acid (7) with compound 4 to afford title compound Q34 (yield 67%) as a white solid. $^1$H NMR (CDCl$_3$, 400 MHz) δ 1.61 (d, J=6.8 Hz, 3H), 5.11 (q, J=6.8 Hz, 1H), 7.09 (t, J=7.6 Hz, 1H), 7.37 (d, J=8.4 Hz, 2H), 7.60 (d, J=8.8 Hz, 1H), 7.18 (dd, $J_1$=8.8 Hz, $J_2$ 1.6 Hz, 1H), 8.08 (d, J=5.2 Hz, 2H), 8.20 (s, 1H), 8.82 (d, J=5.2 Hz, 2H), 8.99 (s, 1H); $^{13}$C NMR (CDCl$_3$, 100 MHz) δ 18.2, 79.5, 111.1, 112.1, 119.4, 121.2, 126.1, 129.5, 129.6, 134.3, 135.0, 142.4, 148.0, 148.7, 150.9, 169.5, 195.9; ESI-HRMS for $C_{21}H_{16}N_3O_3Cl_2$ (M+H)$^+$ calcd. 428.0569. found 428.0567.

2-(naphthalene-1-yloxy))-N-(2-(pyridine-4-yl) benzo [d]oxazol-5-yl) propanamide (Q11 $R_1$=4-Pyridyl, X=H, $R_2$=2-Naphthyl, $R_3$=Me, Y=O)

The general procedure for compound 8 was followed condensing 2-(naphthalen-1-yloxy) propanoic acid (7) with compound 4 to afford title compound Q11 (73%) as a white solid. $^1$H NMR (CDCl$_3$, 400 MHz) δ 1.84 (d, J=6.4 Hz, 3H), 5.04 (q, J=6.8 Hz, 1H), 6.92 (d, J=7.6 Hz, 1H), 7.39 (t, J=8 Hz, 1H), 7.61-7.48 (m, 5H), 7.89-7.86 (m, 1H), 8.05-8.08 (m, 3H), 8.33-8.36 (m, 1H), 8.41 (s, 1H), 8.80 (s, 2H); $^{13}$C NMR (CDCl$_3$, 100 MHz) δ 19.1, 76.2, 107.3, 111.1, 112.4, 119.6, 121.21, 121.25, 121.5, 122.4, 125.8, 126.0, 126.1, 127.0, 128.1, 134.2, 134.6, 134.9, 142.4, 148.0, 150.9, 152.6, 170.6; ESI-HRMS for $C_{25}H_{20}N_3O_3$ (M+H)$^+$ calcd. 410.1505. found 410.1508.

3-methyl-2-(naphthalene-1-yloxy)-N-(2-(pyridine-4-yl) benzo[d]oxazol-5-yl) butanamide ($R_1$=4-Pyridyl, X=H, $R_2$=2-Naphthyl, $R_3$=Isopropyl, Y=O, Q54)

The general procedure for compound 8 was followed condensing 2-(naphthalen-1-yloxy) propanoic acid (7) with compound 4 to afforded title compound Q54 (67%) as white solid. $^1$H NMR (CDCl$_3$, 400 MHz) δ 1.18 (d, J=6.8 Hz, 3H), 1.25 (d, J=6.8 Hz, 3H), 2.51-2.59 (m, 1H), 4.69 (d, J=4 Hz, 1H), 6.84 (d, J=7.6 Hz, 1H), 7.31 (t, J=8 Hz, 1H), 7.37-7.47 (m, 3H), 7.51-7.54 (m, 2H), 7.80 (t, J=6.4 Hz, 1H), 7.95-

7.97 (m, 3H), 8.34 (d, J=5.6 Hz, 2H), 8.72 (d, J=5.2 Hz, 2H); $^{13}$C NMR (CDCl$_3$, 100 MHz) δ 17.5, 19.6, 32.5, 84.5, 106.7, 111.0, 112.7, 119.9, 121.1, 121.5, 122.1, 125.7, 126.0, 127.0, 128.1, 134.2, 134.4, 134.8, 142.2, 148.0, 150.7, 153.5, 161.6, 169.8; ESI-HRMS for C$_{27}$H$_{24}$N$_3$O$_3$(M+H)$^+$ calcd. 438.1818. found 438.1822.

(R)-2-(naphthalene-1-yloxy))-N-(2-(pyridine-4-yl) benzo [d]oxazol-5-yl) propanamide (R$_1$=4-Pyridyl, X=H, R$_2$=2-Naphthyl, R$_3$=R(Me), Y=O, Q23)

The general procedure for compound 8 was followed condensing (R)-2-(naphthalen-1-yloxy) propanoic acid (7) with compound 4 to afforded title compound Q23 (76%) as white solid. $^1$H NMR (CDCl$_3$, 400 MHz) δ 1.83 (d, J=6.8 Hz, 3H), 5.03 (q, J=6.8 Hz, 1H), 6.91 (d, J=7.6 Hz, 1H), 7.38 (t, J=8 Hz, 1H), 7.50-7.58 (m, 5H), 7.85-7.87 (m, 1H), 8.03-8.07 (m, 3H), 8.34 (t, J=2.8 Hz, 1H), 8.47 (s, 1H), 8.80 (bs, 2H); $^{13}$C NMR (CDCl$_3$, 100 MHz) δ 19.1, 67.3, 76.2, 107.3, 111.1, 112.4, 119.6, 121.2, 121.5, 122.4, 125.8, 126.0, 126.1, 127.0, 128.1, 134.3, 134.6, 134.9, 142.3, 148.0, 150.9, 152.6, 161.7, 170.6; ESI-HRMS for C$_{25}$H$_{20}$N$_3$O$_3$ (M+H)$^+$ calcd. 410.1505. found 410.1508, chiral purity (% ee 98.1, t$_R$=22.87).

(S)-2-(naphthalene-1-yloxy))-N-(2-(pyridine-4-yl) benzo[d]oxazol-5-yl) propanamide (R$_1$=4-Pyridyl, X=H, R$_2$=2-Naphthyl, R$_3$=(S)-Me, Y=O, Q21)

The general procedure for 8 was followed by condensing (S)-2-(naphthalen-1-yloxy) propanoic acid (7) with compound 4 to afforded title compound Q21 (71%) as white solid. $^1$H NMR (CDCl$_3$, 400 MHz) δ 1.78 (d, J=6.8 Hz, 3H), 4.96 (q, J=6.8 Hz, 1H), 6.85 (d, J=7.6 Hz, 1H), 7.30 (t, J=8 Hz, 1H), 7.50-7.42 (m, 5H), 7.77-7.79 (m, 1H), 7.92 (dd, J$_1$=4.4 Hz, 2=1.6 Hz, 2H), 8.02 (s, 1H), 8.26-8.23 (m, 1H), 8.60 (s, 1H), 8.70 (d, J=4.4 Hz, 2H); $^{13}$C NMR (CDCl$_3$, 100 MHz) δ 19.1, 76.2, 107.2, 111.0, 112.5, 119.7, 121.1, 121.5, 122.3, 125.0, 125.8, 126.0, 126.9, 128.0, 134.1, 134.7, 134.8, 142.2, 147.9, 150.8, 152.7, 161.6, 170.7; ESI-HRMS for C$_{25}$H$_{20}$N$_3$O$_3$(M+H)$^+$ calcd. 410.1505. found 410.1507, Chiral purity (% ee 98.9, t=12.08).

(S)-2-(2-chloro-3-(trifluoromethyl) phenoxy)-N-(2-(pyridine-4-yl) benzo[d]oxazol-5-yl) propanamide (R$_1$=4-Pyridyl, X=H, R$_2$=2-Cl,3-trifluoro-Ph, R$_3$=S (Me), Y=O, Q41)

The general procedure for compound 8 was followed condensing (S)-2-(2-chloro-3-(trifluoromethyl) phenoxy propanoic acid (7) with compound 4 to afforded title compound (70%) as creamish solid. $^1$H NMR (CDCl$_3$, 400 MHz) δ 1.78 (d, J=6.8 Hz, 3H), 4.94 (q, J=6.4 Hz, 1H), 7.21 (d, J=7.6 Hz, 1H), 7.37-7.44 (m, 2H), 7.59 (s, 2H), 8.07 (d, J=5.2 Hz 2H), 8.19 (s, 1H), 8.82 (d, J=5.6 Hz, 3H); $^{13}$C NMR (CDCl$_3$, 100 MHz) δ 18.5, 76.9, 111.2, 112.1, 118.4, 119.2, 121.1, 122.3, 124.0, 130.4, 134.2, 134.6, 142.4, 148.0, 150.9, 153.5, 161.8, 168.9; ESI-HRMS for C$_{22}$H$_{16}$N$_3$O$_3$ClF$_3$ (M+H)$^+$ calcd. 462.0832. found 462.0834, Chiral purity (% ee 99.4, t=11.83).

(S)-2-(2-chloro-3-nitrophenoxy)-N-(2-(pyridine-4-yl) benzo[d]oxazol-5-yl) propanamide (R$_1$=4-Pyridyl, X=H, R$_2$=2-Cl,3-nitro-Ph, R$_3$=S(Me), Y=O, Q46)

The general procedure for compound 8 was followed condensing (S)-2-(2-chloro-3-nitrophenoxy propanoic acid (compound 7) with compound 4 to afforded title Q46 (77%) as creamish solid. $^1$H NMR (CDCl$_3$, 400 MHz) δ 1.80 (d, J=6.8 Hz, 3H), 4.97 (q, J=6.8 Hz, 1H), 7.24 (d, J=8.4 Hz, 1H), 7.44 (t, J=8.4 Hz, 1H), 7.53-7.62 (m, 3H), 8.07-8.09 (m, 2H), 8.20 (s, 1H), 8.68 (s, 1H), 8.82-8.84 9m, 2H); $^{13}$C NMR (CDCl$_3$, 100 MHz) δ 18.5, 76.9, 111.3, 112.2, 117.2, 118.0, 118.7, 119.3, 121.2, 128.4, 134.2, 134.4, 142.4, 148.1, 149.9, 150.9, 153.7, 161.9, 168.6; ESI-HRMS for C$_{21}$H$_{16}$N$_4$O$_5$Cl (M+H) calcd. 439.0809. found 439.0805, Chiral purity (% ee >99, t$_R$=35.93).

(S)-2-(2, 3-dimethoxyphenoxy)-N-(2-(pyridine-4-yl) benzo [d]oxazol-5-yl) propanamide (R$_1$=4-Pyridyl, X=H, R$_2$=2,3-dimethoxyPh, R3=S (Me), Y=O, Q42)

The general procedure for compound 8 was followed condensing (S)-2-(2,3-dimethoxy phenoxy propanoic acid (7) with compound 4 to afforded title compound Q42 (79%) as white solid. $^1$H NMR (CDCl$_3$, 400 MHz) δ 1.78 (d, J=6.8 Hz, 3H), 3.89 (s, 3H), 4.01 (s, 3H), 4.78 (q, J=6.8 Hz, 1H), 6.67-6.71 (m, 2H), 7.04 (t, J=5.6 Hz, 1H), 7.55 (d, J=8.8 Hz, 1H), 7.68 (dd, J$_1$=9.2 Hz, J$_2$=2.4 Hz, 1H), 8.07 (dd, J$_1$=4.4 Hz, J$_2$=1.6 Hz, 2H), 8.20 (d, J=2 Hz, 1H), 8.82 (dd, J=4.4 Hz, J$_2$=1.2 Hz, 2H), 9.58 (s, 1H); $^{13}$C NMR (CDCl$_3$, 100 MHz) δ 20.5, 57.0, 62.5, 80.3, 108.3, 111.4, 111.8, 112.7, 120.1, 122.0, 125.7, 135.3, 136.4, 140.4, 143.1, 148.6, 151.7, 152.8, 154.9, 162.4, 171.4; ESI-HRMS for C$_{23}$H$_{22}$N$_3$O$_5$ (M+H)$^+$ calcd. 420.1559. found 420.1557, Chiral purity (% ee >99, t$_R$=17.41).

2-(2, 4-dichlorophenoxy)-N-(2-(phenylbenzo[d] oxazol-S-yl) propanamide (R$_1$=Phenyl, X=H, R$_2$=2, 4-dichloro-Ph, R$_3$=Me, Y=O, Q2)

The general procedure for compound 8 was followed condensing 2-(2,4-dichloro phenoxy propanoic acid (7) with compound 4 to afforded title compound (73%) as white solid. $^1$H NMR (CDCl$_3$, 400 MHz) δ 1.74 (d, J=6.8 Hz, 3H), 4.84 (q, J=6.8 Hz, 1H), 6.94 (d, J=8.8 Hz, 1H), 7.23 (dd, J, =8.8 Hz, J$_2$=2.4 Hz, 1H), 7.44 (d, J=2.4 Hz, 1H), 7.54-7.51 (m, 4H), 7.56 (d, J=2 Hz, 1H), 7.59 (d, J=2 Hz, 1H), 8.05 (d, J=1.6 Hz, 1H), 8.24 (dd, J=8 Hz, 2H), 8.75 (s, 1H); $^{13}$C NMR (CDCl$_3$, 100 MHz) δ 18.6, 76.9, 110.8, 111.6, 116.4, 118.0, 124.7, 127.1, 127.8, 128.0, 128.4, 129.1, 130.6, 131.9, 134.2, 142.8, 148.0, 151.3, 164.2, 169.1; ESI-HRMS for C$_{22}$H$_{17}$N$_2$O$_3$Cl$_2$ (M+H)$^+$ calcd. 427.0616 found 427.0619.

(S)-2-(naphthalene-1-yloxy)-N-(2-(thiazol-5-yl) benzo[d]oxazol-5-yl) propanamide (R$_1$=5-thiazole, X=H, R$_2$=2-Naphthyl, R$_3$=S(Me), Y=O, Q26)

The general procedure for compound 8 was followed condensing (S)-2-(naphthalene-1-yloxy propanoic acid (7) with compound 4 to afforded title compound Q26 (yield 78%) as white solid. $^1$H NMR (CDCl$_3$, 400 MHz) δ 1.81 (d, J=6.8 Hz, 3H), 5.01 (q, J=6.4 Hz, 1H), 6.89 (d, J=7.6 Hz, 1H), 7.35 (t, J=7.6 Hz, 1H), 7.45-7.54 (m, 5H), 7.82 (t, J=4.8 Hz, 1H), 7.96 (s, 1H), 8.29 (d, J=5.2 Hz, 1H), 8.55 (d, J=21.6 Hz, 2H), 8.91 (s, 1H); $^{13}$C NMR (CDCl$_3$, 100 MHz) δ 19.1, 76.2, 107.3, 110.7, 112.0, 119.0, 121.5, 122.3, 125.6, 125.8, 126.0, 126.1, 127.0, 128.0, 134.6, 134.8, 142.2, 145.6, 147.6, 152.6, 156.4, 157.8, 170.6; ESI-HRMS for C$_{23}$H$_{18}$N$_3$O$_3$S (M+H)$^+$ calcd. 416.1069. found 416.1075, Chiral purity (% ee 98.7, t$_R$=12.53).

(S)-2-(2, 3-dichlorophenoxy)-N-(2-(thiazol-5-yl) benzo[d]oxazol-5-yl) propanamide (R₁=5-thiazole, X=H, R₂=2,3-di-Cl Ph, R₃=S(Me), Y=O, Q40)

The general procedure for compound 8 was followed condensing (S)-2-(2,3-dichloro-phenoxy propanoic acid (compound 7) with compound 4 to afforded title compound Q40 (76%) as white solid. $^1$H NMR (CDCl$_3$, 400 MHz) δ 1.76 (d, J=6.8 Hz, 3H), 4.89 (q, J=6.8 Hz, 1H), 6.92 (dd, J$_1$=7.2 Hz, J$_2$=2.4 Hz, 1H), 7.17-7.22 (m, 2H), 7.55 (q, J=8.8 Hz, 2H), 8.09 (s, 1H), 8.64 (s, 1H), 8.81 (s, 1H); $^{13}$C NMR (CDCl$_3$, 100 MHz) δ 18.6, 76.9, 110.9, 111.6, 113.2, 118.6, 120.5, 122.9, 124.3, 125.7, 128.1, 134.7, 142.4, 145.7, 147.6, 153.7, 156.4, 158.0, 169.1; ESI-HRMS for C$_{19}$H$_{14}$N$_3$O$_3$SCl$_2$ (M+H)$^+$ calcd. 434.0133. found 434.0136, Chiral purity (% ee 99.1, t$_R$=15.5).

(S)-2-(2, 3-dichlorophenoxy)-N-(2-(thiazol-2-yl) benzo[d]oxazol-5-yl) propanamide (R₁=2-thiazole, X=H, R₂=2,3-diCl Ph, R₃=S(Me), Y=O, Q58)

The general procedure for compound 8 was followed condensing (S)-2-(2,3-dichloro-phenoxy propanoic acid (compound 7) with compound 4 (R₁=2-thiazole) to afforded title compound (69%) as white solid. $^1$H NMR (CDCl$_3$, 400 MHz) δ 1.72 (d, J=6.8 Hz, 3H), 4.85 (q, J=6.8 Hz, 1H), 6.89 (dd, J$_1$=8 Hz, J$_2$=2 Hz, 1H), 7.12-7.18 (m, 2H), 7.55 (bs, 2H), 7.59 (d, J=2.8 Hz, 1H), 8.03 (d, J=3.2 Hz, 1H), 8.14 (d, J=1.2 Hz, 1H); $^{13}$C NMR (CDCl$_3$, 100 MHz) δ 18.6, 77.0, 111.5, 112.0, 113.2, 119.5, 122.9, 123.5, 124.3, 128.0, 134.5, 134.9, 142.0, 145.3, 147.8, 153.7, 154.7, 158.0, 169.2; ESI-HRMS for C$_{19}$H$_{14}$N$_3$O$_3$SCl$_2$ (M+H)$^+$ calcd. 434.0133. found 434.0132, Chiral purity (% ee >99, t$_R$=12.88).

N-(2-(1H-pyrrol-2-yl) benzo[d]oxazol-5-yl) 2-(naphthalene-1-yloxy) propanamide (R₁=2-pyrrole, X=H, R₂=2-Naphthyl, R₃=Me, Y=O, Q14)

The general procedure for compound 8 was followed condensing 2-(naphthalene-1-yloxy) propanoic acid (7) with compound 4 (R₁=2-pyrrole) to afforded title compound (70%) as white solid. $^1$H NMR (CDCl$_3$, 400 MHz) δ 1.82 (d, J=6.8 Hz, 3H), 5.02 (q, J=6.4 Hz, 1H), 6.36 (dd, J$_1$=2.4 Hz, J$_2$=6 Hz, 1H), 6.91 (d, J=8 Hz, 1H), 7.06 (d, J=1.6 Hz, 2H), 7.32-7.43 (m, 3H), 7.52-7.60 (m, 3H), 7.85-7.89 (m, 2H), 8.34 (d, J=12 Hz, 2H), 9.87 (d, J=1.6 Hz, 1H); $^{13}$C NMR (CDCl$_3$, 100 MHz) δ 19.1, 76.2, 107.3, 110.4, 111.0, 111.1, 113.7, 117.5, 119.5, 120.5, 121.5, 122.3, 123.6, 126.0, 126.0, 126.1, 127.0, 128.1, 134.1, 134.9, 142.0, 147.2, 152.6, 159.0, 170.5; ESI-HRMS for C$_{24}$H$_{20}$N$_3$O$_3$ (M+H)$^+$ calcd. 398.1505. found 398.1509.

2-(naphthalene-1-yloxy)-N-(2-(pyrimidin-2-yl) benzo[d]oxazol-5-yl) propanamide (R₁=2-pyrimidine, X=H, R₂=2-Naphthyl, R₃=Me, Y=O, Q15)

The general procedure for compound 8 was followed condensing 2-(naphthalene-1-yloxy) propanoic acid (compound 7) with compound 4 (R₁=2-pyrimidine) to afforded title compound (63%) as white solid. $^1$H NMR (CDCl$_3$, 400 MHz) δ 1.83 (d, J=6.8 Hz, 3H), 5.04 (q, J=6.8 Hz, 1H), 6.93 (d, J=7.6 Hz, 1H), 7.39 (t, J=8.4 Hz, 1H), 7.61-7.53 (m, 4H), 7.88-7.86 (m, 1H), 8.09 (s, 1H), 8.34 (d, J=7.2 Hz, 1H), 8.44 (s, 1H), 8.99 (d, J=4.8 Hz, 2H); $^{13}$C NMR (CDCl$_3$, 100 MHz) δ 19.1, 76.4, 107.5, 111.7, 111.7, 113.1, 120.5, 121.5, 122.2, 122.4, 125.9, 126.0, 126.1, 127.0, 128.1, 134.8, 134.9, 142.2, 148.4, 152.7, 155.2, 158.2, 170.7; ESI-HRMS for C$_{24}$H$_{19}$N$_4$O$_3$ (M+H)$^+$ calcd. 411.1457. found 411.1460.

2-(4-chloronaphthalen-1-yloxy)-N-(2-(pyridin-4-yl) benzo[d]oxazol-5-yl) propanamide (R₁=4-pyridyl, X=H, R₂=2-(4-Cl-naphthyl), R3=Me, Y=O, Q29)

The general procedure for compound 8 was followed condensing 2-(4-Cl-naphthalene-1-yloxy) propanoic acid (compound 7) with compound 4 to afforded title compound Q29 (68%) as white solid. $^1$H NMR (CDCl$_3$, 400 MHz) δ 1.83 (d, J=6.8 Hz, 3H), 5.0 (q, J=6.8 Hz, 1H), 6.84 (d, J=8.4 Hz, 1H), 7.46-7.50 (m, 2H), 7.54 (d, J=8.8 Hz, 1H), 7.63-7.71 (m, 2H), 8.04-8.07 (m, 3H), 8.27 (d, J=8 Hz, 1H), 8.36 (d, J=8 Hz, 2H), 8.81 (d, J=4 Hz, 2H); $^{13}$C NMR (CDCl$_3$, 100 MHz) 19.0, 76.5, 107.3, 111.1, 112.5, 119.6, 121.1, 122.0, 124.9, 125.5, 125.9, 126.9, 128.1, 131.8, 134.2, 134.4, 134.4, 134.7, 142.4, 148.1, 150.9, 151.7, 161.8, 170.3; ESI-HRMS for C$_{25}$H$_{19}$N$_3$O$_3$Cl (M+H)$^+$ calcd. 444.1115. found 444.1119.

2-(4-chloronaphthalen-1-yloxy)-N-(2-(thiazol-5-yl) benzo[d]oxazol-5-yl) propanamide (R₁=5-thiazole, X=H, R₂=2-(4-Cl-naphthyl), R₃=Me, Y=O, Q30)

The general procedure for compound 8 was followed condensing 2-(4-Cl-naphthalene-1-yloxy) propanoic acid (7) with compound 4 (R₁=5-thiazole) to afford Q30 (64%) as a white solid. $^1$H NMR (CDCl$_3$, 400 MHz) δ 1.82 (d, J=6.8 Hz, 3H), 4.99 (q, J=6.8 Hz, 1H), 6.83 (d, J=8.4 Hz, 1H), 7.44-7.50 (m, 3H), 7.62-7.71 (m, 2H), 7.98 (d, J=2 Hz, 1H), 8.25-8.37 (m, 3H), 8.62 (s, 1H), 8.96 (s, 1H); $^{13}$C NMR (CDCl$_3$, 100 MHz) δ 19.1, 76.6, 107.4, 110.9, 112.1, 119.0, 122.0, 125.0, 125.6, 126.0, 126.9, 127.0, 128.2, 131.8, 134.5, 142.4, 145.8, 147.8, 151.7, 156.5, 161.8, 166.4, 170.3; ESI-HRMS for C$_{23}$H$_{17}$N$_3$O$_3$SCl (M+H)$^+$ calcd. 450.0679. found 450.0680.

N-(2-(pyridin-4-yl)benzo[d]oxazol-5-yl)-2,3-dihydrobenzo[b][1,4]dioxine-2-carboxamide (R₁=4-pyridyl, X=H, Q20)

The general procedure for compound 8 was followed using starting materials 2,3-dihydrobenzo [b][1,4]dioxine-2-carboxylic acid and compound 4 (5-thiazole) to give title compound Q20 (73%) as a white solid. $^1$H NMR (CDCl$_3$, 400 MHz) δ 4.31 (dd, J, =11.6 Hz, J$_2$=7.2 Hz, 1H), 4.66 (dd, J$_1$=12 Hz, J$_2$=2.8 Hz, 1H), 4.86 (dd, J, =7.4 Hz, J$_2$=2.8 Hz, 1H), 6.93-6.96 (m, 3H), 7.06-7.08 (m, 1H), 7.59 (s, 2H), 8.07-8.08 (m, 2H), 8.14 (s, 1H), 8.43 (s, 1H), 8.83 (d, J=5.6 Hz, 2H); $^{13}$C NMR (CDCl$_3$, 100 MHz) δ 65.5, 73.5, 111.2, 112.6, 117.3, 118.0, 119.6, 121.2, 122.3, 123.0, 134.2, 134.3, 141.5, 142.4, 143.4, 148.2, 150.9, 161.9, 165.4; ESI-HRMS for C$_{21}$H$_{16}$N$_3$O$_4$(M+H)$^+$ calcd. 374.1141. found 374.1138.

(S)—N-(7-chloro-2-(pyridin-4-yl)benzo[d]oxazol-5-yl)-2-(2,3-dichlorophenoxy)propanamide (R₁=4-pyridyl, R₂=(S)-2,3-Di-Cl-Ph, R₃=(S) Me, X=Cl, Y=O, Q39)

The general procedure for compound 8 was followed condensing (S)-2-(2,3-dichlorophenyl) propanoic acid 7, with compound 4 to afforded title compound (68%) as white solid. $^1$H NMR (CDCl$_3$, 400 MHz) δ 1.73 (d, J=6.8 Hz, 3H), 4.87 (q, J=6.8 Hz, 1H), 6.90 (dd, J, =6.4 Hz, J$_2$=3.2 Hz, 1H), 7.18-7.23 (m, 2H), 7.75 (d, J=2 Hz, 1H), 7.97 (d, J=1.6 Hz, 1H), 8.08 (d, J=5.2 Hz, 2H), 8.82 (d, J=8 Hz, 3H); $^{13}$C NMR (CDCl$_3$, 100 MHz) δ 18.5, 77.0, 110.4, 113.3, 116.5, 119.2, 121.3, 124.5, 128.1, 133.7, 134.6, 135.3, 143.2, 144.8, 150.9, 153.6, 162.1, 162.6, 169.3; ESI-HRMS for C$_{21}$H$_{15}$N$_3$O$_3$Cl$_3$ (M+H)$^+$ calcd. 462.0179 found 462.0182, Chiral purity (% ee >99, t$_R$=4.52).

2-(2,3-dichlorophenylamino)-N-(2-(pyridine-4-yl)benzo[d]oxazol-5-yl)propanamide (R$_1$=4-pyridyl, R$_2$=2,3-Di-Cl-Ph, R$_3$=(S) Me, X=H, Y=N, Q60)

Similarly prepared as per compound 8 procedure, using (S)-2-(2,3-dichlorophenyl) propanoic acid 7 and compound 4 (4-pyridine) to obtained title compound Q60 as white solid (71%). $^1$H NMR (CDCl$_3$, 400 MHz) δ 1.72 (d, J=6.8 Hz, 3H), 3.95 (dq, J=7.2 Hz, J=3.2 Hz, 1H), 4.79 (d, J=2.8 Hz, 1H), 6.56 (d, J=8.4 Hz, 1H), 6.96 (d, J=8 Hz, 1H), 7.09 (t, J=8 Hz, 1H), 7.46 (dd, J=9.2 Hz, J$_2$=2 Hz, 1H), 7.54 (d, J=8.4 Hz, 1H), 8.06 (d, J=4 Hz, 2H), 8.09 (d, J=1.6 Hz, 1H), 8.56 (s, 1H), 8.8 (bs, 2H); $^{13}$C NMR (CDCl$_3$, 100 MHz) δ 20.0, 56.4, 110.8, 111.1, 112.4, 118.6, 119.6, 120.9, 121.2, 128.4, 133.5, 134.3, 134.7, 142.4, 144.1, 148.0, 150.9, 161.7, 171.7; C$_{21}$H$_{17}$N$_4$O$_2$Cl$_2$ (M+H)$^+$ calcd. 427.0729 found 427.0724.

2-methyl-3-phenyl-N-(2-(pyridine-4-yl)benzo[d]oxazol-5-yl)propanamide (R$_1$=4-pyridyl, X=H, Q44)

Similarly prepared as per compound 8 procedure, using starting materials 2-methyl-3-phenylpropanoic acid and compound 4 to obtained title compound as white solid (75%). $^1$H NMR (CDCl$_3$, 400 MHz) δ 1.29 (d, J=6 Hz, 3H), 2.63 (q, J=6.4 Hz, 1H), 2.77 (dd, J$_1$=16 Hz, J$_2$=5.6 Hz, 1H), 3.02 (dd, J$_1$=16 Hz, J$_2$=9.2 Hz, 1H), 7.17-7.25 (m, 5H), 7.34-7.44 (m, 3H), 7.75 (s, 1H), 7.99 (d, J=4 Hz, 2H), 8.75 (s, 2H); $^{13}$C NMR (CDCl$_3$, 100 MHz) δ 18.0, 40.9, 44.9, 110.9, 112.5, 120.0, 121.2, 126.7, 128.8, 129.1, 134.4, 135.3, 139.8, 142.1, 147.8, 150.8, 174.3; ESI-HRMS for C$_{22}$H$_{20}$N$_3$O$_2$ (M+H)$^+$ calcd. 358.1556 found 358.1556.

2-phenyl-N-(2-(pyridine-4-yl)benzo[d]oxazol-yl)propanamide (R$_1$=4-pyridyl, X=H, Q45)

Similarly prepared as per compound 8, using starting materials 2-phenylpropanoic acid and compound 4 (4-pyridine) to obtained Q45 as white solid (77%). $^1$H NMR (CDCl$_3$, 400 MHz) δ 1.61 (d, J=7.2 Hz, 3H), 3.74 (q, J=7.2 Hz, 1H), 7.17 (s, 1H), 7.23 (s, 1H), 7.29-7.32 (m, 1H), 7.37-7.41 (m, 4H), 7.47 (d, J=8.8 Hz, 1H), 7.91 (d, J=1.6 Hz, 1H), 8.01 (dd, J=1.6 Hz, J$_2$=1.2 Hz, 2H), 8.77 (d, J=5.6 Hz, 2H); $^{13}$C NMR (CDCl$_3$, 100 MHz) δ 18.8, 48.3, 110.9, 112.1, 119.4, 121.1, 127.92, 127.94, 129.4, 134.3, 135.4, 140.9, 142.3, 147.8, 150.9, 161.6, 172.5; ESI-HRMS for C$_{21}$H$_{18}$N$_3$O$_2$(M+H)$^+$ calcd. 344.1399. found 344.1400.

(S)-2-phenyl-N-(2-(pyridine-4-yl)benzo[d]oxazol-5-yl)propanamide (R$_1$=4-pyridyl, X=H, Q48)

Similarly prepared as per compound 8, using starting materials (S)-2-phenylpropanoic acid and compound 4 (R,=2-pyridine) to obtained Q48 as white solid (77%). $^1$H NMR (CDCl$_3$, 400 MHz) δ 1.52 (d, J=7.2 Hz, 3H), 3.67 (q, J=7.2 Hz, 1H), 7.15 (t, J=8.4 Hz, 1H), 7.21-7.35 (m, 5H), 7.69 (s, 1H), 7.83 (s, 1H), 7.91 (d, J=5.6 Hz, 2H), 8.68 (d, J=5.2 Hz, 2H); $^{13}$C NMR (CDCl$_3$, 100 MHz) δ 18.9, 31.1, 42.7, 48.0, 110.8, 112.2, 119.7, 120.5, 121.1, 127.7, 127.8, 128.1, 129.3, 134.3, 135.6, 141.1, 142.1, 147.7, 148.4, 149.1, 150.8, 161.4, 172.9; ESI-HRMS for C$_{21}$H$_{18}$N$_3$O$_2$(M+H)$^+$ calcd. 344.1399. found 344.1397 purity (% ee >99, t$_R$=8.07 min).

(R)-2-phenyl-N-(2-(pyridine-4-yl)benzo[d]oxazol-5-yl)propanamide (R$_1$=4-pyridyl, X=H, Q49)

Similarly prepared as per compound 8 procedure, using starting materials (R)-2-phenylpropanoic acid and compound 4 (4-pyridine) to obtain title compound Q49 as white solid (78%). $^1$H NMR (CDCl$_3$, 400 MHz) δ 1.59 (d, J=7.2 Hz, 3H), 3.76 (q, J=6.8 Hz, 1H), 7.21-7.29 (m, 1H), 7.32-7.41 (m, 6H), 7.90 (s, 1H), 7.97 (d, J=4.8 Hz, 3H), 8.74 (s, 2H); $^{13}$C NMR (CDCl$_3$, 100 MHz) δ 18.9, 48.0, 110.8, 112.3, 119.8, 121.2, 127.7, 127.8, 129.2, 134.3, 135.6, 141.1, 142.1, 147.7, 150.7, 161.4, 172.9; ESI-HRMS for C$_{21}$H$_{18}$N$_3$O$_2$ (M+H)$^+$ calcd. 344.1399. found 344.1393 (% ee 99, t$_R$=11.29 min).

Example 10

Synthesis of (S)-2-(naphthalen-1-ylamino)-N-(2-(pyridin-4-yl)benzo[d]oxazol-5-yl)propanamide 15 (Q74) (R$_1$=Pyridyl, X=H)

General procedure for the synthesis of (R) or (S)-2-((2,3-dichlorophenyl)amino)propanoic acid 11

A mixture of (R) or (S)-2-aminopropanoic acid 10 (163 mg, 1.82 mmol), 2, 3-dichloro iodo benzene (500 mg, 1.83 mmol), CS$_2$CO$_3$ (1.19 g, 3.65 mmol), CuI (69.7 mg, 0.36 mmol) were dissolved in DMF (3 mL) under N$_2$ atmosphere, heated up to 90° C. and stirred it for 48 h. The mixture was cooled to room temperature and diluted with water and adjusted to pH 3-5 by adding conc. HCl. Extracted with DCM and washed with brine solution. Organic layer was dried on MgSO$_4$, filtered, concentrated under vacuum. The corresponding product was purified by using flash column chromatography on silica using ethyl acetate/n-hexane (50:50) to afforded (R) or (S)-2-(2, 3-dichlorophenylamino) propanoic acid 11 (240 mg, 57%) as a brown solid. $^1$H NMR (CDCl$_3$, 400 MHz) δ 1.60 (d, J=7.2 Hz, 3H), 4.17 (q, J=7.2 Hz, 1H), 6.48 (d, J=8 Hz, 1H), 6.85 (d, J=8 Hz, 1H), 7.05 (t, J=8.4 Hz, 1H).

Synthesis of (R)-2-(2,3-dichlorophenylamino)-N-(2-(pyridine-4-yl)benzo[d]oxazol-yl)propanamide Q66 (R$_1$=pyridyl, X=H)

The general procedure for compound 8 was followed using compound 11 ((R)-2-(2,3-dichlorophenylamino) propanoic acid and 4 to yielded (68%) as a brown solid. $^1$H NMR (CDCl$_3$, 400 MHz) δ 1.72 (d, J=6.8 Hz, 3H), 3.95 (dq, J=7.2 Hz, J$_2$-3.2 Hz, 1H), 4.79 (d, J=2.8 Hz, 1H), 6.56 (d, J=8.0 Hz, 1H), 6.96 (d, J=8 Hz, 1H), 7.09 (t, J=8 Hz, 1H), 7.47 (dd, J$_1$=8.8 Hz, J$_2$=2 Hz, 1H), 7.54 (d, J=8.8 Hz, 1H), 8.08 (d, J=8 Hz, 2H), 8.09 (s, 1H), 8.56 (s, 1H), 8.8 (bs, 2H); $^{13}$C NMR (CDCl$_3$, 100 MHz) δ 20.0, 56.4, 110.8, 111.1, 112.4, 118.6, 119.6, 120.9, 121.3, 128.4, 133.5, 134.3, 134.7, 142.4, 144.1, 148.0, 150.8, 161.7, 171.8; ESI-HRMS for C$_{21}$H$_{17}$N$_4$O$_2$Cl$_2$ (M+H)$^+$ calcd. 427.0729 found 427.0726, Chiral purity (% ee 78.5, t$_R$=43.53 min).

Synthesis of (S)-2-(2,3-dichlorophenylamino)-N-(2-(pyridine-4-yl)benzo[d]oxazol-5-yl)propanamide Q67 (R$_1$=Pyridyl, X=H)

The general procedure for compound 8 was followed using compound 11 ((S)-2-(2,3-dichlorophenylamino) propanoic acid and 4 to yielded (70%) as a brown solid. $^1$H NMR (CDCl$_3$, 400 MHz) δ 1.72 (d, J=6.8 Hz, 3H), 3.95 (dq, J=7.2 Hz, J$_2$=3.2 Hz, 1H), 4.79 (d, J=2.8 Hz, 1H), 6.56 (d, J=8.0 Hz, 1H), 6.96 (d, J=8 Hz, 1H), 7.09 (t, J=8 Hz, 1H), 7.47 (d, J=8.4 Hz, 1H), 7.54 (d, J=8.8 Hz, 1H), 8.08 (d (broad), 3H), 8.56 (s, 1H), 8.8 (bs, 2H); $^{13}$C NMR (CDCl$_3$, 100 MHz) δ 19.9, 56.35, 110.7, 111.0, 112.5, 118.5, 119.7, 120.7, 121.2, 128.3, 133.5, 134.3, 134.8, 142.3, 144.1, 148.0, 150.8, 161.6, 171.9; ESI-HRMS for C$_{21}$H$_{17}$N$_4$O$_2$Cl$_2$ (M+H)$^+$ calcd. 427.0729 found 427.0731, Purity (% ee 90.5, t$_1$=20.49 min).

Preparation of (S)-methyl 2-(naphthalen-1-ylamino)propanoate 13

To a dry round bottom flask equipped with a stir bar was added L-alanine methyl ester hydrochloride (500 mg, 3.58 mmol), 1-Naphthalene boronic acid (1000 mg, 5.81 mmol), dry Cu(OAc)$_2$ (715 mg, 3.93 mmol), 4 A° molecular sieves (1.34 g). The flask was sealed with septum, evacuated and back filled with O$_2$ atmosphere. Triethyl amine (0.92 mL), and dry DCM (30 mL) were added at room temperature, stirred for 48 h. The reaction mixture was quenched with 13 mL 2M NH$_3$ in methanol. The volatiles were removed in vacuo and the resulting crude oil was purified by silica gel flash chromatography ethyl acetate/n-hexane (10:90) to give 280 mg of the title compound as brown viscous oil (34% yield).

Preparation of (S)-2-(naphthalen-1-ylamino) propanoic add 14

(S)-methyl 2-(naphthalen-1-ylamino) propanoate 13 (40 mg, 0.174 mmol) was dissolved in anhydrous methanol (1 mL) and 1 M NaOH (0.18 mmol, 1.1 eq) was added drop wise to this solution. Stirred at room temperature for 12 h. The resulting reaction mixture was concentrated and extracted from 10% Na$_2$CO$_3$ and dichloro methane, the aqueous layer was acidified with 1 M HCl, precipitate was collected and washed with DCM. Isolated from flash column chromatography ethyl acetate/n-Hexane (40:70) to yielded 67% (25 mg) as a brown solid. $^1$H NMR (CDCl$_3$, 400 MHz) δ 1.60 (d, J=6.8 Hz, 3H), 4.24 (q, J=6.8 Hz, 1H), 6.49 (d, J$_1$=6 Hz, J$_2$=1.6 Hz, 1H), 7.18-7.25 (m, 2H), 7.39-7.41 (m, 2H), 7.72-7.81 (m, 2H).

Synthesis of (S)-2-(naphthalen-1-ylamino)-N-(2-(pyridin-4-yl)benzo[d]oxazol-5-yl)propanamide 15 (Q74) (R$_1$=Pyridyl, X=H)

The general procedure for compound 8 was followed using compound 13 (S)-2-(naphthalen-1-ylamino) propanoic acid and 4 to yielded (60%) as a brown solid. $^1$H NMR (CDCl$_3$, 400 MHz) δ 1.79 (d, J=6.8 Hz, 3H), 4.13 (q, J=6.8 Hz, 1H), 4.69 (bs, 1H), 6.66 (d, J=7.2 Hz, 1H), 7.56-7.32 (m, 6H), 7.87 (d, J=7.2 Hz, 1H), 7.95 (d, J=8 Hz, 1H), 8.08 (bs, 3H), 8.79 (bs, 3H); $^{13}$C NMR (CDCl$_3$, 100 MHz) δ 20.2, 56.4, 106.9, 110.9, 112.4, 119.6, 12.7, 120.3, 121.1, 123.6, 125.7, 126.3, 126.6, 129.2, 134.3, 134.4, 135.0, 141.4, 142.3, 147.9, 150.9, 161.6, 172.4; LCMS (ESI pos ion) m/z: calcd for C$_{25}$H$_{20}$N$_4$O$_2$, 408.16. found 409.26 (M+H), Chiral purity (% ee 97.7, t$_a$36.4 min).

Example 11

Synthesis of (R)-2-(2, 3-dichlorophenyl-N-(2-(pyridine-4-yl) benzo[d]oxazol-5-yl) propanamide (22, Q71, R$_1$=Pyridyl)

Preparation of 2-(2,3-dichlorophenyl) acetyl chloride compound 17

2,3-dichloro phenyl acetic acid 15 (500 Mg, 2.43 mmol) was dissolved in thionyl chloride (4 mL) under N$_2$ atmosphere at 0° C. in dried 100 mL RBF flask. Stirred it at 90° C. for 2 hr. After that distilled out the thionyl chloride by vacuum and dried to afforded corresponding acid chloride 17 as a colourless liquid. Proceeded to next reaction.

Preparation of (R)-4-benzyl-3-(2-(2,3-dichlorophenyl) acetyl) oxazolidin-2-one (compd 19)

(R)-4-benzyloxazolidin-2-one 18 (212.6 mg, 1.19 mmol) was dissolved in dried 100 mL round-bottom flask containing anhydrous THF (8 mL) under N$_2$ atmosphere. Cooled to −78° C. 2.5M solution of n-butyl lithium in hexanes (0.9 mL, 1.2 mmol) was added dropwise. Continuing the same temperature, 16 (2.4 mmol) was added to the reaction mixture and allowed to stir for 15 min. Then reaction mixture was warmed from −78° C. to 0° C. and allowed to stir for 30 min. The reaction mixture was quenched with aq. NH$_4$Cl. The solvent was removed in vacuo, extracted with DCM and washed with brine, dried (MgSO$_4$), filtered, and concentrated. The crude product was isolated by column chromatography eluting with (EtOAC/n-hexane, 20:80) to yield 19 (350 mg, 80%) as a brown semisolid. $^1$H NMR (CDCl$_3$, 400 MHz) δ 2.77 (t, J=12 Hz, 1H), 3.29 (d, J=12.8 Hz, 1H), 4.23 (m, 2H), 4.35 (d, J=18.4 Hz, 1H), 4.47 (d, J=18.4 Hz, 1H), 4.67 (m, 1H), 7.16-7.30 (m, 7H), 7.40 (dd, J, =4 Hz, J$_2$=2.4 Hz, 1H).

Preparation of (4R)-4-benzyl-3-(2-(2,3-dichlorophenyl) propanoyl) oxazolidin-2-one 20

To a solution of 19 (250 mg, 0.686 mmol) in dry THF (10 mL) was added sodium bis (trimethyl silyl) amide (0.61 mL, 0.617 mmol) at −78° C. under N$_2$ atmp. After stirring 1h, methyl iodide (0.192 mL, 3 mmol) was added slowly. The reaction mixture was stirred for 2h at −78° C. and allowed to warm to rt over 5 h. Reaction mixture was quenched with saturated NH$_4$Cl. The mixture was diluted with DCM and washed with water, sat.sodium sulfite (Na$_2$SO$_3$) and brine. The organic phase was dried over MgSO$_4$ and solvent was remove under reduced pressure. The crude product was purified by flash chromatography eluting with a linear gradient ranging from 5 to 20% ethyl acetate/hexane to provided compound 20 (200 mg, 77%) as white foam. $^1$H NMR (CDCl$_3$, 400 MHz) δ 1.56 (d, J=6.8 Hz, 3H), 2.79 (t, J=12.0 Hz, 1H), 3.28 (d, J=13.6 Hz, 1H), 4.09-4.16 (m, 2H), 4.66 (bs, 1H), 5.37 (q, J=6.8 Hz, 1H), 7.19-7.37 (m, 8H).

Preparation of (R)-2-(2,3-dichlorophenyl) propanoic acid (21)

To a solution of compound 20 (160 mg, 0.42 mmol) in THF (5 mL) and water at 0° C., was added a solution of lithium peroxide (prepared by adding 30% hydrogen peroxide (2.9 mL, 2.10 mmol) to lithium hydroxide (17.6 mg, 0.41 mmol) in water (0.679 mL)) dropwise. The mixture was stirred for 0° C. for 1h, quenched with sat.Na$_2$SO$_3$ (1.28 mL), solvent was removed in vacuo. The mixture was diluted with water and aqueous solution was extracted with DCM twice. The aq.layer was acidified with Conc.HCl and extracted with EtOAc twice. Combined organic layers were washed with brine and dried over MgSO$_4$, concentrated. Purified by column chromatography (EtOAc/n-Hexane 40:60) to afforded compound 21 (80 mg, 86.9%) as a white solid. $^1$H NMR (CDCl$_3$, 400 MHz) δ 1.51 (d, J=7.2 Hz, 3H), 4.27 (q, J=6.8 Hz, 1H), 7.16-7.24 (m, 2H), 7.37 (d, J=7.6 Hz, 1H)).

General procedure for the synthesis of (R)-2-(2, 3-dichlorophenyl-N-(2-(pyridine-4-yl) benzo[d]oxazol-5-yl) propanamide (Compd 22, Q71, R$_1$=Pyridyl)

22 was prepared by following general procedure for 8 condensation of 21 and compound 4 yielded 22 as a white solid (70%). $^1$H NMR (CDCl$_3$, 400 MHz) δ 1.61 (d, J=7.2 Hz, 3H), 4.31 (q, J=6.8 Hz, 1H), 7.26 (t, J=8 Hz, 1H), 7.42-7.54 (m, 4H), 7.98 (s, 1H), 8.05 (d, J=4.4 Hz, 2H), 8.80 (d, J=4 Hz, 2H); 13C NMR (CDCl$_3$, 100 MHz) δ 17.8, 45.0, 111.0, 112.4, 119.7, 121.2, 126.8, 128.2, 129.7, 132.0, 133.7, 134.3, 135.4, 140.9, 142.3, 147.9, 150.8, 161.6, 171.3. Chiral purity (% ee 83, t$_R$=1.58 min).

Example 12

Preparation of 2-Phenoxy-N-(2-pyridin-4-yl)-1H-benzo[d] imidazole-5-yl) propanamide (26, Q37)

Synthesis of 5-nitro-2-(pyridine-4-yl)-H-benzo[d]imidazole (24)

Compound 4-nitro-1, 2-diamine (500 mg, 3.26 mmol) (23) and 4-puridinecarboxaldehyde (419 mg, 3.91 mmol) were dissolved in in DMF (10 mL) and added desodium metabisulfite (742 mg, 3.91 mmol). Reaction heated at 120° C. for 10 h under N$_2$ atmosphere. After cooling, volatiles were removed under reduced pressure the reaction mixture was diluted with water and extracted from DCM. Organic layer was dried on MgSO$_4$, filtered and evaporated in vacuo. Purified by column chromatography on silica using MeOH/CHCl$_3$ (5:95) solvent system to give 5-nitro-2-(pyridine-4-yl)-H-benzo[d]imidazole 24 (480 mg, 61%) as a red solid. $^1$H NMR (CDCl$_3$, 400 MHz) 8.7 (d, J=9.2 Hz, 2H), 8.1 (d, J=2.4 Hz, 1H), 8.03 (d, J=8.2 Hz, 2H), 7.92 (dd, J$_1$=8.0 Hz, J$_2$=2.4 Hz, 1H), 7.82 (s, 1H).

Synthesis of 2-(pyridin-4-yl)-1H-benzo[d]imidazole-5-amine (25)

Title compound 25 was prepared from compound 24 as per general procedure of compound 4 in 64% yield. $^1$H NMR (CDCl$_3$, 400 MHz) 8.50 (d, J=8.2 Hz, 2H), 7.44 (d, J=8.2 Hz, 2H), 6.70 (dd, J, =8 Hz, J$_2$=2 Hz, 1H), 6.20-6.17 (dd, J$_1$=8 Hz, J$_2$=2 Hz, 1H), 6.10 (s, 1H), 4.30 (s, 2H).

Preparation of 2-Phenoxy-N-(2-pyridin-4-yl)-1H-benzo[d]imidazole-5-yl) propanamide (Compd 26, Q37)

To a solution of 2-(pyridin-4-yl)-1H-benzo[d]imidazole-5-amine 25 (50 mg, 0.237 mmol) was dissolved in anhydrous THF (6 mL), and added 2-phenoxypropanoyl chloride (52.5 mg, 0.284 mmol), Et$_3$N (36.2 mg, 0.355 mmol), 4-DMAP (2.89 mg, 0.023 mmol) at ° C. The mixture was stirred it for 30 min at room temperature. The reaction mixture was extracted with DCM, washed with brine. The corresponding crude product was purified by column on silica using MeOH/CHCl$_3$ (10:90) to furnish title compound 26 (60 mg, 70%) as a brown solid. $^1$H NMR (CDCl$_3$, 400 MHz) δ 1.68 (d, J=6.8 Hz, 3H), 4.85 (q, J=6.4 Hz, 1H), 6.95-7.05 (m, 4H), 7.26-7.32 (m, 2H), 7.52 (d, J=8.4 Hz, 1H), 7.86 (d, J=5.2 Hz, 2H), 8.08 (s, 1H), 8.57 (d, J=5.2 Hz, 2H), 8.65 (s, 1H); $^{13}$C NMR (CDCl$_3$, 100 MHz) δ 18.9, 75.5, 115.9, 117.72, 117.74, 120.8, 122.8, 130.1, 132.8, 137.6, 150.0, 150.3, 156.7, 171.5; ESI-HRMS for C$_{21}$H$_{16}$N$_3$O$_3$Cl$_2$ (M+H)$^+$ calcd. 428.0569 found 428.0578.

Example 13

Preparation of 5-(4-(1-phenoxyethyl)-1H-1,2,3-triazol-1-yl)-2-(thiazol-5-yl) benzo[d]oxazole (30, Q35)

Synthesis of (But-3-yn-2-yloxy) Benzene (28) via Mitsonobu reaction

Phenol 27 (422.9 mg, 4.49 mmol), But-3-yn-2-ol (300 mg, 4.28 mmol) were dissolved in anhydrous THF (10 mL) under N$_2$ atmosphere, at 0° C. was added Ph$_3$P (1.12 g, 4.26 mmol) portion wise, stirred it for 10 min, and then DEAD (894.6 mg, 5.14 mmol) added slowly. The resultant solution was heated up to 70° C. stirred for 20 h. To the reaction mixture water added and extracted with DCM and dried organic layer on MgSO$_4$, filtered, concentrated. Purified by flash chromatography using ethylacetate/n-hexane, 5:95) provided compound 28 (450 mg, 69%) as a solid. $^1$H NMR (CDCl$_3$, 400 MHz) δ 1.67 (d, J=6.8 Hz, 3H), 2.47 (d, J=2 Hz, 1H), 4.88 (q, J=2 Hz, 1H), 6.97-7.03 (m, 3H), 7.28-7.32 (m, 2H).

Preparation of 5-azido-2-(thiazol-5-yl) benzo[d]oxazole (29)

2-(thiazol-5-yl)benzo[d]oxazol-5-amine (4, R$_1$=thiazole, X=H) (50 mg, 0.23 mmol) dissolved in 2 mL HCl: H$_2$O (1:1) was cooled at −5° C. by ice-salt mixture. Then a solution of sodium nitrite (31.7 mg, 0.459 mmol) dissolved in water (15 mL) was added slowly at, stirred it for 60 min. Neutralized the reaction mixture with sodium acetate (37.7 mg, 0.459 mmol). Following this, a solution of NaN$_3$ (29.9 mg, 0.49 mmol) in water (0.5 mL) was added slowly over the period of 30 min by maintaining temperature between 0° C. to 5° C. After stirring 30 min, the solution was allowed to warm room temperature. Extracted with ethyl acetate, organic layer dried on MgSO$_4$ and concentrated to yielded 5-azido-2-(thiazol-5-yl) benzo [d]oxazole 29 (50 mg, 89%) as a solid.

Preparation of 5-(4-(1-phenoxyethyl)-1H-1, 2,3-triazol-1-yl)-2-(thiazol-5-yl) benzo [d]oxazole (30, Q35)

A mixture of 5-azido-2-(thiazol-5-yl) benzo[d]oxazole 29 (37 mg, 0.15 mmol) and (But-3-yn-2-yloxy) Benzene 28 (20 mg, 0.13 mmol) were dissolved in anhydrous acetonitrile (3 mL) under nitrogen atmosphere. Then added DIPEA (53 mg, 0.40 mmol) stirred at rt for 10 min. After that added CuI (51.7 mg, 0.27 mmol) portion wise, stirred for 30 mins. The mixture was quenched with NH$_4$Cl, diluted with water and extracted with DCM. Organic layer dried on MgSO$_4$, filtered and concentrated under vacuo. Corresponding crude product was isolated by using silica column (ethyl acetate/n-hexane 50:50) to furnish 5-(4-(1-phenoxyethyl)-1H-1, 2,3-triazol-1-yl)-2-(thiazol-5-yl) benzo [d]oxazole 30 (43 mg, 84%) as a solid. $^1$H NMR (CDCl$_3$, 400 MHz) δ 1.77 (d, J=6.4 Hz, 3H), 5.69 (q, J=6.4 Hz, 1H), 6.90-6.97 (m, 3H), 7.22-7.24 (m, 2H), 7.66 (d, J=8.8 Hz, 1H), 7.74 (dd, J$_1$=8 Hz, J$_2$=2 Hz, 1H), 7.90 (s, 1H), 7.99 (d, J=2 Hz, 1H), 8.66 (s, 1H), 8.98 (s, 1H); 13C NMR (Pyridine-d$_5$, 100 MHz) δ 22.1, 69.5, 112.3, 112.5, 116.6, 119.1, 121.7, 121.8, 125.8, 130.3, 135.3, 143.2, 146.9, 150.5, 151.1, 158.5, 159.0, 159.3; ESI-HRMS for C$_{20}$H$_{16}$N$_5$O$_2$S (M+H)$^+$ calcd. 390.1025. found 390.1031.

Example 14

Preparation of (S)—N-(3-(2-(2, 3-dichlorophenoxy) propanamido) phenyl) isonicotinamide 34 (Q43)

Preparation of N-(3-nitrophenyl) isonicotinamide 32

The general procedure for 8 was followed using 3-nitro aniline 31 and isonicotinic acid to afforded (68%) as a yellow solid. $^1$H NMR (DMSO-d$_6$, 400 MHz) δ 7.67-7.71 (m, 1H), 7.89-7.91 (m, 2H), 8.01 (dd, J, =8.4 Hz, J$_2$=1.6 Hz, 1H), 8.19 (dd, J, =8 Hz, J$_2$=1.6 Hz, 1H), 8.79-8.83 (m, 3H), 10.9 (NH, s, 1H).

Preparation of N-(3-aminophenyl) isonicotinamide 33

N-(3-nitrophenyl) isonicotinamide 32 was hydrogenated using general procedure 4 to yield 33 as a brown solid in 65% yield.

Preparation of (S)—N-(3-(2-(2, 3-dichlorophenoxy) propanamido) phenyl) isonicotinamide 34 (Q43)

The general procedure for compound 8 was followed condensing 33 and 7, (R$_2$=2,3-di-Cl-Ph, Y=O, R$_3$=S (Me)) (S)-2-(2,3-dichlorophenyl) propanoic acid to afforded 34 (63%) as white solid. $^1$H NMR (CDCl$_3$, 400 MHz) δ 1.67 (d, J=6.8 Hz, 3H), 4.79 (q, J=6.8 Hz, 1H), 6.84-6.88 (m, 1H), 7.15-7.23 (m, 3H), 7.31 (t, J=8 Hz, 1H), 7.59 (d, J=8 Hz, 1H), 7.68 (d, J=4.4 Hz, 2H), 8.02 (s, 1H), 8.24 (s, 1H), 8.68 (s, 1H), 8.75 (s, 2H); 13C NMR (CDCl$_3$, 100 MHz) δ 18.5, 77.0, 111.9, 113.3, 116.5, 117.0, 121.2, 123.0, 124.4, 128.0, 130.0, 134.5, 137.8, 138.3, 142.1, 150.8, 153.7, 164.0, 169.5; ESI-HRMS for C$_{21}$H$_{18}$N$_3$O$_3$Cl$_2$ (M+H)$^+$ calcd. 430.0725 found 430.0725, Chiral purity (% ee >99, t$_R$=10.54).

Example 15

Synthesis of N-(1-phenylethyl) 2-pyridin-4-yl) benzo [d] oxazole-5-carboxamide (compound 36, Q63)

The general procedure for compound 8 was followed condensing of 35 with alpha methyl benzyl amine to give 36 (71%) as white solid. $^1$H NMR (CDCl$_3$, 400 MHz) δ 1.57 (d, J=6.8 Hz, 3H), 5.29 (q, J=6.8 Hz, 1H), 6.41 (d, J=7.2 Hz, 1H), 7.19-7.25 (m, 1H), 7.27-7.36 (m, 4H), 7.58 (d, J=8.4 Hz, 1H), 7.85 (d, J=8.4 Hz, 1H), 8.00 (d, J=4.8 Hz, 2H), 8.13 (s, 1H), 8.77 (bs, 2H); $^{13}$C NMR (CDCl$_3$, 100 MHz) δ 21.9, 49.7, 111.2, 119.6, 121.3, 126.0, 126.4, 127.8, 129.0, 132.4, 134.0, 142.0, 143.1, 151.0, 152.8, 162.1, 166.1; ESI-HRMS for C$_{21}$H$_{11}$N$_3$O$_2$(M+H)$^+$ calcd. 344.1399 found 344.1403.

Example 16

(S)-2-(2,3-dichlorophenoxy)-N-(2-(pyridin-4-yl) benzo [d] oxazol-6-yl) propanamide (comd 40, R$_2$= (S)-2,3-DiCl-Ph, R$_3$=(S) Me, R$_5$=4-Pyridyl, Y=O, Q59)

Preparation of 6-nitro-2-(pyridin-4-yl) benzo [d]oxazole (compd 38)

The general procedure 3 was followed using 2-amino-5-nitro phenol (37) and 4-pyridyl carboxaldehyde to give 38 (75%) as yellow solid.

Preparation of 2-(pyridin-4-yl) benzo [d]oxazol-6-amine (Compd 39)

The general procedure 4 was followed using 6-nitro-2-(pyridin-4-yl) benzo [d]oxazole (38) to obtained 39 (85%) as yellow solid. $^1$H NMR (DMSO-d$_6$, 400 MHz) 5.61 (s, 2H), 6.66 (dd, J, =8 Hz, J$_2$=2 Hz, 1H), 6.79 (d, J=1.6 Hz, 1H), 7.44 (d, J=8.8 Hz, 1H), 7.92 (d, J=6 Hz, 2H), 8.71 (d, J=6 Hz, 2H).

(S)-2-(2,3-dichlorophenoxy)-N-(2-(pyridin-4-yl) benzo [d]oxazol-6-yl) propanamide (compd 40, R$_2$=(S)-2,3-DiCl-Ph, R$_3$=(S) Me, R$_5$=4-Pyridyl, Y=O, Q59)

The general procedure for compound 8 was followed condensing (S)-2-(2,3-dichlorophenyl) propanoic acid 7, with compound 39 to afforded 40 (76%) as white solid. $^1$H NMR (CDCl$_3$, 400 MHz) δ 1.71 (d, J=6.8 Hz, 3H), 4.85 (q, J=6.6 Hz, 1H), 6.88 (dd, J$_1$=7.2 Hz, J$_2$=2.8 Hz, 1H), 7.12-7.18 (m, 2H), 7.24 (dd, J, =8.8 Hz, J$_2$=2 Hz, 2H), 7.69 (d, J=8.4 Hz, 1H), 7.99 (d, J=5.6 Hz, 2H), 8.33 (s, 1H), 8.75 (d, J=5.2 Hz, 2H), 8.91 (s, 1H); $^{13}$C NMR (CDCl$_3$, 100 MHz) δ 18.3, 76.7, 102.6, 113.0, 117.4, 120.5, 120.7, 122.6, 124.1, 127.8, 134.0, 134.2, 135.6, 138.3, 150.6, 151.1, 153.4, 160.8, 169.0; ESI-HRMS for C$_{21}$H$_{16}$N$_3$O$_3$Cl$_2$ (M+H)$^+$ calcd. 428.0569. found 428.0567, Chiral purity (% ee >99, t$_R$=21.0).

(S)-2-(2,3-dichlorophenoxy)-N-(2-(thiazol-5-yl) benzo[d]oxazol-6-yl) propanamide (R$_2$=(S)-2,3-dichlorophenyl, R$_3$=(S)-Me, R$_5$=5-thiazole, Y=O, Q64)

The general procedure for compound 8 was followed condensing (S)-2-(2,3-dichlorophenyl) propanoic acid 7, with compound 38 to afforded title compound (70%) as white solid. $^1$H NMR (CDCl$_3$, 400 MHz) δ 1.73 (d, J=6.8 Hz, 3H), 4.88 (q, J=6.4 Hz, 1H), 6.89-6.92 (m, 1H), 7.17-7.19 (m, 1H), 7.23-7.26 (m, 2H), 7.66 (d, J=8.8 Hz, 1H), 8.29 (s, 1H), 8.61 (s, 1H), 8.85 (s, 1H), 8.94 (s, 1H); $^{13}$C NMR (CDCl$_3$, 100 MHz) δ 18.5, 76.9, 102.8, 113.2, 117.5, 120.1, 122.9, 124.3, 125.7, 128.1, 134.5, 135.4, 138.6, 142.4, 151.0, 153.6, 153.68, 156.2, 157.3, 169.2; ESI-HRMS for C$_{19}$H$_{14}$N$_3$O$_3$SCl$_2$ (M+H)$^+$ calcd. 434.0133 found 434.0139, Chiral purity (% ee >99, t=22.5).

Synthesis and Biological Evaluation of D Series Compounds

Scheme 9. General procedure for the synthesis of phthalazinone derivatives.

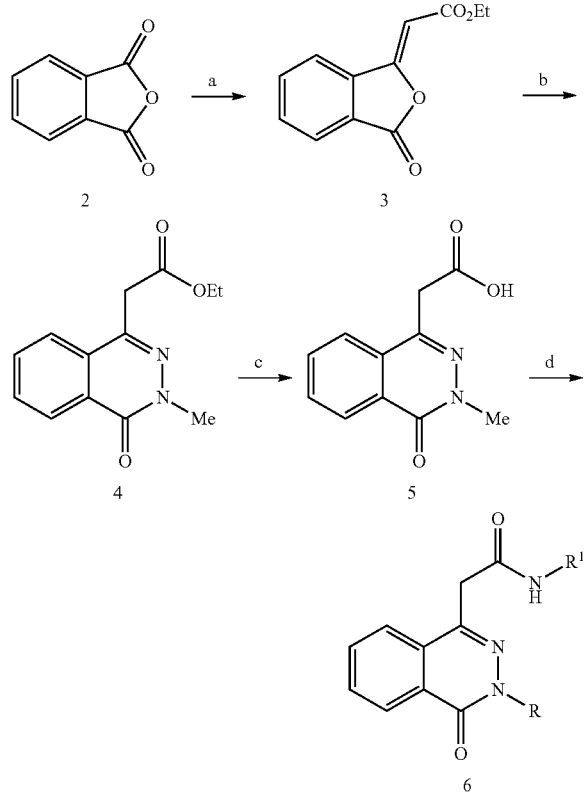

Reagents and Conditions: a) Ph₃PCHCO₂Et, CHCl₃, reflux, 16 h, b) NH₂NH₂ or NH₂NHMe, EtOH, reflux, 3 h. c) 3M NaOH/THF, reflux, 2 h followed by acidification. d) R¹—NH₂, EDC, HOBt, DIPEA, DMSO, 3-5 h.

Example 17

¹H NMR Data of Selected D Series Compounds (D62) N-(2-methylbenzofuran-5-yl)-2-(3-methyl-4-oxo-3,4-dihydrophthalazin-1-yl)-acetamide ¹H-NMR (DMSO $d_6$, 400 MHz) δ 10.23 (s, 1H), 8.30 (d, 1H, J=8 Hz), 7.92-8.00 (m, 2H), 7.82-7.88 (m, 2H), 7.41 (d, 1H, J=10 Hz), 7.31 (d, 1H, J=10 Hz), 6.52 (s, 1H), 4.09 (s, 2H), 3.72 (s, 3H), 2.40 (s, 3H).

(D64) N-(benzo[d]oxazol-5-yl)-2-(3-methyl-4-oxo-3,4-dihydrophthalazin-1-yl)acetamide ¹H-NMR (DMSO $d_6$, 400 MHz) δ 10.69 (s, 1H), 8.68 (s, 1H), 8.29-8.31 (m, 1H), 8.19 (bs, 1H), 7.92-7.90 (m, 2H), 7.85-7.89 (m, 1H), 7.74 (d, 1H, J=9 Hz), 7.43 (dd 1H, $J_1$=8 Hz, $J_2$=1.6 Hz, 1H), 4.15 (s, 2H), 3.73 (s, 3H).

(D67) N-(6,7,8,9-tetrahydrodibenzo[b,d]furan-5-yl)-2-(3-methyl-4-oxo-3,4-dihydro-phthalazin-1-yl)acetamide ¹H-NMR (DMSO $d_6$, 400 MHz) δ 10.21 (s, 1H), 8.26 (d, 1H, J=8 Hz), 7.88-7.96 (m, 2H), 7.88-7.96 (m, 2H), 7.80-7.84 (m, 1H), (7.76, d, J=2 Hz, 1H), (7.35, d, 1H, J=9 Hz), J=7.24 (dd, $J_1$=7 Hz, $J_2$=2 Hz, 1H 4.06 (s, 2H), 3.68 (s, 3H), 2.63 (br, 2H), 1.70-1.81 (m, 6H).

(D70) N-(9H-carbazol-3-yl)-2-(3-methyl-4-oxo-3,4-dihydrophthalazin-1-yl)acetam-de ¹H-NMR (DMSO $d_6$, 400 MHz) δ 11.19 (s, 1H), 10.36 (s, 1H), (8.38, s, 1H), 8.31 (d, 1H, J=8 Hz), 7.86-8.05 (m, 4H), 7.33-7.50 (m, 4H), 7.09-7.13 (m, 1H), 4.13 (s, 2H), 3.75 (s, 3H).

(D71) N-(9-ethyl-9H-carbazol-3-yl)-2-(3-methyl-oxo-3,4-dihydrophthalazin-1-yl) acetamide ¹H-NMR (DMSO $d_6$, 400 MHz) δ 10.39 (s, 1H) 8.41 (s, 1H), 8.31 (d, 1H, J 8 Hz), 8.01-8.05 (m, 2H), 7.94-7.97 (m, 1H), 7.85-7.89 (m, 1H), 7.56-7.58 (m, 3H), 7.41-7.45 (m, 1H), 7.13-7.17 (m, 1H), 4.40 (q, 2H, J=6.8 Hz), 4.14 (s, 2H), 3.74 (s, 3H), 1.29 t, 3H, J=6.8 Hz).

(D72) N-(dibenzo[b,d]furan-3-yl)-2-(3-methyl-4-oxo-3,4-dihydrophthalazin-1-yl)acetamide ¹H-NMR (DMSO $d_6$, 400 MHz) δ (10.57, s, 1H), J=8.32 (d, 1H, J=9 Hz), 7.93-8.08 (m, 5H), 7.86-7.90 (m, 1H), (7.66, d, 1H, J=9 Hz), 7.44-7.50 (m, 2H), 7.35-7.39 (m, 1H), (4.17, s, 2H), (3.74, s, 3H).

(D73) N-(dibenzo[b,d]furan-2-yl)-2-(3-methyl-4-oxo-3,4-dihydrophthalazin-1-yl)acetamide ¹H-NMR (DMSO $d_6$, 400 MHz) δ 10.70 (s, 1H), 8.45 (d, J=1.6 Hz, 1H), 8.32 (d, 1H, J=8 Hz), 8.13 (s, 1H), 7.95-8.09 (m, 4H), 7.87-7.91 (m, 1H), 7.67-7.71 (m, 2H), 7.59-7.62 (m, 1H), 7.47-7.55 (m, 2H), 7.37-7.41 (m, 1H), 4.18 (s, 2H), (3.74, s, 3H).

(D74) N-(4-bromo-3-methylphenyl)-2-(3-methyl-4-oxo-3,4-dihydrophthalazin-1-yl)-acetamide ¹H-NMR (DMSO $d_6$, 400 MHz) δ 10.44 (s, 1H), 8.30 (d, 1H, J=10 Hz), 7.92-7.97 (m, 2H), 7.85-7.89 (m, 1H), 7.50 (d, J=8.8 Hz, 1H), 7.36 (dd, $J_1$=9 Hz, $J_2$=2 Hz, 1H) 4.10 (s, 2H), 3.73, (s, 3H), 2.26, (s, 3H).

(D76) N-(4-cyan-3-methylphenyl)-2-(3-methyl-4-oxo-3,4-dihydrophthalazin-1-yl) acetamide ¹H-NMR (DMSO $d_6$, 400 MHz) δ 10.74 (s, 1H), 8.30 (d, 1H, J=8 Hz), 7.87-7.94 (m, 3H), 7.70 (d, 2H, J=8.8 Hz), 7.58 (d, 1H, J=8.4 Hz), 4.15 (s, 2H), 3.71 (s, 3H), 2.42 (s, 3H).

(D78) 2-(methyl-4-oxo-3,4-dihydrophthalazin-1-yl)-N-(1,2,4-trimethyl-1,2,3,4-tetrahydrobenzofuro[3,2-c]pyridin-8-yl)acetamide ¹H-NMR (DMSO d, 400 MHz) δ 10.46 (s, 1H), 8.36 (d, 1H, J=9 Hz), 8.06 (d, 1H, J=8 Hz), 8.0 (t, 2H, J=8 Hz), 7.93 (t, 1H, J=6.8 Hz), 7.51 (d, 1H, J=8 Hz), 7.39 (d, 1H, J=8 Hz), 4.17 (s, 2H), 3.79 (s, 3H), 3.40 (s, 2H), 3.14 (s, 2H), 2.56 (s, 3H), 2.46 (s, 3H), 2.31 (s, 1H), 1.40 (s, 3H), 1.28 (s, 1H), 1.24 (d, 3H, J=9 Hz).

(D84) N-(4-chloro-3-(trifluoromethyl)phenyl)-2-(3,5-diethyl-4-oxo-3,4-dihydrophthalazin-1-yl)acetamide $^1$H-NMR (DMSO-d$_6$, 400 MHz) δ 10.78 (s, 1H), 8.17 (d, 1H, J=1.6 Hz), 7.75-7.77 (m, 2H), 7.67 (d, J=8.8 Hz, 1H), 7.62 (d, 1H, J=6.8 Hz), 4.08 (s, 2H), 3.66 (s, 3H), 2.86 (s, 3H).

(D85) N-(4-chloro-3-methoxyphenyl)-2-(3,5-dimethyl-4-oxo-3,4-dihydrophthalazin-1-yl)acetamide $^1$H-NMR (DMSO-d$_6$, 400 MHz) δ 10.54 (s, 1H), 7.79-7.83 (m, 2H), 7.68 (d, J=8.4 Hz, 1H), 7.59 (s, 1H), 7.39 (d, J=8.4 Hz, 1H), 7.18 (d, 1H, J=9.2 Hz), 4.12 (s, 2H), 3.84 (s, 3H), 3.73 (s, 3H), 2.92 (s, 3H).

(D87) N-(dibenzo[b,d]furan-2-yl)-2-(hydroxy-3-methyl-4-oxo-3,4-dihydrophthalazin-1-yl)acetamide $^1$H-NMR (DMSO-d$_6$, 400 MHz) δ 12.71 (s, 1H), 10.58 (s, 1H), 8.48 (s, 1H), 8.12 (d, J=7.6 Hz, 1H), 7.18 (t, J=8.0 Hz, 1H), 7.75-7.71 (m, 2H), 7.64 (d, J=8.8 Hz, 1H), 7.59-7.56 (m, 1H), 7.52-7.42 (m, 2H), 7.27 (d, J=8 Hz, 1H), 4.17 (s, 2H), 3.81 (s, 3H).

(D89) N-(dibenzo[b,d]furan-2-yl)-2-(3,5-dimethyl-4-oxo-3,4-dihydrophthalazin-1-yl)acetamide $^1$H-NMR (DMSO-d$_6$, 400 MHz) δ 10.57 (s, 1H), 8.48 (d, J=2 Hz, 1H), 7.87-7.85 (m, 2H), 7.75-7.65 (m, 4H), 7.44 (t, J=8 Hz, 1H), 4.16 (2H, s), 3.75 (s, 3H), 2.93 (s, 3H).

(D90) N-(dibenzo[b]furan-2-yl)-2-(3,5-dimethyl-4-oxo-3,4-dihydrophthalazin-1-yl)acetamide $^1$H-NMR (DMSO-d$_6$, 400 MHz) δ 10.89 (s, 1H), 8.37 (d, J=7.6 Hz, 1H), 8.04-8.0 (m, 3H), 7.96-7.92 (m, 3H), 7.86-7.84 (m, 2H), 7.76 (d, J=10 Hz, 1H), 4.23 (s, 2H). 3.79 (s, 3H), 2.15 (s, 3H).

(D91) N-(3-chlorophenyl)-2-(3-methyl-4-oxo-3,4-dihydrophthalazin-1-yl)acetamide $^1$H-NMR (DMSO-d$_6$, 400 MHz) δ 10.55 (s, 1H), 8.30 (d, J=7.6 Hz, 1H), 7.97-7.94 (m, 2H), 7.89-7.79 (m, 1H), 7.79 (d, J=8.4 Hz, 1H), 7.12 (d, J=8.1 Hz, 1H), 7.34 (t, J=8.4 Hz, 1H), 7.12 (d, J=8.1 Hz, 1H), 4.11 (s, 2H), 3.72 (s, 3H).

Example 18

SAR Study of D Series Compounds and *C. parvum* IMPDH Screen

Inspired by the results with D41, a variety of fused heterocycles were explored as replacements of the 2-naphthylene. Although the 5-benzofuranyl analog D61 had reduced activity and the 5-benzoxazolyl analog D64 was inactive, the 2-methyl-5-benzofuranyl derivative D62 retained activity with an IC$_{50}$ of 70 nM. Furthermore, incorporation of an additional ring (D67) resulted in enhanced potency. Unsaturation of the ring further increased activity with D73 demonstrating an IC$_{50}$ of 4 nM. However, the regioisomer D72 and two carbazoles D70 and D71 were not active.

Compounds with IC$_{50}$ values less than 30 nM were candidates for evaluation of antiparasitic activity in a *Toxoplasma gondii* model of *C. parvum* infection. In this model, the endogenous *T. gondii* IMPDH and hypoxanthine-guanine-xanthine phosphoribosyltransferase genes have been knocked out and the CpIMPDH gene inserted to create *T. gondii*/CpIMPDH, a model parasite that relies on CpIMPDH for the production of guanine nucleotides. Both wild-type and *T. gondii*/CpIMPDH were cultured in human foreskin fibroblasts immortalized with hTERT, so this assay also reports on host cell toxicity. Compounds D45, D48, D67 and D73 all displayed sub-micromolar activity against *T. gondii*/CpIMPDH. However, only D48 displayed selectivity ≥30 versus the wild-type strain, strongly indicating that antiparasitic activity results from the inhibition of CpIMPDH.

Example 19

Inhibition of CPIMPDH

A compound of the invention (below) displayed sub-micromolar activity against *T. gondii*/CpIMPDH and selectivity >30 versus the wild-type strain. This strongly indicates that antiparasitic activity results from inhibition of CpIMPDH.

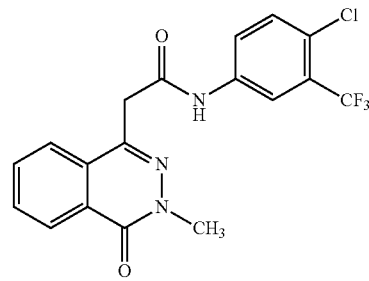 [SMILES: Cn1nc(CC(=O)Nc2ccc(Cl)c(C(F)(F)F)c2)c2ccccc2c1=O]

Figure 25:
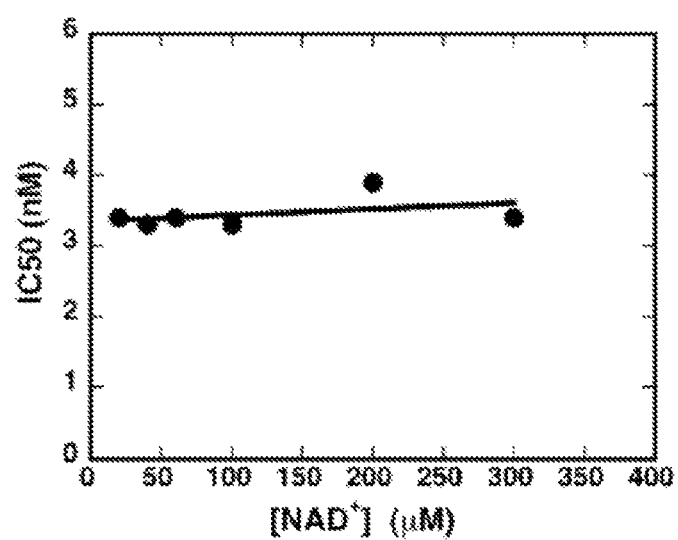

The inhibition of CpIMPDH by this compound was characterized further. Whereas some compounds are mixed inhibitors of CpIMPDH with respect to NAD$^+$ (K$_{is}$=1.8 μM, K$_{ii}$=7 μM), the above-mentioned compound is a pure noncompetitive inhibitor (K$_{is}$=K$_{ii}$=3.4±0.2 nM; FIG. 25).

This compound displayed good stability in mouse liver microsomes (T$_{1/2}$=79 min). This compound was advanced into the IL12 knockout mouse model of *C. parvum* infection. Additional optimization of pharmacokinetic properties may also be necessary for this compound series in order to achieve in vivo efficacy.

Example 20

Figure 27:
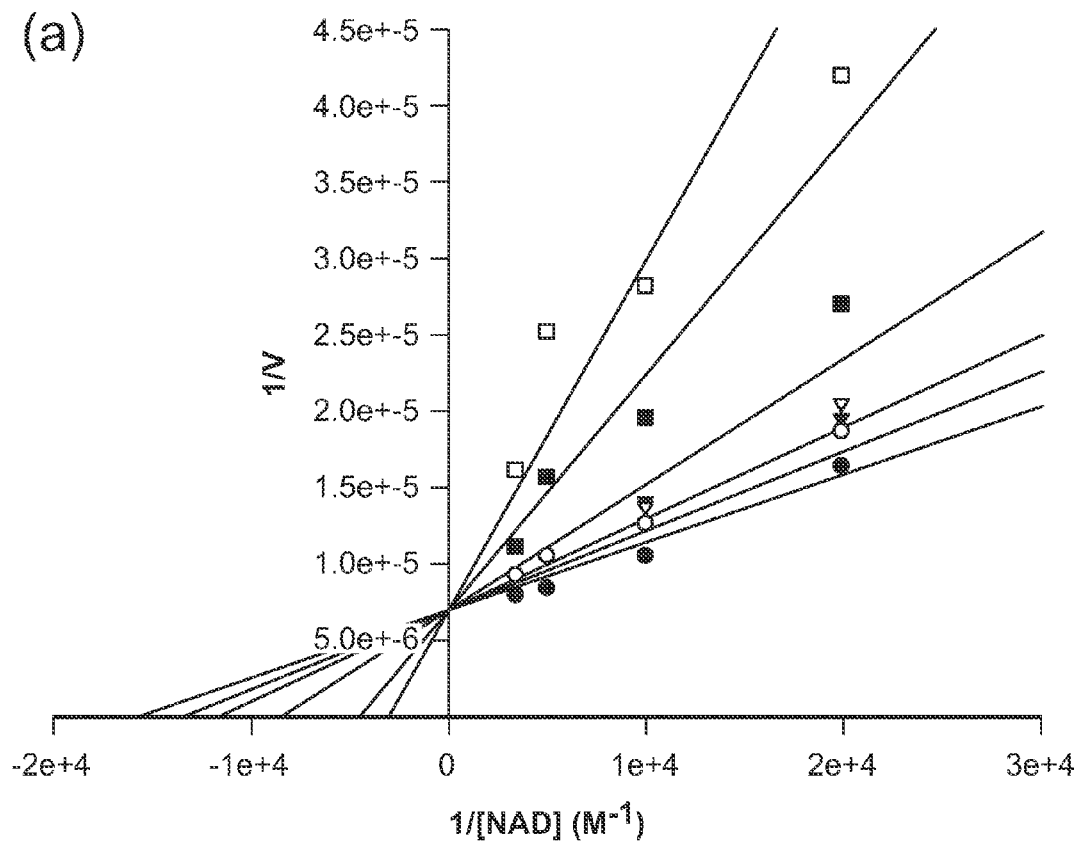

Evaluation of the Kinetic Mechanism of CpIMPDH Inhibition of Benzoxazole Compounds The high throughput screen was designed to target the cofactor site, since this site is the most diverged and therefore most likely to yield inhibitors selective for the parasite enzyme. CpIMPDH, like other IMPDHs characterized to date, has a kinetic mechanism wherein substrates bind randomly and hydride transfer occurs forming a covalent E-XMP* intermediate and NADH. Products dissociate in an ordered fashion, with NADH release occurring before the hydrolysis of E-XMP*. In principle, IMPDH inhibitors that bind in the cofactor site can be competitive, uncompetitive, or noncompetitive, depending on their relative affinities for the E, E-IMP, and E-XMP* complexes. In practice, most such inhibitors are noncompetitive, suggesting comparable affinities for E-IMP and E-XMP*. Uncompetitive inhibition is also commonly observed, indicating a strong preference for E-XMP*. The inhibition mechanisms of four representative inhibitors were evaluated. Surprisingly, the inhibition data with respect to $NAD^+$ for all four compounds were best fit by competitive mechanism (FIG. 27). However, the fit to a noncompetitive/mixed inhibition was not significantly inferior. This ambiguity is a consequence of $NAD^+$ substrate inhibition, which prevents the use of saturating $NAD^+$ concentrations. This observation suggests that these compounds have a strong preference for E-IMP. All four compounds are noncompetitive inhibitors with respect to IMP.

Example 21

Mouse Liver Microsomal Stability of Benzoxazole Compounds

Figure 28:
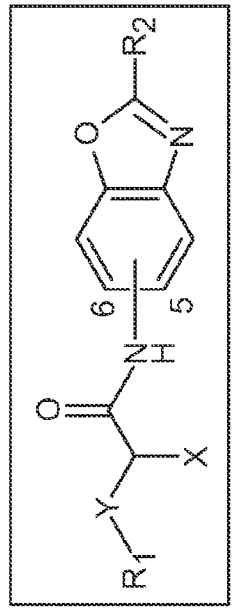
Figure 35:
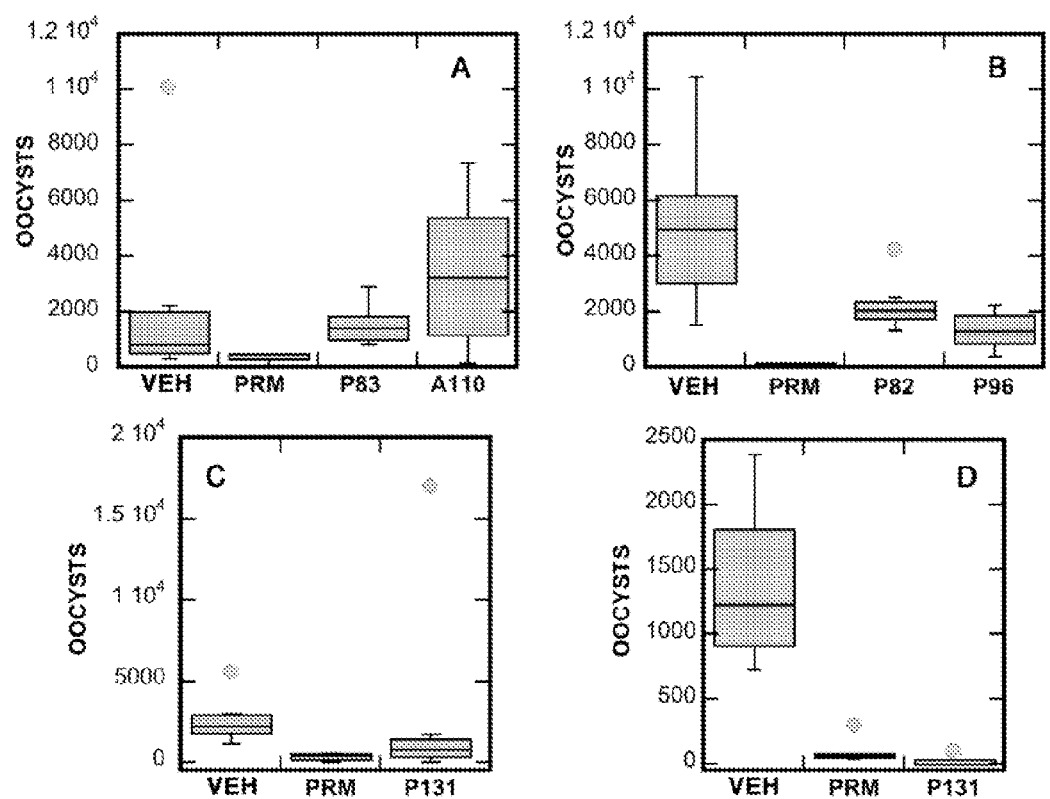
FIG. 35 depicts antiparasitic activity of CpIMPDH inhibitors. Each panel reflects a separate experiment. A, B and C) IL-12 knockout mice were infected with 1,000 *C. parvum* oocysts and treated with single daily doses of vehicle, paromomycin (2000 mg/kg) or compound by oral gavage. All compounds, with the exception of A110, were dosed at 250 mg/kg. A110 was dosed at 100 mg/kg. Fecal oocysts were counted on day 7 post infection. A) Experiment 2; B) Experiment 5; C) Experiment 7; D) Experiment 9; IL-12 knockout mice were infected with 10,000 *C. parvum* oocysts and treated with three daily doses of either vehicle, paromomycin (670 mg/kg) or P131 (83 mg/kg). Fecal oocysts were counted on day 5 post infection.

A selected set of the CpIMPDH inhibitors was evaluated for metabolic stability in mouse liver microsomes (FIG. 28). Compounds were incubated with microsomes at 37° C. in the presence and absence of NADPH. The percentage of compound remaining at various time points was determined, and then the data were fit to a first-order decay model to determine the half-life. Three ether derivatives (55, 62, and 40a) demonstrated poor stability in both the presence and absence of NADPH ($t_{1/2} \leq 12$ min), whereas 54 was moderately more stable ($t_{1/2}=30$ min). In the case of two phenylacetamide derivatives, the unsubstituted inhibitor 72 proved to be more stable ($t_{1/2}=43$ min) compared to the 2,3-dichlorophenyl inhibitor 22 ($t_{1/2}=25$ min) in the presence of NADPH. Both compounds were quite stable in the absence of NADPH. For the amine derivatives, the 2,3-dichlorophenyl inhibitor 15a also displayed moderate stability in the presence of NADPH ($t_{1/2}=44$ min), whereas the naphthyl derivative 15b was less stable in the presence or absence of NADPH ($t_{1/2}=18$ and 27 min, respectively).

Example 22

Evaluation of Antiparasitic Activity of Benzoxazole Compounds

Although the generation of potent CpIMPDH inhibitors has been accomplished with several structurally distinct compound classes, achieving antiparasitic activity in *C. parvum* remains a challenge. This organism cannot be continuously cultured in vitro, so such assays are poor mimics of in vivo infection in addition to having a poor dynamic range. However, the related intracellular parasite *T. gondii* has proven to be a well behaved organism that can be engineered to express fluorescent markers, facilitating its use in screening. Previously, we genetically engineered a *T. gondii* strain that relies on CpIMPDH (Toxo/CpIMPDH) to synthesize guanine nucleotides. In contrast, the wild type *T. gondii* strain RH (Toxo/WT) contains a eukaryotic IMPDH that is resistant to CpIMPDH inhibitors, thus providing target validation as well as a measure of host cell cytotoxicity.

A set of 22 CpIMPDH inhibitors were evaluated for activity in both Toxo/CpIMPDH and Toxo/WT assays (FIG. 29). Four compounds demonstrated $EC_{50}$ values of 5250 nM in the Toxo/CpIMPDH assay and selectivity of >30-fold versus Toxo/WT. Thus, the 2,3-dichlorophenyl or 1-naphthyl ethers or amines at either the 5- or 6-position of the 2-(4-pyridyl)- or 2-(thiazolyl)benzoxazole translated into encouraging antiparasitic activity. Furthermore, two of these compounds demonstrated $EC_{50}$ values of ≤30 nM and selectivity of >150-fold, indicating that the 2,3-dichlorophenyl ether or amine at either the 5- or 6-position of the 2-(4-pyridyl)benzoxazole might be interesting. On the basis of the in vitro and cellular properties, these compounds are candidates for evaluation in an animal model of cryptosporidiosis.

Example 23

Evaluation of Mammalian Cytotoxicity Activity

A subset of compounds were also evaluated for cytotoxicity against four mammalian cell lines (HeLa, HEK293, COS, and CHO). Viability was determined by monitoring metabolic activity with an alamarBlue assay. None of the compounds displayed significant toxicity ($LD_{50}>50$ μM) against the four cell lines except one, which exhibited $LD_{50} \approx 12.5$ μM in HEK293 cells.

Example 24

Validation of IMP Dehydrogenase as a Target for Anticryptosporidial Therapy in a Mouse Model of Acute Disease Results
Selection of the Compounds
Urea-based CpIMPDH inhibitors were initially identified in a high throughput screen. Reasoning that the inhibitors must traverse the gastrointestinal tract and cross both host and parasite membranes to reach the parasite target, optimization chiefly followed the guidelines for oral bioavailability, e.g., Lipinski's and Veber's Rules, with respect to molecular weight, hydrogen bond donors and acceptors, hydrophobicity (log P), topological polar surface area (tPSA) and number of rotatable bonds. One compound, P131, was designed to increase intestinal exposure, and therefore exceeded the recommended tPSA (tPSA ≤140 Å$^2$). Compounds were evaluated for enzyme inhibition and antiparasitic activity against a reporter *T. gondii* strain (*T. gondii*/CpIMPDH) engineered to rely on CpIMPDH for the production of guanine nucleotides. Compounds that performed well in these two assays, with $IC_{50} \leq 20$ nM and $EC_{50} \leq 2$ μM, were candidates for testing in the IL-12 knockout mouse model of acute cryptosporidiosis.

Several additional assays were performed to further prioritize compounds for testing in the mouse model. Compounds were evaluated for stability in mouse liver microsomes, which serve as a convenient model for liver metabolism. However, since the tissue distribution required for in vivo antiparasitic activity has not been defined, this information was not used to eliminate candidates. Instead, compounds were selected to have a range of metabolic stabilities. Antiparasitic activity was also assessed in a tissue culture model of *C. parvum* infection (FIG. 30). However, since parasite proliferation is limited and does not recapitulate the full life cycle in vitro, candidates were only eliminated if the value of $EC_{50}$ exceeded 20 μM. It is worth noting that the efficacies of nitazoxanide and paromomycin vary depending upon which stage of the life cycle is assayed, further justifying using a "loose filter" in the in vitro *C. parvum* assay.

Several compounds were chosen to test in the mouse model. These compounds represent a wide range of hydrophobicity (log P), polarity (tPSA) and metabolic stability.

Antiparasitic Activity in an Immunosuppressed Mouse Model of Acute Cryptosporidiosis In vivo antiparasitic activity was evaluated in the IL-12 knockout mouse model of acute disease. IL-12 knockout mice are highly susceptible to *C. parvum*.

Infection results in moderate to heavy shedding of oocysts beginning 3 days after infection with a peak at days 4-7. Mice resolve the infection and recover within 2-3 weeks, which closely resembles infections observed in immunocompetent individuals. Toxicity was assessed prior to antiparasitic activity by orally administering compounds at 250 mg/kg daily to uninfected C57BL/6 mice for five days. Animal weight and behavior (e.g., grooming) were noted daily. No overt signs of acute toxicity were observed.

Figure 39:
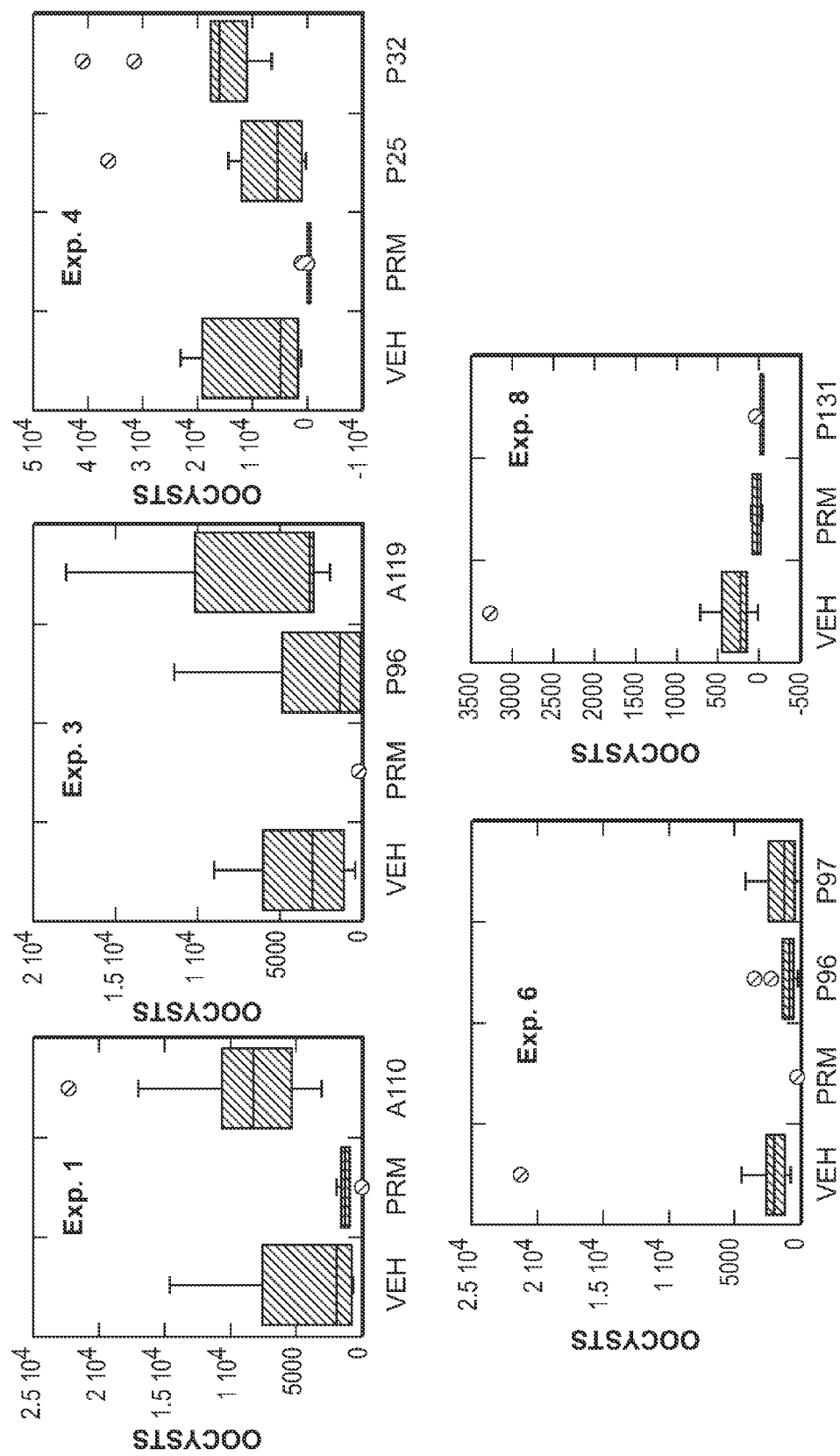
FIG. 39 depicts antiparasitic activity of CpIMPDH inhibitors. IL-12 knockout mice were infected with 1,000 *C. parvum* oocysts and treated with single daily doses of vehicle, paromomycin (2000 mg/kg) or compound (250 mg/kg) by oral gavage. Fecal oocysts were counted on day 7 post infection. Each panel displays a separate experiment.

The CpIMPDH inhibitors were evaluated in nine separate experiments (FIGS. 31, 35, 39, and 41). Mice were infected with 1000 oocysts, and treatment was initiated after 4 h and continued for seven days. Mice were treated daily via oral gavage, with either 250 mg/kg of CpIMPDH inhibitor, vehicle, or 2000 mg/kg paromomycin (note that nitazoxanide has little to no efficacy in mouse models. Infections were monitored by counting fecal oocysts at peak infection using flow cytometry. The average number of fecal oocysts from mice treated with vehicle ranged from 600 to 9000. Paromomycin reduced oocysts by an average of 89% (73-99%, FIG. 41). Most of the compounds failed to significantly change the numbers of fecal oocysts (FIG. 31, FIGS. 35A and 39). Fecal oocyst counts also appeared higher when mice were treated with P32, although in these cases the differences were not statistically significant. Three inhibitors, P82, P96 and P131, significantly reduced oocyst numbers (55-72%; FIGS. 35B and C). P83 is very similar to P82, and is converted into P82, so the failure of P83 was somewhat surprising. Taken together, the antiparasitic activity of P82, P96 and P131 provide proof-of-concept in an animal model and validate CpIMPDH as a target for the treatment of cryptosporidiosis.

The antiparasitic activity of P131 was particularly interesting because this compound is a 10-fold less potent inhibitor of CpIMPDH than P82 and P96 (FIG. 31). To further investigate the In vivo efficacy of P131, we also evaluated antiparasitic activity in a multiple daily dose regime (3×83 mg/kg). The infection protocol was modified to accommodate the increased dosing by shortening the treatment period. Infection was increased from 1000 to 10,000 oocysts, and fecal oocysts were counted on day 4 post-infection. Multiple dosing did not improve the efficacy of paromomycin (88-95% reduction of fecal oocysts; FIG. 35B). In contrast, the efficacy of P131 improved with multiple dosing, reducing fecal oocysts by 93-99% in two separate trials. The antiparasitic activity of P131 surpassed the activity of paromomycin (FIG. 35B).

Plasma Pharmacokinetic Properties.

Given the limited efficacy of current treatments, the pharmacokinetic and physicochemical properties required for in vivo efficacy have not been established. In order to investigate the relationship between anticryptosporidial activity and systemic exposure, we measured the plasma pharmacokinetics for 250 mg/kg single oral doses of compounds P82, P83, P96 and P131 (FIG. 32). P82 is the primary product of P83 metabolism, so the concentration of P82 in plasma was also measured during P83 treatment. As expected, the five compounds displayed a range of plasma pharmacokinetic behavior. Maximal plasma concentrations ($C_{max}$) was as low as 9 µM (P131) while plasma half-life ($\tau_{1/2}$) was as low as 4 h (P83 and P131). The values of $C_{max}$ exceeded the values of $IC_{50}$ for enzyme inhibition by at least 400-fold for all five compounds. The values of $C_{max}$ also exceeded the values of $EC_{50}$ for the *Toxoplasma* reporter assay by at least a factor of 9. Thus, if the plasma concentrations were comparable to concentrations within the parasite, all five compounds should have displayed antiparasitic activity. These observations suggest that plasma-distributed compounds cannot adequately access the parasite. Interestingly, the compound with the highest plasma concentration and longest half-life, P83, failed to display antiparasitic activity. This observation suggests that systemic distribution may be a liability.

Compound P131 Accumulates in Intestinal Cells.

Figure 36:
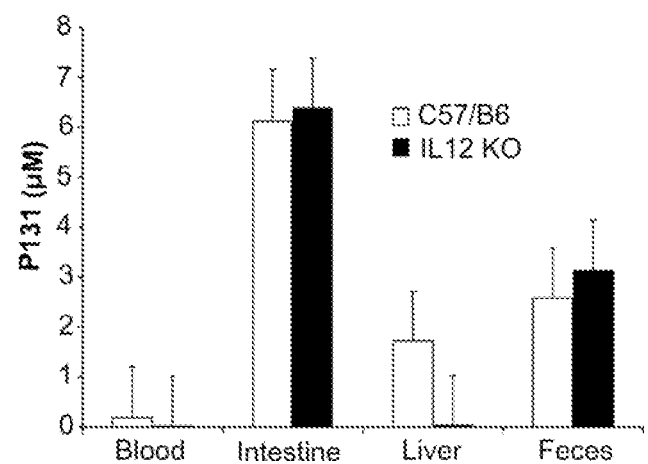
FIG. 36 depicts the concentration of P131 in various tissues 24 h after the first 83 mg/kg dose. Concentration in tissue is reported assuming 1 g of tissue is equivalent to 1 mL of liquid. An alternative way to express concentration is nmol/g.

The superior performance of P131 in vivo relative to its potency in the enzyme inhibition prompted a more thorough investigation of its tissue distribution in both C57BL/6 and IL-12 knockout mice. Tissues were harvested 24 h after a single 83 mg/kg oral dose. No significant difference was noted between the two mice strains, justifying the use of C57BL/6 mice for routine pharmacokinetic evaluations. As expected from the plasma pharmacokinetic experiments, little P131 was found in blood after 24 h (FIG. 36). Higher concentrations were found in the liver, suggesting that liver metabolism might limit the systemic distribution of P131. The highest concentrations of P131 were present in the intestine and feces (3-6 µM). These concentrations are more than 100-fold higher than the $IC_{50}$ value for CpIMPDH inhibition. These findings suggest that in vivo antiparasitic activity requires the accumulation of CpIMPDH inhibitors in gastrointestinal tract.

Compound P131 Accumulates in Caco-2 Cells.

To further investigate the relationship between intestinal accumulation and antiparasitic activity, we measured the uptake of the CpIMPDH inhibitors in Caco-2 cells, a widely used model of human intestinal epithelial cells. Uptake varied over a range of 2000-fold among the eight CpIMPDH inhibitors (FIG. 33). The lowest uptake was observed for the two inactive compounds, P25 and P32. The intracellular concentrations of these compounds did not reach the extracellular concentration (10 µM). All of the other compounds accumulated intracellular concentrations in excess of the extracellular concentration. P131 had the highest uptake/accumulation, reaching millimolar concentrations. The concentrations of all the other compounds were lower by at least a factor of 10, but nevertheless exceeded the concentrations required to inhibit CpIMPDH.

We also measured the permeability of the CpIMPDH inhibitors across a Caco-2 cell monolayer (FIG. 33). This assay is commonly used to model intestinal absorption. All of the compounds displayed good permeability ($P > 1 \times 10^{-5}$ cm/sec), though permeability varied 20-fold among the compounds. In all cases, permeability was similar in both the apical to basal (A→B) and basal to apical (B→A) directions, suggesting that none of the compounds are substrates for an efflux pump (efflux ratio ≤2).

Figure 37:
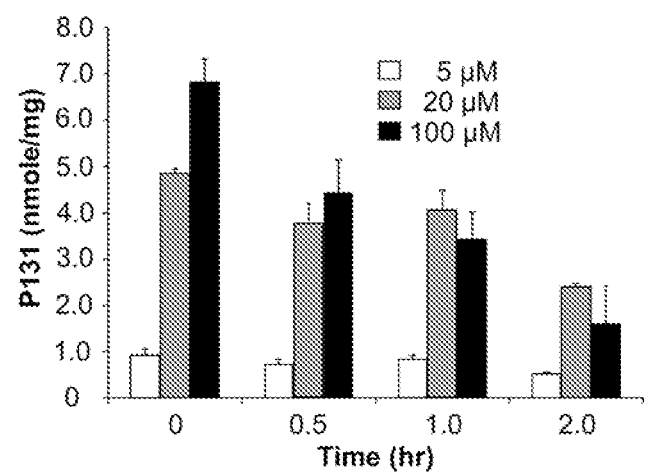
FIG. 37 depicts the amount of P131 remaining in Caco-2 cells after the cells were loaded with different concentrations of P131 for 2 h at 37° C. in HBSS. The efflux tin is ~1 h for loading at 100 μM and 2 h for 20 μM and 5 μM.

The high accumulation of P131 suggested that the efflux of P131 from Caco-2 cells might be unusually slow. We preloaded Caco-2 cells with 5, 20 or 100 µM P131, then measured efflux (FIG. 37). The initial intracellular concentrations of P131 were dose dependent and scaled with the extracellular concentration for the 5 and 20 µM preincubation conditions. Some cytotoxicity was noted when cells were preincubated with 100 µM P131, which may account for the somewhat lower than expected intracellular concentration at this concentration. P131 efflux was very slow under all three conditions, with tin of 1-2 h. In contrast, the values of $t_{1/2}$ for the efflux of amino acids and other nutrients are on the order of 15-30 min.

The Area Compounds do not Perturb the Gut Microbiota.

We hypothesized that the ability of compounds to promote C. parvum infection might result from perturbation of gut microbiota. CpIMPDH inhibitors do inhibit some bacterial IMPDHs, and many commensal bacteria contain IMPDHs that should be sensitive to CpIMPDH inhibitors. Whether this sensitivity translates into antibacterial activity will be determined by uptake as well as the ability of the bacteria to salvage purines and bypass IMPDH, so it is impossible to predict which bacteria may be affected.

We analyzed fecal bacteria in IL-12 knockout mice to investigate the effects of CpIMPDH inhibitors on gut microbiota. Groups of ten mice were treated orally with vehicle or P131 for 7 days. Individual fecal samples were collected prior to treatment (Day 0) and on Day 7. Total genomic DNA was isolated and 16S rRNA gene libraries were constructed and sequenced. Phyla were identified using the GreenGenes 16S rRNA database with UCLUST. A summary of phyla distribution among the three treatment groups is given in FIG. 38A.

Figure 38:
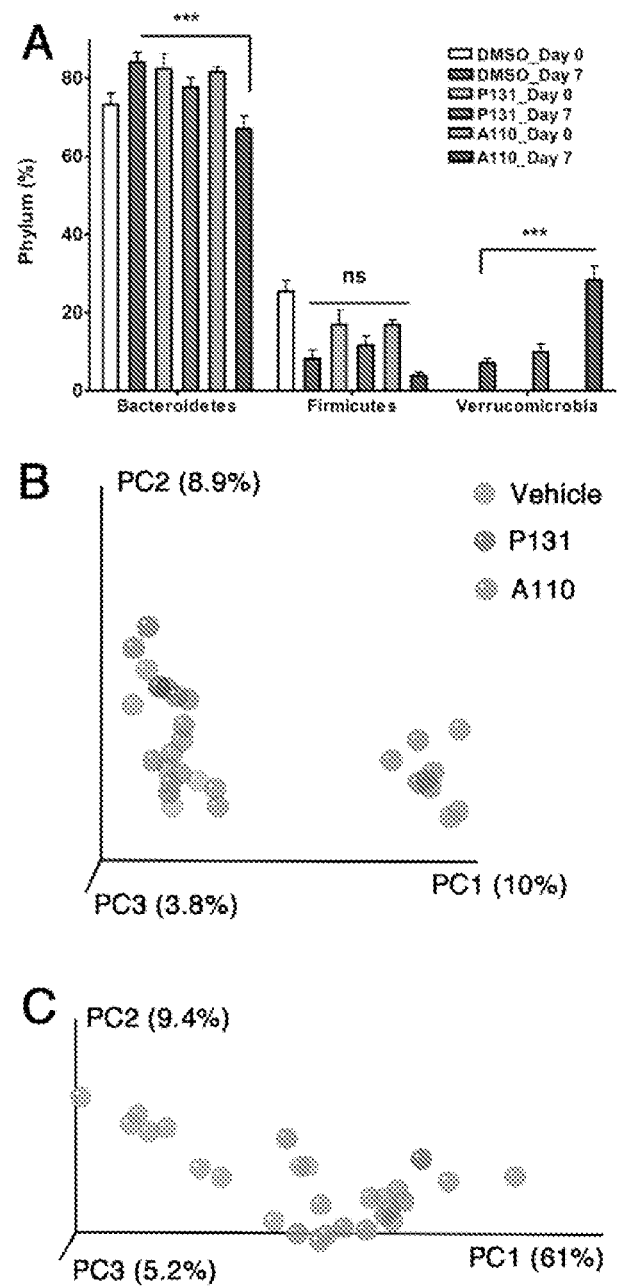
FIG. 38 depicts effects of vehicle, A110 and P131 on gut microbiota. IL-12 knockout mice were treated with vehicle, A110 or P131 (250 mg/kg) for seven days. Each treatment group contained 10 mice. Fecal samples were collected and the 16S rRNA gene content was sequenced using 454 pyrosequencing and analyzed with the QIIME platform. A) The change in phyla distribution of the three treatment groups is shown. Statistical analysis was performed using Mann-Whitney U test (*** =P<0.001). B) and C) Beta diversity plots to compare the bacterial taxa between the treatments. Unweighted UniFrac (B) or weighted UniFrac (C) were used to generate a matrix of pairwise distances between communities and scatter plots were generated from matrix of distances using Principal Coordinate Analysis (PCA). The p values generated from the original UniFrac Matrix using QIIME scripts.
Figure 40:
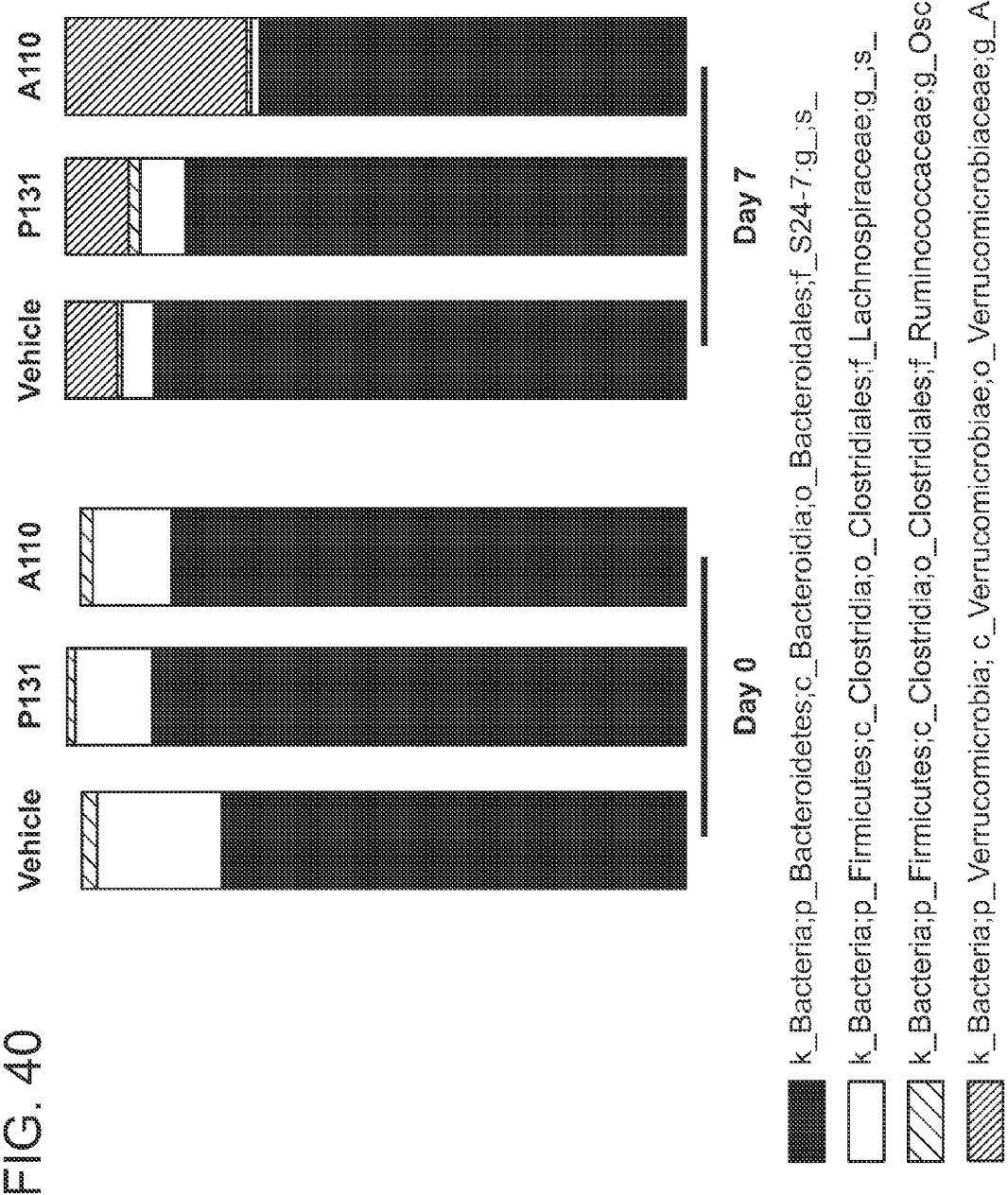
FIG. 40 depicts the effect of vehicle, A110 and P131 on fecal microbiota at the species level. The cumulative relative distribution of species in different treatments is listed.
Figure 44:
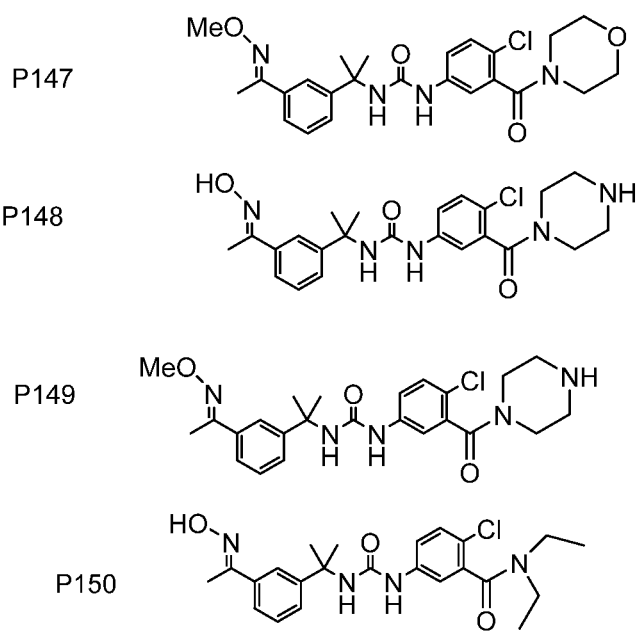

Treatment with vehicle alone induced significant changes in two phyla (FIG. 34 and FIG. 38A). Firmicules bacteria decreased from 25% to 8% between Day 0 and Day 7, accompanied by a remarkable increase of ~90-fold in Verrucomicrobia (from 0.08 to 7%, P <0.0001). Analysis at the species level revealed that the increase in Verrucomicrobia resulted from expansion of *Akkermansii muciniphila*, while the decrease in *Firmicues* derived from a reduction of Lachnospiracea (p<0.0001; FIG. 40). Similar changes were observed when mice were treated with P131, suggesting that this compound has no additional impact on fecal microbiota.

Discussion

Validation of CpIMPDH as a Target for the Treatment of Cryptosporidiosis.

Our results demonstrate that three compounds, P82, P96 and P131, have anticryptosporidial activity in the IL1-2 knockout mouse model of acute disease. At present, no clinically validated, and few experimentally validated, targets exist for *Cryptosporidium* treatment, so the demonstration of in vivo efficacy for CpIMPDH inhibitors represents a milestone in *Cryptosporidium* drug discovery. Impressively, P131 is more effective than paromomycin when administered in split doses. Further optimization of the dosing schedule may improve the efficacy of P131 and additional CpIMPDH inhibitors.

The Pharmacokinetic Requirements of Anticryptosporidial Activity.

We evaluated the pharmacokinetics of closely related compounds with varying efficacies in order to gain insight into the drug distribution required for in vivo antiparasitic activity. The best plasma pharmacokinetic behavior was observed with the inactive compound P3. In contrast, P131 has poor systemic distribution, but accumulates to high concentrations in intestinal tissue. Paromomycin also has poor oral bioavailability. Nitazoxanide is systemically distributed, though it is recycled to the intestine via glucuronidation. Interestingly, the glucuronidated nitazoxanide metabolite has comparable antiparasitic activity in vitro. In vivo anticryptosporidial activity has also been reported for pyrvinium pamoate and dication carbazole compounds that have poor systemic bioavailability. Trifluoromethylthymidine has significant anticryptosporidial activity in an immunosuppressed mouse model even though it is rapidly metabolized in plasma. These observations suggest that systemic exposure is not required for anticryptosporidial activity in the gastrointestinal tract, and may actually be a liability.

The above results strongly suggest that accumulation in host cells is the key to antiparasitic activity. All three active compounds attain concentrations in Caco-2 cells that far exceed their values of $IC_{50}$ for enzyme inhibition. The accumulation of P131 is especially high, reflecting its unusually slow efflux. Paromomycin also displays high accumulation in Caco-2 cells. We propose that the design of anticryptosporidial drugs should focus on retention in intestinal tissue rather than for systemic bioavailability, and that accumulation in Caco-2 cells is a useful assay during inhibitor optimization.

Systemic exposure may be required to treat the extraintestinal infections that can arise in immunocompromised patients. We believe that this is currently an open question, and note that nitazoxanide is only marginally superior to paromomycin in treating biliary infections in the immunosuppressed gerbil model of cryptosporidiosis, despite its systemic distribution. The varying pharmacokinetic properties of P82, P96 and P131 should provide useful tools to address this question.

Materials and Methods

Materials. Compounds were synthesized as previously described. Properties were calculated using ChemBioDraw Ultra version 12.0.3.1216.

Cell Culture Model of C. Parvum Infection.

Oocysts are excysted, and the sporozoites are allowed to infect confluent human ileocecal adenocarcinoma epithelial cells (HCT-8) or Madin-Darby canine kidney cells (MDCK). The monolayer is washed after 3 h, and the parasites are cultured for 48 h. Cultures are fixed and counted using an anti-*C. parvum* fluorescein-labeled monoclonal antibody (C3C3-FITC) or a high content imaging assay. The values of $EC_{50}$ were calculated using the Hill-Slope model (eq1) using Prism v5 (GraphPad Software Inc., La Jolla, Calif.):

$$\% \text{ Growth} = (\text{Max} - \text{Min})/(1 + (EC_{50}/[I])^n) \quad \text{eq1}$$

where n is the Hill coefficient.

In Vivo Toxicity Evaluation.

Compound toxicity was evaluated in uninfected C57BL/6 mice treated for 10 days (5 mice/group). Toxicity was assessed by weight loss and signs of distress (e.g., ruffled fur, hunched shoulders and decreased appetite). Mice were sacrificed on day 11 and serum was collected to assess liver function by measuring levels of alanine aminotransferase, aspartate aminotransferase, and alkaline phosphatase. Livers were also qualitatively assessed for hepatic icterus and assigned a score of 0 to 4 based on the degree of discoloration. In addition, major organs were removed and weighed. Standard statistical analyses will be performed to evaluate the compound toxicity.

Mouse Model of C. parvum Infection.

The anticryptosporidial activity of the CpIMPDH inhibitors was assessed in the IL-12 knockout mouse model that resembles the acute human disease. Mice (6-10 per group) were inoculated with 1,000 oocysts. Treatment by gavage began 4 h post infection with either vehicle (10% DMSO in corn oil), 250 mg/kg compound or 2000 mg/kg paromomycin. Compounds were given for 7 days and mice sacrificed on day 8 (peak infection). Parasite load was quantified by FACS assays for the presence of the oocysts in the feces at days 0, 4 and 7. Fecal pellets were routinely collected daily and homogenized in adjusted volumes of 2.5% potassium dichromate. Aliquots (200 µL) of vortexed samples were processed over micro-scale sucrose gradients as previously described. The oocyst-containing fraction was collected, washed and treated with monoclonal antibody (OW50-FITC) for 20 min. Samples were adjusted to 600 µl and a portion (100 μL) was assayed with a 102-s sampling interval using logical gating of forward/side scatter and OW50-FITC fluorescence signal on a Becton Dickinson FACScan flow cytometer. Flow cytometry data were evaluated by analysis of variance (KaleidaGraph, Synergy Software, Reading Pa.; Microsoft Excel; Microsoft Corporation, Redmond, Wash.).

Pharmacokinetics.

PK was assessed at either the Stony Brook Translation Experimental Laboratory Therapeutics (Stony Brook, NY) or GVK Biosciences (Hyderabad, India).

DNA Isolation and Microbiota Sequencing.

The total genomic DNA was isolated from fecal pellets from individual mice using the Maxwell automated DNA isolation method as implemented in a Promega genomic DNA isolation kit. The 16S rRNA genes were amplified using the universal primer pair 27f (AGAGTTTGATCCTG-GCTCAG) and 534r (ATTACCGCGGCTGCTGG), which produce an amplicon containing variable regions V1-V3. The primers were anchored with adapters and barcodes to identify each sample in a multiplexed 454 sequencing reaction. PCR amplification was performed with a FastStart Hifidelity PCR system (Roche) using 0.5 μM primer concentrations. The PCR cycling conditions were 95° C. for 5 min, followed by 30 cycles of 94° C. for 30 sec, 56° C. for 30 sec, and 72° C. for 1 min and 30 sec with a final extension period of 8 min at 72° C. Each PCR reaction was performed in triplicate and pooled for gel purification. The PCR amplicon products were pooled and purified using QIAGEN gel purification columns. The amplicon pool was quantified using a QuatiT Picogreen kit (Invitrogen). The pooled purified amplicons were sequenced using a 454Roche Jr instrument according to manufacturer's protocols.

Microbiota Sequence Analysis.

The bacterial 16S rRNA gene sequence analysis was performed using the QIIME pipeline (QIIME 1.6.0, www.qiime.org) developed and maintained by the Knight group. Briefly, the quality sequences (200-650 bp lengths) were demultiplexed based on their barcodes. The 16S rRNA Operational Taxonomic Units (OTUs) were picked based on 97% sequence identity using UCLUST against the Green-Genes 16S rRNA database (gg_otus-12_10). The Green-Gene taxonomies were used to generate the taxa summaries at different levels of phylogeny (phylum, order, class, family, genus, species). Each OTU was represented by a single sequence that was aligned by Python Nearest Alignment Space Termination (PyNAST) for phylogenetic tree-based analyses. To standardize the sequences across the samples with uneven sampling, the sequences were rarified at 1000 randomly selected sequences per sample. The phylogenetic tree was built with FastTree. The beta-diversity (diversity between the samples) was measured using both weighted and unweighted UniFrac measurements. The detailed analytical protocols and scripts can be found at www.qiime.org.

Example 25

IMPDH Inhibitors as Broad Spectrum Antibiotics

Microbial infections are now the second leading cause of death worldwide. Many commonly used antibiotics have been rendered ineffective by the upsurge of drug resistance, and years of neglect have left a mere trickle of new antibiotics in the pipeline. This proposal outlines a project to develop novel antibacterial drugs with activity against a wide variety of Gram-positive and Gram-negative bacteria. Potentially susceptible organisms include including eight biowarfare agents, MRSA, XDR-TB and other drug resistant pathogens.

IMPDH catalyzes a key step in the production of guanine nucleotides, and is therefore required for proliferation. To this end, we will determine the efficacy of the IMPDH inhibitors developed in our previous work targeting *Cryptosporidium parvum* IMPDH (CpIMPDH) against a panel of pathogenic bacteria chosen to define the SAR in terms of the structural variation of the target enzyme and the permeability properties of the bacteria. The panel includes three Gram-positives (*Bacillus anthracis, Listeria monocytogenes* and *Staphylococcus aureus*) and three Gram-negatives (*Francisella tularensis, Burkholderia mallei/pseudomallei* and *Acinetobacter baumannii*).

A. Testing CpIMPDH Inhibitors for Antibacterial Activity.

We have completed the initial evaluation of antibacterial activity of >110 compounds against *A. baumannii* ATCC 17961; *B. anthracis* Sterne 7702; *Bu. cenocepacia* K56-2 and *Bu. thailandensis* E264 (models for *Bu. mallei/pseudomallei*), *F. tularensis* Schu S4 and *L. monocytogenes* 10403S. We also expanded the evaluation of antibacterial activity to *Campylobacter jejuni* 81-176, *Helicobacter pylori* G27, *Staphylococcus aureus* NCTC 8325 and *Mycobacterium tuberculosis* H37Rv (assays performed by Helena Boshoff at the Tuberculosis Research Section, NIAID). In addition, compounds were tested against *Clostridia perfringens, Escherichia coli, Enterococcus faecalis, Enterococcus facium, Salmonella* spp. and *Streptococcus uberis*. We also provided compounds for testing in *Pseudomonas aeruginosa*. We have 14 compounds with MIC values ≤12 μM against two or more bacteria, and 8 compounds with MIC values ≤3 μM against one bacterium (FIG. 43). Antibacterial activity (MIC <12 μM) is associated with compounds in the D, P and Q series.

We have 17 compounds with MIC values ≤12 μM against *B. anthracis*. In general, lower MICs track with greater potency in the enzyme inhibition assay (FIG. 42), suggesting that the antibacterial activity results from inhibition of IMPDH. We have 8 compounds with MIC ≤1 μM against *F. tularensis* Schu S4. However, in contrast to *B. anthracis*, there is little correspondence between MIC values and enzyme inhibition (FIG. 42). Several of these compounds are equally effective against a ΔguaB strain that should lack IMPDH, so we are concerned that the antibacterial activity may be off-target. The ΔguaB strain grows very poorly, so we are not confident about this conclusion. We will perform an additional test of verify that IMPDH is the target for all active compounds by determining if the value MIC increases in the presence of excess guanine. In the case of *M. tuberculosis*, the values of MIC increased in the presence of guanine for 7/7 compounds, indicating that these compounds inhibit IMPDH as expected.

B. Determining SAR for IMPDHs from Pathogenic Bacteria Using Compounds "in Hand" and Identify Inhibitors with Broadest Spectrum.

We have evaluated the inhibition of over 174 compounds for IMPDHs from *A. baumannii, B. anthracis, Bu. mallei/pseudomallei, F. tularensis, L. monocytogenes, P. aeruginosa, Sta. aureus*, and *Str. pyogenes*. We have identified potent inhibitors ($IC_{50}$<20 nM) for all of the enzymes except *P. aeruginosa* (best $IC_{50}$=36 nM) and *Sr. pyogenes* (best $IC_{50}$=3.8 μM) IMPDHs. Interestingly, results suggest that the failure to observe antibacterial activity results from lack of uptake. We have used cluster analysis to analyze the relationships between both inhibitors and enzymes. Intriguingly, *B. anthracis* and *L. monocytogenes* IMPDHs have very similar inhibition profiles, as do the *Bu. mallei* and *Sta. aureus* enzymes. These relationships were not predicted by phylogeny.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A compound, or a pharmaceutically acceptable salt or ester thereof, selected from the group consisting of

P98

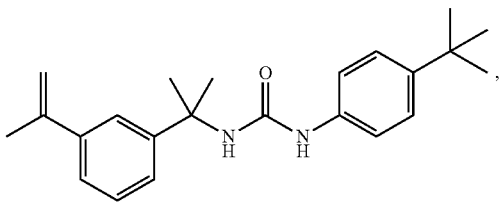

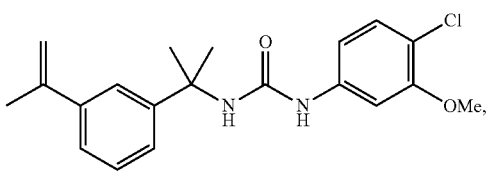

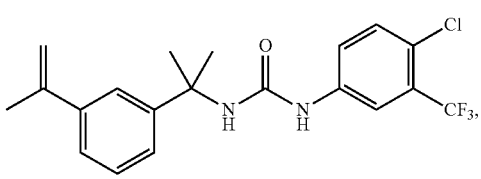

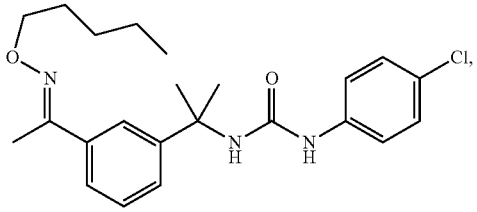

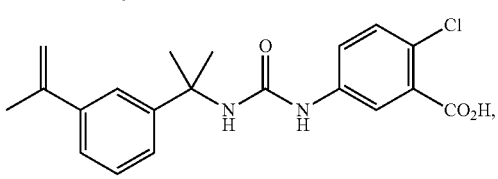

-continued

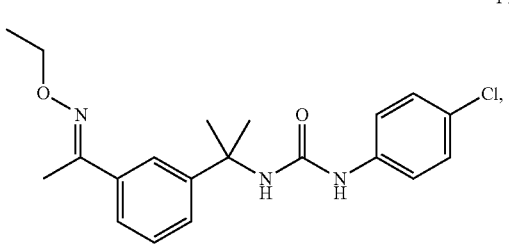

P109

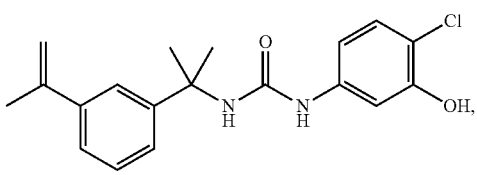

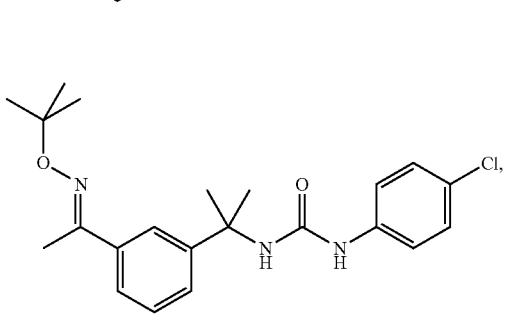

195
-continued
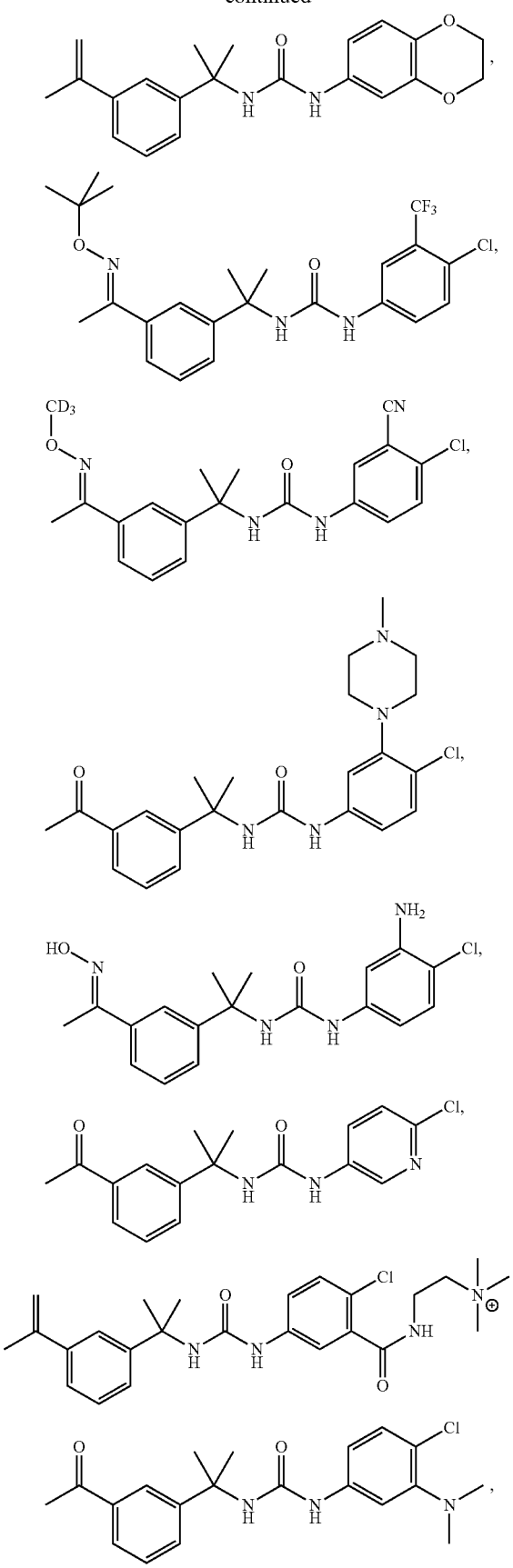
196
-continued
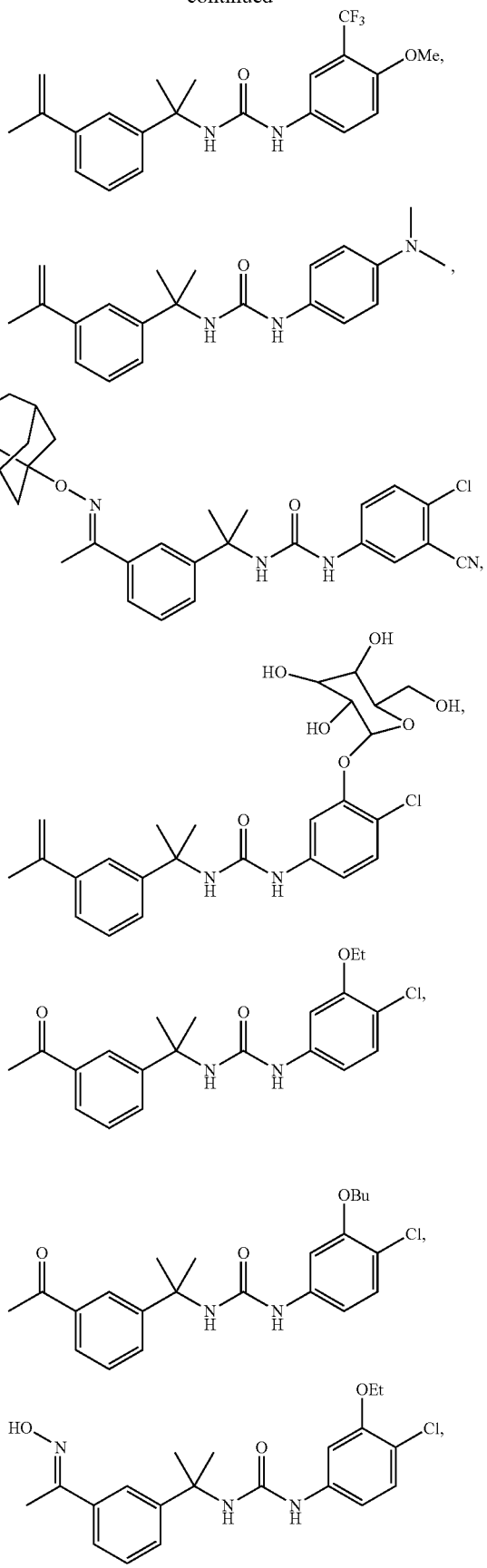

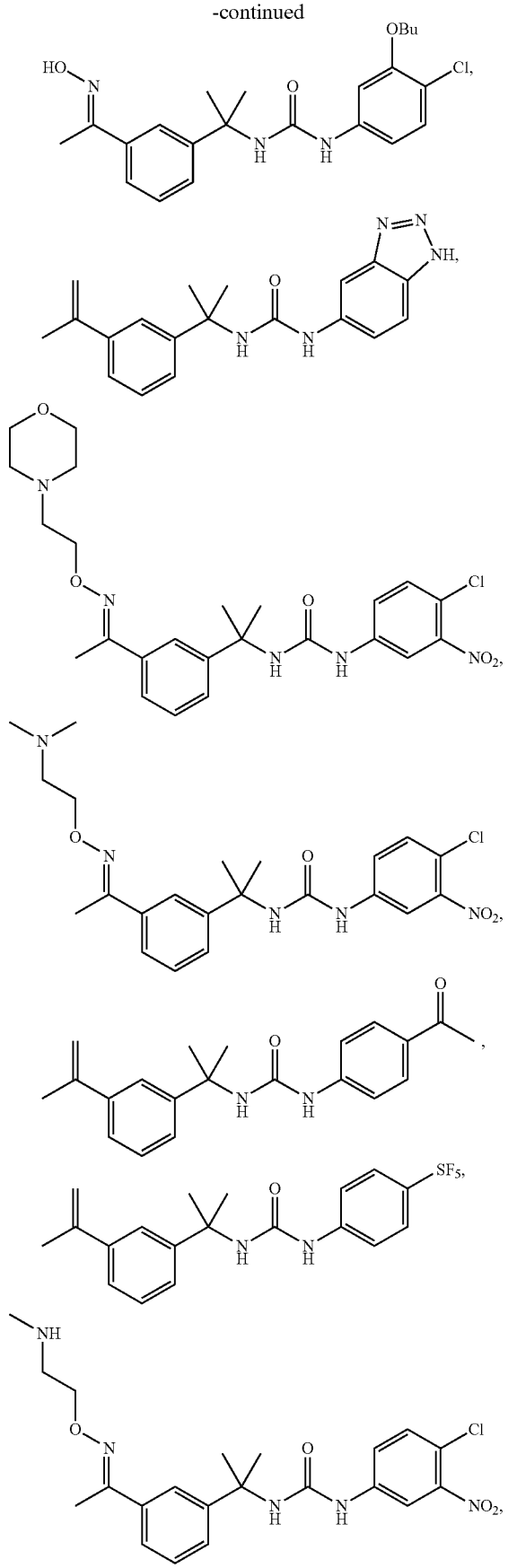
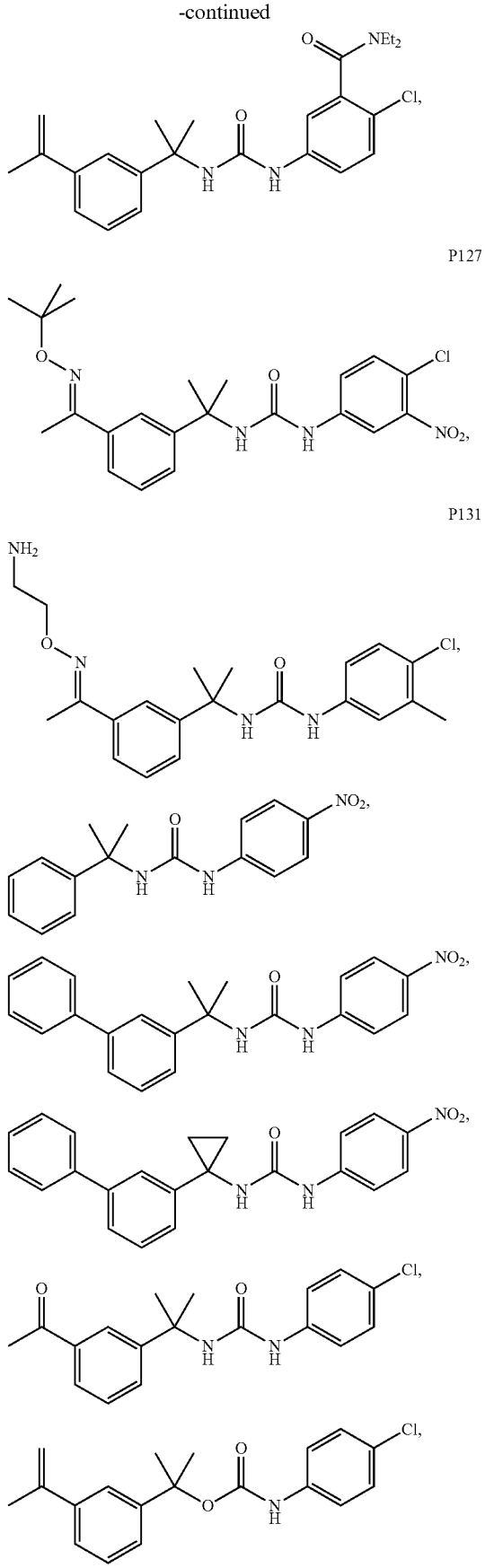

199
-continued
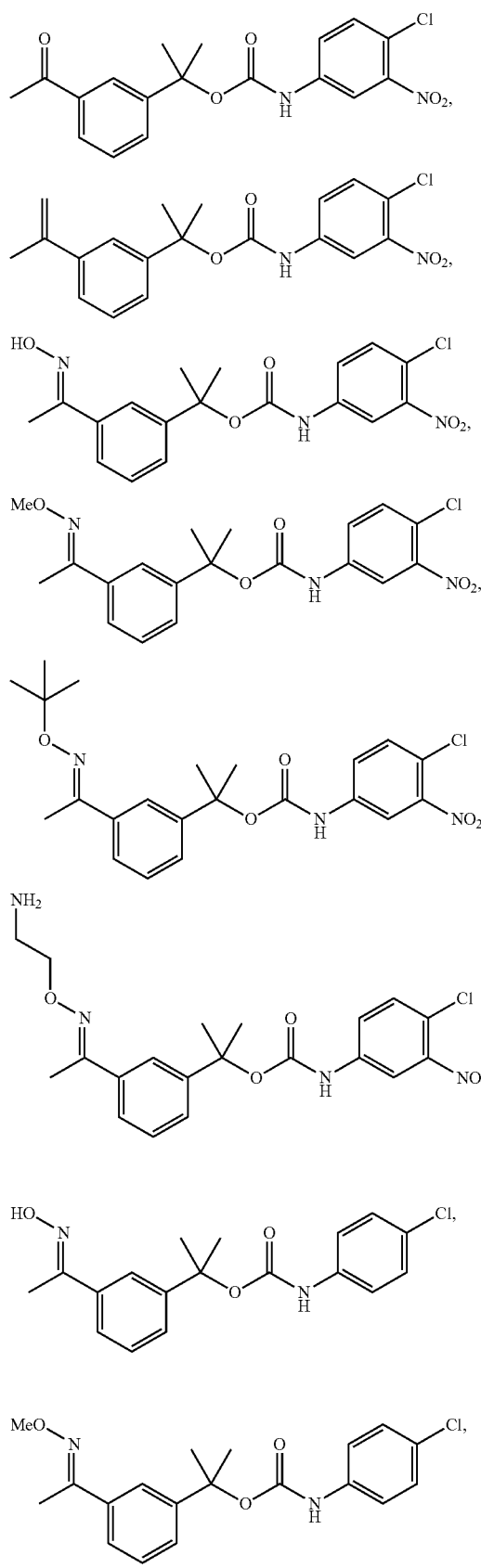
200
-continued
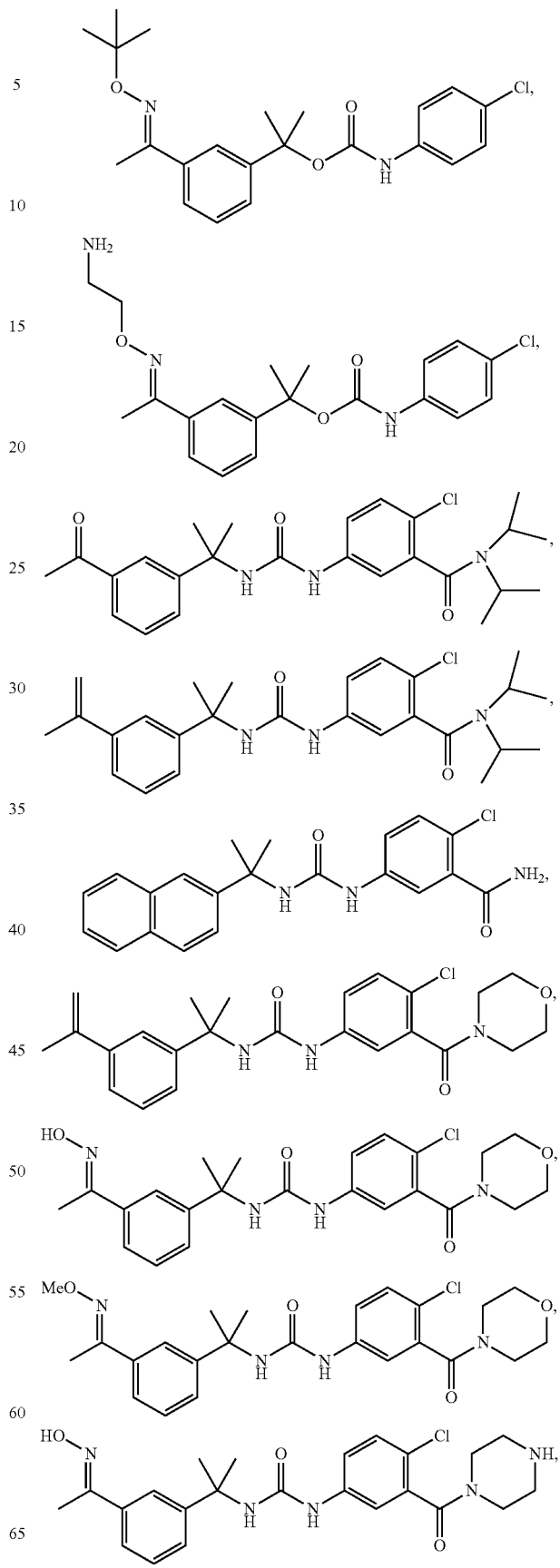

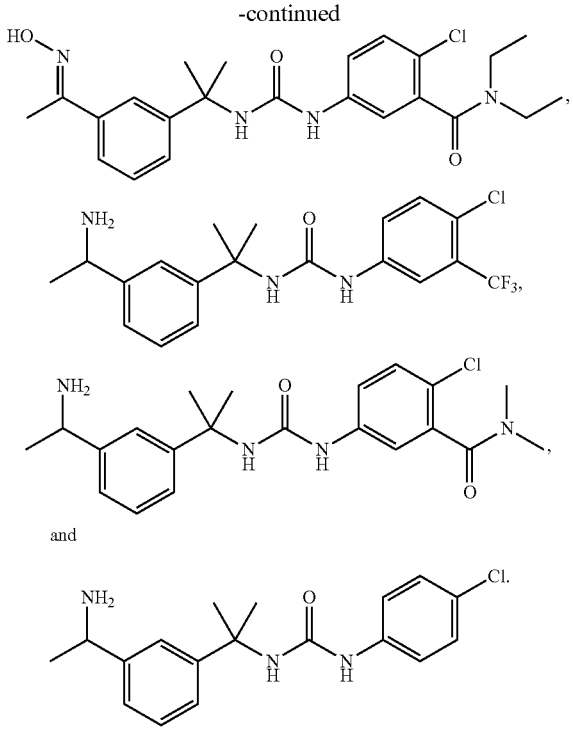

and

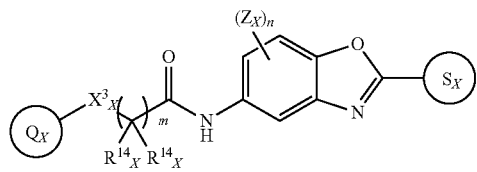

2. A compound, or a pharmaceutically acceptable salt or ester thereof, represented by Formula X or Formula XIII:

Formula X

wherein, independently for each occurrence, $X^3_X$ is $C(R')_2$, S, or NR';
  wherein R' is hydrogen, halide, alkyl, alkenyl, alkynyl, cycloalkyl, heterocyclyl, aryl, heteroaryl, acyl, aracyl, or heteroaracyl;

m is 0, 1, or 2;

n is 0, 1, 2, or 3;

$R^{14}_X$ is hydrogen, alkyl, alkenyl, alkynyl, cycloalkyl, heterocyclyl, aryl, heteroaryl, acyl, aracyl, heteroaracyl sulfonate, sulfonyl, sulfonamido, formyl, carboxyl, alkoxycarbonyl, or acyloxy, or two $R^{14}_X$ groups taken together form a non-aromatic 3-8 membered ring, or two $R^{14}_X$ groups taken together form the side chain of a natural or non-natural D or L amino acid;

$Z_X$ is hydrogen, halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, sulfhydryl, formyl, cyano, or isocyano;

is hydrogen, halogen, alkyl, alkenyl, alkynyl, aralkyl, heteroaralkyl, halogen, amino, amido, acyl, aracyl, heteroaracyl, alkoxy, hydroxyl, carboxyl, alkoxylcarbonyl, acyloxy, silyl, alkylthio, sulfonate, sulfonyl, sulfonamido, sulfhydryl, formyl, cyano, isocyano, monocyclic or bicyclic cycloalkyl, monocyclic or bicyclic heterocyclyl, monocyclic or bicyclic aryl or monocyclic or bicyclic heteroaryl; and

is monocyclic or bicyclic cycloalkyl, monocyclic or bicyclic heterocyclyl, monocyclic or bicyclic aryl or monocyclic or bicyclic heteroaryl;

Formula XIII

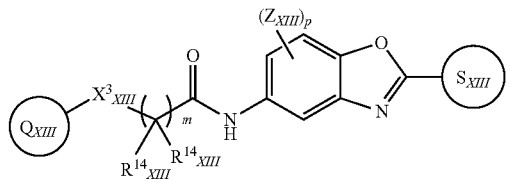

wherein, independently for each occurrence, $X^3_{XIII}$ is absent, O, $C(R')_2$, S, or NR';

$R^{14}_{XIII}$ is hydrogen, alkyl, alkenyl, alkynyl, cycloalkyl, heterocyclyl, aryl, heteroaryl, acyl, aracyl, heteroaracyl sulfonate, sulfonyl, sulfonamido, formyl, carboxyl, alkoxycarbonyl, or acyloxy, or two $R^{14}_{XIII}$ groups taken together form a non-aromatic 3-8 membered ring, or two $R^{14}_{XIII}$ groups taken together form the side chain of a natural or non-natural D or L amino acid;

$Z_{XIII}$ is halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, sulfhydryl, formyl, cyano, or isocyano;

$S_{XIII}$ is hydrogen, alkyl, alkenyl, alkynyl, aralkyl, heteroaralkyl, halogen, amino, amido, acyl, aracyl, heteroaracyl, alkoxy, hydroxyl, carboxyl, alkoxylcarbonyl, acyloxy, silyl, alkylthio, sulfonate, sulfonyl, sulfonamido, sulfhydryl, formyl, cyano, isocyano, monocyclic or bicyclic cycloalkyl, monocyclic or bicyclic heterocyclyl, monocyclic or bicyclic aryl or monocyclic or bicyclic heteroaryl;

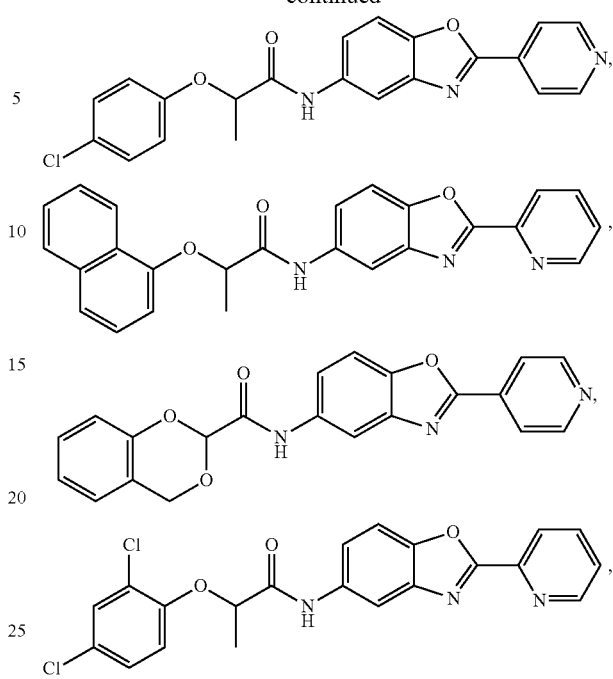

is monocyclic or bicyclic cycloalkyl, monocyclic or bicyclic heterocyclyl, or monocyclic or bicyclic heteroaryl;

p is 1, 2, or 3; and wherein R' and m are as defined for Formula X;

wherein, any of the aforementioned alkyl, aryl, or heteroaryl may be substituted with one or more groups independently selected from the group consisting of halo, azido, alkyl, haloalkyl, aralkyl, alkenyl, alkynyl, cycloalkyl, heterocyclyl, aryl, heteroaryl, heteroaralkyl, hydroxy, alkoxy, aryloxy, heteroaryloxy, amino, nitro, sulfhydryl, imino, amido, phosphonate, phosphinate, acyl, carboxyl, alkoxycarbonyl, acyloxy, silyl, alkylthio, sulfonate, sulfonyl, sulfonamido, sulfhydryl, formyl, cyano, and isocyano.

3. A compound or a pharmaceutically acceptable salt or ester thereof, selected from the group consisting of

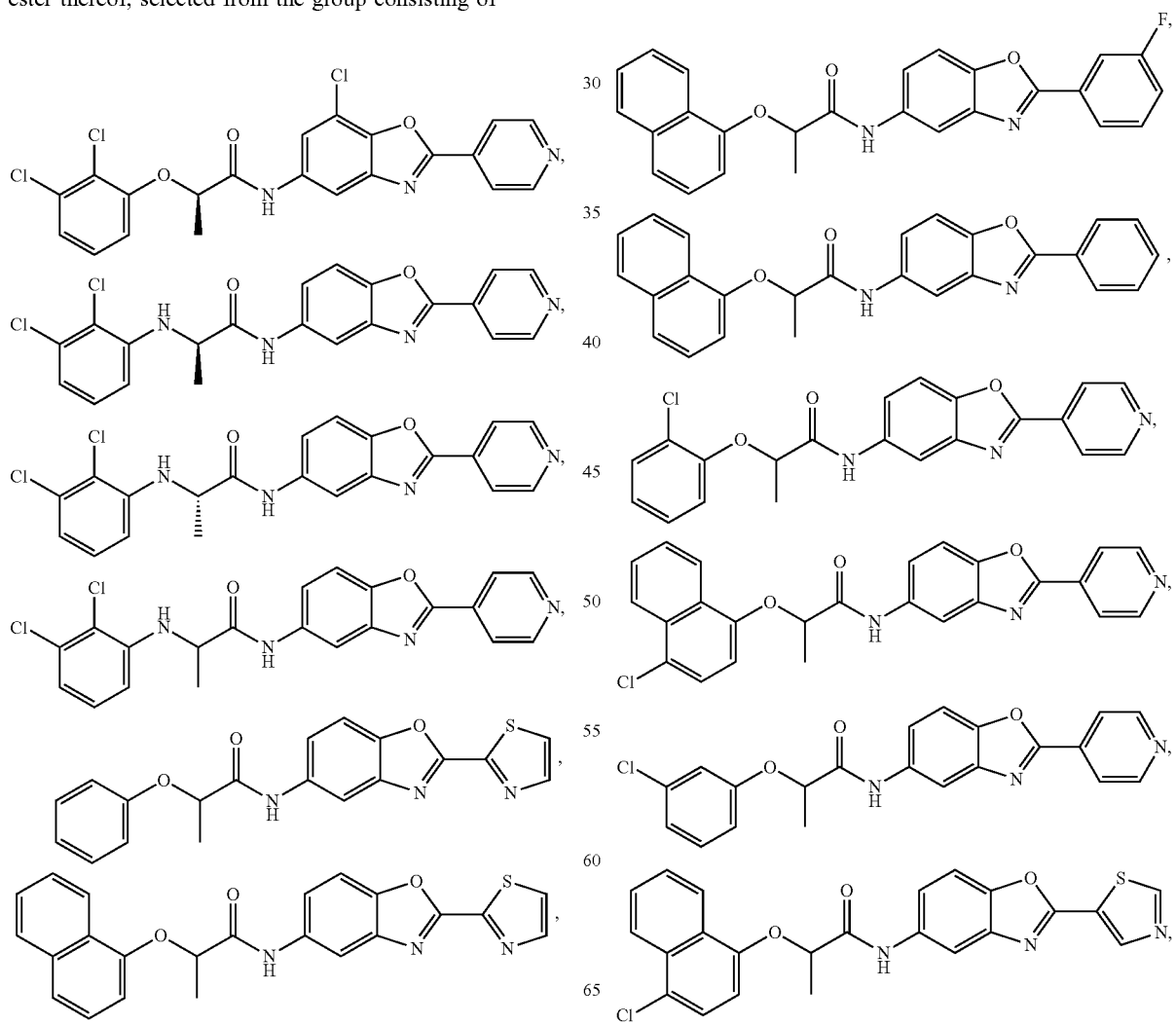

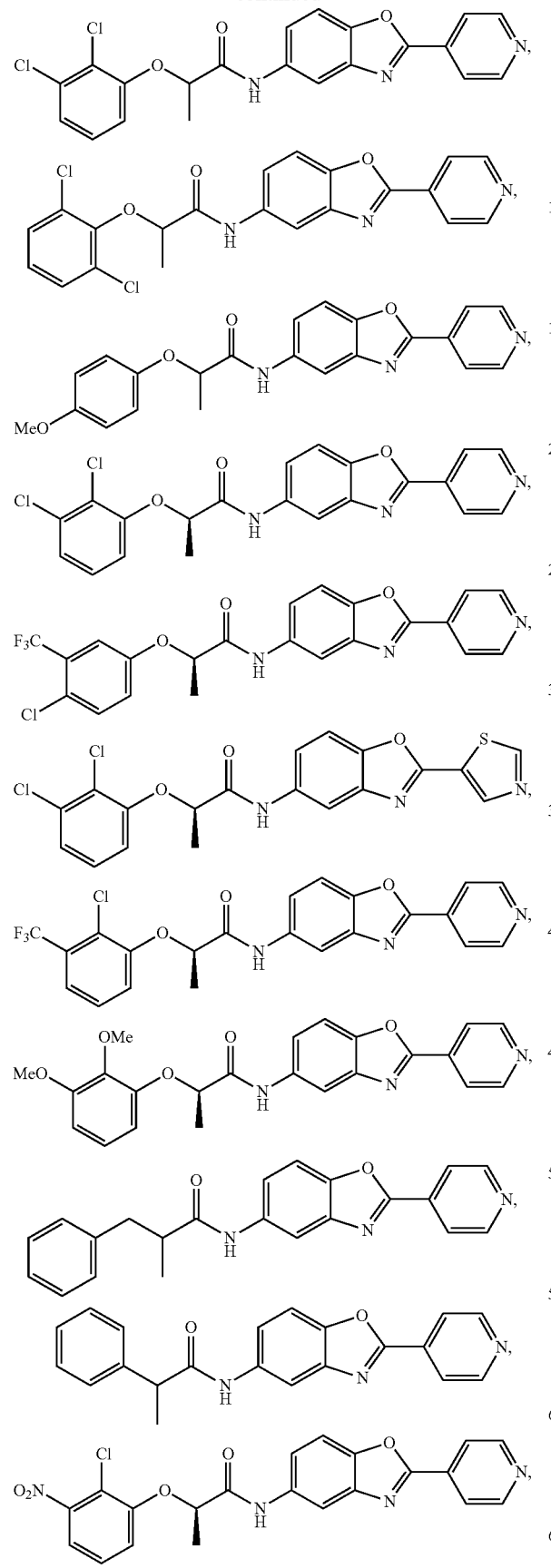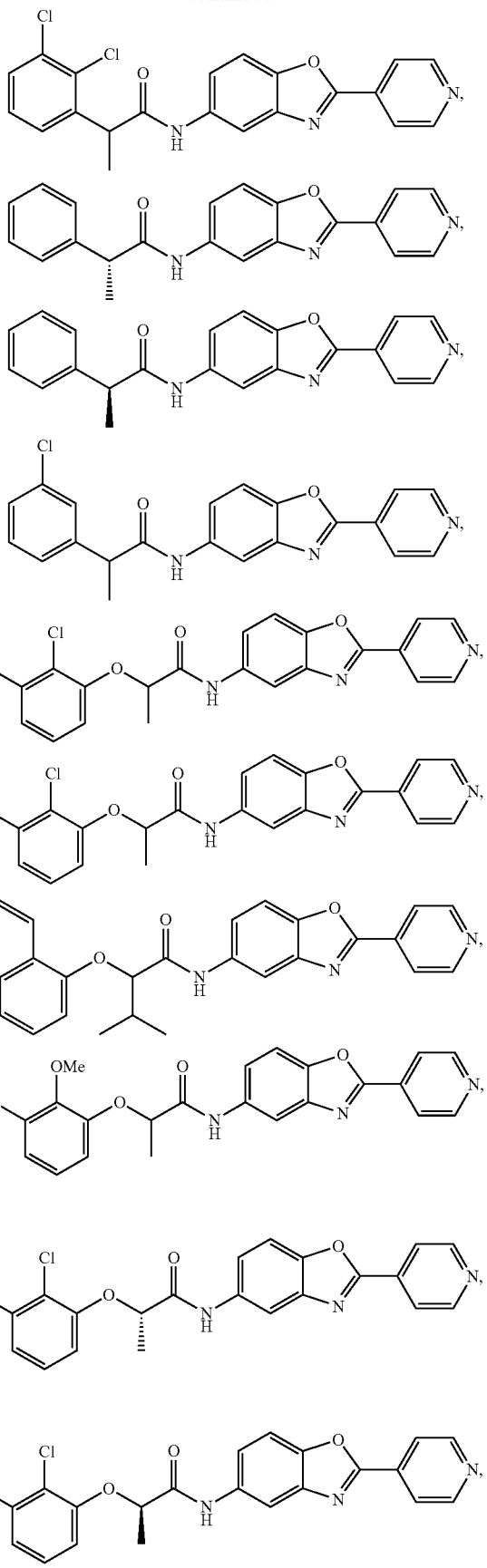

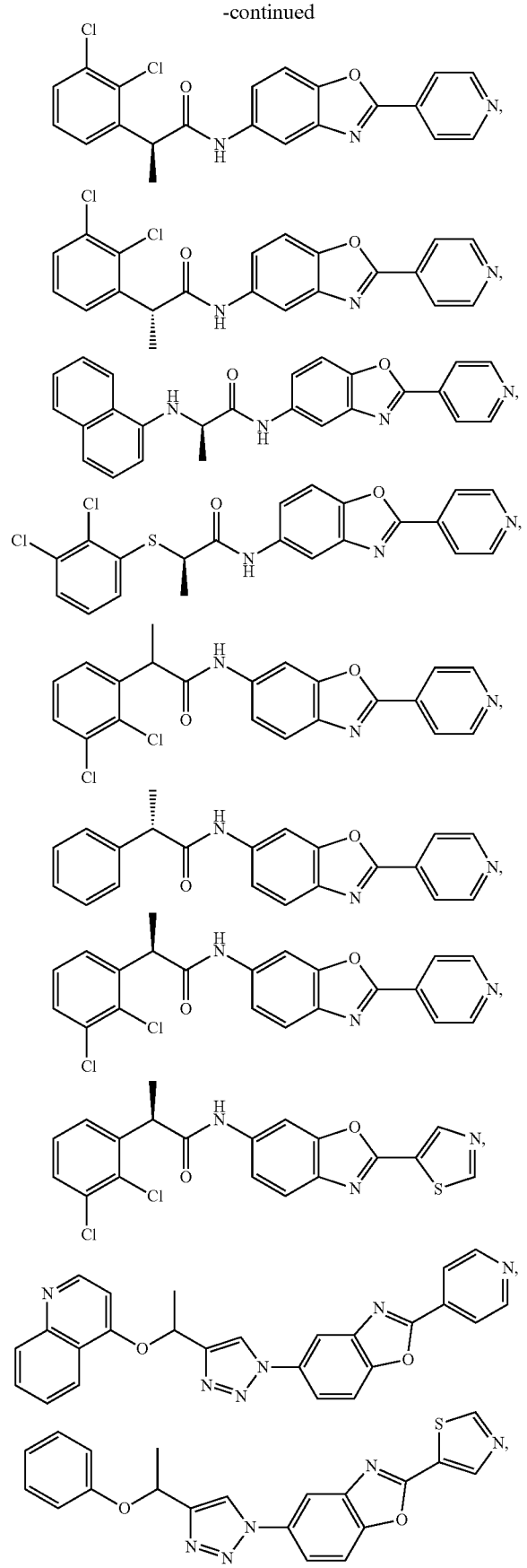
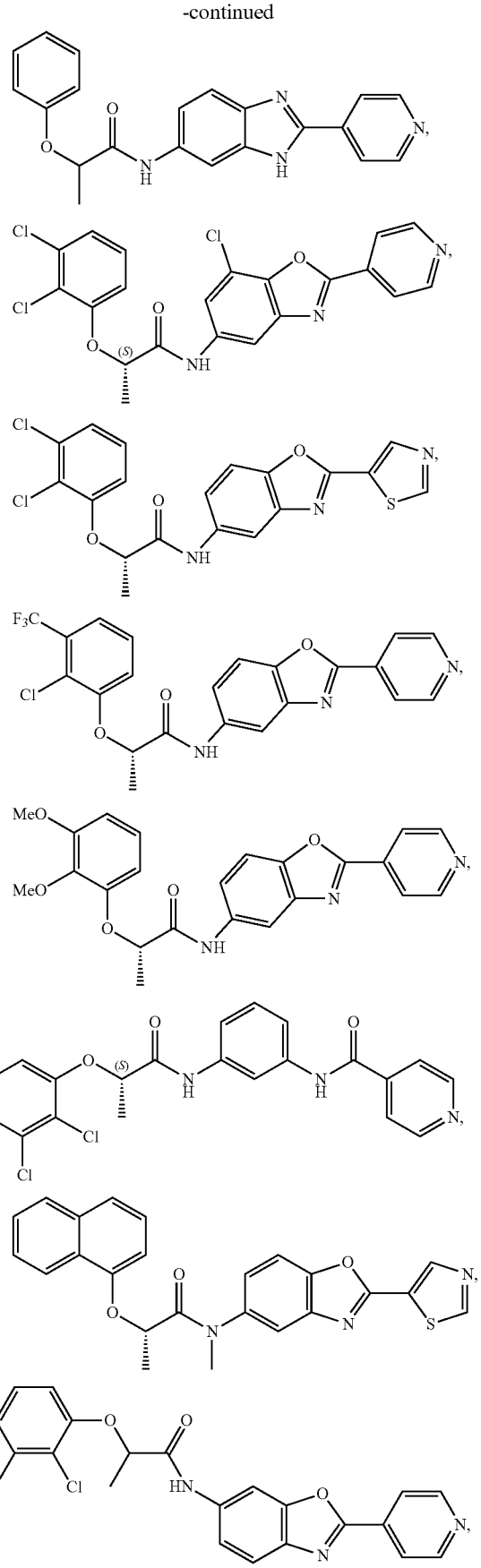

-continued

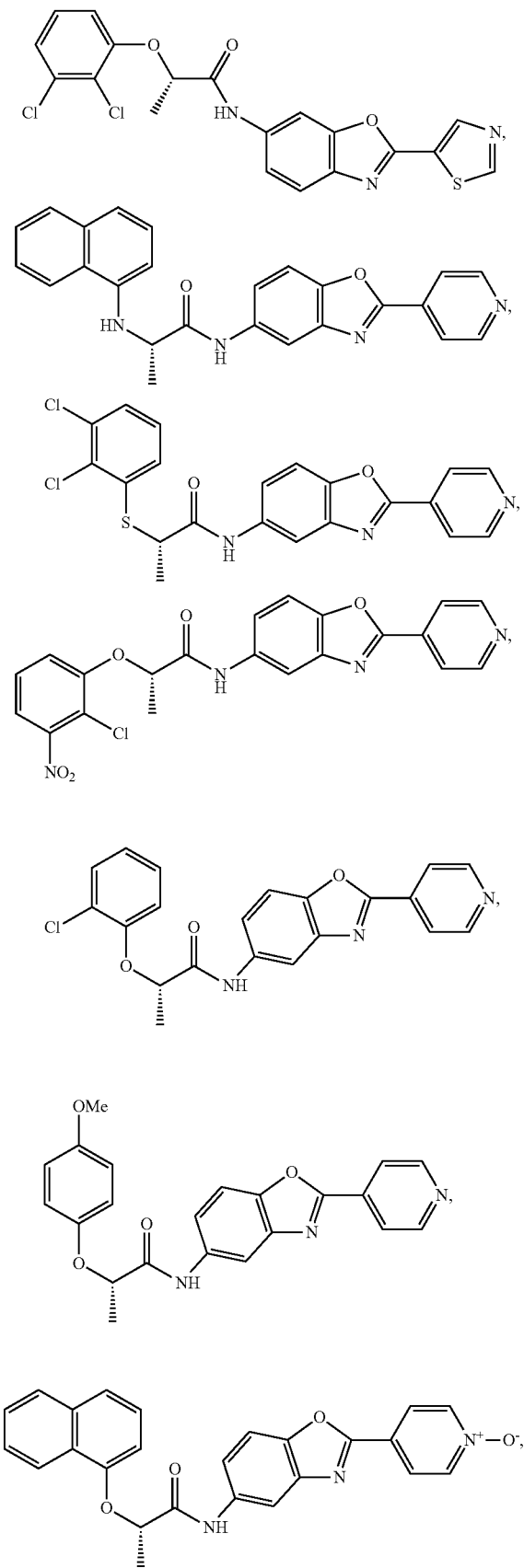

and

-continued

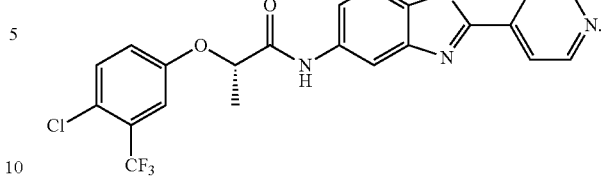

4. A method of killing or inhibiting the growth of a microbe, comprising the step of contacting said microbe with an effective amount of a compound of claim 1.

5. The method of claim 4, wherein said microbe is a protozoan or a bacterium.

6. The method of claim 4, wherein said microbe is a protozoan or a bacterium selected from the group consisting of the genera *Toxoplasma, Eimeria, Cryptosporidium, Plasmodium, Babesia, Theileria, Neospora, Sarcocystis, Giardia, Entamoeba, Tritrichomonas, Leishmania, Trypanosoma, Helicobacter, Borrelia, Salmonella, Shigella, Yersinia, Streptococcus, Campylobacter, Arcobacter, Bacteroides, Fusobacterium, Burkholderia, Clostridia, Neisseria, Mycobacterium,* and *Acinetobacter*.

7. The method of claim 5, wherein said microbe is a protozoan; and said protozoan is selected from the group consisting of the genera *Cryptosporidium, Entamoeba, Leishmania* and *Trypanosoma*.

8. The method of claim 7, wherein said protozoan is selected from the genus *Cryptosporidium*.

9. The method of claim 5, wherein said microbe is a bacterium; and said bacterium is selected from the group consisting of the genera *Acinetobacter, Arcobacter, Bacillus, Bacteroides, Borrelia, Brachyspira, Brucella, Burkholderia, Campylobacter, Clostridia, Coxiella, Enterococcus, Erysipelothrix, Francisella, Fusobacterium, Helicobacter, Lactobacillus, Listeria, Mycobacterium, Neisseria, Pseudomonas, Staphylococcus* and *Streptococcus*.

10. A method of treating or preventing a microbial infection in a mammal or bird comprising the step of administering to a mammal or bird in need thereof a therapeutically effective amount of a compound of claim 1.

11. The method of claim 10, wherein said microbial infection is caused by a protozoan or bacterium.

12. The method of claim 10, wherein said microbial infection is caused by a protozoan or a bacterium selected from the group consisting of the genera *Cryptosporidium, Entamoeba, Leishmania, Trypanosoma, Acinetobacter, Arcobacter, Bacillus, Bacteroides, Borrelia, Brachyspira, Brucella, Burkholderia, Campylobacter, Clostridia, Coxiella, Enterococcus, Erysipelothrix, Francisella, Fusobacterium, Helicobacter, Lactobacillus, Listeria, Mycobacterium, Neisseria, Pseudomonas, Staphylococcus* and *Streptococcus*.

13. The method of claim 11, wherein said microbial infection is caused by a protozoan; and said protozoan is selected from the group consisting of the genera *Cryptosporidium, Entamoeba, Leishmania* and *Trypanosoma*.

14. The method of claim 13, wherein said protozoan is selected from the genus *Cryptosporidium*.

15. The method of claim 11, wherein said microbial infection is caused by a bacterium; and said bacterium is selected from the group consisting of the genera *Acinetobacter, Arcobacter, Bacillus, Bacteroides, Borrelia, Brachyspira, Brucella, Burkholderia, Campylobacter,*

*Clostridia, Coxiella, Enterococcus, Erysipelothrix, Francisella, Fusobacterium, Helicobacter, Lactobacillus, Listeria, Mycobacterium, Neisseria, Pseudomonas, Staphylococcus* and *Streptococcus*.

16. The method of claim 10, further comprising the step of co-administering to a mammal or bird in need thereof a therapeutically effective amount of an antimicrobial agent.

17. The method of claim 16, wherein said antimicrobial agent is an antibiotic.

18. The method of claim 16, wherein said antimicrobial agent is an antiparasitic.

19. The method of claim 10, wherein said infection is in a mammal; and the mammal is a primate, a bovine, an ovine, an equine, a porcine, a rodent, a feline, a mustelid, or a canine.

20. The method of claim 10, wherein said infection is in a mammal; and the mammal is a human.

\* \* \* \* \*